US008603969B2

(12) United States Patent
Levy et al.

(10) Patent No.: US 8,603,969 B2
(45) Date of Patent: *Dec. 10, 2013

(54) PANCREATIC POLYPEPTIDE FAMILY MOTIFS AND POLYPEPTIDES COMPRISING THE SAME

(75) Inventors: Odile Esther Levy, San Diego, CA (US); Carolyn M. Jodka, Encinitas, CA (US); Soumitra S. Ghosh, San Diego, CA (US); David G. Parkes, Del Mar, CA (US); Richard A. Pittner, San Diego, CA (US); Lawrence J. D'Souza, San Diego, CA (US); John S. Ahn, San Diego, CA (US); Kathryn S. Prickett, San Diego, CA (US)

(73) Assignees: Amylin Pharmaceuticals, LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 1472 days.

This patent is subject to a terminal disclaimer.

(21) Appl. No.: 11/055,098

(22) Filed: Feb. 11, 2005

(65) Prior Publication Data

US 2006/0094653 A1    May 4, 2006

Related U.S. Application Data

(60) Provisional application No. 60/543,406, filed on Feb. 11, 2004, provisional application No. 60/543,407, filed on Feb. 11, 2004.

(51) Int. Cl.
*A61K 38/22* (2006.01)

(52) U.S. Cl.
USPC .......................................................... 514/5.2

(58) Field of Classification Search
None
See application file for complete search history.

(56) References Cited

U.S. PATENT DOCUMENTS

| | | | |
|---|---|---|---|
| 4,265,884 A | 5/1981 | Kofod | |
| 4,353,888 A | 10/1982 | Sefton | |
| 4,391,909 A | 7/1983 | Lim | |
| 4,533,494 A | 8/1985 | Uchiyama et al. | |
| 4,683,195 A | 7/1987 | Mullis et al. | |
| 4,683,202 A | 7/1987 | Mullis | |
| 4,839,343 A | 6/1989 | Waeber et al. | |
| 4,891,357 A | 1/1990 | Kala | |
| 4,892,538 A | 1/1990 | Aebisher et al. | |
| 5,106,627 A | 4/1992 | Aebischer et al. | |
| 5,308,701 A | 5/1994 | Cohen et al. | |
| 5,459,039 A | 10/1995 | Modrich et al. | |
| 5,498,531 A | 3/1996 | Jarrell | |
| 5,574,010 A | 11/1996 | McFadden | |
| 5,604,203 A | 2/1997 | Balasubramaniam | |
| 5,696,093 A | 12/1997 | Tseng | |
| 5,739,106 A | 4/1998 | Rink et al. | |
| 5,824,778 A | 10/1998 | Ishikawa et al. | |
| 5,824,784 A | 10/1998 | Kinstler et al. | |
| 5,912,227 A | 6/1999 | Croom, Jr. et al. | |
| 5,939,462 A | 8/1999 | Connell et al. | |
| 5,968,819 A | 10/1999 | Gerald et al. | |
| 5,980,945 A | 11/1999 | Ruiz | |
| 6,013,622 A | 1/2000 | Bruno et al. | |
| 6,315,203 B1 | 11/2001 | Ikeda et al. | |
| 6,355,478 B1 | 3/2002 | Baez et al. | |
| 6,391,343 B1 | 5/2002 | Yen | |
| 6,420,532 B1 | 7/2002 | Gerald et al. | |
| 6,506,724 B1 | 1/2003 | Hiles et al. | |
| 6,528,486 B1 | 3/2003 | Larsen et al. | |
| 6,558,708 B1 | 5/2003 | Lin | |
| 6,569,832 B1 | 5/2003 | Knudsen et al. | |
| 6,734,166 B1 | 5/2004 | Croom, Jr. et al. | |
| 7,459,432 B2 * | 12/2008 | Cowley et al. | 514/1.1 |
| 2002/0094346 A1 | 7/2002 | Lin | |

(Continued)

FOREIGN PATENT DOCUMENTS

EA         004791        8/2004
EP     0 992 239 B1     3/2003

(Continued)

OTHER PUBLICATIONS

Pollock, H. G. et al. "Isolation and structures of alligator gar (Lepisosteus spatula) insulin and pancreatic polypeptide," General and Comparative Endocrinology (1987), 67(3), 375-82.*

(Continued)

*Primary Examiner* — Thomas Heard
(74) *Attorney, Agent, or Firm* — Womble Carlyle Sandridge & Rice, LLP; Mark Pino; Alireza Behrooz

(57) ABSTRACT

The present invention relates to novel Pancreatic Polypeptide Family ("PPF") polypeptides. The PPF polypeptides of the invention generally include at least two PPF motif, have at least 50% sequence identity to PYY (3-36) over its length and will generally retain, at least in part, a biological activity of a PP, PYY or NPY. Preferred PPF polypeptides of the invention are those having a potency in one of the assays described herein (preferably food intake, gastric emptying, pancreatic secretion, or weight reduction assays) which is greater than the potency of PP, NPY, PYY, or PYY(3-36) in that same assay. In one aspect, the PPF polypeptides of the invention include novel PYY analog polypeptides. In another aspect, the PPF polypeptides of the invention include PPF chimeric polypeptides including a fragment of a PP family polypeptide linked to a second PP family polypeptide, wherein each of the first and second fragments includes a PPF motif. Methods of using the PPF polypeptides of the invention, and pharmaceutical compositions including the PPF polypeptides of the invention are also disclosed.

3 Claims, 23 Drawing Sheets

(56) References Cited

U.S. PATENT DOCUMENTS

| | | | |
|---|---|---|---|
| 2002/0141985 A1* | 10/2002 | Pittner et al. | 424/94.1 |
| 2003/0224983 A1 | 12/2003 | Nielsen | |
| 2004/0115135 A1 | 6/2004 | Quay | |
| 2004/0228846 A1 | 11/2004 | Pang et al. | |

FOREIGN PATENT DOCUMENTS

| | | | |
|---|---|---|---|
| EP | 1421950 A1 | | 5/2004 |
| JP | 06133731 | | 5/1994 |
| WO | WO 83/04053 | | 11/1983 |
| WO | WO 89/01967 | | 3/1989 |
| WO | WO 90/02580 | | 3/1990 |
| WO | WO 90/15637 | | 12/1990 |
| WO | WO 91/10425 | | 7/1991 |
| WO | WO 91/10470 | | 7/1991 |
| WO | WO 94/16101 | | 7/1994 |
| WO | WO 96/40196 | | 12/1996 |
| WO | WO 97/26321 | | 7/1997 |
| WO | WO 98/20885 | | 5/1998 |
| WO | WO 98/28427 | | 7/1998 |
| WO | WO 99/07404 | | 2/1999 |
| WO | WO 99/15516 | | 4/1999 |
| WO | WO 99/25727 | | 5/1999 |
| WO | WO 99/25728 | | 5/1999 |
| WO | WO 00/47219 | | 8/2000 |
| WO | WO 00/68197 | | 11/2000 |
| WO | WO 01/51078 A1 | | 7/2001 |
| WO | WO 01/62737 | | 8/2001 |
| WO | WO 01/76631 | | 10/2001 |
| WO | WO 02/46227 | | 6/2002 |
| WO | WO 03/011892 A2 | | 2/2003 |
| WO | WO 03/026591 A2 | | 4/2003 |
| WO | WO 03/057235 | | 5/2003 |
| WO | WO 03/105763 | | 12/2003 |
| WO | WO 2004/056313 A2 | | 7/2004 |
| WO | WO 2004/089279 | | 10/2004 |
| WO | WO 2005/077094 | | 8/2005 |
| WO | WO 2006/066024 | | 6/2006 |
| WO | WO 2006/108234 | | 10/2006 |

OTHER PUBLICATIONS

Conlon, J.M., "Neuropeptide Y-Related Peptides From the Pancreas of a Teleostean Eel Holostean Bowfin and Elasmobranch Skate Fish," Peptides, 1991, 221-226, vol. 12, No. 2.
Kofod, "Secretin and the Endocrine Pancreas", Acta Endocrinologica 126 (Suppl. 1.): 8-41 (1992).
Geoghegan and Pappas, "Clinical Uses of Gut Peptides", Annals of Surgery 225 (2) 145-154 (1997).
Nicholl et al., "The Hormonal Regulation of Food Intake, Digestion and Absorption", Ann. Rev. Nutr. 5: 213-239 (1995).
Nishitani et al., "Transcriptional Regulation of Secretin Gene Expression", J. Clin. Gastroenterology 2 (Suppl. 1.) : S50-S55 (1995).
Townsend et al., "Gastrointestinal Hormones and Cell Proliferation", Surgery Today (Jpn J Surg) 24 : 772-777 (1984).
Ulrich II et al., "Secretin and Vasoactive Intestinal Peptide Receptors:Members of a Unique Family of G Protein-Coupled Receptors", Gastroenterology 114: 382-397 (1998).
Funakoshi et al., "Changes in Insulin Secretion After Secretin Administration and the Implication in Diabetes Mellitus", Endocrinologica Japonoca 32 (4): 473-479 (1985).
Kofod et al., "Secretin and Its C-terminal Hexapeptide Potentiates Insulin Release in Mouse Islets", American Journal of Psychology, 250:E107-E113 (1986).
Lerner et al., "Augmentation by Secretin of Glucose Stimulated Insulin Responses in diabetes Subjects", Clinical Research 25: 126A (1997).
McCrea et al., 2-36[K, RYYSA]PP a novel Y5-receptor preferring ligand with strong stimulatory effect on food intake, Regulatory Peptides 87 (2000) 47-58.

Bork, Peer, "Powers and Pitfalls in Sequence Analysis: The 70% Hurdle." Genome Research, 10:398-400, 2000.
Bork, Peer, "Go hunting in sequence databases but watch out for traps." Trends in Genetics, vol. 12. No. 10. pp. 425-427, 1996.
Brenner, S.E., "Errors in genome annotation." Trends in Genetics, vol. 15. No. 4. pp. 132-133, 1999.
Doerks, Tobias, Protein annotation: detective work for function prediction. Trends in Genetics, vol. 14. No. 6. pp. 248-250, 1998.
Ngo, Thomas J., "Computational Complexity, Protein Structure Prediction and the Levinthal Paradox." In Merz and Le Grand (Eds.) The Protein Folding Problem and Tertiary Structure Predication, Birkhauser Boston, pp. 492-495, 1992.
Skolnick, Jeffrey et al., "From genes to protein structure and function: novel applications of computational approaches in the genomic era." Tibtech, vol. 18. No. 1. pp. 34-39, 2000.
Smith, Temple F. et al., "The challenges of genome sequence annotation or The devil is in the details". Nature Biotechnology, vol. 15. pp. 1222-1223, 1997.
Wells, J.A., "Additivity of Mutational Effects in Proteins." Biochemistry, vol. 29. No. 37. pp. 8509-8517, 1990.
Halford, Jason, et al., "The Psychopharmacology of Appetite: Targets for Potential Anti-Obesity Agents", Central Nervous System Agents in Medicinal Chemistry, Bentham Science Publishers Ltd., vol. 3, No. 4, pp. 283-310 (2003).
Howl, John, et al., "Chimeric Strategies for the Rotational Design of Bioactive Analogs of Small Peptide Hormones", FASEB Journal, Fed. of American Soc. for Experimental Biology, vol. 11, No. 7, pp. 582-590 (2007).
Chasrzad, Montrose-Rafizadeh, et al., "High Potency Antagonists of the Pancreatic Glucagon-like Peptide-1 Receptor", Journal of Biological Chemistry, American Soc. of Biochemical Biologists, vol. 272, No. 34, pp. 21201-21206 (1997).
Balasubramaniam, et al., "Antagonistic properties of centrally truncated analogs of (D-Trp-32)NPY", Journal of Medicine Chemistry, vol. 39, Nov. 5, 1996, pp. 1142-1147.
Ei-Salhy, et al., "Peptide YY in gastrointestinal disorders", Peptides, Elsevier, Amsterdam, US, vol. 23, Feb. 2002, pp. 397-402.
Adrian, T.E., et al., Gastroenterology (1985) 89, 1070-1077.
Adrian, T.E., et al. Digestion (1981) 21, 214-218.
Ahren, B. et al., Eur J Endocrinol (1996) 134, 362-365.
Allen, J.M., et al., Digestion (1984) 30, 255-262.
Ando, R., et al., Eur J Pharmacol (2001) 427, 53-59.
Andres, C.J., et al., Bioorg Med Chem Lett (2003) 13, 2883-2885.
Aponte, G.W., et al. FASEB J (1989) 3, 1949-55.
Asakawa, a., et al., Peptides (1999) 20, 1445-1448.
Bader, R., et al., Biochemistry (2002) 41, 8031-8042.
Balasubramaniam, A., et al., Peptides (1993) 14, 1011-1016.
Balasubramaniam, A., et al., Int J Pept Protein Res (1987) 29, 78-83.
Balasubramaniam, A., et al., Pept Res(1988) 1, 32-35.
Balasubramaniam, A., et al., Peptides (2002) 23, 1485-1490.
Balasubramaniam, A., et al., J Med Chem (2000) 43, 3420-3427.
Balasubramaniam, A. Peptides (1997) 18, 445-457.
Barany, F. Proc Natl Acad Sci U S A (1991) 88, 189-193.
Bartlett PA, et al. Bioorg Chem. 1986; 14:356-377.
Batterham, R.L., et al., N Engl J Med (2003) 349, 941-948.
Batterham, R.L., et al., Nature (2002) 418, 650-654.
Beck, A., et al., FEBS Lett (1989) 244, 119-122.
Beck-Sickinger, A.G., et al., J Recept Res (1993) 13, 215-228.
Beltowski, J. et al., Pol J Pharmacol (2004) 56, 5-27.
Berge, S.M., et al., J Pharm Sci (1977) 66, 1-19.
Berglund, M.M., et al., Exp Biol Med (Maywood) (2003) 228, 217-244.
Bertrand, G., et al., Pancreas (1992) 7, 595-600.
Birdsall, N.J.M. et al., Trends Pharmacol Sci (1983) 4, 459-463.
Bischoff, A. et al., Trends Pharmacol Sci (1999) 20, 104-106.
Bonaz, B., et al., Neurosci Lett (1993) 163, 77-80.
Bottcher, G., et al., Pancreas (1989) 4, 282-288.
Boublik, J.H., et al., J Med Chem (1989) 32, 597-601.
Bourguet E, et al., Bioorg Med Chem Lett. (2003) 13:1561-1564.
Brown, K.K., et al., Diabetes (1999) 48, 1415-1424.
Cabrele, C. et al., J Pept Sci (2000) 6, 97-122.
Cabrele, C., et al., J Biol Chem (2000) 275, 36043-36048.
Cabrele, C., et al., Biochemistry (2002) 41, 8043-8049.

(56) References Cited

OTHER PUBLICATIONS

Cabrele, C., Peptides (2001) 22, 365-378.
Camilleri, M., et al., Gut (1981) 22, 14-18.
Campfield, L.A., et al., Science (1995) 269, 546-549.
Chen, C.H. et al., Am J Physiol (1995) 269, R787-R792.
Chen, C.H., et al., Regul Pept (1996) 61, 95-98.
Chen, C.H., et al., Neurogastroenterol Motil (1997) 9, 109-116.
Chen, M.H., et al., Gastroenterology (1984) 87, 1332-1338.
Chen, Z., et al., FEBS Lett (2001) 492, 119-122.
Clark, J.T., et al., Endocrinology (1984) 115, 427-429.
Clark, J.T., et al., Regul Pept (1987) 17, 31-39.
Conlon, J.M. Peptides (2002) 23, 269-278.
Cook, D.L. et al., Nature (1984) 311, 271-273.
Corp, E.S., et al., Peptides (2001) 22, 493-499.
Corp, E.S., et al., Am J Physiol (1990) 259, R317-R323.
Coruzzi, G., et al, Arch Int Pharmacodyn Ther (1989) 302, 232-241.
Cotton, R.G. Mutat Res (1993) 285, 125-144.
Cotton, R.G., et al., Proc Natl Acad Sci U S A (1988) 85, 4397-4401.
Cox, H.M. et al., Br J Pharmacol (1990) 101, 247-252.
Cox, H.M., et al., J Physiol (1988) 398, 65-80.
Cox, H.M., et al., Regul Pept (1998) 75-76, 3-8.
Dea, D., et al., Gastroenterology (1989) 96, 695-703.
Deng, X., et al., Dig Dis Sci (2001) 46, 156-165.
Dox, I.G., et al., Definition of 'islet'. In: Anonymous The HarperCollins Illustrated Medical Dictionary, (1993) 1st edn. pp. 227 New York: HarperCollins Publishers, Inc.
Dumont, Y., et al., Brain Res Mol Brain Res (1994) 26, 320-324.
Dumont, Y., et al., Eur J Pharrnacol (1993) 238, 37-45.
Dumont Y, et al., Society for Neuroscience Abstracts. 1993;19:726. Abstract 299.8.
Eberlein, G.A., et al., Peptides (1989) 10, 797-803.
Ebert, R. Z Gastroenterol Verh (1988) 23, 165-170.
Eto, B., et al., Peptides (1995) 16, 1403-1409.
Fackelmann USA Today, Health and Science Gut hormone could curb urge to overeat. (Aug. 7, 2002).
Feinstein, R.D., et al., J Med Chem (1992) 35, 2836-2843.
Ferber, S., et al., Journal of Biological Chemistry (1994) 269, 11523-11529.
Fournier, A., et al., Mol Pharmacol (1994) 45, 93-101.
Freshney, R.I. Freshney, R.I., (Ed.) Culture of Animal Cells: A Manual of Basic Technique, (1983) pp. 4 New York: Alan R. Liss, Inc.
Garlicki, J., et al., Am J Physiol (1990) 258, E40-E45.
Gedulin, B., et al., Gastroenterology (1995) 108, A604.
Gehlert, D.R. Proc Soc Exp Biol Med (1998) 218, 7-22.
Gibbs, R.A., et al., Nucleic Acids Res (1989) 17, 2437-2448.
Gobbi, M., et al., J Neurochem (1999) 72, 1663-1670.
Gold, G., et al., Diabetes (1981) 30, 77-82.
Gomez, G., et al., Am J Physiol (1995) 268, G71-G81.
Gordon, E.A., et al., Neurosci Lett (1990) 119, 187-190.
Grandt, D., et al., Regul Pept (1994) 51, 151-159.
Grandt, D., et al Biochem Biophys Res Commun (1992) 186, 1299-1306.
Greeley, G.H et al., Proc Soc Exp Biol Med (1988) 189, 325-328.
Greeley, G.H. et al., Am J Physiol (1988) 254, E513-E517.
Grieco P, et al., Tetrahedron Lett. 2002;43:6297-6299.
Groth, C.G., et, al. Transplant Proc (1992) 24, 972-973.
Grouzmann, E., et al., Endocrine Society Program & Abstracts 75th Annual Meeting, Las Vegas, NV, Jun. 9-12 (1993) 180. Abstract 519B.
Grundemar, L., et al. Regul Pept (1996) 62, 131-136.
Gu X, et al., Tetrahedron Lett. 2003;44:5863-5866.
Guan, D., et al., Endocrinology (1991) 128, 911-916.
Gue, M., et al., Br J Pharmacol (1996) 118, 237-242.
Gustaysson, S., et al., Scand J Gastroenterol (1977) 12, 993-997.
Hagan, M.M. et al., Pharmacol Biochem Behav (1993) 45, 941-944.
Halaas, J.L., et al., Science (1995) 269, 543-546.
Halatchev, I.G., et al., Endocrinology (2004) 145, 2585-2590.
Hanessian S, et al., Tetrahedron. 1997;53:12789-12854.
Harding, R.K. et al., Peptides (1989) 10, 21-24.
Haynes, J.M., et al., Br J Pharmacol (1997) 122, 1530-1536.
Henry, M.et al., Obes Res (2005) 13, 36-47.
Hoentjen, F., et al., Scand J Gastroenterol (2000) 35, 166-171.
Holliday, N.D. et al., Br J Pharmacol (1996) 119, 321-329.
Hsu, I.C., et al., Carcinogenesis (1994) 15, 1657-1662.
Hu, Y., et al., J Biol Chem (1996) 271, 26315-26319.
Hughes, S.D., et al., Proceedings of the National Academy of Sciences of the United States of America (1992) 89, 688-692.
Inui, A. Trends Pharmacol Sci (1999) 20, 43-46.
Iyengar, S., et al., J Pharmacol Exp Ther (1999) 289, 1031-1040.
Jackerott, M. et al., Endocrinology (1997) 138, 5013-5018.
Jackerott, M., et al., J Histochem Cytochem (1996) 44, 809-817.
Johnson, J.H., et al., Science (1990) 250, 546-549.
Jones, P.M. et al., Endocr Rev (1998) 19, 429-461.
Kanatani, A., et al., Biochem Biophys Res Commun (2000) 272, 169-173.
Kanatani, A. et al., Biochem Biophys Res Commun (1999) 266, 88-91.
Kanatani, A., et al., Endocrinology (2000) 141, 1011-1016.
Karlsson S, et al., Acta Physiol Scand. 1996;157:305-306.
Kato, K., et al., Peptides (1995) 16, 1257-1262.
Kawakubo, K., et al., (2000) Brain Res 854, 30-34.
Keire, D.A., et al., Peptides (2002) 23, 305-321.
Keire, D.A., et al., Biochemistry (2000) 39, 9935-9942.
Keire, D.A., et al., Am J Physiol (2000) 279, G126-G131.
Kimmel, J.R., et al., Endocrinology (1968) 83, 1323-1330.
Kirby, D.A., et al., J Med Chem (1993) 36, 3802-3808.
Kirby, D.A., et al., J Med Chem (1995) 38, 4579-4586.
Kopelman, P.G. Nature (2000) 404, 635-643.
Korsgren, O., et al., Transplantation (1988) 45, 509-514.
Krasinski, S.D., et al., Mol Endocrinol (1991) 5, 433-440.
Krstenansky, J.L., et al., Proc Natl Acad Sci (1989) U S A 86, 4377-4381.
Krstenansky, J.L., et al., Neuropeptides (1990) 17, 117-120.
Kruger, D.F., et al., Diabetes Educ (1999) 25, 389-397; quiz 398.
Kumagai Braesch, M., et, al., Transplant Proc (1992) 24, 679-680.
Kushi, A., et al., Proc Natl Acad Sci U S A (1998) 95, 15659-15664.
Lacy, P.E., et al., Science (1991) 254, 1782-1784.
Landegren, U., et al., Science (1988) 241, 1077-1080.
Leban, J.J., et al., J Med Chem (1995) 38, 1150-1157.
Leibowitz, S.F. et al., Peptides (1991) 12, 1251-1260.
Liu, C.D., et al., J Gastrointest Surg (2001) 5, 147-152.
Liu, X.M., et al., Diabetes (1991) 40, 858-66.
Lloyd, K.C.K., et al., Am J Physiol (1996) 270, G123-G127.
Lluis, F., et al., Gastroenterology (1988) 94, 137-144.
Lundberg, J.M., et al., Proc Natl Acad Sci U S A (1982) 79, 4471-4475.
Lundell, I., et al., J Biol Chem (1995) 270, 29123-29128.
Lyznicki JM, et al., Am Fam Physician. 2001;63:2185-2196.
Makimura, H. et al., Obesity Poster Abstract No. 118 "Adrenalectomy stimulated hypothalamic proopiomelanocortin mRNA but does not correct obesity in diet-induced obese mice.".
Malaisse-Lagae, F., et al., Experientia (1977) 33, 915-917.
Markison S., et al., Obesity Poster Abstract No. 119 "Selective melanin-concentrating hormone receptor antagonists decrease feeding in rodents.".
Marsh, D.J., et al., Nat Med (1998) 4, 718-721.
Martin, J.R. Brain Res (2004) 1002, 11-20.
Martin, N.M., et al., Int J Obes Relat Metab Disord (2004) 28, 886-893.
Mashiko, S., et al., Endocrinology(2003) 144, 1793-1801.
Mashiko et al., Obesity Poster Abstract No. 120 "Characterization of neuropeptide Y Y5 receptor mediated obesity in mice.".
Maxam, A.M. et al., Proc Natl Acad Sci U S A (1977) 74, 560-564.
Mazelin L, et al., J Auton Nerv Syst. 1998;73:38-45.
Medeiros, M.D. et al., Endocrinology (1994) 134, 2088-2094.
Michel, M.C., et al., Pharmacol Rev (1998) 50, 143-150.
Morley, J.E. Neuropsychobiology (1989) 21, 22-30.
Morley, J.E., et al., Life Sci (1987) 41, 2157-2165.
Morley, J.E., et al., Am J Physiol (1994) 267, R178-R184.
Morley, J.E., et al., Brain Res (1985) 341, 200-203.
Morris GP, et al., Gastroenterology. (1989);96:795-803.
Mulder, H., et al., Microscopy Research and Technique (1998) 43, 313-321.

(56) References Cited

OTHER PUBLICATIONS

Mullins, D., et al., Mol Pharmacol (2001) 60, 534-540.
Munson, P.J. et al., Anal Biochem (1980) 107, 220-239.
Murakami, Y., et al., J Med Chem (1999) 42, 2621-2632.
Murase, S., et al., J Biochem (Tokyo) (1996) 119, 37-41.
Myers, R.M., et al., Science (1985) 230, 1242-1246.
Myers, R.M., et al., Nature (1985) 313, 495-498.
Naeve, C.W., et al., Biotechniques (1995) 19, 448-453.
Nakajima, M., et al., J Pharmacol Exp Ther (1994) 268, 1010-1014.
Nakazawa, H., et al., Proc Natl Acad Sci U S A (1994) 91, 360-364.
Naslund, E., et al., Int J Obes Relat Metab Disord (1999) 23, 304-311.
Ngo, J.T. et al., The protein folding problem and tertiary structure prediction, (1994) pp. 491-495. Boston: Birkhauser.
Nieuwenhuizen, A.G., et al., Diabetologia (1994) 37, 871-878.
Nightingale, J.M., et al., Gut (1996) 39, 267-272.
Odagiri, H., et al., J Biol Chem (1996) 271, 1909-1915.
Okada, S., et al., Endocrine Society Program & Abstracts 75th Annual Meeting, Las Vegas, NV, Jun. 9-12, 1993 180. Abstract 520B.
Okumura, T., et al., Neuroscience Letters(1994) 178, 167-170.
Orita, M., et al., Proc Natl Acad Sci U S A (1989) 86, 2766-2770.
Otonkoski, T., et al., Diabetes (1988) 37, 286-291.
Pappas, T.N., et al., Gastroenterology (1986) 91, 1386-1389.
Pappas, T.N., et al., Am J Physiol (1985) 248, G118-G123.
Parker, E.M., et al., Eur J Pharmacol (1998) 349, 97-105.
Parker, E.M., et al., Peptides (2000) 21, 393-399.
Parker, S.L. et al., Can J Physiol Pharmacol (2000) 78, 150-161.
Pelleymounter, M.A., et al., Science (1995) 269, 540-543.
Pheng, L.H., et al., Br J Pharmacol (2003) 139, 695-704.
Pironi, L., et al., Gastroenterology (1993) 105, 733-739.
Pokrovsky, V.I. (1996) Nephrotomy: renal insufficiency. In: Academician of RAMS, (Ed.) Small Medical Encyclopedia, pp. 59-62. Moscow: Meditisina Publishers) (w/ trnsltn).
Potter, E.K., et al., Eur J Pharmacol (1994) 267, 253-262.
Randle, P.J. Diabetes Metab Rev(1998) 14, 263-283.
Renshaw, D. et al., Curr Drug Targets (2005) 6, 171-179.
Rhodes, C.J. et al., J Cell Biol (1987) 105, 145-153.
Rico, L. et al., Obesity Poster Abstract No. 117 "Early and dissociated leptin and insulin resistance in transgenic mice overexpressing leptin from keratinocytes."
Rissanen, A., et al., BMJ (1990) 301, 835-837.
Rist, B., et al., Eur J Biochem (1997) 247, 1019-1028.
Rist, B., et al., FEBS Lett (1996) 394, 169-173.
Robbins, L.S., et al., The Endocrine Pancreas. In: Robbins, L.S., Cotran, R.S. and Kumar, V., (Eds.) Pathologic Basis of Disease, (1984) 3rd edn. pp. 972-990. Philadelphi:.
Saiki, R.K., et al., Nature (1986) 324, 163-166.
Saiki, R.K., et al., Proc Natl Acad Sci U S A (1989) 86, 6230-6234.
Sainsbury, A.,et al., Genes Dev (2002) 16, 1077-1088.
Saleeba, J.A. et al., Methods Enzymol (1993) 217, 286-295.
Sandberg M, et al., J Med Chem. 1998;41:2481-2491.
Sander, M., et al., Proc Natl Acad Sci U S A (1998) 95, 11572-11577.
Sanger, F., et al., Proc Natl Acad Sci U S A (1977) 74, 5463-5467.
Sato, N., et al., J Med Chem (2003) 46, 666-669.
Savage, A.P., et al., Gut (1987) 28, 166-170.
Scatchard, G. Ann NY Acad Sci (1949) 51, 660.
Scheen, A.J. Drugs (1997) 54, 355-368.
Schuit, F.C. Horm Res (1996) 46, 99-106.
Schwartz, M.W., et al., Nature (2000) 404, 661-671.
Servin, A.L., et al., Endocrinology (1989) 124, 692-700.
Shan, L., et al., Science (2002) 297, 2275-2279.
Sheikh, S.P. Am J Physiol (1991) 261, G701-G715.
Silva, A.P., et al., Clin Chim Acta (2002) 326, 3-25.
Simeonovic, C.J. et al., Aust J Exp Biol Med Sci (1982) 60 Pt 4, 383-390.
Slack, J.M. Development (1995) 121, 1569-1580.
Small, C.J., et al., Proc Natl Acad Sci U S A (1997) 94, 11686-11691.
Soil, R.M., et al., Eur J Biochem (2001) 268, 2828-2837.
Souers AJ, et al., Tetrahedron. 2001;57:7431-7448.
Stanley, B.G., et al., Peptides (1985) 6, 1205-1211.
Sullivan, S.J., et al., Science (1991) 252, 718-721.
Surwit, R.S., et al., Metabolism—Clinical and Experimental (1995) 44, 645-651.
Suzuki, T., et al., Gastroenterology (1983) 85, 114-121.
Taniguchi, H., et al., Eur J Pharmacol(1996) 312, 227-233.
Tatemoto, K. Proc Natl Acad Sci U S A (1982) 79, 2514-2518.
Tatemoto, K. Proc Natl Acad Sci U S A (1982) 79, 5485-5489.
Tatemoto, K., et al., Nature (1982) 296, 659-660.
Tatemoto, K., et al., Proc Natl Acad Sci U S A (1992) 89, 1174-1178.
Tatemoto, K., et al., Biochem Biophys Res Commun (1988) 157, 713-717.
Taylor, I.L. J Dairy Sci (1993) 76, 2094-2101.
Taylor, I.L. Am J Physiol (1985) 248, G277-G28.
Teyssen, S., et al., Pancreas (1996) 13, 80-88.
Thorens, B,et al., Proceedings of the National Academy of Sciences of the United States of America (1990) 87, 6492-6496.
Thum, A., et al., Exp Clin Endocrinol Diabetes (2002) 110, 113-118.
Tito JM, et al., Am J Surg. 1993;165:690-696.
Totheroh, G., "Science Offers Promising Treatment for an Overweight Nation" CBN News (Sep. 4, 2003).
Tsai JH, et al., Bioorg Med Chem. 1999;7:29-38.
Tschop, M., et al., Nature (2004) 430, 1 p following 165; discussion 2 p following 165.
Tseng, W.W. et al., Peptides (2002) 23, 389-395.
Tuch, B.E., et al., J Endocrinol (1992) 132, 159-167.
Turnbull, A.V., et al., Diabetes (2002) 51, 2441-2449.
Ueno, N., et al., Gastroenterology (1999) 117, 1427-1432.
Upchurch, B.H., et al., Development (1994) 120, 245-252.
Valera, A., et al., J Biol Chem (1994) 269, 28543-28546.
van Santbrink, E.J. et al., J Clin Endocrinol Metab (1997) 82, 3597-602.
Verchere, C.B., et al., Endocrine Society Program & Abstracts 75th Annual Meeting, Las Vegas, NV, Jun. 9-12, 1993 180. Abstract 517B.
Virgilio AA, et al., Tetrahedron. 1997;53:6635-6644.
Voisin, T., et al., J Biol Chem (1993) 268, 20547-20554.
Wager-Page, S.A., et al., Can J Physiol Pharmacol (1993) 71, 768-775.
Wahoff, D.C., et al., Transplant Proc (1994) 26, 804.
Walker, M.W., et al., J Neurosci (1988) 8, 2438-2446.
Walker, M.W., et al., Peptides (1997) 18, 609-612.
Wang, Z.L., et al., Endocrine Society Program & Abstracts 75th Annual Meeting, Las Vegas, NV, Jun. 9-12, 1993 180. Abstract 518B.
Weinberg, D.H., et al., J Biol Chem (1996) 271, 16435-16438.
Wells, J.A. Biochemistry (1990) 29, 8509-8517.
Widdowson, P.S., et al., Brain Res (1997) 778, 242-250.
Wilding, J.P. Diabet Med (2002) 19, 619-627.
Wiley, J.W., et al., Gastroenterology (1991) 100, 865-872.
Wilson, J.D., et al., Diabetes (1989) 38 Suppl 1, 217-219.
Wimalawansa, S.J. Crit Rev Neurobiol (1997) 11, 167-239.
Yang, H., et al., Br J Pharmacol (1998) 123, 1549-1554.
Yang, H. et al., Am J Physiol (1995) 268, G943-G948.
Yoshinaga, K., et al Am J Physiol (1992) 263, G695-G701.
Young, A.A. et al., Program and Abstracts, 10th International Congress of Endocrinology (1996) 419 (poster P2-58).
Young, A.A., et al., Metabolism (1996) 45, 1-3.
Zai, H., et al., Regul Pept (1996) 61, 181-188.
Towfigh et al., Surgical Forum vol. 50: 25-27 (1999).
Aponte, G.W. (2002) Peptides 23, 367-376.
Bousquet-Melou, A., et al. (1995) J Lipid Res 36, 451-461.
Pi-Sunyer, F.X. (2002) Obes Surg 12 Suppl 1, 6S-11S.
St-Onge, M.P. et al., (2002) J Nutr 132, 329-332.
Valet, P., et al., (1990) J Clin Invest 85, 291-295.

\* cited by examiner

Peptides with Combination of Substitutions Are Active in Appetite Suppression

Food Intake Assay, Mouse, Dose: 10 nmol/kg i.p.

PPF Polypeptides with Unnatural AA Substitution or N-Terminus Modification Retain Anorectic Effect PPF Chimeric Polypeptides Are Active in Appetite Suppression PPF Chimeric Polypeptides Are Active in Appetite Suppression Peptides with Combination of Substitutions Are Active in DIO Mouse Model DIO Assay, Fattened C57BL/6 Mouse Dose: 75 nmol/kg/day, s.c. pump infusion PPF Polypeptide Shows efficacy in *in-vivo* Assays

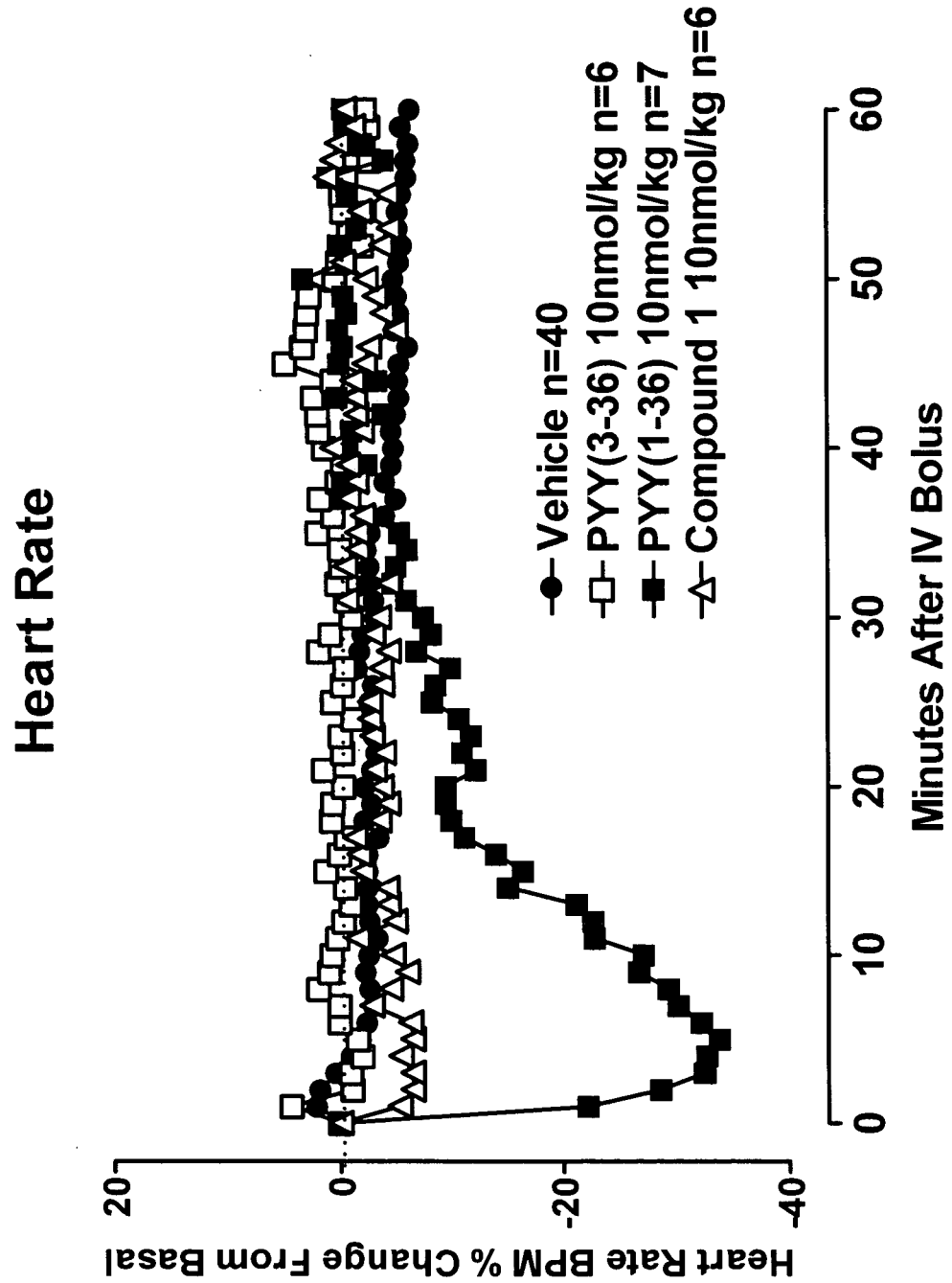
Figure 9-A

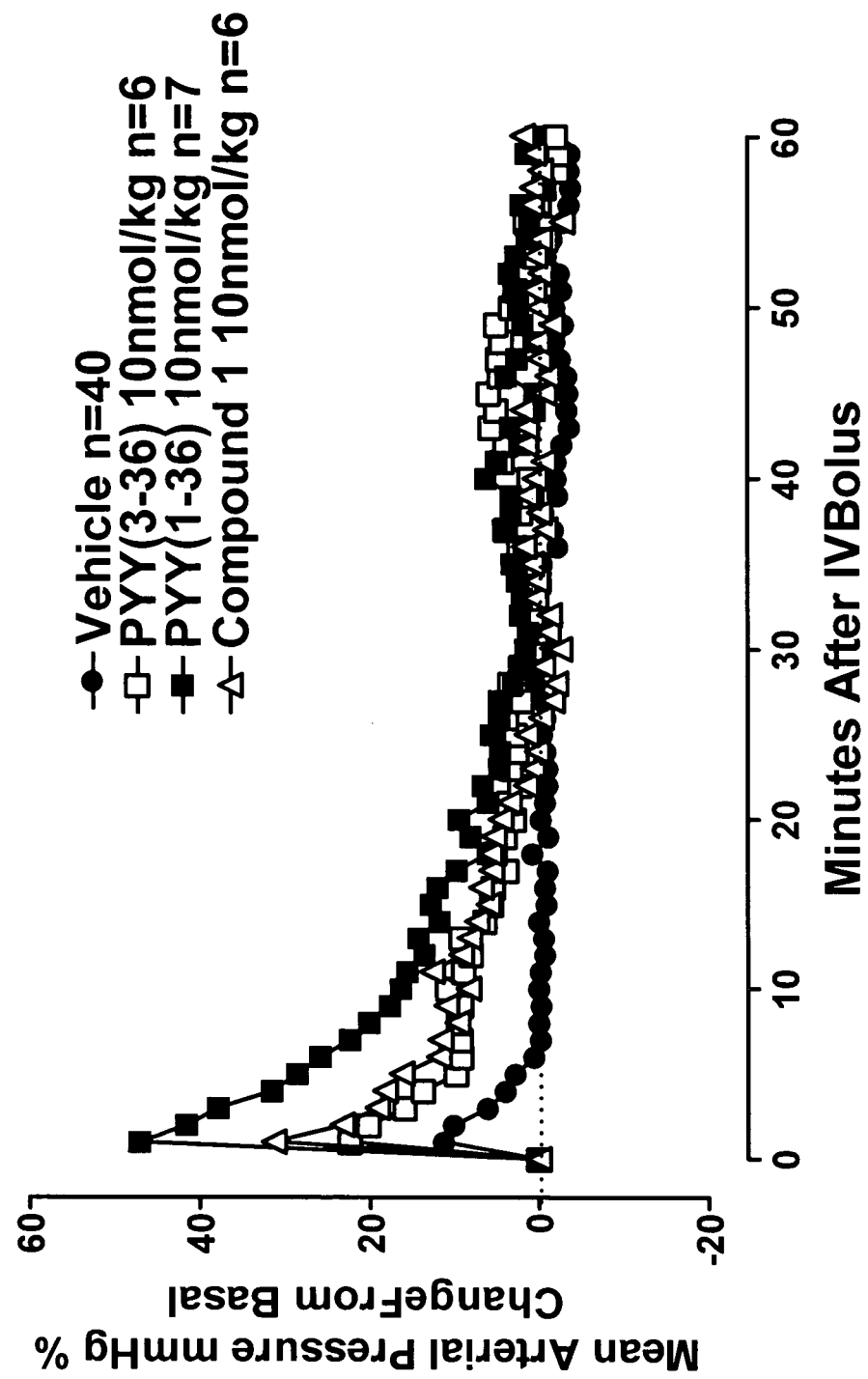
Figure 9-B

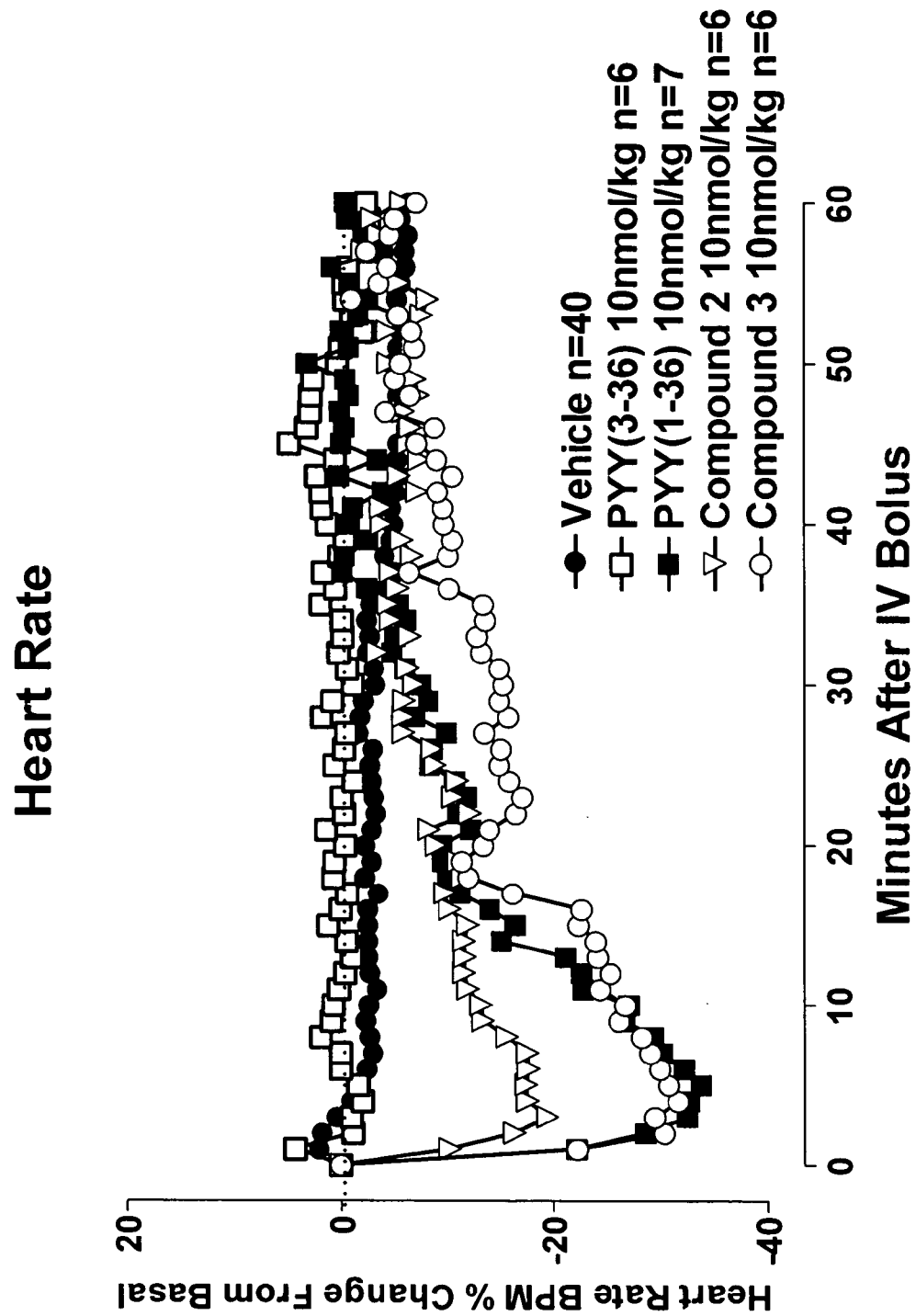
Figure 9-C

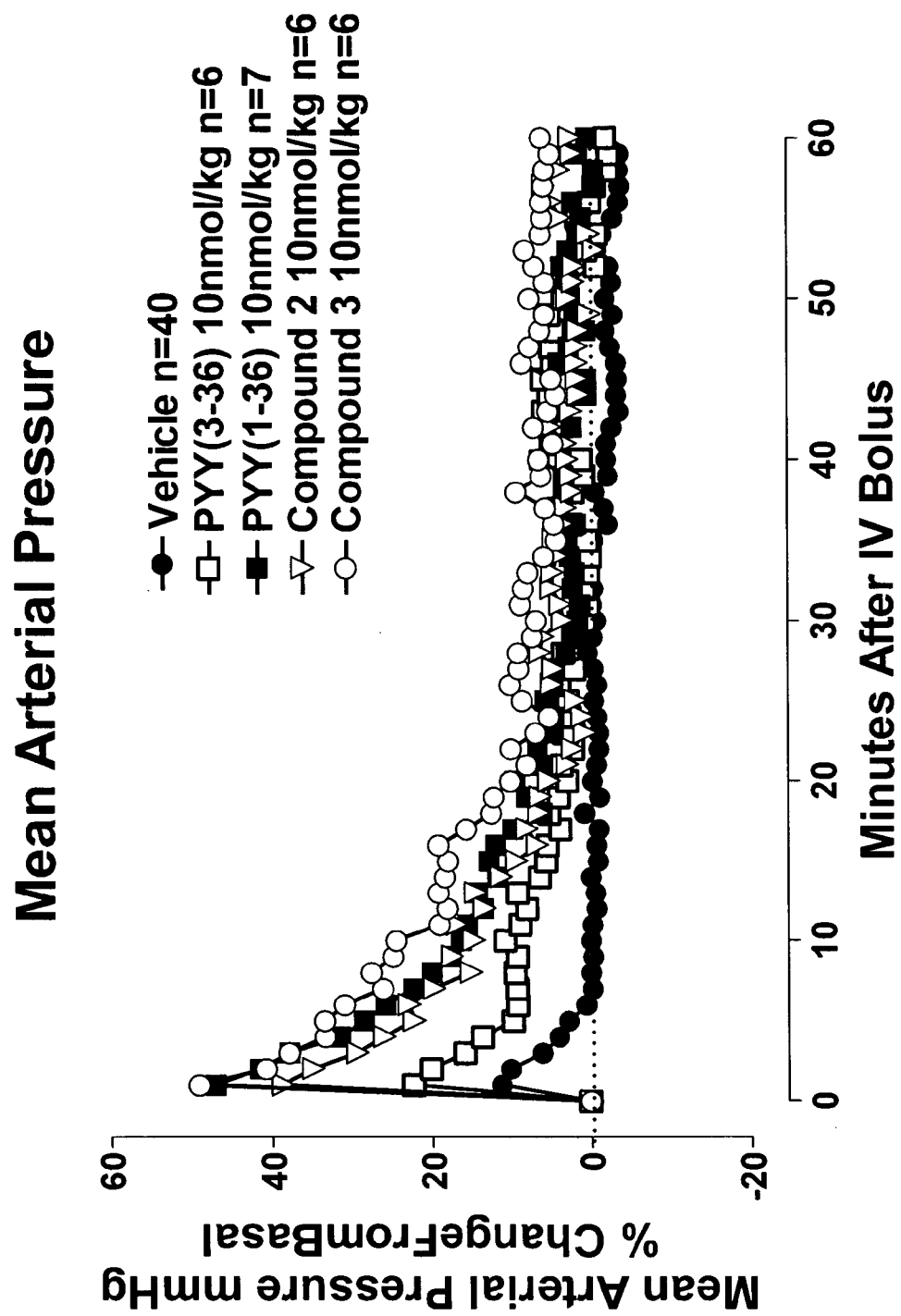
Figure 9-D

* P< 0.05 compared to saline

```
                          SEQUENCE LISTING

<160> NUMBER OF SEQ ID NOS: 435

<210> SEQ ID NO 1
<211> LENGTH: 36
<212> TYPE: PRT
<213> ORGANISM: Homo sapiens

<400> SEQUENCE: 1

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 2
<211> LENGTH: 36
<212> TYPE: PRT
<213> ORGANISM: Homo sapiens

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 34
<212> TYPE: PRT
<213> ORGANISM: Homo sapiens

<400> SEQUENCE: 3

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 4
<211> LENGTH: 36
<212> TYPE: PRT
<213> ORGANISM: Homo sapiens

<400> SEQUENCE: 4

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 5
<211> LENGTH: 36
<212> TYPE: PRT
```

<213> ORGANISM: Homo sapiens
<220> FEATURE:
<221> NAME/KEY: MOD_RES
<222> LOCATION: (32)
<223> OTHER INFORMATION: Aib

<400> SEQUENCE: 5

Ala Pro Leu Glu Pro Val Tyr Pro Gly Asp Asn Ala Thr Pro Glu Gln
1               5                   10                  15
Met Ala Arg Tyr Tyr Ser Ala Leu Arg His Tyr Ile Asn Leu Ala Xaa
            20                  25                  30
Arg Gln Arg Tyr
        35

<210> SEQ ID NO 6
<211> LENGTH: 36
<212> TYPE: PRT
<213> ORGANISM: Homo sapiens

<400> SEQUENCE: 6

Ala Pro Leu Glu Pro Val Tyr Pro Gly Asp Asn Ala Thr Pro Glu Gln
1               5                   10                  15
Met Ala Arg Tyr Tyr Ser Ala Leu Arg His Tyr Ile Asn Leu Ile Thr
            20                  25                  30
Arg Gln Arg Tyr
        35

<210> SEQ ID NO 7
<211> LENGTH: 36
<212> TYPE: PRT
<213> ORGANISM: Raja rhina

<400> SEQUENCE: 7

Tyr Pro Pro Lys Pro Glu Ser Pro Gly Glu Asn Ala Thr Pro Glu Glu
1               5                   10                  15
Leu Ala Lys Tyr Ile Ser Ala Asp Arg His Tyr Ile Asn Leu Val Thr
            20                  25                  30
Arg Gln Arg Tyr
        35

<210> SEQ ID NO 8
<211> LENGTH: 34
<212> TYPE: PRT
<213> ORGANISM: Raja rhina

<400> SEQUENCE: 8

Pro Lys Pro Glu Ser Pro Gly Glu Asn Ala Thr Pro Glu Glu Leu Ala
1               5                   10                  15
Lys Tyr Ile Ser Ala Asp Arg His Tyr Ile Asn Leu Val Thr Arg Gln
            20                  25                  30
Arg Tyr

<210> SEQ ID NO 9
<211> LENGTH: 36
<212> TYPE: PRT
<213> ORGANISM: Danio rerio

<400> SEQUENCE: 9

Ala Pro Pro Lys Pro Glu His Pro Gly Asp Asp Ala Pro Ala Glu Asp
1               5                   10                  15
Val Ala Lys Tyr Tyr Thr Ala Leu Arg His Tyr Ile Asn Leu Ile Thr
            20                  25                  30

Arg Gln Arg Tyr
        35

<210> SEQ ID NO 10
<211> LENGTH: 34
<212> TYPE: PRT
<213> ORGANISM: Danio rerio

<400> SEQUENCE: 10

Pro Lys Pro Glu His Pro Gly Asp Asp Ala Pro Ala Glu Asp Val Ala
1               5                   10                  15

Lys Tyr Tyr Thr Ala Leu Arg His Tyr Ile Asn Leu Ile Thr Arg Gln
            20                  25                  30

Arg Tyr

<210> SEQ ID NO 11
<211> LENGTH: 34
<212> TYPE: PRT
<213> ORGANISM: Raja rhina

<400> SEQUENCE: 11

Pro Lys Pro Glu Asn Pro Gly Glu Asp Ala Pro Pro Glu Glu Leu Ala
1               5                   10                  15

Lys Tyr Tyr Ser Ala Leu Arg His Tyr Ile Asn Leu Ile Thr Arg Gln
            20                  25                  30

Arg Tyr

<210> SEQ ID NO 12
<211> LENGTH: 37
<212> TYPE: PRT
<213> ORGANISM: Gallus gallus

<400> SEQUENCE: 12

Ala Tyr Pro Pro Lys Pro Glu Ser Pro Gly Asp Ala Ala Ser Pro Glu
1               5                   10                  15

Glu Ile Ala Gln Tyr Phe Ser Ala Leu Arg His Tyr Ile Asn Leu Val
            20                  25                  30

Thr Arg Gln Arg Tyr
        35

<210> SEQ ID NO 13
<211> LENGTH: 36
<212> TYPE: PRT
<213> ORGANISM: Rana ridibunda

<400> SEQUENCE: 13

Met Pro Pro Lys Pro Asp Asn Pro Ser Ser Asp Ala Ser Pro Glu Glu
1               5                   10                  15

Leu Ser Lys Tyr Met Leu Ala Val Arg Asn Tyr Ile Asn Leu Ile Thr
            20                  25                  30

Arg Gln Arg Tyr
        35

<210> SEQ ID NO 14
<211> LENGTH: 34
<212> TYPE: PRT
<213> ORGANISM: Rana ridibunda

<400> SEQUENCE: 14

Pro Lys Pro Asp Asn Pro Ser Ser Asp Ala Ser Pro Glu Glu Leu Ser
1               5                   10                  15

```
Lys Tyr Met Leu Ala Val Arg Asn Tyr Ile Asn Leu Ile Thr Arg Gln
            20                  25                  30

Arg Tyr

<210> SEQ ID NO 15
<211> LENGTH: 34
<212> TYPE: PRT
<213> ORGANISM: Ichthyomyzon gagei

<400> SEQUENCE: 15

Pro Lys Pro Asp Asn Pro Gly Asp Asn Ala Ser Pro Glu Gln Met Ala
1               5                   10                  15

Arg Tyr Lys Ala Ala Val Arg His Tyr Ile Asn Leu Ile Thr Arg Gln
            20                  25                  30

Arg Tyr

<210> SEQ ID NO 16
<211> LENGTH: 34
<212> TYPE: PRT
<213> ORGANISM: Raja rhina

<400> SEQUENCE: 16

Pro Lys Pro Glu Asn Pro Gly Asp Asn Ala Ser Pro Glu Glu Met Ala
1               5                   10                  15

Lys Tyr Phe Ser Ala Leu Arg His Tyr Ile Asn Leu Val Thr Arg Gln
            20                  25                  30

Arg Tyr

<210> SEQ ID NO 17
<211> LENGTH: 34
<212> TYPE: PRT
<213> ORGANISM: Rana ridibunda

<400> SEQUENCE: 17

Thr Lys Pro Glu Asn Pro Gly Asn Asp Ala Ser Pro Gln Glu Met Ala
1               5                   10                  15

Lys Tyr Met Thr Ala Leu Arg His Tyr Val Asn Leu Ile Thr Arg Gln
            20                  25                  30

Arg Tyr

<210> SEQ ID NO 18
<211> LENGTH: 36
<212> TYPE: PRT
<213> ORGANISM: Rana ridibunda

<400> SEQUENCE: 18

Tyr Pro Pro Lys Pro Glu Asn Pro Gly Glu Asp Ala Ser Pro Glu Glu
1               5                   10                  15

Met Thr Lys Tyr Leu Thr Ala Leu Arg His Tyr Ile Asn Leu Val Thr
            20                  25                  30

Arg Gln Arg Tyr
        35

<210> SEQ ID NO 19
<211> LENGTH: 34
<212> TYPE: PRT
<213> ORGANISM: Rana ridibunda

<400> SEQUENCE: 19

Pro Lys Pro Glu Asn Pro Gly Glu Asp Ala Ser Pro Glu Glu Met Thr
```

```
                1               5                   10                  15
Lys Tyr Leu Thr Ala Leu Arg His Tyr Ile Asn Leu Val Thr Arg Gln
                20                  25                  30
Arg Tyr

<210> SEQ ID NO 20
<211> LENGTH: 34
<212> TYPE: PRT
<213> ORGANISM: Danio rerio

<400> SEQUENCE: 20

Ile Lys Pro Glu Ala Pro Gly Glu Asp Ala Ser Pro Glu Glu Leu Ala
1               5                   10                  15
Lys Tyr Tyr Thr Ala Leu Arg His Tyr Ile Asn Leu Ile Thr Arg Gln
                20                  25                  30
Arg Tyr

<210> SEQ ID NO 21
<211> LENGTH: 34
<212> TYPE: PRT
<213> ORGANISM: Amia calva

<400> SEQUENCE: 21

Ser Lys Pro Asp Asn Pro Gly Glu Asp Ala Pro Ala Glu Asp Met Ala
1               5                   10                  15
Lys Tyr Tyr Thr Ala Leu Arg His Tyr Ile Asn Leu Ile Thr Arg Gln
                20                  25                  30
Arg Tyr

<210> SEQ ID NO 22
<211> LENGTH: 34
<212> TYPE: PRT
<213> ORGANISM: Homo sapien

<400> SEQUENCE: 22

Pro Lys Pro Glu His Pro Gly Asp Asp Ala Pro Ala Glu Asp Val Asn
1               5                   10                  15
Arg Tyr Tyr Ala Ser Leu Arg His Tyr Leu Asn Leu Val Thr Arg Gln
                20                  25                  30
Arg Tyr

<210> SEQ ID NO 23
<211> LENGTH: 34
<212> TYPE: PRT
<213> ORGANISM: Ovis Aries

<400> SEQUENCE: 23

Pro Lys Pro Glu His Pro Gly Asp Asp Ala Pro Ala Glu Asp Val Asn
1               5                   10                  15
Arg Tyr Tyr Ala Ala Leu Arg Ala Tyr Leu Asn Leu Val Thr Arg Gln
                20                  25                  30
Arg Tyr

<210> SEQ ID NO 24
<211> LENGTH: 34
<212> TYPE: PRT
<213> ORGANISM: Ovis Aries

<400> SEQUENCE: 24

Pro Lys Pro Glu His Pro Gly Asp Asp Ala Pro Ala Glu Asp Val Ala
```

```
                1               5                   10                  15
Gln Tyr Ala Ala Asp Leu Arg Arg Tyr Ile Asn Met Leu Thr Arg Gln
                20                  25                  30

Arg Tyr

<210> SEQ ID NO 25
<211> LENGTH: 33
<212> TYPE: PRT
<213> ORGANISM: Ovis Aries

<400> SEQUENCE: 25

Ile Pro Glu His Pro Gly Asp Asp Ala Pro Ala Glu Asp Val Ala Arg
1               5                   10                  15

Tyr Tyr Ser Ala Leu Arg Ala Tyr Ile Asn Leu Ile Thr Arg Gln Arg
                20                  25                  30

Tyr

<210> SEQ ID NO 26
<211> LENGTH: 34
<212> TYPE: PRT
<213> ORGANISM: Ovis Aries

<400> SEQUENCE: 26

Pro Lys Pro Glu His Pro Gly Asp Asp Ala Pro Ala Glu Asp Val Ala
1               5                   10                  15

Arg Tyr Tyr Ser Ala Leu Arg His Tyr Ile Asn Leu Ile Thr Arg Gln
                20                  25                  30

Arg Tyr

<210> SEQ ID NO 27
<211> LENGTH: 34
<212> TYPE: PRT
<213> ORGANISM: Ovis Aries

<400> SEQUENCE: 27

Pro Lys Pro Glu His Pro Gly Asp Asp Ala Pro Ala Glu Asp Val Ala
1               5                   10                  15

Arg Tyr Tyr Ser Ala Leu Arg Ala Tyr Ile Asn Leu Ile Thr Arg Gln
                20                  25                  30

Arg Tyr

<210> SEQ ID NO 28
<211> LENGTH: 36
<212> TYPE: PRT
<213> ORGANISM: Raja rhina

<400> SEQUENCE: 28

Tyr Pro Pro Lys Pro Glu Ala Pro Gly Glu Asp Ala Ser Pro Glu Glu
1               5                   10                  15

Leu Ala Lys Tyr Tyr Ala Ala Leu Arg His Tyr Ile Asn Leu Val Thr
                20                  25                  30

Arg Gln Arg Tyr
            35

<210> SEQ ID NO 29
<211> LENGTH: 34
<212> TYPE: PRT
<213> ORGANISM: Rana ridibunda

<400> SEQUENCE: 29
```

```
Ala Lys Pro Glu Asn Pro Gly Asp Asn Ala Pro Ala Glu Gln Met Ala
1               5                   10                  15

Lys Tyr Leu Thr Ala Leu Arg Ala Tyr Val Asn Leu Ile Thr Arg Gln
                20                  25                  30

Arg Tyr

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Tyr, Ala, Phe, Trp, or absent
<220> FEATURE:
<221> NAME/KEY: MOD_RES
<222> LOCATION: (2)
<223> OTHER INFORMATION: Pro, Gly, d-Ala, homoPro, hydroxyPro, or absent
<220> FEATURE:
<221> NAME/KEY: MOD_RES
<222> LOCATION: (3)
<223> OTHER INFORMATION: Ile, Ala, NorVal, Val, Leu, Pro, Ser, Thr,
      or absent
<220> FEATURE:
<221> NAME/KEY: MOD_RES
<222> LOCATION: (4)
<223> OTHER INFORMATION: Lys, Ala, Gly, Arg, d-Ala, homoLys, homo-Arg,
      Glu Asp, or absent
<220> FEATURE:
<221> NAME/KEY: MOD_RES
<222> LOCATION: (6)
<223> OTHER INFORMATION: Glu, Ala, Val, Asp, Asn, or Gln
<220> FEATURE:
<221> NAME/KEY: MOD_RES
<222> LOCATION: (7)
<223> OTHER INFORMATION: Ala, Asn, His, Ser, or Tyr
<220> FEATURE:
<221> NAME/KEY: MOD_RES
<222> LOCATION: (9)
<223> OTHER INFORMATION: Gly, Ala, Ser, Sarcosine, Pro, or Aib
<220> FEATURE:
<221> NAME/KEY: MOD_RES
<222> LOCATION: (10)
<223> OTHER INFORMATION: Glu, Ala, Asp, Asn, Gln, Pro, Aib, or Gly
<220> FEATURE:
<221> NAME/KEY: MOD_RES
<222> LOCATION: (11)
<223> OTHER INFORMATION: Asp, Ala, Glu, Asn, Gln, Pro, Aib, or Gly
<220> FEATURE:
<221> NAME/KEY: MOD_RES
<222> LOCATION: (12)
<223> OTHER INFORMATION: Ala or d-Ala
<220> FEATURE:
<221> NAME/KEY: MOD_RES
<222> LOCATION: (13)
<223> OTHER INFORMATION: Ser, Ala, Thr, Pro, or homoSer
<220> FEATURE:
<221> NAME/KEY: MOD_RES
<222> LOCATION: (14)
<223> OTHER INFORMATION: Pro, Ala, homoPro, hydroxyPro, Aib, or Gly
<220> FEATURE:
<221> NAME/KEY: MOD_RES
<222> LOCATION: (15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)
<223> OTHER INFORMATION: Glu, Ala, Asp, Asn, or Gln
<220> FEATURE:
<221> NAME/KEY: MOD_RES
<222> LOCATION: (17)
<223> OTHER INFORMATION: Leu, Ala, Met, Trp, Ile, Val, or NorVal
<220> FEATURE:
<221> NAME/KEY: MOD_RES
```

```
<222> LOCATION: (18)
<223> OTHER INFORMATION: Asn, Asp, Ala, Glu, Gln, Ser, or Thr
<220> FEATURE:
<221> NAME/KEY: MOD_RES
<222> LOCATION: (19)
<223> OTHER INFORMATION: Arg, Tyr, Lys, Ala, Gln, or N(Me)Ala
<220> FEATURE:
<221> NAME/KEY: MOD_RES
<222> LOCATION: (21)
<223> OTHER INFORMATION: Tyr, Ala, Met, Phe, or Leu
<220> FEATURE:
<221> NAME/KEY: MOD_RES
<222> LOCATION: (22)
<223> OTHER INFORMATION: Ala, Ser, Thr, or d-Ala
<220> FEATURE:
<221> NAME/KEY: MOD_RES
<222> LOCATION: (23)
<223> OTHER INFORMATION: Ser, Ala, Asp, Thr, or homoSer
<220> FEATURE:
<221> NAME/KEY: MOD_RES
<222> LOCATION: (25)
<223> OTHER INFORMATION: Arg, homoArg, Lys, homoLys, Orn, or Cit
<220> FEATURE:
<221> NAME/KEY: MOD_RES
<222> LOCATION: (26)
<223> OTHER INFORMATION: His, Ala, Arg, homoArg, homoLys, Orn, or Cit
<220> FEATURE:
<221> NAME/KEY: MOD_RES
<222> LOCATION: (27)
<223> OTHER INFORMATION: Tyr or Phe
<220> FEATURE:
<221> NAME/KEY: MOD_RES
<222> LOCATION: (28)
<223> OTHER INFORMATION: Leu, Ile, Val, or Ala
<220> FEATURE:
<221> NAME/KEY: MOD_RES
<222> LOCATION: (29)
<223> OTHER INFORMATION: Asn or Gln
<220> FEATURE:
<221> NAME/KEY: MOD_RES
<222> LOCATION: (30)
<223> OTHER INFORMATION: Leu, Ala, NorVal, Val, Ile, or Met
<220> FEATURE:
<221> NAME/KEY: MOD_RES
<222> LOCATION: (31)
<223> OTHER INFORMATION: Ala, Val, Ile, or Leu
<220> FEATURE:
<221> NAME/KEY: MOD_RES
<222> LOCATION: (36)
<223> OTHER INFORMATION: Tyr, N(Me)Tyr, His, Trp, or Phe

<400> SEQUENCE: 30

Xaa Xaa Xaa Xaa Pro Xaa Xaa Pro Xaa Xaa Xaa Xaa Xaa Xaa Xaa Xaa
1               5                   10                  15

Xaa Xaa Xaa Tyr Xaa Xaa Xaa Leu Xaa Xaa Xaa Xaa Xaa Xaa Xaa Thr
            20                  25                  30

Arg Gln Arg Xaa
        35

<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 31

Tyr Pro Ile Lys Pro Glu Ala Pro Gly Glu Asp Ala Ser Pro Glu Glu
1               5                   10                  15
```

Leu Asn Arg Tyr Tyr Ala Ser Leu Arg His Tyr Leu Asn Leu Val Thr
            20                  25                  30

Arg Gln Arg Tyr
        35

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 32

Tyr Pro Ile Lys Pro Ala Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 33

Tyr Pro Ile Lys Pro Glu Ala Pro Ala Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 34

Tyr Pro Ile Lys Pro Glu Ala Pro Gly Ala Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 35

Tyr Pro Ile Lys Pro Glu Ala Pro Gly Glu Ala Ser Pro Glu Glu
1               5                   10                  15

-continued

Leu Asn Arg Tyr Tyr Ala Ser Leu Arg His Tyr Leu Asn Leu Val Thr
            20                  25                  30

Arg Gln Arg Tyr
        35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 36

Tyr Pro Ile Lys Pro Glu Ala Pro Gly Glu Asp Ala Ala Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 37

Tyr Pro Ile Lys Pro Glu Ala Pro Gly Glu Asp Ala Ser Ala Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 38

Tyr Pro Ile Lys Pro Glu Ala Pro Gly Glu Asp Ala Ser Pro Ala Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 39

Tyr Pro Ile Lys Pro Glu Ala Pro Gly Glu Asp Ala Ser Pro Glu Ala
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 40

Tyr Pro Ile Lys Pro Glu Ala Pro Gly Glu Asp Ala Ser Pro Glu Glu
1               5                   10                  15

Ala Asn Arg Tyr Tyr Ala Ser Leu Arg His Tyr Leu Asn Leu Val Thr
            20                  25                  30

Arg Gln Arg Tyr
        35

<210> SEQ ID NO 41
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 41

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Leu Asn Leu Val Thr
            20                  25                  30

Arg Gln Arg Tyr
        35

<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 42

Tyr Pro Ile Lys Pro Glu Ala Pro Gly Glu Asp Ala Ser Pro Glu Glu
1               5                   10                  15

Leu Asn Lys Tyr Tyr Ala Ser Leu Arg His Tyr Leu Asn Leu Val Thr
            20                  25                  30

Arg Gln Arg Tyr
        35

<210> SEQ ID NO 43
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 43

Tyr Pro Ile Lys Pro Glu Ala Pro Gly Glu Asp Ala Ser Pro Glu Glu
1               5                   10                  15

-continued

```
Leu Asn Arg Tyr Ala Ala Ser Leu Arg His Tyr Leu Asn Leu Val Thr
            20                  25                  30

Arg Gln Arg Tyr
        35

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 44

Tyr Pro Ile Lys Pro Glu Ala Pro Gly Glu Asp Ala Ser Pro Glu Glu
1               5                   10                  15

Leu Asn Arg Tyr Tyr Ala Ala Leu Arg His Tyr Leu Asn Leu Val Thr
            20                  25                  30

Arg Gln Arg Tyr
        35

<210> SEQ ID NO 45
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 45

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg Ala Tyr Leu Asn Leu Val Thr
            20                  25                  30

Arg Gln Arg Tyr
        35

<210> SEQ ID NO 46
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 46

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Ala Val Thr
            20                  25                  30

Arg Gln Arg Tyr
        35

<210> SEQ ID NO 47
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 47

Tyr Pro Ile Lys Pro Glu Ala Pro Gly Glu Asp Ala Ser Ala Glu Glu
1               5                   10                  15
```

```
Leu Ala Arg Tyr Tyr Ala Ser Leu Arg His Tyr Leu Asn Leu Val Thr
            20                  25                  30

Arg Gln Arg Tyr
        35

<210> SEQ ID NO 48
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 48

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg Ala Tyr Leu Asn Leu Val Thr
            20                  25                  30

Arg Gln Arg Tyr
        35

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 49

Tyr Pro Ile Lys Pro Glu Ala Pro Gly Glu Asp Ala Ser Ala Glu Glu
1               5                   10                  15

Leu Ala Arg Tyr Tyr Ala Ser Leu Arg Ala Tyr Leu Asn Leu Val Thr
            20                  25                  30

Arg Gln Arg Tyr
        35

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 50

Ala Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 51

Phe Pro Ile Lys Pro Glu Ala Pro Gly Glu Asp Ala Ser Pro Glu Glu
1               5                   10                  15
```

-continued

Leu Asn Arg Tyr Tyr Ala Ser Leu Arg His Tyr Leu Asn Leu Val Thr
            20                  25                  30

Arg Gln Arg Tyr
        35

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: d-Ala

<400> SEQUENCE: 52

Tyr Ala Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 53
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 53

Tyr Gly Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 54
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 54

Ala Tyr Pro Ile Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35

<210> SEQ ID NO 55
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 55

```
Tyr Ala Pro Ile Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35
```

<210> SEQ ID NO 56
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 56

```
Tyr Pro Ala Ile Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35
```

<210> SEQ ID NO 57
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 57

```
Tyr Pro Ile Ala Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35
```

<210> SEQ ID NO 58
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 58

```
Tyr Pro Ile Lys Ala Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
            35
```

<210> SEQ ID NO 59
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 59

Tyr Pro Ile Lys Pro Ala Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
                20                  25                  30

Thr Arg Gln Arg Tyr
            35

<210> SEQ ID NO 60
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 60

Tyr Pro Ile Lys Pro Glu Ala Ala Pro Gly Glu Asp Ala Ser Pro Glu
1               5                   10                  15

Glu Leu Asn Arg Tyr Tyr Ala Ser Leu Arg His Tyr Leu Asn Leu Val
                20                  25                  30

Thr Arg Gln Arg Tyr
            35

<210> SEQ ID NO 61
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 61

Tyr Pro Ile Lys Pro Glu Ala Pro Ala Gly Glu Asp Ala Ser Pro Glu
1               5                   10                  15

Glu Leu Asn Arg Tyr Tyr Ala Ser Leu Arg His Tyr Leu Asn Leu Val
                20                  25                  30

Thr Arg Gln Arg Tyr
            35

<210> SEQ ID NO 62
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 62

Tyr Pro Ile Lys Pro Glu Ala Pro Gly Ala Glu Asp Ala Ser Pro Glu
1               5                   10                  15

Glu Leu Asn Arg Tyr Tyr Ala Ser Leu Arg His Tyr Leu Asn Leu Val
                20                  25                  30

Thr Arg Gln Arg Tyr
            35

<210> SEQ ID NO 63
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 63

Tyr Pro Ile Lys Pro Glu Ala Pro Gly Glu Ala Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 64
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 64

Tyr Pro Ile Lys Pro Glu Ala Pro Gly Glu Asp Ala Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 65

Tyr Pro Ile Lys Pro Glu Ala Pro Gly Glu Asp Ala Ser Ala Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 66
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 66

Tyr Pro Ile Lys Pro Glu Ala Pro Gly Glu Asp Ala Ser Pro Ala Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 67
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 67

```
Tyr Pro Ile Lys Pro Glu Ala Pro Gly Glu Asp Ala Ser Pro Glu Ala
1               5                   10                  15

Glu Leu Asn Arg Tyr Tyr Ala Ser Leu Arg His Tyr Leu Asn Leu Val
            20                  25                  30

Thr Arg Gln Arg Tyr
            35

<210> SEQ ID NO 68
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 68

Tyr Pro Ile Lys Pro Glu Ala Pro Gly Glu Asp Ala Ser Pro Glu Glu
1               5                   10                  15

Ala Leu Asn Arg Tyr Tyr Ala Ser Leu Arg His Tyr Leu Asn Leu Val
            20                  25                  30

Thr Arg Gln Arg Tyr
            35

<210> SEQ ID NO 69
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 69

Tyr Pro Ile Lys Pro Glu Ala Pro Gly Glu Asp Ala Ser Pro Glu Glu
1               5                   10                  15

Leu Ala Asn Arg Tyr Tyr Ala Ser Leu Arg His Tyr Leu Asn Leu Val
            20                  25                  30

Thr Arg Gln Arg Tyr
            35

<210> SEQ ID NO 70
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 70

Tyr Pro Ile Lys Pro Glu Ala Pro Gly Glu Asp Ala Ser Pro Glu Glu
1               5                   10                  15

Leu Asn Ala Arg Tyr Tyr Ala Ser Leu Arg His Tyr Leu Asn Leu Val
            20                  25                  30

Thr Arg Gln Arg Tyr
            35

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 71
```

Tyr Pro Ile Lys Pro Glu Ala Pro Gly Glu Asp Ala Ser Pro Glu Glu
1               5                   10                  15

Leu Asn Arg Ala Tyr Tyr Ala Ser Leu Arg His Tyr Leu Asn Leu Val
            20                  25                  30

Thr Arg Gln Arg Tyr
            35

<210> SEQ ID NO 72
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 72

Tyr Pro Ile Lys Pro Glu Ala Pro Gly Glu Asp Ala Ser Pro Glu Glu
1               5                   10                  15

Leu Asn Arg Tyr Ala Tyr Ala Ser Leu Arg His Tyr Leu Asn Leu Val
            20                  25                  30

Thr Arg Gln Arg Tyr
            35

<210> SEQ ID NO 73
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 73

Tyr Pro Ile Lys Pro Glu Ala Pro Gly Glu Asp Ala Ser Pro Glu Glu
1               5                   10                  15

Leu Asn Arg Tyr Tyr Ala Ala Ser Leu Arg His Tyr Leu Asn Leu Val
            20                  25                  30

Thr Arg Gln Arg Tyr
            35

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 74

Tyr Pro Ile Lys Pro Glu Ala Pro Gly Glu Asp Ala Ser Pro Glu Glu
1               5                   10                  15

Leu Asn Arg Tyr Tyr Ala Ser Ala Leu Arg His Tyr Leu Asn Leu Val
            20                  25                  30

Thr Arg Gln Arg Tyr
            35

<210> SEQ ID NO 75
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 75

```
Tyr Pro Ile Lys Pro Glu Ala Pro Gly Glu Asp Ala Ser Pro Glu Glu
1               5                   10                  15

Leu Asn Arg Tyr Tyr Ala Ser Leu Ala Arg His Tyr Leu Asn Leu Val
            20                  25                  30

Thr Arg Gln Arg Tyr
        35
```

<210> SEQ ID NO 76
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 76

```
Tyr Pro Ile Lys Pro Glu Ala Pro Gly Glu Asp Ala Ser Pro Glu Glu
1               5                   10                  15

Leu Asn Arg Tyr Tyr Ala Ser Leu Arg Ala His Tyr Leu Asn Leu Val
            20                  25                  30

Thr Arg Gln Arg Tyr
        35
```

<210> SEQ ID NO 77
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 77

```
Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Ala Tyr Leu Asn Leu Val
            20                  25                  30

Thr Arg Gln Arg Tyr
        35
```

<210> SEQ ID NO 78
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 78

```
Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Ala Leu Asn Leu Val
            20                  25                  30

Thr Arg Gln Arg Tyr
        35
```

<210> SEQ ID NO 79
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 79

-continued

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Ala Asn Leu Val
            20                  25                  30

Thr Arg Gln Arg Tyr
            35

<210> SEQ ID NO 80
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 80

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Ala Leu Val
            20                  25                  30

Thr Arg Gln Arg Tyr
            35

<210> SEQ ID NO 81
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 81

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Ala Val
            20                  25                  30

Thr Arg Gln Arg Tyr
            35

<210> SEQ ID NO 82
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 82

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Ala
            20                  25                  30

Thr Arg Gln Arg Tyr
            35

<210> SEQ ID NO 83
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 83

```
Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Ala Arg Gln Arg Tyr
            35

<210> SEQ ID NO 84
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 84

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Ala Gln Arg Tyr
            35

<210> SEQ ID NO 85
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 85

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Ala Arg Tyr
            35

<210> SEQ ID NO 86
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 86

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Ala Tyr
            35

<210> SEQ ID NO 87
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 87
```

```
Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr Ala
            35

<210> SEQ ID NO 88
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Tyr, Ala, Phe, Trp, or absent
<220> FEATURE:
<221> NAME/KEY: MOD_RES
<222> LOCATION: (2)
<223> OTHER INFORMATION: Pro, Gly, d-Ala, homoPro, hydroxy-Pro, or
      absent
<220> FEATURE:
<221> NAME/KEY: MOD_RES
<222> LOCATION: (3)
<223> OTHER INFORMATION: Ile, Ala, NorVal, Val, Leu, Pro, Ser, or Thr
<220> FEATURE:
<221> NAME/KEY: MOD_RES
<222> LOCATION: (4)
<223> OTHER INFORMATION: Lys, Ala, Gly, Arg, d-Ala, homoLys, homoArg,
      Glu, or Asp
<220> FEATURE:
<221> NAME/KEY: MOD_RES
<222> LOCATION: (6)
<223> OTHER INFORMATION: Glu, Ala, Val, Asp, Asn, or Gln
<220> FEATURE:
<221> NAME/KEY: MOD_RES
<222> LOCATION: (7)
<223> OTHER INFORMATION: Ala, Asn, His, Ser, or Tyr
<220> FEATURE:
<221> NAME/KEY: MOD_RES
<222> LOCATION: (9)
<223> OTHER INFORMATION: Gly, Ala, Ser, Sarcosine, Pro, or Aib
<220> FEATURE:
<221> NAME/KEY: MOD_RES
<222> LOCATION: (10)
<223> OTHER INFORMATION: Glu, Ala, Asp, Asn, Gln, Pro, Aib, or Gly
<220> FEATURE:
<221> NAME/KEY: MOD_RES
<222> LOCATION: (11)
<223> OTHER INFORMATION: Asp, Ala, Glu, Asn, Gln, Pro, Aib, or Gly
<220> FEATURE:
<221> NAME/KEY: MOD_RES
<222> LOCATION: (12)
<223> OTHER INFORMATION: Ala or d-Ala
<220> FEATURE:
<221> NAME/KEY: MOD_RES
<222> LOCATION: (13)
<223> OTHER INFORMATION: Ser, Ala, Thr, or homoSer
<220> FEATURE:
<221> NAME/KEY: MOD_RES
<222> LOCATION: (14)
<223> OTHER INFORMATION: Pro, Ala, homoPro, hydroxyPro, Aib, or Gly
<220> FEATURE:
<221> NAME/KEY: MOD_RES
<222> LOCATION: (15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)
<223> OTHER INFORMATION: Glu, Ala, Asp, Asn, or Gln
<220> FEATURE:
<221> NAME/KEY: MOD_RES
<222> LOCATION: (17)
<223> OTHER INFORMATION: Leu, Ala, Met, Trp, Ile, Val, or NorVal
```

```
<220> FEATURE:
<221> NAME/KEY: MOD_RES
<222> LOCATION: (18)
<223> OTHER INFORMATION: Asn, Asp, Ala, Glu, Gln, Ser, or Thr
<220> FEATURE:
<221> NAME/KEY: MOD_RES
<222> LOCATION: (19)
<223> OTHER INFORMATION: Arg, Tyr, Lys, Ala, Gln, or N(Me)Ala
<220> FEATURE:
<221> NAME/KEY: MOD_RES
<222> LOCATION: (21)
<223> OTHER INFORMATION: Tyr, Ala, Met, Phe, or Leu
<220> FEATURE:
<221> NAME/KEY: MOD_RES
<222> LOCATION: (22)
<223> OTHER INFORMATION: Ala, Ser, Thr, or d-Ala
<220> FEATURE:
<221> NAME/KEY: MOD_RES
<222> LOCATION: (23)
<223> OTHER INFORMATION: Ser, Ala, Thr, or homoSer
<220> FEATURE:
<221> NAME/KEY: MOD_RES
<222> LOCATION: (26)
<223> OTHER INFORMATION: His or Ala
<220> FEATURE:
<221> NAME/KEY: MOD_RES
<222> LOCATION: (28)
<223> OTHER INFORMATION: Leu, Ile, Val, or Ala
<220> FEATURE:
<221> NAME/KEY: MOD_RES
<222> LOCATION: (30)
<223> OTHER INFORMATION: Leu, Ala, NorVal, Val, Ile, or Met
<220> FEATURE:
<221> NAME/KEY: MOD_RES
<222> LOCATION: (31)
<223> OTHER INFORMATION: Ala, Val, Ile, or Leu
<220> FEATURE:
<221> NAME/KEY: MOD_RES
<222> LOCATION: (36)
<223> OTHER INFORMATION: Tyr, N(Me)Tyr, His, Trp, or Phe

<400> SEQUENCE: 88

Xaa Xaa Xaa Xaa Pro Xaa Xaa Pro Xaa Xaa Xaa Xaa Xaa Xaa Xaa
1               5                   10                  15

Xaa Xaa Xaa Tyr Xaa Xaa Xaa Leu Arg Xaa Tyr Xaa Asn Xaa Xaa Thr
                20                  25                  30

Arg Gln Arg Xaa
            35

<210> SEQ ID NO 89
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 89

Ala Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
                20                  25                  30

Arg Tyr

<210> SEQ ID NO 90
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
```

```
<400> SEQUENCE: 90

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 91
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 91

Ile Gly Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 92
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: d-Ala

<400> SEQUENCE: 92

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 93
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 93

Ile Lys Ala Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 94
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
```

```
<400> SEQUENCE: 94

Ile Lys Pro Ala Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 95
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: d-Ala

<400> SEQUENCE: 95

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 96
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 96

Ile Lys Pro Glu Ala Ala Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 97
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 97

Ile Lys Pro Glu Ala Pro Ala Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 98
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
```

-continued

```
<400> SEQUENCE: 98

Ile Lys Pro Glu Ala Pro Gly Ala Asp Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 99
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 99

Ile Lys Pro Glu Ala Pro Gly Glu Ala Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 100
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (10)
<223> OTHER INFORMATION: d-Ala

<400> SEQUENCE: 100

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 101
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 101

Ile Lys Pro Glu Ala Pro Gly Glu Asp Ala Ala Pro Glu Glu Leu Asn
1               5                   10                  15
Arg Tyr Tyr Ala Ser Leu Arg His Tyr Leu Asn Leu Val Thr Arg Gln
            20                  25                  30
Arg Tyr

<210> SEQ ID NO 102
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
```

```
<400> SEQUENCE: 102

Ile Lys Pro Glu Ala Pro Gly Glu Asp Ala Ser Ala Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 103
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 103

Ile Lys Pro Glu Ala Pro Gly Glu Asp Ala Ser Pro Ala Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 104
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 104

Ile Lys Pro Glu Ala Pro Gly Glu Asp Ala Ser Pro Glu Ala Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 105
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 105

Ile Lys Pro Glu Ala Pro Gly Glu Asp Ala Ser Pro Glu Glu Ala Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 106
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 106

Ile Lys Pro Glu Ala Pro Gly Glu Asp Ala Ser Pro Glu Glu Leu Ala
1               5                   10                  15
```

```
Arg Tyr Tyr Ala Ser Leu Arg His Tyr Leu Asn Leu Val Thr Arg Gln
            20                  25                  30

Arg Tyr

<210> SEQ ID NO 107
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 107

Ile Lys Pro Glu Ala Pro Gly Glu Asp Ala Ser Pro Glu Glu Leu Asn
1               5                   10                  15

Ala Tyr Tyr Ala Ser Leu Arg His Tyr Leu Asn Leu Val Thr Arg Gln
            20                  25                  30

Arg Tyr

<210> SEQ ID NO 108
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 108

Ile Lys Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 109
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)
<223> OTHER INFORMATION: (NMe)Ala

<400> SEQUENCE: 109

Ile Lys Pro Glu Ala Pro Gly Glu Asp Ala Ser Pro Glu Glu Leu Asn
1               5                   10                  15

Ala Tyr Tyr Ala Ser Leu Arg His Tyr Leu Asn Leu Val Thr Arg Gln
            20                  25                  30

Arg Tyr

<210> SEQ ID NO 110
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 110

Ile Lys Pro Glu Ala Pro Gly Glu Asp Ala Ser Pro Glu Glu Leu Asn
1               5                   10                  15
```

```
Arg Ala Tyr Ala Ser Leu Arg His Tyr Leu Asn Leu Val Thr Arg Gln
            20                  25                  30

Arg Tyr

<210> SEQ ID NO 111
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 111

Ile Lys Pro Glu Ala Pro Gly Glu Asp Ala Ser Pro Glu Glu Leu Asn
1               5                   10                  15

Arg Tyr Ala Ala Ser Leu Arg His Tyr Leu Asn Leu Val Thr Arg Gln
            20                  25                  30

Arg Tyr

<210> SEQ ID NO 112
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (20)
<223> OTHER INFORMATION: d-Ala

<400> SEQUENCE: 112

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 113
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 113

Ile Lys Pro Glu Ala Pro Gly Glu Asp Ala Ser Pro Glu Glu Leu Asn
1               5                   10                  15

Arg Tyr Tyr Ala Ala Leu Arg His Tyr Leu Asn Leu Val Thr Arg Gln
            20                  25                  30

Arg Tyr

<210> SEQ ID NO 114
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 114

Ile Lys Pro Glu Ala Pro Gly Glu Asp Ala Ser Pro Glu Glu Leu Asn
1               5                   10                  15
```

Arg Tyr Tyr Ala Ser Ala Arg His Tyr Leu Asn Leu Val Thr Arg Gln
            20                  25                  30

Arg Tyr

<210> SEQ ID NO 115
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 115

Ile Lys Pro Glu Ala Pro Gly Glu Asp Ala Ser Pro Glu Glu Leu Asn
1               5                   10                  15

Arg Tyr Tyr Ala Ser Leu Ala His Tyr Leu Asn Leu Val Thr Arg Gln
            20                  25                  30

Arg Tyr

<210> SEQ ID NO 116
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 116

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Val Thr Arg Gln
            20                  25                  30

Arg Tyr

<210> SEQ ID NO 117
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 117

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 118
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 118

Ile Lys Pro Glu Ala Pro Gly Glu Asp Ala Ser Pro Glu Glu Leu Asn
1               5                   10                  15

Arg Tyr Tyr Ala Ser Leu Arg His Ala Leu Asn Leu Val Thr Arg Gln
            20                  25                  30

Arg Tyr

```
<210> SEQ ID NO 119
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 119
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Ala Asn Leu Val Thr Arg Gln
            20                  25                  30

Arg Tyr

```
<210> SEQ ID NO 120
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 120
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Ala Leu Val Thr Arg Gln
            20                  25                  30

Arg Tyr

```
<210> SEQ ID NO 121
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 121
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Ala Val Thr Arg Gln
            20                  25                  30

Arg Tyr

```
<210> SEQ ID NO 122
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 122
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Ala Thr Arg Gln
            20                  25                  30

Arg Tyr

```
<210> SEQ ID NO 123
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 123

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Ala Arg Gln
            20                  25                  30

Arg Tyr

<210> SEQ ID NO 124
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 124

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Ala Gln
            20                  25                  30

Arg Tyr

<210> SEQ ID NO 125
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 125

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Lys Gln
            20                  25                  30

Arg Tyr

<210> SEQ ID NO 126
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 126

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Ala
            20                  25                  30

Arg Tyr

<210> SEQ ID NO 127
<211> LENGTH: 34
<212> TYPE: PRT
<213> ORGANISM: Artificial Sequence
<220> FEATURE:
```

<223> OTHER INFORMATION: Description of Artificial Sequence: Synthetic
      peptide construct

<400> SEQUENCE: 127

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Ala Tyr

<210> SEQ ID NO 128
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 128

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Ala

<210> SEQ ID NO 129
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 129

Ser Lys Pro Asp Asn Pro Gly Glu Asp Ala Pro Ala Glu Asp Met Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 130
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 130

Pro Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 131
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES

```
<222> LOCATION: (1)
<223> OTHER INFORMATION: Isocaproyl-Pro

<400> SEQUENCE: 131

Pro Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 132
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Ac-Pro

<400> SEQUENCE: 132

Pro Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 133
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: (NMe)Tyr

<400> SEQUENCE: 133

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 134
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 134

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg His

<210> SEQ ID NO 135
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 135

Ile Lys Pro Glu Ala Pro Gly Glu Asp Ala Ser Pro Glu Glu Leu Asn
1               5                   10                  15
Arg Tyr Tyr Ala Ser Leu Arg Ala Tyr Leu Asn Leu Val Thr Arg Gln
            20                  25                  30
Arg His

<210> SEQ ID NO 136
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 136

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Trp

<210> SEQ ID NO 137
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 137

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Leu Val Thr Arg Gln
            20                  25                  30
Arg Phe

<210> SEQ ID NO 138
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 138

Ile Lys Pro Glu Ala Pro Gly Glu Asp Ala Ser Pro Glu Glu Leu Asn
1               5                   10                  15
Arg Tyr Tyr Ala Ser Leu Arg Ala Tyr Leu Asn Leu Val Thr Arg Gln
            20                  25                  30
Arg Phe

<210> SEQ ID NO 139
<211> LENGTH: 34
<212> TYPE: PRT
<213> ORGANISM: Artificial Sequence
<220> FEATURE:
```

```
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Tyr(CH2SO3)

<400> SEQUENCE: 139

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 140
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Pro(OH)

<400> SEQUENCE: 140

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Pro

<210> SEQ ID NO 141
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (33)
<223> OTHER INFORMATION: homo-Arg

<400> SEQUENCE: 141

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 142
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 142

Ile Lys Pro Glu Ala Pro Gly Glu Asp Ala Ser Ala Glu Glu Leu Ala
1               5                   10                  15

Arg Tyr Tyr Ala Ser Leu Arg His Tyr Leu Asn Leu Val Thr Arg Gln
            20                  25                  30
```

Arg Tyr

<210> SEQ ID NO 143
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 143

Ile Lys Pro Glu Ala Pro Gly Glu Asp Ala Ser Pro Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 144
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 144

Ile Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 145
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 145

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 146
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)
<223> OTHER INFORMATION: Ser(Ac)

<400> SEQUENCE: 146

Ile Lys Pro Glu Ala Pro Gly Glu Asp Ala Ser Pro Glu Glu Leu Asn
1               5                   10                  15

-continued

Arg Tyr Tyr Ala Ser Leu Arg His Tyr Leu Asn Leu Val Thr Arg Gln
            20                  25                  30

Arg Tyr

<210> SEQ ID NO 147
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (21)
<223> OTHER INFORMATION: Ser(Ac)

<400> SEQUENCE: 147

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 148
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)
<223> OTHER INFORMATION: homo-Arg

<400> SEQUENCE: 148

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 149
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (23)
<223> OTHER INFORMATION: homo-Arg

<400> SEQUENCE: 149

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 150
<211> LENGTH: 34
<212> TYPE: PRT
<213> ORGANISM: Artificial Sequence

```
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: FmocSO3H-Ile
<220> FEATURE:
<221> NAME/KEY: MOD_RES
<222> LOCATION: (2)
<223> OTHER INFORMATION: Lys(FmocSO3H)

<400> SEQUENCE: 150

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 151
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile

<400> SEQUENCE: 151

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 152
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile

<400> SEQUENCE: 152

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 153
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isobutyloxycarbonyl-Ile
```

-continued

```
<400> SEQUENCE: 153

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 154
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isopropyloxycarbonyl-Ile

<400> SEQUENCE: 154

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 155
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: N-butyloxycarbonyl-Ile

<400> SEQUENCE: 155

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 156
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Ethoxycarbonyl-Ile

<400> SEQUENCE: 156

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr
```

-continued

```
<210> SEQ ID NO 157
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 157

Ile Lys Pro Glu Ala Pro Gly Glu Asp Ala Ser Pro Glu Glu Leu Ser
1               5                   10                  15

Arg Tyr Tyr Ala Ser Leu Arg His Tyr Leu Asn Leu Val Thr Arg Gln
            20                  25                  30

Arg Tyr

<210> SEQ ID NO 158
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (16)
<223> OTHER INFORMATION: NorVal

<400> SEQUENCE: 158

Ile Lys Pro Glu Ala Pro Gly Glu Asp Ala Ser Pro Glu Glu Leu Xaa
1               5                   10                  15

Arg Tyr Tyr Ala Ser Leu Arg His Tyr Leu Asn Leu Val Thr Arg Gln
            20                  25                  30

Arg Tyr

<210> SEQ ID NO 159
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 159

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 160
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile
<220> FEATURE:
<221> NAME/KEY: MOD_RES
<222> LOCATION: (2)
```

-continued

```
<223> OTHER INFORMATION: homo-Lys

<400> SEQUENCE: 160

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 161
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)
<223> OTHER INFORMATION: homo-Arg

<400> SEQUENCE: 161

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 162
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile
<220> FEATURE:
<221> NAME/KEY: MOD_RES
<222> LOCATION: (17)
<223> OTHER INFORMATION: homo-Arg

<400> SEQUENCE: 162

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 163
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys
<220> FEATURE:
<221> NAME/KEY: MOD_RES
<222> LOCATION: (17)
<223> OTHER INFORMATION: homo-Arg

<400> SEQUENCE: 163
```

```
Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 164
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile
<220> FEATURE:
<221> NAME/KEY: MOD_RES
<222> LOCATION: (2)
<223> OTHER INFORMATION: homo-Lys
<220> FEATURE:
<221> NAME/KEY: MOD_RES
<222> LOCATION: (17)
<223> OTHER INFORMATION: homo-Arg

<400> SEQUENCE: 164

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 165
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 165

Ile Lys Pro Glu Ala Pro Gly Glu Asp Ala Ser Pro Glu Glu Met Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 166
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 166

Ile Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30
```

Arg Tyr

```
<210> SEQ ID NO 167
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys
<220> FEATURE:
<221> NAME/KEY: MOD_RES
<222> LOCATION: (17)
<223> OTHER INFORMATION: homo-Arg

<400> SEQUENCE: 167
```

Ile Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

```
<210> SEQ ID NO 168
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys
<220> FEATURE:
<221> NAME/KEY: MOD_RES
<222> LOCATION: (11)
<223> OTHER INFORMATION: homo-Ser
<220> FEATURE:
<221> NAME/KEY: MOD_RES
<222> LOCATION: (17)
<223> OTHER INFORMATION: homo-Arg

<400> SEQUENCE: 168
```

Leu Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

```
<210> SEQ ID NO 169
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 169
```

Ile Lys Pro Glu Ala Pro Gly Glu Asp Ala Ser Ala Gln Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 170
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 170

Ile Lys Ala Pro Glu Ala Pro Gly Glu Asp Ala Ser Pro Glu Leu
1               5                   10                  15

Asn Arg Tyr Tyr Ala Ser Leu Lys His Tyr Leu Asn Leu Val Thr Arg
            20                  25                  30

Gln Arg Tyr
        35

<210> SEQ ID NO 171
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 171

Ile Lys Pro Glu Cys Pro Gly Glu Asp Ala Ser Pro Glu Glu Cys Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 172
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 172

Leu Glu Pro Val Tyr Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 173
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 173

Leu Glu Pro Val Tyr Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

```
<210> SEQ ID NO 174
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 174

Ile Lys Pro Glu Ala Pro Gly Glu Asp Ala Ser Pro Glu Glu Leu Asn
1               5                   10                  15

Arg Tyr Tyr Tyr Ala Ser Leu Arg His Tyr Leu Asn Ala Val Thr Arg
            20                  25                  30

Gln Arg Tyr
        35

<210> SEQ ID NO 175
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 175

Pro Glu Ala Pro Gly Glu Asp Ala Ser Pro Glu Glu Leu Asn Arg Tyr
1               5                   10                  15

Tyr Ala Ser Leu Arg His Tyr Leu Asn Leu Val Thr Arg Gln Arg Tyr
            20                  25                  30

<210> SEQ ID NO 176
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 176

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 177
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 177

Glu Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct
```

-continued

```
<400> SEQUENCE: 178

Tyr Tyr Ala Ser Leu Arg His Tyr Leu Asn Leu Val Thr Arg Gln Arg
1               5                   10                  15

Tyr

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 179

Arg His Tyr Leu Asn Leu Val Thr Arg Gln Arg Tyr
1               5                   10

<210> SEQ ID NO 180
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: Aca

<400> SEQUENCE: 180

Tyr Pro Ile Lys Xaa Pro Glu Glu Leu Asn Arg Tyr Tyr Ala Ser Leu
1               5                   10                  15

Arg His Tyr Leu Asn Leu Val Thr Arg Gln Arg Tyr
            20                  25

<210> SEQ ID NO 181
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: Aca

<400> SEQUENCE: 181

Tyr Pro Ile Lys Xaa Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 182
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: Aca

<400> SEQUENCE: 182

Tyr Pro Ile Lys Xaa Glu Leu Asn Arg Tyr Tyr Ala Ser Leu Arg His
1               5                   10                  15
```

```
Tyr Leu Asn Leu Val Thr Arg Gln Arg Tyr
            20                  25

<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: Aca

<400> SEQUENCE: 183

Tyr Pro Ile Lys Xaa Ala Ser Leu Arg His Tyr Leu Asn Leu Val Thr
1               5                   10                  15

Arg Gln Arg Tyr
            20

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: Aca

<400> SEQUENCE: 184

Tyr Pro Ile Lys Xaa Arg His Tyr Leu Asn Leu Val Thr Arg Gln Arg
1               5                   10                  15

Tyr

<210> SEQ ID NO 185
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 185

Tyr Pro Ile Lys Pro Glu Ala Pro Gly Glu Ala Asn Arg Tyr Tyr Ala
1               5                   10                  15

Ser Leu Arg His Tyr Leu Asn Leu Val Thr Arg Gln Arg Tyr
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)
<223> OTHER INFORMATION: Ado

<400> SEQUENCE: 186

Tyr Pro Ile Lys Pro Glu Ala Pro Gly Glu Xaa Asn Arg Tyr Tyr Ala
1               5                   10                  15
```

-continued

Ser Leu Arg His Tyr Leu Asn Leu Val Thr Arg Gln Arg Tyr
            20                  25                  30

<210> SEQ ID NO 187
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile
<220> FEATURE:
<221> NAME/KEY: MOD_RES
<222> LOCATION: (2)
<223> OTHER INFORMATION: Lys(PEG5000)

<400> SEQUENCE: 187

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 188
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Lys(PEG5000)

<400> SEQUENCE: 188

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 189
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile
<220> FEATURE:
<221> NAME/KEY: MOD_RES
<222> LOCATION: (17)
<223> OTHER INFORMATION: Lys(PEG5000)

<400> SEQUENCE: 189

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

```
<210> SEQ ID NO 190
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: PEG5000-Ile

<400> SEQUENCE: 190

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 191
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)
<223> OTHER INFORMATION: Ser(OAc)

<400> SEQUENCE: 191

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 192
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (21)
<223> OTHER INFORMATION: Ser(OAc)

<400> SEQUENCE: 192

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 193
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
```

```
<223> OTHER INFORMATION: Fmoc-Ile
<220> FEATURE:
<221> NAME/KEY: MOD_RES
<222> LOCATION: (17)
<223> OTHER INFORMATION: Lys(Oct)

<400> SEQUENCE: 193

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 194
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)
<223> OTHER INFORMATION: Lys(Oct)

<400> SEQUENCE: 194

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 195
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Octanoic acid-Ile

<400> SEQUENCE: 195

Ile Ala Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 196
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile
<220> FEATURE:
<221> NAME/KEY: MOD_RES
<222> LOCATION: (17)
<223> OTHER INFORMATION: Lys(stearyl)

<400> SEQUENCE: 196
```

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 197
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)
<223> OTHER INFORMATION: Lys(stearyl)

<400> SEQUENCE: 197

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 198
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Ac-Glu

<400> SEQUENCE: 198

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 199
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Stearyl-Glu

<400> SEQUENCE: 199

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 200
<211> LENGTH: 27
<212> TYPE: PRT
<213> ORGANISM: Artificial Sequence
<220> FEATURE:

```
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Octyl-Glu

<400> SEQUENCE: 200

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 201
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Succinyl-Glu

<400> SEQUENCE: 201

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Stearyl-Ala

<400> SEQUENCE: 202

Ala Ser Leu Arg His Tyr Leu Asn Leu Val Thr Arg Gln Arg Tyr
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Octyl-Ala

<400> SEQUENCE: 203

Ala Ser Leu Arg His Tyr Leu Asn Leu Val Thr Arg Gln Arg Tyr
1               5                   10                  15

<210> SEQ ID NO 204
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
```

```
<220> FEATURE:
<221> NAME/KEY: MOD_RES
<222> LOCATION: (14)
<223> OTHER INFORMATION: Lys(PEG)

<400> SEQUENCE: 204

Ile Ala Pro Glu Ala Pro Gly Glu Asp Ala Ser Pro Glu Lys Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 205
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (14)
<223> OTHER INFORMATION: Lys(Oct)

<400> SEQUENCE: 205

Ile Ala Pro Glu Ala Pro Gly Glu Asp Ala Ser Pro Glu Lys Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 206
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile
<220> FEATURE:
<221> NAME/KEY: MOD_RES
<222> LOCATION: (14)
<223> OTHER INFORMATION: Lys(Oct)

<400> SEQUENCE: 206

Ile Ala Pro Glu Ala Pro Gly Glu Asp Ala Ser Pro Glu Lys Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 207
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Tyr(8-Am-3,6-dioxaoct)

<400> SEQUENCE: 207
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 208
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Tyr(11-Am-undecanoyl)

<400> SEQUENCE: 208

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 209
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Tyr(12 Ado)

<400> SEQUENCE: 209

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 210
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Tyr(8-Oct)

<400> SEQUENCE: 210

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 211
<211> LENGTH: 5

```
<212> TYPE: PRT
<213> ORGANIZM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 352

<400> SEQUENCE: 211

Ile Lys Pro Glu Ala
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 353

<400> SEQUENCE: 212

Ile Lys Pro Glu Ala Pro
1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 354

<400> SEQUENCE: 213

Ile Lys Pro Glu Ala Pro Gly
1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 355

<400> SEQUENCE: 214

Ile Lys Pro Glu Ala Pro Gly Glu
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 356

<400> SEQUENCE: 215

Ile Lys Pro Glu Ala Pro Gly Glu Asp
1               5

<210> SEQ ID NO 216
<211> LENGTH: 10
```

<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 357

<400> SEQUENCE: 216

Ile Lys Pro Glu Ala Pro Gly Glu Asp Ala
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 358

<400> SEQUENCE: 217

Ile Lys Pro Glu Ala Pro Gly Glu Asp Ala Ser
1               5                   10

<210> SEQ ID NO 218
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (7)
<223> OTHER INFORMATION: Aib

<400> SEQUENCE: 218

Ile Lys Pro Glu Ala Ala Xaa Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 219
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (8)
<223> OTHER INFORMATION: Aib

<400> SEQUENCE: 219

Ile Lys Pro Glu Ala Pro Ala Xaa Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 220
<211> LENGTH: 34
<212> TYPE: PRT
<213> ORGANISM: Artificial Sequence

```
<220> FEATURE:
<223> OTHER INFORMATION: Description of Artificial Sequence: Synthetic
      peptide construct
<220> FEATURE:
<221> NAME/KEY: MOD_RES
<222> LOCATION: (9)
<223> OTHER INFORMATION: Aib

<400> SEQUENCE: 220

Ile Lys Pro Glu Ala Pro Gly Ala Xaa Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 221
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (10)
<223> OTHER INFORMATION: Aib

<400> SEQUENCE: 221

Ile Lys Pro Glu Ala Pro Gly Glu Ala Xaa Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 222
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)
<223> OTHER INFORMATION: Aib

<400> SEQUENCE: 222

Ile Lys Pro Glu Ala Pro Gly Glu Asp Ala Xaa Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 223
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (12)
<223> OTHER INFORMATION: Aib

<400> SEQUENCE: 223

Ile Lys Pro Glu Ala Pro Gly Glu Asp Ala Ala Xaa Glu Glu Leu Asn
```

```
                 1               5                  10                 15
Arg Tyr Tyr Ala Ser Leu Arg His Tyr Leu Asn Leu Val Thr Arg Gln
                20                 25                 30

Arg Tyr

<210> SEQ ID NO 224
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (13)
<223> OTHER INFORMATION: Aib

<400> SEQUENCE: 224

Ile Lys Pro Glu Ala Pro Gly Glu Asp Ala Ser Ala Xaa Glu Leu Asn
1               5                  10                 15

Arg Tyr Tyr Ala Ser Leu Arg His Tyr Leu Asn Leu Val Thr Arg Gln
                20                 25                 30

Arg Tyr

<210> SEQ ID NO 225
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 225

Ile Lys Pro Glu Ala Ala Pro Glu Asp Ala Ser Pro Glu Glu Leu Asn
1               5                  10                 15

Arg Tyr Tyr Ala Ser Leu Arg His Tyr Leu Asn Leu Val Thr Arg Gln
                20                 25                 30

Arg Tyr

<210> SEQ ID NO 226
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 226

Ile Lys Pro Glu Ala Pro Ala Pro Asp Ala Ser Pro Glu Glu Leu Asn
1               5                  10                 15

Arg Tyr Tyr Ala Ser Leu Arg His Tyr Leu Asn Leu Val Thr Arg Gln
                20                 25                 30

Arg Tyr

<210> SEQ ID NO 227
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 227

Ile Lys Pro Glu Ala Pro Gly Ala Pro Ala Ser Pro Glu Glu Leu Asn
```

```
                1               5                  10                  15
Arg Tyr Tyr Ala Ser Leu Arg His Tyr Leu Asn Leu Val Thr Arg Gln
                20                  25                  30

Arg Tyr

<210> SEQ ID NO 228
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 228

Ile Lys Pro Glu Ala Pro Gly Glu Ala Pro Ser Pro Glu Glu Leu Asn
1               5                  10                  15

Arg Tyr Tyr Ala Ser Leu Arg His Tyr Leu Asn Leu Val Thr Arg Gln
                20                  25                  30

Arg Tyr

<210> SEQ ID NO 229
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 229

Ile Lys Pro Glu Ala Pro Gly Glu Asp Ala Pro Pro Glu Glu Leu Asn
1               5                  10                  15

Arg Tyr Tyr Ala Ser Leu Arg His Tyr Leu Asn Leu Val Thr Arg Gln
                20                  25                  30

Arg Tyr

<210> SEQ ID NO 230
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 230

Ile Lys Pro Glu Ala Pro Gly Glu Asp Ala Ser Ala Pro Glu Leu Asn
1               5                  10                  15

Arg Tyr Tyr Ala Ser Leu Arg His Tyr Leu Asn Leu Val Thr Arg Gln
                20                  25                  30

Arg Tyr

<210> SEQ ID NO 231
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 359

<400> SEQUENCE: 231

Ile Lys Pro Glu Ala
1               5
```

```
<210> SEQ ID NO 232
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 360

<400> SEQUENCE: 232

Ile Lys Pro Glu Ala Pro
1               5

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 361

<400> SEQUENCE: 233

Ile Lys Pro Glu Ala Pro Gly
1               5

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 362

<400> SEQUENCE: 234

Ile Lys Pro Glu Ala Pro Gly Glu
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 363

<400> SEQUENCE: 235

Ile Lys Pro Glu Ala Pro Gly Glu Asp
1               5

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 364

<400> SEQUENCE: 236

Ile Lys Pro Glu Ala Pro Gly Glu Asp Ala
1               5                   10
```

-continued

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 365

<400> SEQUENCE: 237

Ile Lys Pro Glu Ala Pro Gly Glu Asp Ala Ser
1               5                   10

<210> SEQ ID NO 238
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 238

Ala Pro Leu Glu Pro Val Tyr Pro Gly Asp Asn Ala Thr Pro Glu Gln
1               5                   10                  15

Met Ala Arg Tyr Tyr Ser Ala Leu Arg His Tyr Ile Asn Leu Ala Thr
            20                  25                  30

Arg Gln Arg Tyr
        35

<210> SEQ ID NO 239
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 239

Tyr Pro Ile Lys Pro Glu Ala Pro Gly Glu Asp Ala Ser Pro Glu Glu
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 240
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 240

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 241
<211> LENGTH: 34
<212> TYPE: PRT
<213> ORGANISM: Artificial Sequence -continued

```
<220> FEATURE:
<223> OTHER INFORMATION: Description of Artificial Sequence: Synthetic
      peptide construct

<400> SEQUENCE: 241

Ile Lys Pro Glu Ala Pro Gly Glu Asp Ala Ser Pro Glu Glu Leu Ala
1               5                   10                  15

Lys Tyr Tyr Ser Ala Leu Arg His Tyr Ile Asn Leu Ile Thr Arg Gln
            20                  25                  30

Arg Tyr

<210> SEQ ID NO 242
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile

<400> SEQUENCE: 242

Ile Lys Pro Glu Ala Pro Gly Glu Asp Ala Ser Pro Glu Glu Leu Ala
1               5                   10                  15

Lys Tyr Tyr Ser Ala Leu Arg His Tyr Ile Asn Leu Ile Thr Arg Gln
            20                  25                  30

Arg Tyr

<210> SEQ ID NO 243
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 243

Ile Pro Glu Ala Pro Gly Glu Asp Ala Ser Pro Glu Glu Leu Ala Arg
1               5                   10                  15

Tyr Tyr Ser Ala Leu Arg His Tyr Ile Asn Leu Ile Thr Arg Gln Arg
            20                  25                  30

Tyr

<210> SEQ ID NO 244
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 244

Tyr Pro Ile Pro Glu Ala Pro Gly Glu Asp Ala Ser Ala Glu Glu Leu
1               5                   10                  15

Ala Arg Tyr Tyr Ser Ala Leu Arg Ala Tyr Ile Asn Leu Ile Thr Arg
            20                  25                  30

Gln Arg Tyr
        35

<210> SEQ ID NO 245
<211> LENGTH: 36
<212> TYPE: PRT
```

<213> ORGANISM: Artificial Sequence
<220> FEATURE:
<223> OTHER INFORMATION: Description of Artificial Sequence: Synthetic
      peptide construct

<400> SEQUENCE: 245

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

Arg Gln Arg Tyr
        35

<210> SEQ ID NO 246
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 246

Ile Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 247
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 247

Tyr Pro Ile Lys Pro Glu Ala Pro Gly Glu Asp Ala Ser Ala Glu Glu
1               5                   10                  15

Leu Ala Arg Tyr Tyr Ser Ala Leu Arg Ala Tyr Ile Asn Leu Ile Thr
            20                  25                  30

Arg Gln Arg Tyr
        35

<210> SEQ ID NO 248
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 248

Tyr Pro Ile Lys Pro Glu Ala Pro Gly Glu Asp Ala Ser Ala Glu Glu
1               5                   10                  15

Leu Ala Arg Tyr Tyr Ala Ser Leu Arg Ala Tyr Ile Asn Leu Ile Thr
            20                  25                  30

Arg Gln Arg Tyr
        35

<210> SEQ ID NO 249
<211> LENGTH: 36
<212> TYPE: PRT
<213> ORGANISM: Artificial Sequence

```
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 249

Tyr Pro Ile Lys Pro Glu Ala Pro Gly Glu Asp Ala Ser Pro Glu Glu
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 250
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 250

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 251
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 251

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

Arg Gln Arg Tyr
        35

<210> SEQ ID NO 252
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 252
```

-continued

Ile Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 253
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 253

Pro Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 254
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 254

Pro Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 255
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 255

Pro Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 256
<211> LENGTH: 34
<212> TYPE: PRT
<213> ORGANISM: Artificial Sequence
<220> FEATURE:

<223> OTHER INFORMATION: Description of Artificial Sequence: Synthetic
      peptide construct

<400> SEQUENCE: 256

Pro Lys Pro Glu His Pro Gly Glu Asp Ala Pro Ala Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 257
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 257

Pro Lys Pro Glu Ala Pro Gly Glu Asp Ala Pro Ala Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 258
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 258

Tyr Pro Ile Lys Pro Glu Ala Pro Gly Glu Asp Ala Ser Pro Glu Glu
1               5                   10                  15

Leu Ala Arg Tyr Tyr Ser Ala Leu Arg Ala Tyr Ile Asn Leu Ile Thr
            20                  25                  30

Arg Gln Arg Tyr
        35

<210> SEQ ID NO 259
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 259

Ile Lys Pro Glu Ala Pro Gly Glu Asp Ala Ser Pro Glu Glu Leu Ala
1               5                   10                  15

Arg Tyr Tyr Ser Ala Leu Arg Ala Tyr Ile Asn Leu Ile Thr Arg Gln
            20                  25                  30

Arg Tyr

```
<210> SEQ ID NO 260
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 260

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg Ala Tyr Ile Asn Leu Ile Thr
            20                  25                  30

Arg Gln Arg Tyr
        35

<210> SEQ ID NO 261
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 261

Ile Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 262
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 262

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 263
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 263
```

```
Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 264
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 264

Pro Pro Lys Pro Glu Ala Pro Gly Glu Asp Ala Ser Pro Glu Glu Leu
1               5                   10                  15

Ala Arg Tyr Tyr Ala Ser Leu Arg Ala Tyr Ile Asn Leu Ile Thr Arg
            20                  25                  30

Gln Arg Tyr
        35

<210> SEQ ID NO 265
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 265

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 266
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 266

Pro Lys Pro Glu His Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 267
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 267
```

Tyr Pro Ile Arg Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
                20                  25                  30

Arg Gln Arg Tyr
            35

<210> SEQ ID NO 268
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 268

Tyr Pro Ile Arg Pro Glu Ala Pro Gly Glu Asp Ala Ser Pro Glu Glu
1               5                   10                  15

Leu Ala Arg Tyr Tyr Ala Ser Leu Arg Ala Tyr Ile Asn Leu Ile Thr
                20                  25                  30

Arg Gln Arg Tyr
            35

<210> SEQ ID NO 269
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 269

Ile Arg Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
                20                  25                  30

Arg Tyr

<210> SEQ ID NO 270
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 270

Pro Arg Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
                20                  25                  30

Arg Tyr

<210> SEQ ID NO 271
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: 8-amino-octanoyl-Ile

```
<400> SEQUENCE: 271

Ile Arg Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 272
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 272

Tyr Pro Ile Arg Pro Glu Ala Pro Gly Glu Asp Ala Ser Pro Glu Glu
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 273
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 273

Tyr Pro Ile Lys Pro Glu Ala Pro Gly Glu Asp Ala Pro Ala Glu Glu
1               5                   10                  15

Leu Ala Arg Tyr Tyr Ala Ser Leu Arg Ala Tyr Ile Asn Leu Ile Thr
            20                  25                  30

Arg Gln Arg Tyr
        35

<210> SEQ ID NO 274
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 274

Ile Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 275
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 275
```

```
Pro Tyr Pro Ile Lys Pro Glu Ala Pro Gly Glu Asp Ala Pro Ala Glu
1               5                   10                  15

Glu Leu Ala Arg Tyr Tyr Ala Ser Leu Arg Ala Tyr Ile Asn Leu Ile
                20                  25                  30

Thr Arg Gln Arg Tyr
            35

<210> SEQ ID NO 276
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: 8-amino-octanoyl-Lys

<400> SEQUENCE: 276

Lys Pro Glu Ala Pro Gly Glu Asp Ala Pro Ala Glu Glu Leu Ala Arg
1               5                   10                  15

Tyr Tyr Ala Ser Leu Arg Ala Tyr Ile Asn Leu Ile Thr Arg Gln Arg
                20                  25                  30

Tyr

<210> SEQ ID NO 277
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 277

Pro Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
                20                  25                  30

Arg Tyr

<210> SEQ ID NO 278
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 278

Pro Lys Pro Glu Ala Pro Gly Glu Asp Ala Pro Ala Glu Glu Leu Ala
1               5                   10                  15

Arg Tyr Tyr Ala Ser Leu Arg His Tyr Ile Asn Leu Ile Thr Arg Gln
                20                  25                  30

Arg Tyr

<210> SEQ ID NO 279
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
```

```
<221> NAME/KEY: MOD_RES
<222> LOCATION: (1)
<223> OTHER INFORMATION: Isocaproyl-Pro

<400> SEQUENCE: 279

Pro Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 280
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Tyr

<400> SEQUENCE: 280

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

Arg Gln Arg Tyr
        35

<210> SEQ ID NO 281
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile

<400> SEQUENCE: 281

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 282
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Gly(Oct)

<400> SEQUENCE: 282

Gly Ile Lys Pro Glu Ala Pro Gly Glu Asp Ala Ser Pro Glu Glu Leu
1               5                   10                  15

Ala Arg Tyr Tyr Ser Ala Leu Arg His Tyr Ile Asn Leu Ile Thr Arg
```

```
            20                  25                  30

Gln Arg Tyr
        35

<210> SEQ ID NO 283
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Gly(Oct)

<400> SEQUENCE: 283

Gly Ile Lys Pro Glu Ala Pro Gly Glu Asp Ala Ser Pro Glu Glu Leu
1               5                   10                  15

Ala Arg Tyr Tyr Ser Ala Leu Arg His Tyr Ile Asn Leu Ile Thr Arg
            20                  25                  30

Gln Arg Tyr
        35

<210> SEQ ID NO 284
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Gly(Oct)

<400> SEQUENCE: 284

Gly Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 285
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 285

Tyr Pro Ser Lys Pro Asp Asn Pro Gly Glu Asp Ala Pro Ala Glu Asp
1               5                   10                  15

Met Ala Arg Tyr Tyr Ala Ser Leu Arg His Tyr Leu Asn Leu Val Thr
            20                  25                  30

Arg Gln Arg Tyr
        35

<210> SEQ ID NO 286
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
```

<400> SEQUENCE: 286

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30

Arg Gln Arg Tyr
        35

<210> SEQ ID NO 287
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 287

Leu Glu Pro Val Tyr Pro Gly Asp Asn Ala Thr Pro Glu Gln Met Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 288
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 288

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Phe Leu Asn Leu Val Thr
            20                  25                  30

Arg Gln Arg Tyr
        35

<210> SEQ ID NO 289
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 289

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Ala Pro
            20                  25                  30

Arg Gln Arg Tyr
        35

<210> SEQ ID NO 290
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:

```
<221> NAME/KEY: MOD_RES
<222> LOCATION: (32)
<223> OTHER INFORMATION: Aib

<400> SEQUENCE: 290

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Ala Xaa
                20                  25                  30

Arg Gln Arg Tyr
            35

<210> SEQ ID NO 291
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (32)
<223> OTHER INFORMATION: Sar

<400> SEQUENCE: 291

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Ala Xaa
                20                  25                  30

Arg Gln Arg Tyr
            35

<210> SEQ ID NO 292
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 292

Ala Pro Leu Glu Pro Val Tyr Pro Gly Asp Asn Ala Thr Pro Glu Gln
1               5                   10                  15

Met Asn Arg Tyr Tyr Ser Ala Leu Arg His Tyr Leu Asn Leu Val Thr
                20                  25                  30

Arg Gln Arg Tyr
            35

<210> SEQ ID NO 293
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 293

Ala Pro Leu Glu Pro Val Tyr Pro Gly Asp Asn Ala Thr Pro Glu Gln
1               5                   10                  15

Met Asn Lys Tyr Tyr Ala Ser Leu Arg His Tyr Leu Asn Leu Val Thr
                20                  25                  30

Arg Gln Arg Tyr
            35
```

```
<210> SEQ ID NO 294
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 294

Ala Pro Leu Glu Pro Val Tyr Pro Gly Asp Asn Ala Thr Pro Glu Gln
1               5                   10                  15

Met Ala Arg Tyr Tyr Ala Ser Leu Arg His Tyr Leu Asn Leu Val Thr
            20                  25                  30

Arg Gln Arg Tyr
        35

<210> SEQ ID NO 295
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 295

Ala Pro Leu Glu Pro Val Tyr Pro Gly Asp Asn Ala Thr Pro Glu Gln
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 296
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 296

Ala Pro Leu Glu Pro Val Tyr Pro Gly Asp Asn Ala Thr Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 297
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 297

Ala Pro Leu Glu Pro Val Tyr Pro Gly Asp Asn Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35
```

-continued

```
<210> SEQ ID NO 298
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 298

Ala Pro Leu Glu Pro Val Tyr Pro Gly Asp Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 299
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 299

Ala Pro Leu Glu Pro Val Tyr Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 300
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 300

Ala Pro Leu Glu Pro Val Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 301
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 301

Ala Pro Leu Glu Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35
```

```
<210> SEQ ID NO 302
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 302

Ala Pro Leu Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr
        35

<210> SEQ ID NO 303
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ala

<400> SEQUENCE: 303

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
                20                  25                  30

Arg Gln Arg Tyr
        35

<210> SEQ ID NO 304
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (19)
<223> OTHER INFORMATION: homo-Arg

<400> SEQUENCE: 304

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
                20                  25                  30

Arg Gln Arg Tyr
        35

<210> SEQ ID NO 305
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ala
<220> FEATURE:
```

```
<221> NAME/KEY: MOD_RES
<222> LOCATION: (19)
<223> OTHER INFORMATION: homo-Arg

<400> SEQUENCE: 305

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30

Arg Gln Arg Tyr
        35

<210> SEQ ID NO 306
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (19)
<223> OTHER INFORMATION: homo-Lys

<400> SEQUENCE: 306

Ala Pro Leu Glu Pro Val Tyr Pro Gly Asp Asn Ala Thr Pro Glu Gln
1               5                   10                  15

Met Asn Lys Tyr Tyr Ala Ser Leu Arg His Tyr Leu Asn Leu Val Thr
            20                  25                  30

Arg Gln Arg Tyr
        35

<210> SEQ ID NO 307
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 307

Ala Pro Met Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30

Arg Gln Arg Tyr
        35

<210> SEQ ID NO 308
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 308

Ala Pro Leu Glu Pro Val Tyr Pro Gly Asp Asn Ala Thr Pro Glu Gln
1               5                   10                  15

Met Asn Arg Tyr Tyr Ala Ser Leu Arg Ala Tyr Leu Asn Leu Val Thr
            20                  25                  30

Arg Gln Arg Tyr
        35
```

```
<210> SEQ ID NO 309
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 309

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Pro Arg Tyr
        35

<210> SEQ ID NO 310
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 310

Ile Lys Pro Glu Ala Pro Gly Glu Asp Ala Ser Pro Glu Glu Leu Ala
1               5                   10                  15

Gln Tyr Ala Ala Asp Leu Arg Arg Tyr Ile Asn Met Leu Thr Arg Pro
            20                  25                  30

Arg Tyr

<210> SEQ ID NO 311
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 311

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 312
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 312

Ile Lys Pro Glu Ala Pro Gly Glu Asp Ala Ser Pro Glu Glu Leu Ala
1               5                   10                  15

Gln Tyr Ala Ala Asp Leu Arg Arg Tyr Ile Asn Met Leu Thr Arg Gln
            20                  25                  30

Arg Tyr

<210> SEQ ID NO 313
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 313

Tyr Pro Ile Lys Pro Glu Ala Pro Gly Glu Asp Ala Ser Pro Glu Glu
1               5                   10                  15

Leu Ala Gln Tyr Ala Ala Ser Leu Arg His Tyr Ile Asn Met Leu Thr
            20                  25                  30

Arg Gln Arg Tyr
        35

<210> SEQ ID NO 314
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 314

Tyr Pro Ile Lys Pro Glu Ala Pro Gly Glu Asp Ala Ser Pro Glu Glu
1               5                   10                  15

Leu Ala Gln Tyr Ala Ser Ala Leu Arg His Tyr Ile Asn Met Leu Thr
            20                  25                  30

Arg Gln Arg Tyr
        35

<210> SEQ ID NO 315
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 315

Tyr Pro Ile Lys Pro Glu Ala Pro Gly Glu Asp Ala Ser Pro Glu Glu
1               5                   10                  15

Leu Ala Gln Tyr Ala Ala Asp Leu Arg His Tyr Ile Asn Met Leu Thr
            20                  25                  30

Arg Gln Arg Tyr
        35

<210> SEQ ID NO 316
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 316

Tyr Pro Ile Lys Pro Glu Ala Pro Gly Glu Asp Ala Ser Pro Glu Glu
1               5                   10                  15

Leu Asn Gln Tyr Ala Ala Asp Leu Arg Arg Tyr Ile Asn Met Leu Thr
            20                  25                  30

Arg Gln Arg Tyr
        35

<210> SEQ ID NO 317
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 317

Tyr Pro Ile Lys Pro Glu Ala Pro Gly Glu Asp Ala Ser Pro Glu Glu
1               5                   10                  15

Leu Asn Gln Tyr Ala Ala Ser Leu Arg Arg Tyr Ile Asn Met Leu Thr
            20                  25                  30

Arg Gln Arg Tyr
        35

<210> SEQ ID NO 318
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: d-Ala

<400> SEQUENCE: 318

Tyr Ala Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 319
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 319

Ala Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 320
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Tyr

<400> SEQUENCE: 320

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
```

-continued

```
                20                  25                  30
Arg Gln Arg Tyr
        35

<210> SEQ ID NO 321
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)
<223> OTHER INFORMATION: homo-Lys

<400> SEQUENCE: 321

Tyr Pro Ile Lys Pro Glu Ala Pro Gly Glu Asp Ala Ser Pro Glu Glu
1               5                   10                  15

Leu Ala Gln Tyr Ala Ala Asp Leu Lys Arg Tyr Ile Asn Met Leu Thr
                20                  25                  30

Arg Gln Arg Tyr
        35

<210> SEQ ID NO 322
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)
<223> OTHER INFORMATION: homo-Arg

<400> SEQUENCE: 322

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
                20                  25                  30

Arg Gln Arg Tyr
        35

<210> SEQ ID NO 323
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)
<223> OTHER INFORMATION: Orn

<400> SEQUENCE: 323

Tyr Pro Ile Lys Pro Glu Ala Pro Gly Glu Asp Ala Ser Pro Glu Glu
1               5                   10                  15

Leu Ala Gln Tyr Ala Ala Asp Leu Xaa Arg Tyr Ile Asn Met Leu Thr
                20                  25                  30

Arg Gln Arg Tyr
        35

<210> SEQ ID NO 324
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)
<223> OTHER INFORMATION: Cit

<400> SEQUENCE: 324

Tyr Pro Ile Lys Pro Glu Ala Pro Gly Glu Asp Ala Ser Pro Glu Glu
1               5                   10                  15

Leu Ala Gln Tyr Ala Ala Asp Leu Xaa Arg Tyr Ile Asn Met Leu Thr
            20                  25                  30

Arg Gln Arg Tyr
        35

<210> SEQ ID NO 325
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)
<223> OTHER INFORMATION: homo-Lys

<400> SEQUENCE: 325

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Lys Tyr Ile Asn Met Leu Thr
            20                  25                  30

Arg Gln Arg Tyr
        35

<210> SEQ ID NO 326
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)
<223> OTHER INFORMATION: homo-Arg

<400> SEQUENCE: 326

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 327
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)
```

```
<223> OTHER INFORMATION: Orn

<400> SEQUENCE: 327

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Xaa Tyr Ile Asn Met Leu Thr
            20                  25                  30

Arg Gln Arg Tyr
        35

<210> SEQ ID NO 328
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)
<223> OTHER INFORMATION: Cit

<400> SEQUENCE: 328

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Xaa Tyr Ile Asn Met Leu Thr
            20                  25                  30

Arg Gln Arg Tyr
        35

<210> SEQ ID NO 329
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)..(26)
<223> OTHER INFORMATION: homo-Arg

<400> SEQUENCE: 329

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 330
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 330

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
```

```
                    20                  25                  30

Arg Gln Arg Tyr
        35

<210> SEQ ID NO 331
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Tyr
<220> FEATURE:
<221> NAME/KEY: MOD_RES
<222> LOCATION: (4)
<223> OTHER INFORMATION: homo-Lys

<400> SEQUENCE: 331

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
                20                  25                  30

Arg Gln Arg Tyr
        35

<210> SEQ ID NO 332
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Arg

<400> SEQUENCE: 332

Tyr Pro Ile Arg Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
                20                  25                  30

Arg Gln Arg Tyr
        35

<210> SEQ ID NO 333
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (8)
<223> OTHER INFORMATION: homo-Pro

<400> SEQUENCE: 333

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
                20                  25                  30

Arg Gln Arg Tyr
        35
```

-continued

```
<210> SEQ ID NO 334
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (8)
<223> OTHER INFORMATION: Aib

<400> SEQUENCE: 334

Tyr Pro Ile Lys Pro Glu Ala Xaa Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 335
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 335

Tyr Pro Ile Lys Pro Glu Ala Gly Pro Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 336
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (14)
<223> OTHER INFORMATION: homo-Pro

<400> SEQUENCE: 336

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 337
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (14)
```

```
<223> OTHER INFORMATION: Aib

<400> SEQUENCE: 337

Tyr Pro Ile Lys Pro Glu Ala Pro Gly Glu Asp Ala Ser Xaa Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 338
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (9)
<223> OTHER INFORMATION: Sar

<400> SEQUENCE: 338

Tyr Pro Ile Lys Pro Glu Ala Pro Xaa Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 339
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (13)
<223> OTHER INFORMATION: homo-Ser

<400> SEQUENCE: 339

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 340
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (13)
<223> OTHER INFORMATION: Dap

<400> SEQUENCE: 340

Tyr Pro Ile Lys Pro Glu Ala Pro Gly Glu Asp Ala Xaa Pro Glu Glu
1               5                   10                  15

Leu Ala Gln Tyr Ala Ala Asp Leu Arg Arg Tyr Ile Asn Met Leu Thr
```

```
                    20                  25                  30

Arg Gln Arg Tyr
        35

<210> SEQ ID NO 341
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 341

Tyr Pro Ile Lys Pro Glu Ala Pro Gly Glu Asp Ala Ser Pro Gln Glu
1               5                   10                  15

Leu Ala Gln Tyr Ala Ala Asp Leu Arg Arg Tyr Ile Asn Met Leu Thr
                20                  25                  30

Arg Gln Arg Tyr
        35

<210> SEQ ID NO 342
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 342

Tyr Pro Ile Lys Pro Glu Ala Pro Gly Glu Asp Ala Ser Pro Asp Glu
1               5                   10                  15

Leu Ala Gln Tyr Ala Ala Asp Leu Arg Arg Tyr Ile Asn Met Leu Thr
                20                  25                  30

Arg Gln Arg Tyr
        35

<210> SEQ ID NO 343
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 343

Tyr Pro Ile Lys Pro Glu Ala Pro Gly Glu Asp Ala Ser Pro Glu Glu
1               5                   10                  15

Met Ala Gln Tyr Ala Ala Asp Leu Arg Arg Tyr Ile Asn Met Leu Thr
                20                  25                  30

Arg Gln Arg Tyr
        35

<210> SEQ ID NO 344
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 344
```

```
Tyr Pro Ile Lys Pro Glu Ala Pro Gly Glu Asp Ala Ser Ala Gln Glu
1               5                   10                  15

Leu Ala Gln Tyr Ala Ala Asp Leu Arg Arg Tyr Ile Asn Met Leu Thr
            20                  25                  30

Arg Gln Arg Tyr
            35

<210> SEQ ID NO 345
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 345

Tyr Pro Ile Lys Pro Glu Ala Pro Gly Glu Asp Ala Ser Ala Ser Glu
1               5                   10                  15

Leu Ala Gln Tyr Ala Ala Asp Leu Arg Arg Tyr Ile Asn Met Leu Thr
            20                  25                  30

Arg Gln Arg Tyr
            35

<210> SEQ ID NO 346
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 346

Tyr Pro Ile Lys Pro Glu Ala Pro Gly Glu Asp Ala Ser Ala Gln Glu
1               5                   10                  15

Met Ala Gln Tyr Ala Ala Asp Leu Arg Arg Tyr Ile Asn Met Leu Thr
            20                  25                  30

Arg Gln Arg Tyr
            35

<210> SEQ ID NO 347
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 347

Tyr Pro Ile Lys Pro Glu Ala Pro Gly Glu Asp Ala Ser Pro Glu Glu
1               5                   10                  15

Leu Ala Gln Tyr Ala Ala Glu Leu Arg Arg Tyr Ile Gln Met Leu Thr
            20                  25                  30

Arg Gln Arg Tyr
            35

<210> SEQ ID NO 348
<211> LENGTH: 36
```

-continued

```
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Tyr, Phe, Trp, or absent
<220> FEATURE:
<221> NAME/KEY: MOD_RES
<222> LOCATION: (2)
<223> OTHER INFORMATION: Pro, Gly, d-Ala, homo-Pro, hyroxy-Pro, or
      absent
<220> FEATURE:
<221> NAME/KEY: MOD_RES
<222> LOCATION: (3)
<223> OTHER INFORMATION: Ile, Ala, NorVal, Val, Leu, Pro, Ser, or Thr
<220> FEATURE:
<221> NAME/KEY: MOD_RES
<222> LOCATION: (4)
<223> OTHER INFORMATION: Lys, Ala, Gly, Arg, d-Ala, homo-Lys, homo-Arg,
      Glu, or Asp
<220> FEATURE:
<221> NAME/KEY: MOD_RES
<222> LOCATION: (6)
<223> OTHER INFORMATION: Glu, Ala, Val, Asp, Asn, or Gln
<220> FEATURE:
<221> NAME/KEY: MOD_RES
<222> LOCATION: (7)
<223> OTHER INFORMATION: Ala, Asn, His, Ser, or Tyr
<220> FEATURE:
<221> NAME/KEY: MOD_RES
<222> LOCATION: (9)
<223> OTHER INFORMATION: Gly, Ala, Ser, Sarcosine, Pro, or Aib
<220> FEATURE:
<221> NAME/KEY: MOD_RES
<222> LOCATION: (10)
<223> OTHER INFORMATION: Glu, Ala, Asp, Asn, Gln, Pro, Aib, or Gly
<220> FEATURE:
<221> NAME/KEY: MOD_RES
<222> LOCATION: (11)
<223> OTHER INFORMATION: Asp, Ala, Glu, Asn, Gln, Pro, Aib, or Gly
<220> FEATURE:
<221> NAME/KEY: MOD_RES
<222> LOCATION: (12)
<223> OTHER INFORMATION: Ala or d-Ala
<220> FEATURE:
<221> NAME/KEY: MOD_RES
<222> LOCATION: (13)
<223> OTHER INFORMATION: Ser, Ala, Thr, Pro, or homo-Ser
<220> FEATURE:
<221> NAME/KEY: MOD_RES
<222> LOCATION: (14)
<223> OTHER INFORMATION: Pro, Ala, homo-Pro, hydroxy-Pro, Aib, or Gly
<220> FEATURE:
<221> NAME/KEY: MOD_RES
<222> LOCATION: (15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)
<223> OTHER INFORMATION: Glu, Ala, Asp, Asn, or Gln
<220> FEATURE:
<221> NAME/KEY: MOD_RES
<222> LOCATION: (17)
<223> OTHER INFORMATION: Leu, Ala, Met, Trp, Ile, Val, or NorVal
<220> FEATURE:
<221> NAME/KEY: MOD_RES
<222> LOCATION: (18)
<223> OTHER INFORMATION: Asn, Asp, Ala, Glu, Gln, Ser, or Thr
<220> FEATURE:
<221> NAME/KEY: MOD_RES
<222> LOCATION: (19)
<223> OTHER INFORMATION: Arg, Tyr, Lys, Ala, Gln, or N(Me)Ala
<220> FEATURE:
<221> NAME/KEY: MOD_RES
<222> LOCATION: (21)
<223> OTHER INFORMATION: Tyr, Ala, Met, Phe, or Leu
<220> FEATURE:
```

-continued

```
<221> NAME/KEY: MOD_RES
<222> LOCATION: (22)
<223> OTHER INFORMATION: Ala, Ser, Thr, or d-Ala
<220> FEATURE:
<221> NAME/KEY: MOD_RES
<222> LOCATION: (23)
<223> OTHER INFORMATION: Ser, Ala, Thr, or homo-Ser
<220> FEATURE:
<221> NAME/KEY: MOD_RES
<222> LOCATION: (26)
<223> OTHER INFORMATION: His or Ala
<220> FEATURE:
<221> NAME/KEY: MOD_RES
<222> LOCATION: (28)
<223> OTHER INFORMATION: Leu, Ile, Val, or Ala
<220> FEATURE:
<221> NAME/KEY: MOD_RES
<222> LOCATION: (30)
<223> OTHER INFORMATION: Leu, Ala, NorVal, Val, Ile, or Met
<220> FEATURE:
<221> NAME/KEY: MOD_RES
<222> LOCATION: (31)
<223> OTHER INFORMATION: Ala, Val, Ile, or Leu
<220> FEATURE:
<221> NAME/KEY: MOD_RES
<222> LOCATION: (36)
<223> OTHER INFORMATION: Tyr, N(Me)Tyr, His, Trp, or Phe

<400> SEQUENCE: 348

Xaa Xaa Xaa Xaa Pro Xaa Xaa Pro Xaa Xaa Xaa Xaa Xaa Xaa Xaa Xaa
 1               5                  10                  15

Xaa Xaa Xaa Tyr Xaa Xaa Xaa Leu Arg Xaa Tyr Xaa Asn Xaa Xaa Thr
                20                  25                  30

Arg Gln Arg Xaa
            35

<210> SEQ ID NO 349
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Tyr, Phe, Trp, or absent
<220> FEATURE:
<221> NAME/KEY: MOD_RES
<222> LOCATION: (2)
<223> OTHER INFORMATION: Pro, Gly, d-Ala, homo-Pro, hydroxy-Pro, or
      absent
<220> FEATURE:
<221> NAME/KEY: MOD_RES
<222> LOCATION: (3)
<223> OTHER INFORMATION: Ile, Ala, NorVal, Val, Leu, Pro, Ser, or Thr
<220> FEATURE:
<221> NAME/KEY: MOD_RES
<222> LOCATION: (4)
<223> OTHER INFORMATION: Lys, Ala, Gly, Arg, d-Ala, homo-Lys, homo-Arg,
      Glu, or Asp
<220> FEATURE:
<221> NAME/KEY: MOD_RES
<222> LOCATION: (6)
<223> OTHER INFORMATION: Glu, Ala, Val, Asp, Asn, or Gln
<220> FEATURE:
<221> NAME/KEY: MOD_RES
<222> LOCATION: (7)
<223> OTHER INFORMATION: Ala, Asn, His, Ser, or Tyr
<220> FEATURE:
<221> NAME/KEY: MOD_RES
<222> LOCATION: (9)
<223> OTHER INFORMATION: Gly, Ala, Ser, Sarcosine, Pro, or Aib
<220> FEATURE:
<221> NAME/KEY: MOD_RES
<222> LOCATION: (10)
```

```
<223> OTHER INFORMATION: Glu, Ala, Asp, Asn, Gln, Pro, Aib, or Gly
<220> FEATURE:
<221> NAME/KEY: MOD_RES
<222> LOCATION: (11)
<223> OTHER INFORMATION: Asp Ala, Glu, Asn, Gln, Pro, Aib, or Gly
<220> FEATURE:
<221> NAME/KEY: MOD_RES
<222> LOCATION: (12)
<223> OTHER INFORMATION: Ala or d-Ala
<220> FEATURE:
<221> NAME/KEY: MOD_RES
<222> LOCATION: (13)
<223> OTHER INFORMATION: Ser, Ala, Thr, or homo-Ser
<220> FEATURE:
<221> NAME/KEY: MOD_RES
<222> LOCATION: (14)
<223> OTHER INFORMATION: Pro, Ala, homo-Pro, hydroxy-Pro, Aib, or Gly
<220> FEATURE:
<221> NAME/KEY: MOD_RES
<222> LOCATION: (15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)
<223> OTHER INFORMATION: Glu, Ala, Asp, Asn, or Gln
<220> FEATURE:
<221> NAME/KEY: MOD_RES
<222> LOCATION: (17)
<223> OTHER INFORMATION: Leu, Ala, Met, Trp, Ile, Val, or NorVal
<220> FEATURE:
<221> NAME/KEY: MOD_RES
<222> LOCATION: (18)
<223> OTHER INFORMATION: Asn, Asp, Ala, Glu, Gln, Ser, or Thr
<220> FEATURE:
<221> NAME/KEY: MOD_RES
<222> LOCATION: (19)
<223> OTHER INFORMATION: Arg, Tyr, Lys, Ala, Gln, or N(Me)Ala
<220> FEATURE:
<221> NAME/KEY: MOD_RES
<222> LOCATION: (21)
<223> OTHER INFORMATION: Tyr, Ala, Met, Phe, or Leu
<220> FEATURE:
<221> NAME/KEY: MOD_RES
<222> LOCATION: (22)
<223> OTHER INFORMATION: Ala, Ser, Thr, or d-Ala
<220> FEATURE:
<221> NAME/KEY: MOD_RES
<222> LOCATION: (23)
<223> OTHER INFORMATION: Ser, Ala, Thr, or homo-Ser
<220> FEATURE:
<221> NAME/KEY: MOD_RES
<222> LOCATION: (26)
<223> OTHER INFORMATION: His or Ala
<220> FEATURE:
<221> NAME/KEY: MOD_RES
<222> LOCATION: (28)
<223> OTHER INFORMATION: Leu, Ile, Val, or Ala
<220> FEATURE:
<221> NAME/KEY: MOD_RES
<222> LOCATION: (30)
<223> OTHER INFORMATION: Leu, Ala, NorVal, Val, Ile, or Met
<220> FEATURE:
<221> NAME/KEY: MOD_RES
<222> LOCATION: (31)
<223> OTHER INFORMATION: Ala, Val, Ile, or Leu
<220> FEATURE:
<221> NAME/KEY: MOD_RES
<222> LOCATION: (36)
<223> OTHER INFORMATION: Tyr, N(Me)Tyr, His, Trp, or Phe

<400> SEQUENCE: 349

Xaa Xaa Xaa Xaa Pro Xaa Xaa Pro Xaa Xaa Xaa Xaa Xaa Xaa Xaa
1               5                   10                  15

Xaa Xaa Xaa Tyr Xaa Xaa Xaa Leu Arg Xaa Tyr Xaa Asn Xaa Xaa Thr
                20                  25                  30

Arg Gln Arg Xaa
            35
```

```
<210> SEQ ID NO 350
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Ile, Ala, Pro, Ser, Thr, or NorVal
<220> FEATURE:
<221> NAME/KEY: MOD_RES
<222> LOCATION: (2)
<223> OTHER INFORMATION: Lys, Ala, Gly, Glu, Asp, d-Ala, homo-Lys, or
      homo-Arg
<220> FEATURE:
<221> NAME/KEY: MOD_RES
<222> LOCATION: (4)
<223> OTHER INFORMATION: Glu, Ala, Val, Asp, Asn, or Gln
<220> FEATURE:
<221> NAME/KEY: MOD_RES
<222> LOCATION: (5)
<223> OTHER INFORMATION: Ala, Asn, His, Ser, or Tyr
<220> FEATURE:
<221> NAME/KEY: MOD_RES
<222> LOCATION: (7)
<223> OTHER INFORMATION: Gly, Ala, Ser, Sarcosine, Pro, or Aib
<220> FEATURE:
<221> NAME/KEY: MOD_RES
<222> LOCATION: (8)
<223> OTHER INFORMATION: Glu, Ala, Asp, Asn, Gln, Pro, Aib, or Gly
<220> FEATURE:
<221> NAME/KEY: MOD_RES
<222> LOCATION: (9)
<223> OTHER INFORMATION: Asp, Ala, Glu, Asn, Gln, Pro, Aib, or Gly
<220> FEATURE:
<221> NAME/KEY: MOD_RES
<222> LOCATION: (10)
<223> OTHER INFORMATION: Ala or d-Ala
<220> FEATURE:
<221> NAME/KEY: MOD_RES
<222> LOCATION: (11)
<223> OTHER INFORMATION: Ser, Ala, Thr, or homo-Ser
<220> FEATURE:
<221> NAME/KEY: MOD_RES
<222> LOCATION: (12)
<223> OTHER INFORMATION: Pro, Ala, homo-Pro, hydroxy-Pro, Aib, or Gly
<220> FEATURE:
<221> NAME/KEY: MOD_RES
<222> LOCATION: (13)
<223> OTHER INFORMATION: Glu, Ala, Asp, Asn, Gln, Pro, Aib, or Gly
<220> FEATURE:
<221> NAME/KEY: MOD_RES
<222> LOCATION: (14)
<223> OTHER INFORMATION: Glu, Ala, Asp, Asn, or Gln
<220> FEATURE:
<221> NAME/KEY: MOD_RES
<222> LOCATION: (15)
<223> OTHER INFORMATION: Leu, Ala, Met, Trp, Ile, Val, or NorVal
<220> FEATURE:
<221> NAME/KEY: MOD_RES
<222> LOCATION: (16)
<223> OTHER INFORMATION: Asn, Asp, Ala, Glu, Gln, Ser or Thr
<220> FEATURE:
<221> NAME/KEY: MOD_RES
<222> LOCATION: (17)
<223> OTHER INFORMATION: Arg, Tyr, Lys, Ala, Gln, or N(Me)Ala
<220> FEATURE:
<221> NAME/KEY: MOD_RES
<222> LOCATION: (19)
<223> OTHER INFORMATION: Tyr, Ala, Met, Phe, or Leu
<220> FEATURE:
<221> NAME/KEY: MOD_RES
<222> LOCATION: (20)
<223> OTHER INFORMATION: Ala, Ser, Thr, or d-Ala
<220> FEATURE:
<221> NAME/KEY: MOD_RES
```

```
<222> LOCATION: (21)
<223> OTHER INFORMATION: Ser, Ala, Thr, or homo-Ser
<220> FEATURE:
<221> NAME/KEY: MOD_RES
<222> LOCATION: (24)
<223> OTHER INFORMATION: His or Ala
<220> FEATURE:
<221> NAME/KEY: MOD_RES
<222> LOCATION: (26)
<223> OTHER INFORMATION: Leu or Ala
<220> FEATURE:
<221> NAME/KEY: MOD_RES
<222> LOCATION: (28)
<223> OTHER INFORMATION: Leu, Ala, NorVal, or Ile
<220> FEATURE:
<221> NAME/KEY: MOD_RES
<222> LOCATION: (29)
<223> OTHER INFORMATION: Ala or Val
<220> FEATURE:
<221> NAME/KEY: MOD_RES
<222> LOCATION: (34)
<223> OTHER INFORMATION: Tyr, N(Me)Tyr, His, or Trp

<400> SEQUENCE: 350

Xaa Xaa Pro Xaa Xaa Pro Xaa Xaa Xaa Xaa Xaa Xaa Xaa Xaa Xaa
1               5                   10                  15

Xaa Tyr Xaa Xaa Xaa Leu Arg Xaa Tyr Xaa Asn Xaa Xaa Thr Arg Gln
            20                  25                  30

Arg Xaa

<210> SEQ ID NO 351
<211> LENGTH: 4
<212> TYPE: PRT
<213> ORGANISM: Homo sapiens

<400> SEQUENCE: 351

Thr Arg Gln Arg
1

<210> SEQ ID NO 352
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 211

<400> SEQUENCE: 352

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 353
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 212

<400> SEQUENCE: 353

Asp Ala Ser Pro Glu Glu Leu Asn Arg Tyr Tyr Ala Ser Leu Arg His
1               5                   10                  15

Tyr Leu Asn Leu Val Thr Arg Gln Arg Tyr
```

20                  25

<210> SEQ ID NO 354
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 213

<400> SEQUENCE: 354

Ala Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 355
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 214

<400> SEQUENCE: 355

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 356
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 215

<400> SEQUENCE: 356

Pro Glu Glu Leu Asn Arg Tyr Tyr Ala Ser Leu Arg His Tyr Leu Asn
1               5                   10                  15

Leu Val Thr Arg Gln Arg Tyr
            20

<210> SEQ ID NO 357
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 216

<400> SEQUENCE: 357

Glu Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 358

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 217

<400> SEQUENCE: 358

Glu Leu Asn Arg Tyr Tyr Ala Ser Leu Arg His Tyr Leu Asn Leu Val
1               5                   10                  15

Thr Arg Gln Arg Tyr
            20

<210> SEQ ID NO 359
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 231

<400> SEQUENCE: 359

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 360
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 232

<400> SEQUENCE: 360

Asp Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 361
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 233

<400> SEQUENCE: 361

Ala Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 362
<211> LENGTH: 24
<212> TYPE: PRT
<213> ORGANISM: Artificial Sequence
<220> FEATURE:
```

<223> OTHER INFORMATION: Description of Artificial Sequence: Synthetic
      peptide construct
<220> FEATURE:
<223> OTHER INFORMATION: N-term Mimic B linker to SEQ ID NO: 234

<400> SEQUENCE: 362

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 363
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 235

<400> SEQUENCE: 363

Pro Glu Glu Leu Asn Arg Tyr Tyr Ala Ser Leu Arg His Tyr Leu Asn
1               5                   10                  15

Leu Val Thr Arg Gln Arg Tyr
            20

<210> SEQ ID NO 364
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 236

<400> SEQUENCE: 364

Glu Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 365
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 237

<400> SEQUENCE: 365

Glu Leu Asn Arg Tyr Tyr Ala Ser Leu Arg His Tyr Leu Asn Leu Val
1               5                   10                  15

Thr Arg Gln Arg Tyr
            20

<210> SEQ ID NO 366
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 366

```
Pro Ser Lys Pro Asp Asn Pro Gly Glu Asp Ala Pro Ala Glu Asp Met
1               5                   10                  15

Ala Arg Tyr Tyr Ser Ala Leu Arg His Tyr Ile Asn Leu Ile Thr Arg
            20                  25                  30

Gln Arg Tyr
        35

<210> SEQ ID NO 367
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 367

Lys Pro Asp Asn Pro Gly Glu Asp Ala Pro Ala Glu Asp Met Ala Arg
1               5                   10                  15

Tyr Tyr Ser Ala Leu Arg His Tyr Ile Asn Leu Ile Thr Arg Gln Arg
            20                  25                  30

Tyr

<210> SEQ ID NO 368
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 368

Pro Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Val Thr Arg
            20                  25                  30

Gln Arg Tyr
        35

<210> SEQ ID NO 369
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 369

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 370
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 370

Pro Leu Glu Pro Val Tyr Pro Gly Asp Asn Ala Thr Pro Glu Gln Met
```

```
                1               5                  10                 15
Ala Gln Tyr Ala Ala Asp Leu Arg Arg Tyr Ile Asn Met Leu Thr Arg
            20                  25                 30

Pro Arg Tyr
        35

<210> SEQ ID NO 371
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 371

Glu Pro Val Tyr Pro Gly Asp Asn Ala Thr Pro Glu Gln Met Ala Gln
1               5                   10                  15

Tyr Ala Ala Asp Leu Arg Arg Tyr Ile Asn Met Leu Thr Arg Pro Arg
            20                  25                  30

Tyr

<210> SEQ ID NO 372
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 372

Ala Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 373
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 373

Tyr Pro Ala Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 374
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 374

Tyr Pro Ser Ala Pro Asp Asn Pro Gly Glu Asp Ala Pro Ala Glu Asp
1               5                   10                  15
```

Met Ala Arg Tyr Tyr Ser Ala Leu Arg His Tyr Ile Asn Leu Ile Thr
            20                  25                  30

Arg Gln Arg Tyr
        35

<210> SEQ ID NO 375
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 375

Tyr Pro Ser Lys Pro Ala Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 376
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 376

Tyr Pro Ser Lys Pro Asp Ala Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 377
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 377

Tyr Pro Ser Lys Pro Lys Tyr Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 378
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 378

Tyr Pro Ser Lys Pro Asp Asn Pro Ala Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 379
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 379

Tyr Pro Ser Lys Pro Asp Asn Pro Gly Ala Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 380
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 380

Tyr Pro Ser Lys Pro Asp Asn Pro Gly Glu Ala Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 381
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 381

Tyr Pro Ser Lys Pro Asp Asn Pro Gly Glu Asp Ala Ala Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 382
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 382

Tyr Pro Ser Lys Pro Asp Asn Pro Gly Glu Asp Ala Pro Gly Glu Asp
1               5                   10                  15

```
Met Ala Arg Tyr Tyr Ser Ala Leu Arg His Tyr Ile Asn Leu Ile Thr
            20                  25                  30

Arg Gln Arg Tyr
        35

<210> SEQ ID NO 383
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 383

Tyr Pro Ser Lys Pro Asp Asn Pro Gly Glu Asp Ala Pro Ala Ala Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 384
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 384

Tyr Pro Ser Lys Pro Asp Asn Pro Gly Glu Asp Ala Pro Ala Glu Ala
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 385
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 385

Tyr Pro Ser Lys Pro Asp Asn Pro Gly Glu Asp Ala Pro Ala Glu Asp
1               5                   10                  15

Ala Ala Arg Tyr Tyr Ser Ala Leu Arg His Tyr Ile Asn Leu Ile Thr
            20                  25                  30

Arg Gln Arg Tyr
        35

<210> SEQ ID NO 386
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 386

Tyr Pro Ser Lys Pro Asp Asn Pro Gly Glu Asp Ala Pro Ala Glu Asp
1               5                   10                  15
```

Met Ala Ala Tyr Tyr Ser Ala Leu Arg His Tyr Ile Asn Leu Ile Thr
            20                  25                  30

Arg Gln Arg Tyr
        35

<210> SEQ ID NO 387
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 387

Tyr Pro Ser Lys Pro Asp Asn Pro Gly Glu Asp Ala Pro Ala Glu Asp
1               5                   10                  15

Met Ala Lys Tyr Tyr Ser Ala Leu Arg His Tyr Ile Asn Leu Ile Thr
            20                  25                  30

Arg Gln Arg Tyr
        35

<210> SEQ ID NO 388
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 388

Tyr Pro Ser Lys Pro Asp Asn Pro Gly Glu Asp Ala Pro Ala Glu Asp
1               5                   10                  15

Met Ala Arg Tyr Ala Ser Ala Leu Arg His Tyr Ile Asn Leu Ile Thr
            20                  25                  30

Arg Gln Arg Tyr
        35

<210> SEQ ID NO 389
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 389

Tyr Pro Ser Lys Pro Asp Asn Pro Gly Glu Asp Ala Pro Ala Glu Asp
1               5                   10                  15

Met Ala Arg Tyr Tyr Ala Ala Leu Arg His Tyr Ile Asn Leu Ile Thr
            20                  25                  30

Arg Gln Arg Tyr
        35

<210> SEQ ID NO 390
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 390

Tyr Pro Ser Lys Pro Asp Asn Pro Gly Glu Asp Ala Pro Ala Glu Asp
1               5                   10                  15

```
Met Ala Arg Tyr Tyr Ser Ala Leu Lys His Tyr Ile Asn Leu Ile Thr
            20                  25                  30

Arg Gln Arg Tyr
        35

<210> SEQ ID NO 391
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 391

Tyr Pro Ser Lys Pro Asp Asn Pro Gly Glu Asp Ala Pro Ala Glu Asp
1               5                   10                  15

Met Ala Arg Tyr Tyr Ser Ala Leu Arg Ala Tyr Ile Asn Leu Ile Thr
            20                  25                  30

Arg Gln Arg Tyr
        35

<210> SEQ ID NO 392
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 392

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Phe Ile Asn Leu Ile Thr
            20                  25                  30

Arg Gln Arg Tyr
        35

<210> SEQ ID NO 393
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 393

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ala Asn Leu Ile Thr
            20                  25                  30

Arg Gln Arg Tyr
        35

<210> SEQ ID NO 394
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 394

Tyr Pro Ser Lys Pro Asp Asn Pro Gly Glu Asp Ala Pro Ala Glu Asp
1               5                   10                  15
```

Met Ala Arg Tyr Tyr Ser Ala Leu Arg His Tyr Ile Gln Leu Ile Thr
            20                  25                  30

Arg Gln Arg Tyr
        35

<210> SEQ ID NO 395
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 395

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Ala Ile Thr
            20                  25                  30

Arg Gln Arg Tyr
        35

<210> SEQ ID NO 396
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 396

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ala Thr
            20                  25                  30

Arg Gln Arg Tyr
        35

<210> SEQ ID NO 397
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 397

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Phe
        35

<210> SEQ ID NO 398
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 398

Tyr Pro Ser Lys Pro Asp Asn Pro Gly Glu Asp Ala Pro Ala Glu Asp
1               5                   10                  15

```
Met Ala Arg Tyr Tyr Ser Ala Leu Arg His Tyr Ile Asn Leu Ile Thr
            20                  25                  30

Arg Gln Arg His
        35

<210> SEQ ID NO 399
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 399

Leu Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 400
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 400

Val Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 401
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 401

Tyr Pro Ile Lys Pro Glu Ala Pro Gly Glu Asp Ala Pro Ala Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 402
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 402

Ala Pro Leu Glu Pro Val Tyr Tyr Pro Ser Lys Pro Lys Asn Pro Gly
1               5                   10                  15

Glu Asp Ala Pro Ala Glu Asp Leu Ala Arg Tyr Tyr Ser Ala Leu Arg
```

```
                   20                  25                  30

His Tyr Ile Asn Leu Ile Thr Arg Gln Arg Tyr
        35                  40

<210> SEQ ID NO 403
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 403

Ala Pro Leu Glu Pro Val Tyr Pro Gly Asp Asn Ala Thr Pro Glu Gln
1               5                   10                  15

Met Tyr Pro Ser Lys Pro Lys Asn Pro Gly Glu Asp Ala Pro Ala Glu
            20                  25                  30

Asp Leu Ala Arg Tyr Tyr Ser Ala Leu Arg His Tyr Ile Asn Leu Ile
        35                  40                  45

Thr Arg Gln Arg Tyr
    50

<210> SEQ ID NO 404
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 404

Gln Tyr Ala Ala Asp Tyr Pro Ser Lys Pro Lys Asn Pro Gly Glu Asp
1               5                   10                  15

Ala Pro Ala Glu Asp Leu Ala Arg Tyr Tyr Ser Ala Leu Arg His Tyr
            20                  25                  30

Ile Asn Leu Ile Thr Arg Gln Arg Tyr
        35                  40

<210> SEQ ID NO 405
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 405

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Leu Val Thr Arg Gln
            20                  25                  30

Arg Tyr

<210> SEQ ID NO 406
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 406

Ile Lys Pro Glu Ala Pro Gly Glu Asp Ala Ser Pro Glu Glu Leu Asn
1               5                   10                  15
```

```
Arg Tyr Tyr Ala Ser Leu Arg His Tyr Ile Asn Leu Val Thr Arg Gln
            20                  25                  30

Arg Tyr

<210> SEQ ID NO 407
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 407

Ile Lys Pro Glu Ala Pro Gly Glu Asp Ala Ser Pro Glu Glu Leu Asn
1               5                   10                  15

Arg Tyr Tyr Ala Ser Leu Arg His Tyr Val Asn Leu Val Thr Arg Gln
            20                  25                  30

Arg Tyr

<210> SEQ ID NO 408
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 408

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Val Thr Arg Gln
            20                  25                  30

Arg Tyr

<210> SEQ ID NO 409
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 409

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Val Thr Arg Gln
            20                  25                  30

Arg Tyr

<210> SEQ ID NO 410
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 410

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Ile Thr Arg Gln
            20                  25                  30
```

Arg Tyr

<210> SEQ ID NO 411
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 411

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Tyr

<210> SEQ ID NO 412
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 412

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Phe

<210> SEQ ID NO 413
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 413

Ile Lys Pro Glu Ala Pro Gly Glu Asp Ala Ser Pro Glu Glu Leu Asn
1               5                   10                  15

Arg Tyr Tyr Ala Ser Leu Lys His Phe Leu Asn Leu Val Thr Arg Gln
            20                  25                  30

Arg Tyr

<210> SEQ ID NO 414
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 414

Ile Lys Pro Glu Ala Pro Gly Glu Asp Ala Ser Pro Glu Glu Leu Asn
1               5                   10                  15

Arg Tyr Tyr Ala Ser Leu Lys His Tyr Ile Asn Leu Val Thr Arg Gln
            20                  25                  30

Arg Tyr

<210> SEQ ID NO 415

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 415

Ile Lys Pro Glu Ala Pro Gly Glu Asp Ala Ser Pro Glu Glu Leu Asn
1               5                   10                  15

Arg Tyr Tyr Ala Ser Leu Lys His Tyr Val Asn Leu Val Thr Arg Gln
            20                  25                  30

Arg Tyr

<210> SEQ ID NO 416
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 416

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Gln Leu Val Thr Arg Gln
            20                  25                  30

Arg Tyr

<210> SEQ ID NO 417
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 417

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Val Val Thr Arg Gln
            20                  25                  30

Arg Tyr

<210> SEQ ID NO 418
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 418

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Ile Thr Arg Gln
            20                  25                  30

Arg Tyr

<210> SEQ ID NO 419
<211> LENGTH: 34
<212> TYPE: PRT
<213> ORGANISM: Artificial Sequence
<220> FEATURE:
```

-continued

<223> OTHER INFORMATION: Description of Artificial Sequence: Synthetic
     peptide construct

<400> SEQUENCE: 419

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Leu Thr Arg Gln
            20                  25                  30

Arg Tyr

<210> SEQ ID NO 420
<211> LENGTH: 34
<212> TYPE: PRT
<213> ORGANISM: Artificial Sequence
<220> FEATURE:
<223> OTHER INFORMATION: Description of Artificial Sequence: Synthetic
     peptide construct

<400> SEQUENCE: 420

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Val Thr Arg Gln
            20                  25                  30

Arg Phe

<210> SEQ ID NO 421
<211> LENGTH: 34
<212> TYPE: PRT
<213> ORGANISM: Artificial Sequence
<220> FEATURE:
<223> OTHER INFORMATION: Description of Artificial Sequence: Synthetic
     peptide construct

<400> SEQUENCE: 421

Ile Lys Pro Glu Ala Pro Gly Glu Asp Ala Ser Pro Glu Glu Leu Asn
1               5                   10                  15

Arg Tyr Tyr Ala Ser Leu Arg His Phe Ile Asn Leu Val Thr Arg Gln
            20                  25                  30

Arg Tyr

<210> SEQ ID NO 422
<211> LENGTH: 34
<212> TYPE: PRT
<213> ORGANISM: Artificial Sequence
<220> FEATURE:
<223> OTHER INFORMATION: Description of Artificial Sequence: Synthetic
     peptide construct

<400> SEQUENCE: 422

Ile Lys Pro Glu Ala Pro Gly Glu Asp Ala Ser Pro Glu Glu Leu Asn
1               5                   10                  15

Arg Tyr Tyr Ala Ser Leu Arg His Phe Val Asn Leu Val Thr Arg Gln
            20                  25                  30

Arg Tyr

<210> SEQ ID NO 423
<211> LENGTH: 34
<212> TYPE: PRT
<213> ORGANISM: Artificial Sequence
<220> FEATURE:
<223> OTHER INFORMATION: Description of Artificial Sequence: Synthetic
     peptide construct

<400> SEQUENCE: 423

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Gln Leu Val Thr Arg Gln
            20                  25                  30

Arg Tyr

<210> SEQ ID NO 424
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 424

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Val Val Thr Arg Gln
            20                  25                  30

Arg Tyr

<210> SEQ ID NO 425
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 425

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Leu Ile Thr Arg Gln
            20                  25                  30

Arg Tyr

<210> SEQ ID NO 426
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 426

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Leu Leu Thr Arg Gln
            20                  25                  30

Arg Tyr

<210> SEQ ID NO 427
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 427

Ile Lys Pro Glu Ala Pro Gly Glu Asp Ala Ser Pro Glu Glu Leu Asn
1               5                   10                  15

-continued

Arg Tyr Tyr Ala Ser Leu Arg His Phe Leu Asn Leu Val Thr Arg Gln
            20                  25                  30

Arg Phe

<210> SEQ ID NO 428
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 428

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Val Val Thr Arg Gln
            20                  25                  30

Arg Tyr

<210> SEQ ID NO 429
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 429

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Ile Thr Arg Gln
            20                  25                  30

Arg Tyr

<210> SEQ ID NO 430
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 430

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Leu Thr Arg Gln
            20                  25                  30

Arg Tyr

<210> SEQ ID NO 431
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 431

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Val Thr Arg Gln
            20                  25                  30

Arg Phe

```
<210> SEQ ID NO 432
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 432

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Ile Thr Arg Gln
            20                  25                  30

Arg Tyr

<210> SEQ ID NO 433
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 433

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Leu Thr Arg Gln
            20                  25                  30

Arg Tyr

<210> SEQ ID NO 434
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 434

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Val Thr Arg Gln
            20                  25                  30

Arg Phe

<210> SEQ ID NO 435
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 435

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Phe
```

PANCREATIC POLYPEPTIDE FAMILY MOTIFS AND POLYPEPTIDES COMPRISING THE SAME

RELATED APPLICATIONS

The present application claims priority to U.S. Provisional Application No. 60/543,406, filed Feb. 11, 2004, and U.S. Provisional Application No. 60/543,407, filed Feb. 11, 2004, both of which are hereby incorporated by reference in their entirety.

FIELD OF THE INVENTION

The present invention relates to peptide chemistry, and more particularly to pancreatic polypeptide family ("PPF") polypeptides.

INCORPORATION-BY-REFERENCE OF MATERIAL SUBMITTED ON COMPACT DISCS

The sequence listing in the present application is being submitted on two compact discs labeled "Sequence Listing-Copy 1" and "Sequence Listing-Copy 2"; each containing a file of 206 KB in size named "0406-UTL-5_18528723_seq.txt" created on Aug. 8, 2005, the contents of which are hereby incorporated by reference.

BACKGROUND OF THE INVENTION

A number of related hormones make up the pancreatic polypeptide family ("PPF"). Pancreatic polypeptide ("PP") was discovered as a contaminant of insulin extracts and was named by its organ of origin rather than functional importance (Kimmel et al., *Endocrinology* 83: 1323-30 (1968)). PP is a 36-amino acid peptide (SEQ ID NO: 1) containing distinctive structural motifs. A related peptide was subsequently discovered in extracts of intestine and named Peptide YY ("PYY") (SEQ ID NO: 2) because of the N- and C-terminal tyrosines (Tatemoto, *Proc. Natl. Acad. Sci. USA* 79: 2514-8 (1982)). A third related peptide was later found in extracts of brain and named Neuropeptide Y ("NPY") (SEQ ID NO: 4) (Tatemoto, *Proc. Natl. Acad. Sci. USA* 79: 5485-9 (1982); Tatemoto et al., *Nature* 296: 659-60 (1982)).

These three related peptides have been reported to exert various biological effects. Effects of PP include inhibition of pancreatic secretion and relaxation of the gallbladder. Centrally administered PP produces modest increases in feeding that may be mediated by receptors localized to the hypothalamus and brainstem (reviewed in Gehlert, *Proc. Soc. Exp. Biol. Med.* 218: 7-22 (1998)).

Release of PYY (SEQ ID NO: 2) occurs following a meal. An alternate molecular form of PYY is PYY(3-36) (SEQ ID NO: 3) (Eberlein et al., *Peptides* 10: 797-803 (1989); Grandt et al., *Regul. Pept.* 51: 151-9 (1994)). This fragment constitutes approximately 40% of total PYY-like immunoreactivity in human and canine intestinal extracts and about 36% of total plasma PYY immunoreactivity in a fasting state to slightly over 50% following a meal. It is apparently a dipeptidyl peptidase-IV (DPP4) cleavage product of PYY. PYY(3-36) is reportedly a selective ligand at the Y2 and Y5 receptors, which appear pharmacologically unique in preferring N-terminally truncated (i.e., C-terminal fragments of) NPY analogs. Peripheral administration of PYY reportedly reduces gastric acid secretion, gastric motility, exocrine pancreatic secretion (Yoshinaga et al., *Am. J. Physiol.* 263: G695-701 (1992); Guan et al., *Endocrinology* 128: 911-6 (1991); Pappas et al., *Gastroenterology* 91: 1386-9 (1986)), gallbladder contraction and intestinal motility (Savage et al., *Gut* 28: 166-70 (1987)). The effects of central injection of PYY on gastric emptying, gastric motility and gastric acid secretion, as seen after direct injection in or around the hindbrain/brainstem (Chen and Rogers, *Am. J. Physiol.* 269: R787-92 (1995); Chen et al., *Regul. Pept.* 61: 95-98 (1996); Yang and Tache, *Am. J. Physiol.* 268: G943-8 (1995); Chen et al., *Neurogastroenterol. Motil.* 9: 109-16 (1997)), may differ from those effects observed after peripheral injection. For example, centrally administered PYY had some effects opposite to those described herein for peripherally injected PYY(3-36) in that gastric acid secretion was stimulated, not inhibited. Gastric motility was suppressed only in conjunction with TRH stimulation, but not when administered alone, and was indeed stimulatory at higher doses through presumed interaction with PP receptors. PYY has been shown to stimulate food and water intake after central administration (Morley et al., *Brain Res.* 341: 200-3 (1985); Corp et al., *Am. J. Physiol.* 259: R317-23 (1990)).

Likewise, one of the earliest reported central effects of NPY (SEQ ID NO: 4) was to increase food intake, particularly in the hypothalamus (Stanley et al., *Peptides* 6: 1205-11 (1985)). PYY and PP are reported to mimic these effects, and PYY is more potent or as potent as NPY (Morley et al., *Brain Res.* 341: 200-3 (1985); Kanatani et al., *Endocrinology* 141: 1011-6 (2000); Nakajima et al., *J. Pharmacol. Exp. Ther.* 268: 1010-4 (1994)). Several groups found the magnitude of NPY-induced feeding to be higher than that induced by any pharmacological agent previously tested, and also extremely long-lasting. NPY-induced stimulation of feeding has been reproduced in a number of species. Among the three basic macronutrients (fat, protein, and carbohydrate), the intake of carbohydrates was preferentially stimulated. No tolerance was seen towards the orexigenic effect of NPY, and when administration of the peptide was repeated over 10 days, a marked increase in the rate of weight gain was observed. Following starvation, the concentration of NPY in the hypothalamic PVN increased with time, and returned rapidly to control levels following food ingestion.

Pharmacological studies and cloning efforts have revealed a number of seven transmembrane receptors for the PP family of peptides, and these receptors have been assigned the names Y1 through Y6 (and a putative PYY-preferring receptor Y7). Typical signaling responses of these receptors are similar to those of other $G_i/G_o$-coupled receptors, namely inhibition of adenylate cyclase. Even with fairly low sequence homology among receptors, it is apparent that there is a clustering of amino acid sequence similarity between Y1, Y4 and Y6 receptors, while Y2 and Y5 define other families. Other binding sites have been identified by the rank order of potency of various peptides. The NPY-preferring receptor, which has not been cloned, has been termed Y3, and PYY-preferring receptors have also been shown to exist (putative Y7) (reviewed in Michel et al., *Pharmacol. Rev.* 50: 143-50 (1998); Gehlert, *Proc. Soc. Exp. Biol. Med.* 218: 7-22 (1998)).

The Y5 and Y1 receptors have been suggested as the primary mediators of the food intake response (Marsh et al., *Nat. Med.* 4: 718-21 (1998); Kanatani et al., *Endocrinology* 141: 1011-6 (2000)). The prevalent idea has been that endogenous NPY, via these receptors, increases feeding behavior. Proposed therapies for obesity have invariably been directed toward antagonism of NPY receptors, while therapies for treating anorexia have been directed toward agonists of this ligand family (see, e.g., U.S. Pat. Nos. 5,939,462; 6,013,622; and 4,891,357). In general, PYY and NPY are reported to be equipotent and equally effective in all Y1, Y5 (and Y2) receptor assays studied (Gehlert, *Proc. Soc. Exp. Biol. Med.* 218: 7-22 (1998)).

Pharmacologically, the Y2 receptor is distinguished from Y1 by exhibiting affinity for C-terminal fragments of neuropeptide Y. The Y2 receptor is most often differentiated by the affinity of neuropeptide Y(13-36), although the 3-36 fragment of neuropeptide Y and peptide YY provided improved affinity and selectivity (see Dumont et al., *Soc. for Neurosci. Abstracts* 19:726 (1993)). Signal transmission through both the Y1 and Y2 receptors are coupled to the inhibition of adenylate cyclase. Binding to the Y2 receptor was also found to reduce the intracellular levels of calcium in the synapse by selective inhibition of N-type calcium channels. In addition, the Y2 receptor, like the Y1 receptors, exhibits differential coupling to second messengers (see U.S. Pat. No. 6,355,478). Y2 receptors are found in a variety of brain regions, including the hippocampus, substantia nigra-lateralis, thalamus, hypothalamus, and brainstem. The human, murine, monkey and rat Y2 receptors have been cloned (e.g., see U.S. Pat. No. 6,420,532 and U.S. Pat. No. 6,355,478).

The main characteristic of putative Y3 receptors is that they recognize NPY, while PYY is at least an order of magnitude less potent. The Y3 receptor represents the only binding site/receptor that shows a preference for NPY.

There is an additional binding site/receptor which shows preference for PYYs, termed PYY-preferring receptor, which is referred to herein as the Y7 receptor(s). Different rank orders of binding to this receptor, or class of receptors, have been reported, suggesting that there may be more than one receptor in this family. In most cases it has been applied to describe a receptor where PYY was three to five times more potent than NPY. The International Union of Pharmacology recommendations for the nomenclature of NPY, PYY and PP receptors are that the term PYY-preferring receptor is not used unless a potency difference of at least twenty-fold between PYY and NPY is observed (Michel et al., *Pharmacol. Rev.* 50: 143-50 (1998)). However, for purposes of this disclosure, reference to the Y7 receptor or pharmacology of a PYY-preferring receptor means a receptor having any degree of preference for PYY over NPY.

Obesity and its associated disorders are common and very serious public health problems in the United States and throughout the world. Upper body obesity is the strongest risk factor known for type 2 diabetes mellitus, and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia (see, e.g., Kopelman, *Nature* 404: 635-43 (2000)). It reduces life-span and carries a serious risk of co-morbidities above, as well disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al., *Br. Med. J.* 301: 835-7 (1990)). Obesity is also a risk factor for the group of conditions called insulin resistance syndrome, or "Syndrome X." Recent estimate for the medical cost of obesity and associated disorders is $150 billion worldwide. The pathogenesis of obesity is believed to be multifactorial but the basic problem is that in obese subjects nutrient availability and energy expenditure do not come into balance until there is excess adipose tissue. Obesity is currently a poorly treatable, chronic, essentially intractable metabolic disorder. A therapeutic drug useful in weight reduction of obese persons could have a profound beneficial effect on their health.

There remains a need to develop further PYY analog polypeptides. Accordingly, it is an object of the present invention to provide such PYY analog polypeptides and methods for producing and using them.

All documents referred to herein are incorporated by reference into the present application as though fully set forth herein.

SUMMARY OF THE INVENTION

The present invention relates generally to pancreatic polypeptide family ("PPF") polypeptides having at least 50% sequence identity to PYY(3-36) over the entire length of PYY(3-36), and also comprise at least two PPF motifs including at least the N-terminal polyproline PPF motif and the C-terminal tail PPF motif. Additional PPF motifs of the invention may correspond to any motif of any of the PP family polypeptides, including PP, PYY and NPY. In certain embodiments, the PPF polypeptides do not include unnatural amino acids. In other embodiments, the PPF polypeptides do not include known naturally occurring species variants.

In one aspect, the PPF polypeptides of the invention include PYY analog polypeptides. In yet another aspect of the invention, the PPF polypeptides of the invention include PPF chimeric polypeptides comprising a fragment of a PP, PYY or NPY polypeptide covalently linked to at least one additional fragment of a PP, PYY or NPY polypeptide, wherein each PP, PYY or NPY fragment includes a PPF motif. Such PPF analog polypeptides and PPF chimeric polypeptides of the invention will exhibit at least 50% sequence identity to a native PYY(3-36) over the entire length of the PYY(3-36). In certain embodiments, desirable PPF chimeric polypeptides include an N-terminal PP fragment in combination with a C-terminal PYY fragment. In other embodiments, PPF chimeric polypeptides include an N-terminal PP fragment in combination with a C-terminal NPY fragment. In other embodiments, PPF chimeric polypeptides include an N-terminal PYY fragment and a C-terminal PP or NPY fragment. In other embodiments, PPF chimeric polypeptides include an N-terminal NPY in combination with a C-terminal PYY or PP. In other embodiments, PPF chimeric polypeptides may not include an N-terminal PP fragment in combination with a C-terminal NPY fragment. In still other embodiments, PPF chimeric polypeptides may not include an N-terminal NPY fragment with a C-terminal PYY fragment.

In another aspect of the invention, methods for treating or preventing obesity are provided, wherein the method comprises administering a therapeutically or prophylactically effective amount of a PPF polypeptide of the invention to a subject in need thereof. In a preferred embodiment, the subject is an obese or overweight subject. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method.

In yet another aspect of the invention, compounds of the invention can be used for methods of reducing food intake, reducing nutrient availability, causing weight loss, affecting body composition, altering body energy content or energy expenditure and improving lipid profile (including reducing LDL cholesterol and triglyceride levels and/or changing HDL cholesterol levels). Thus, in certain embodiments, the methods of the invention are useful for treating or preventing conditions or disorders which can be alleviated by reducing nutrient availability in a subject in need thereof, comprising administering to said subject a therapeutically or prophylactically effective amount of a PPF polypeptide of the invention. Such conditions and disorders include, but are not limited to, hypertension, dyslipidemia, cardiovascular disease, eating disorders, insulin-resistance, obesity, diabetes mellitus of any kind, including Type I, Type II, and gestational diabetes. Compounds of the invention may also be useful in treating or preventing other conditions associated with obesity including stroke, cancer (e.g., endometrial, breast, prostate, and colon cancer), gallbladder disease, sleep apnea, reduced fertility, and osteoarthritis, (see Lyznicki et al, *Am. Fam. Phys.* 63: 2185, 2001).

Compounds of the invention may also be useful for potentiating, inducing, enhancing or restoring glucose responsivity in pancreatic islets or cells. These actions may also be used to treat or prevent conditions associated with metabolic disorders such as those described above and in U.S. patent application No. US20040228846.

In addition to the amelioration of hypertension in subjects in need thereof as a result of reduced food intake, weight loss, and treating obesity, compounds of the invention may be used to treat or prevent hypotension.

Compounds of the invention may also be useful in the treatment or prevention of any number of gastrointestinal disorders that are associated with excess intestinal electrolytes and water secretion as well as decreased absorption, e.g., infectious (e.g., viral or bacterial) diarrhea, inflammatory diarrhea, short bowel syndrome, or the diarrhea which typically occurs following surgical procedure, e.g., ileostomy (see e.g., Harrison's principles of Internal Medicine, McGraw Hill Inc., New York, 12th ed.). Examples of infectious diarrhea include, without limitation, acute viral diarrhea, acute bacterial diarrhea (e.g., salmonella, campylobacter, and clostridium) or diarrhea due to protozoal infections, or travellers' diarrhea (e.g., Norwalk virus or rotavirus). Examples of inflammatory diarrhea include, without limitation, malabsorption syndrome, tropical spue, chronic pancreatitis, Crohn's disease, diarrhea, and irritable bowel syndrome. It has also been discovered that the peptides of the invention can be used to treat or prevent an emergency or life-threatening situation involving a gastrointestinal disorder, e.g., after surgery or due to cholera. Furthermore, the compounds of the invention can be used to treat intestinal dysfunction in patients with Acquired Immune Deficiency Syndrome (AIDS), especially during cachexia. The compounds of the invention may also be useful for inhibiting small intestinal fluid and electrolyte secretion, and augmenting nutrient transport, as well as increasing cell proliferation in the gastrointestinal tract, regulating lipolysis in, e.g., adipase tissue and regulating blood flow in a mammal.

Compounds of the invention may also be useful for treating or preventing the above conditions by their gastrointestinal protective activity. Accordingly, compound of the invention may be used to treat gastrointestinal or muscosal damage. Exemplary types of damage include, but are not limited to, inflammatory bowel disease, bowel atrophy, conditions characterized by loss of bowel mucosa or bowel mucosal function, and other conditions of the gastrointestinal tract, including those which may be brought about by exposure to cytotoxic agents, radiation, toxicity, infection and/or injury. Moreover, these compounds of the invention may be combined with analgesics, anti-inflammatory agents, growth hormone, heparin, or any other therapies that may be used to treat inflammatory bowel disease or other conditions listed above.

Moreover, compounds of the invention are useful in treating or preventing diseases and disorders that can be alleviated or ameliorated by their anti-secretory properties. Such anti-secretory properties include inhibition of gastric and/or pancreatic secretions and can be useful in the treatment or prevention of diseases and disorders including gastritis, pancreatitis, Barrett's esophagus, and Gastroesophageal Reflux Disease. These diseases may also be treated or prevented by the gastrointestinal protective functions of compounds of the invention.

Compounds of the invention may also be useful for reducing aluminum concentrations in the central nervous system of a subject to treat or prevent a disease or condition associated with abnormal aluminum concentrations (e.g., a patient afflicted with Alzheimer's disease or at risk for developing Alzheimer's disease, dialysis dementia, or increased aluminum levels due to occupational exposure).

The present invention also relates to pharmaceutical compositions comprising a therapeutically or prophylactically effective amount of at least one PPF polypeptide of the invention, or a pharmaceutically acceptable salt thereof, together with pharmaceutically acceptable diluents, preservatives, solubilizers, emulsifiers, adjuvants and/or carriers useful in the delivery of the PPF polypeptides.

These and other aspects of the invention will be more clearly understood with reference to the following preferred embodiments and detailed description.

BRIEF DESCRIPTION OF THE DRAWINGS

FIGS. 9A-9D demonstrate the effect of PPF polypeptides of the invention on heart rate and blood pressure, as compared to PYY and PYY(3-36).

DETAILED DESCRIPTION OF THE INVENTION

Figure 1:
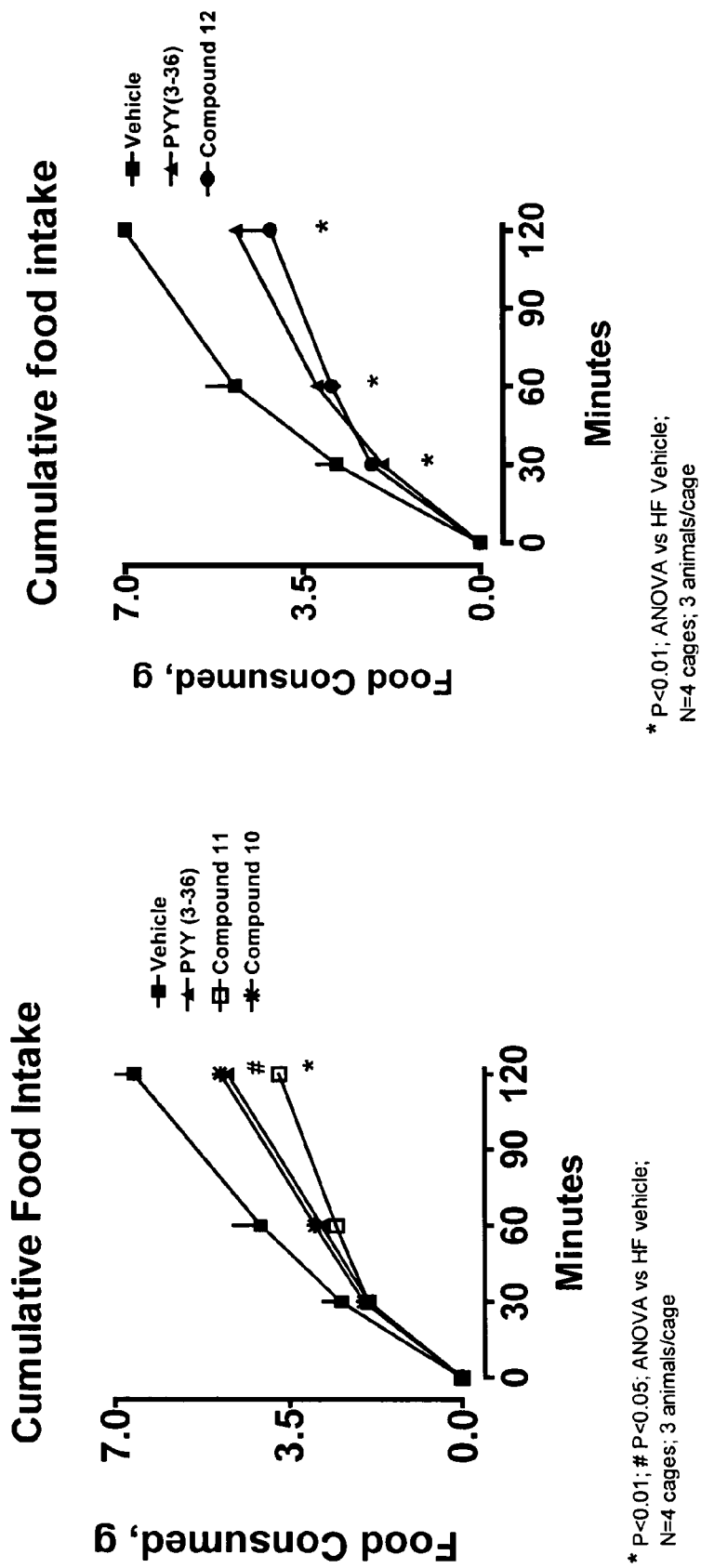
FIG. 1 demonstrates the activity of certain PPF polypeptides of the invention in a food intake assay.
Figure 2:
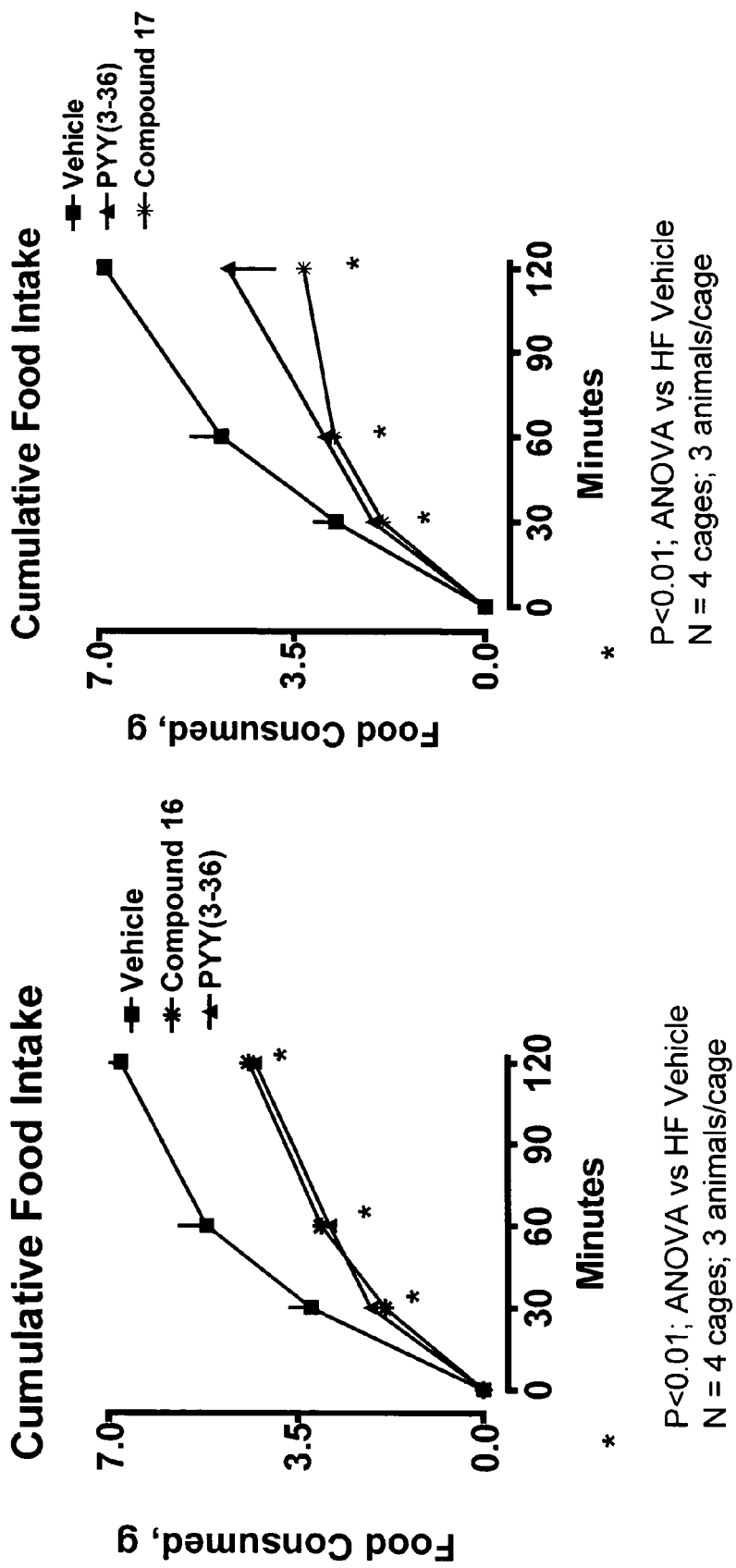
FIG. 2 demonstrates the activity of additional PPF polypeptides of the invention in a food intake assay.
Figure 3:
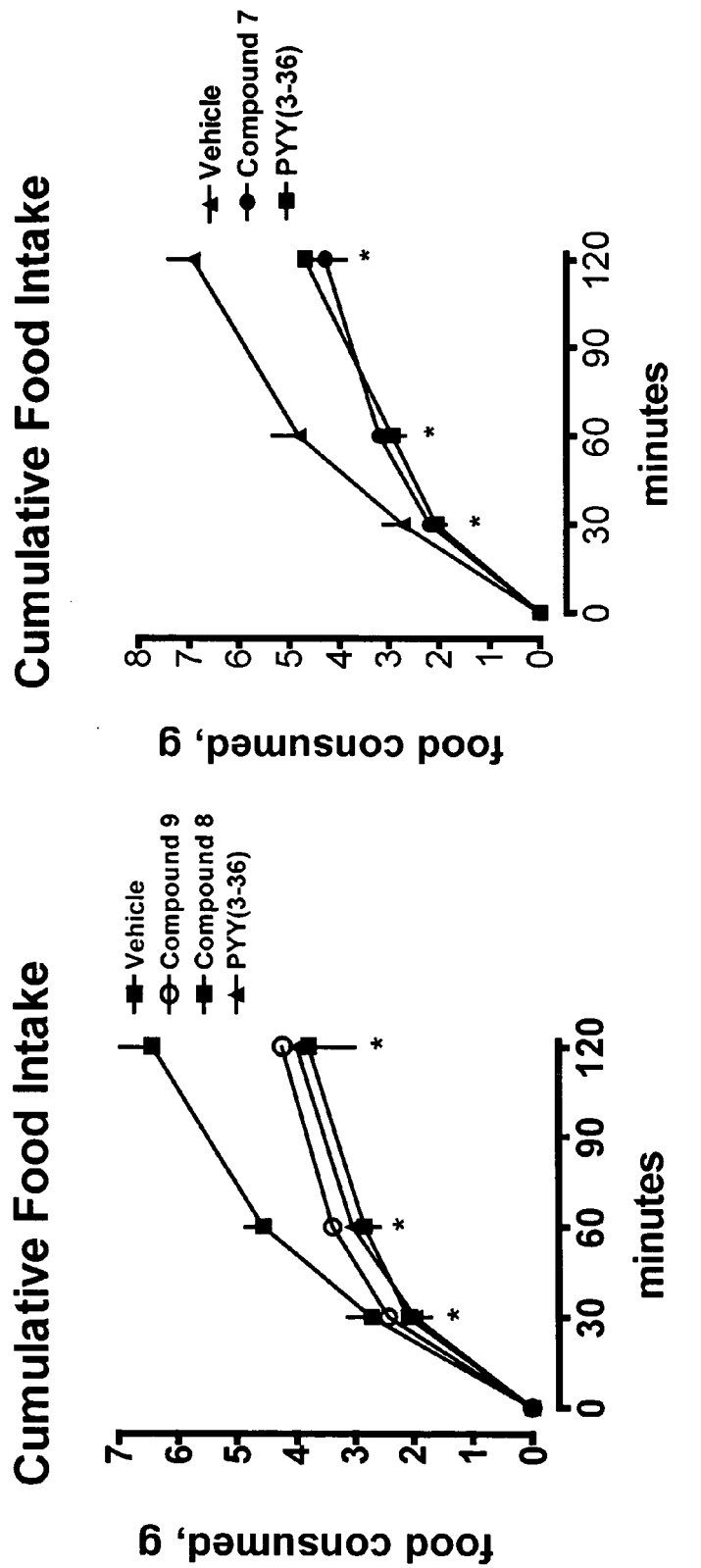
FIG. 3 demonstrates the activity of yet additional PPF polypeptides of the invention in a food intake assays.
Figure 4:
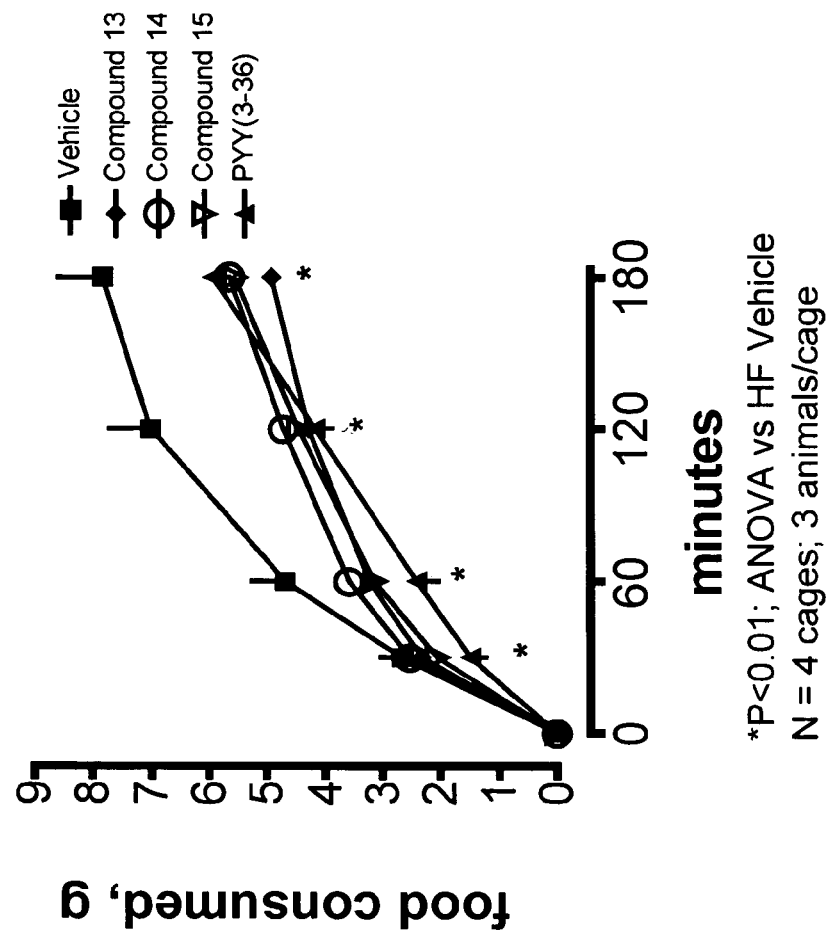
FIG. 4 demonstrates the activity of yet additional PPF polypeptides of the invention in a food intake assay.

The present invention relates generally to pancreatic polypeptide family ("PPF") polypeptides having at least 50% sequence identity to PYY(3-36) over the entire length of PYY(3-36). The PPF polypeptides of the invention also comprise at least two PPF motifs including at least the N-terminal polyproline PPF motif and the C-terminal tail PPF motif. Additional PPF motifs of the invention may correspond to a motif of any of the PP family polypeptides, including PP, PYY and NPY, for example the type II β-turn region motif of PYY, or the α-helical motif at the C-terminal end of PYY. In certain embodiments, the PPF polypeptides of the invention may not include any unnatural amino acids.

The present invention also relates to PPF polypeptides useful in the treatment and prevention of metabolic conditions and disorders. In a preferred embodiment, the PPF polypeptides of the invention may have comparable or higher potency in the treatment and/or prevention of metabolic conditions and disorders, as compared to native human PP, PYY, PYY(3-36) or NPY. Alternatively, preferred PPF polypeptides of the invention may exhibit less potency but may possess other desirable features such as improved ease of manufacture, stability, and/or ease of formulation, as compared to PP, PYY, PYY(3-36), or NPY.

In a preferred embodiment, and without intending to be limited by theory, it is believed that the peripheral administration of the novel PPF polypeptides of the invention to a subject reduces nutrient availability, and thus is useful in the treatment and prevention of obesity and related metabolic conditions or disorders. As such, the present invention provides PPF polypeptide compositions and methods of using them to reduce nutrient availability in a subject in need thereof for treating and preventing metabolic conditions or disorders that may benefit from a reduction in nutrient availability. These methods may be useful in the treatment of, for example, obesity, diabetes, including but not limited to type 2 or non-insulin dependent diabetes, eating disorders, insulin-resistance syndrome, and cardiovascular disease.

The section headings are used herein for organizational purposes only, and are not to be construed as in any way limiting the subject matter described.

A. PPF Polypeptides of the Invention and PPF Motifs

As discussed above, the present invention relates at least in part to novel PPF polypeptides comprising at least two PPF motifs, wherein the at least two PPF motifs include at least the N-terminal polyproline PPF motif and the C-terminal tail PPF motif. The PPF polypeptides of the invention will also exhibit at least 50% sequence identity to a native PYY(3-36) over the entire length of the PYY(3-36). The polypeptides of the present invention will preferably retain, at least in part, a biological activity of native human PP, PYY or NPY, e.g., the polypeptides of the present invention will generally be PP, PYY and/or NPY agonists or antagonists. In a preferred embodiment, the polypeptides of the present invention will exhibit biological activity in the treatment and prevention of metabolic conditions and disorders. Further, the PPF polypeptides of the invention may include internal linker compounds, may include chemical modifications at internal amino acid residues, or may be chemically modified at the N-terminal or C-terminal residue. In a preferred embodiment, the polypeptides of the invention include only natural L amino acid residues and/or modified natural L amino acid residues. Alternatively, in a preferred embodiment, the polypeptides of the invention do not include unnatural amino acid residues.

The PPF motifs of the invention may correspond to any motif of any of the native PP family polypeptides, including PP, PYY and NPY. A "PPF motif" is generally a structural component, primary, secondary, or tertiary, of a native PP family polypeptide that is critical to biological activity, i.e., biological activity is substantially decreased in the absence or disturbance of the motif. Preferred PPF motifs include the N-terminal polyproline type II motif of a native PP family polypeptide, the type II β-turn motif of native PP family polypeptide, the α-helical motif at the C-terminal end of native PP family polypeptide, and the C-terminal tail motif of native PP family polypeptide. More particularly, in the N-terminal polyproline region, amino acids corresponding to residues 5 and 8 of a native PP family polypeptide are generally conserved as a proline. The type II β-turn motif will generally include amino acids corresponding to residues 12-14 of a native PP family polypeptide. The α-helical motif can generally extend from amino acids corresponding to approximately residue 14 of a native PP family polypeptide to any point up to and including the C-terminal end, so long as the α-helical motif includes a sufficient number of amino acid residues such that an α-helical turn is formed in solution. The α-helical motif can also include amino acid substitutions, insertions and deletions to the native PP family sequence, so long as the α-helical turn is still formed in solution. The C-terminal tail motif generally includes amino acids corresponding to approximately the last 10 residues of a native PP family polypeptide, more preferably the last 7, 6, or 5 residues of a native PP family polypeptide, and more preferably amino acid residues 32-35.

In one embodiment, the PPF polypeptides of the invention do not include any unnatural amino acid resides, and further with the provisio that the PPF polypeptides of the invention do not include any native PPF polypeptides (e.g., PP, NPY(1-36), NPY(3-36), PYY(1-36), PYY(3-36), NPY(2-36), NPY(4-36), PYY(2-36), PYY(4-36), PP(3-36), or PP(4-36)). The PPF polypeptides of the invention also preferably do not include: Tyr$^1$hPP, Lys$^4$hPP, Asn$^7$hPP, Arg$^{19}$hPP, Tyr$^{21}$hPP, Glu$^{21}$hPP, Ala$^{23}$hPP, Gln$^{23}$hPP, Gln$^{34}$hPP, Phe$^6$Arg$^{19}$hPP, Phe$^6$Tyr$^{21}$hPP, Phe$^6$Glu$^2$hPP, Phe$^6$Ala$^{23}$hPP, Phe$^6$Gln$^{23}$hPP, Pro$^{13}$Ala$^{14}$hPP, Ile$^{31}$Gln$^{34}$PP, Arg$^{19}$Tyr$^{20}$Tyr$^{21}$Ser$^{22}$Ala$^{23}$hPP, Lys$^4$ Arg$^{19}$Tyr$^{20}$Tyr$^{21}$Ser$^{22}$Ala$^{23}$hPP, Lys$^4$Arg$^{19}$Tyr$^{20}$Tyr$^{21}$Ser 22Ala$^{23}$hPP(2-36), Ala$^1$NPY, Tyr$^1$NPY, Ala$^2$NPY, Leu$^2$ NPY, Phe$^2$NPY, His$^2$NPY, Ala$^3$NPY, Ala$^4$NPY, Ala$^6$NPY, Tyr$^7$pNPY, Ala$^7$NPY, Ala$^9$NPY, Ala$^{10}$NPY, Ala$^{11}$NPY, Gly$^{12}$NPY, Ala$^{13}$NPY, Gly$^{14}$NPY, Ala$^{15}$NPY, Ala$^{16}$NPY, Ala$^{17}$NPY, Gly$^{18}$NPY, Ala$^{19}$NPY, Lys$^{19}$NPY, Ala$^{20}$NPY, Ala$^{21}$NPY, Ala$^{22}$NPY, Gly$^{23}$NPY, Ala$^{24}$NPY, Trp$^{24}$pNPY, Ala$^{25}$NPY, Lys$^{25}$NPY, Ala$^{26}$NPY, Ala$^{27}$NPY, Phe$^{27}$NPY, Ala$^{28}$NPY, Ala$^{29}$NPY, Gln$^{29}$NPY, Ala$^{30}$NPY, Phe$^{30}$NPY, Ala$^{31}$NPY, Trp$^{31}$pNPY, Ala$^{32}$NPY, Trp$^{32}$NPY, Ala$^{33}$NPY, Lys$^{33}$NPY, Ala$^{34}$NPY, Pro$^{34}$NPY, Leu$^{34}$NPY, Ala$^{35}$NPY, Lys$^{35}$NPY, Ala$^{36}$NPY, Phe$^{36}$NPY, His$^{36}$NPY, Glu$^4$Pro$^{34}$pNPY, Arg$^6$Pro$^{34}$pNPY, Phe$^6$Pro$^{34}$pNPY, Cys$^6$Pro$^{34}$pNPY, Asn$^6$Pro$^{34}$pNPY, Phe$^7$Pro$^{34}$pNPY, Arg$^7$Pro$^{34}$pNPY, Cys$^7$Pro$^{34}$pNPY, Asp$^7$Pro$^{34}$ pNPY, Phe$^8$Pro$^{34}$ pNPY, Arg$^8$Pro$^{34}$pNPY, Cys$^8$Pro$^{34}$pNPY, Asp$^8$Pro$^{34}$pNPY, Asn$^8$Pro$^{34}$pNPY, Pro$^{11}$Pro$^{34}$pNPY, Ser$^{13}$Pro$^{14}$pNPY, Trp$^{24,31}$pNPY, Ala$^{31}$Pro$^{32}$pNPY, Cys$^{31}$Pro$^{34}$pNPY, Leu$^{31}$Pro$^{34}$NPY, Phe$^{32}$Pro$^{34}$pNPY, Ala$^{21,25}$Pro$^{34}$pNPY, Pro$^{11}$Tyr$^{13}$Pro$^{14}$Pro$^{34}$pNPY, Ahx(9-22)pNPY, Ahx(9-17) pNPY, des-AA(10-20)-Cys$^{7,21}$Pro$^{34}$-pNPY, des-AA(10-17)- pNPY, des-AA(10-17)-Cys$^{2,27}$-pNPY, des-AA(10-17)-Ala$^{7,21}$-pNPY, des-AA(10-17)-Cys$^{7,21}$-pNPY, des-AA(10-17)-Glu$^7$Lys$^{21}$-pNPY, des-AA(10-17)Cys$^{7,21}$ Pro$^{34}$pNPY, des-AA(10-17)Glu$^7$Lys$^{21}$Pro$^{34}$pNPY, des-AA(10-17) Cys$^{7,21}$Leu$^{31}$Pro$^{34}$pNPY, des-AA(11-17)Cys$^{7,21}$Pro$^{34}$pNPY, Pro$^{34}$PYY, His$^{34}$PYY, Lys$^{25}$hPYY(5-36), Arg$^4$hPYY(4-36), Gln$^4$hPYY(4-36), Asn$^4$hPYY(4-36), Lys$^{25}$hPYY(4-36), Leu$^3$hPYY(3-36), Val$^3$hPYY(3-36), Lys$^{25}$hPYY(3-36), Tyr$^{1,36}$pPYY, Pro$^{13}$Ala$^{14}$hPYY, Leu$^{31}$Pro$^{34}$PYY, FMS-PYY, FMS-PYY(3-36), Fmoc-PYY, Fmoc-PYY(3-36), FMS$_2$-PYY, FMS$_2$-PYY(3-36), Fmoc$_2$-PYY, Fmoc$_2$-PYY(3-36), hPP(1-7)-pNPY, hPP(1-17)-pNPY, hPP(19-23)-pNPY, hPP(19-23)-Pro$^{34}$pNPY, hPP(19-23)-His$^{34}$pNPY, rPP(19-23)-pNPY, rPP(19-23)-Pro$^{34}$pNPY, rPP(19-23)-His$^{34}$pNPY, hPP(1-7)-pNPY, hPP(1-17)-pNPY, hPP(1-17)-His$^{34}$pNPY, pNPY(1-7)-hPP, pNPY(1-7, 19-23-hPP, cPP(1-7)-pNPY(19-23)-hPP, cPP(1-7)-NPY(19-23)-His$^{34}$hPP, hPP(1-17)-His$^{34}$pNPY, hPP(19-23)-pNPY, hPP(19-23)-Pro$^{34}$pNPY, hPP(19-23)-His$^{34}$pNPY, rPP(19-23)-pNPY, rPP(19-23)-Pro$^{34}$pNPY, rPP(19-23)-His$^{34}$pNPY, pNPY(1-7)-hPP, pNPY(19-23)-hPP, pNPY(19-23)-Gln$^{34}$hPP, pNPY(19-23)-His$^{34}$hPP, pNPY(19-23)-Phe$^6$Gln$^{34}$hPP, pNPY(19-23)-Phe$^6$His$^{34}$hPP, pNPY(1-7, 19-23)-hPP, pNPY(1-7, 19-23)-Gln$^{34}$hPP, cPP(20-23)-Pro$^{34}$-pNPY, cPP(21-23)-Pro$^{34}$-pNPY, cPP(22-23)-Pro$^{34}$-pNPY, cPP(1-7)-Pro$^{34}$-pNPY, cPP(20-23)-Pro$^{34}$-pNPY, cPP(1-7,20-23)-Pro$^{34}$-pNPY, cPP(1-7)-pNPY(19-23)-hPP, cPP(1-7)-pNPY(19-23)-His$^{34}$hPP, or cPP(1-7)-gPP(19-23)-hPP.

In another embodiment, such PPF polypeptides of the invention also do not include: Thr$^{27}$hPYY(3-36), Ile$^{30}$hPYY(3-36), Ser$^{32}$hPYY(3-36), Lys$^{33}$hPYY(3-36), Asn$^{34}$hPYY(3-36), Lys$^{35}$hPYY(3-36), Thr$^{36}$hPYY(3-36), Lys$^{25}$Thr$^{27}$hPYY(3-36), Lys$^{25}$Ile$^{30}$hPYY(3-36), Lys$^{25}$Ser$^{32}$hPYY(3-36), Lys$^{25}$Lys$^{33}$hPYY(3-36), Lys$^{25}$Asn$^{24}$hPYY(3-36), Lys$^{25}$Lys$^{35}$hPYY(3-36), Lys$^{25}$Thr$^{36}$hPYY(3-36), Thr$^{27}$Ile$^{28}$hPYY(3-36), Thr$^{27}$Val$^{28}$hPYY(3-36), Thr$^{27}$Gln$^{29}$hPYY(3-36), Thr$^{27}$Ile$^{30}$hPYY(3-36), Thr$^{27}$Val$^{30}$hPYY(3-36), Thr$^{27}$Ile$^3$hPYY(3-36), Thr$^{27}$Leu$^{31}$hPYY(3-36), Thr$^{27}$Ser$^{32}$hPYY(3-36), Thr$^{27}$Lys$^{33}$hPYY(3-36), Thr$^{27}$Asn$^{34}$hPYY(3-36), Thr$^{27}$Lys$^{35}$hPYY(3-36), Thr$^{27}$Thr$^{36}$hPYY(3-36), Thr$^{27}$Phe$^{36}$hPYY(3-36), Phe$^{27}$Ile$^{30}$hPYY(3-36), Phe$^{27}$Ser$^{32}$hPYY(3-36), Phe$^{27}$Lys$^{33}$hPYY(3-36), Phe$^{27}$Asn$^{34}$hPYY(3-36), Phe$^{27}$Lys$^{35}$hPYY(3-36), Phe$^{27}$Thr$^{36}$hPYY(3-36), Gln$^{29}$Ile$^{30}$hPYY(3-36), Gln$^{29}$Ser$^{32}$hPYY(3-36), Gln$^{29}$Leu$^{33}$hPYY(3-36), Gln$^{29}$Asn$^{34}$hPYY(3-36), Gln$^{29}$Leu$^{35}$hPYY(3-36), Gln$^{29}$Thr$^{36}$hPYY(3-36), Ile$^{30}$Ile$^{31}$hPYY(3-36), Ile$^{30}$Leu$^{31}$hPYY(3-36), Ile$^{30}$Ser$^{32}$hPYY(3-36), Ile$^{30}$Lys$^{33}$hPYY(3-36), Ile$^{30}$Asn$^{34}$hPYY(3-36), Ile$^{30}$Lys$^{35}$hPYY(3-36), Ile$^{30}$Thr$^{36}$hPYY(3-36), Ile$^{30}$Phe$^{36}$hPYY(3-36), Val$^{30}$Ser$^{32}$hPYY(3-36), Val$^{30}$Lys$^{33}$hPYY(3-36), Val$^{30}$Asn$^{34}$hPYY(3-36), Val$^{30}$Lys$^{35}$hPYY(3-36), Val$^{30}$Thr$^{36}$hPYY(3-36), Ile$^{31}$Ser$^{32}$hPYY(3-36), Ile$^{31}$Lys$^{33}$hPYY(3-36), Ile$^{31}$Asn$^{34}$hPYY(3-36), Ile$^{31}$Lys$^{35}$hPYY(3-36), Ile$^{31}$Thr$^{36}$hPYY(3-36), Ile$^{31}$Phe$^{36}$hPYY(3-36), Leu$^{31}$Ser$^{32}$hPYY(3-36), Leu$^{31}$Lys$^{33}$hPYY(3-36), Leu$^{31}$Asn$^{34}$hPYY(3-36), Leu$^{31}$Lys$^{35}$hPYY(3-36), Leu$^{31}$Thr$^{36}$hPYY(3-36), Ser$^{32}$Lys$^{33}$hPYY(3-36), Ser$^{32}$Asn$^{34}$hPYY(3-36), Ser$^{32}$Lys$^{35}$hPYY(3-36), Ser$^{32}$Thr$^{36}$hPYY(3-36), Ser$^{32}$Phe$^{36}$hPYY(3-36), Lys$^{33}$Asn$^{34}$hPYY(3-36), Lys$^{33}$Thr$^{36}$hPYY(3-36), Lys$^{33}$Phe$^{36}$hPYY(3-36), Asn$^{34}$Lys$^{35}$hPYY(3-36), Asn$^{34}$Phe$^{36}$hPYY(3-36), Lys$^{35}$Thr$^{36}$hPYY(3-36), Lys$^{35}$Phe$^{36}$hPYY(3-36), Thr$^{27}$hPYY(4-36), Phe$^{27}$hPYY(4-36), Ile$^{28}$hPYY(4-36), Val$^{28}$hPYY(4-36), Gln$^{29}$hPYY(4-36), Ile$^{30}$hPYY(4-36), Val$^{30}$hPYY(4-36), Ile$^{31}$hPYY(4-36), Leu$^{31}$hPYY(4-36), Ser$^{32}$hPYY(4-36), Lys$^{33}$hPYY(4-36), Asn$^{34}$hPYY(4-36), Lys$^{35}$hPYY(4-36), Thr$^{36}$hPYY(4-36), Phe$^{36}$hPYY(4-36), Lys$^{25}$Thr$^{27}$hPYY(4-36), Lys$^{25}$Phe$^{27}$hPYY(4-36), Lys$^{25}$Ile$^{28}$hPYY(4-36), Lys$^{25}$Val$^{28}$hPYY(4-36), Lys$^{25}$Gln$^{29}$hPYY(4-36), Lys$^{25}$Ile$^{30}$hPYY(4-36), Lys$^{25}$Val$^{30}$hPYY(4-36), Lys$^{25}$Ile$^{31}$hPYY(4-36), Lys$^{25}$Leu$^{31}$hPYY(4-36), Lys$^{25}$Ser$^{32}$hPYY(4-36), Lys$^{25}$Lys$^{33}$hPYY(4-36), Lys$^{25}$Asn 24hPYY(4-36), Lys$^{25}$Lys$^{35}$hPYY(4-36), Lys$^{25}$Thr$^{36}$hPYY(4-36), Lys$^{25}$Phe$^{36}$hPYY(4-36), Thr$^{27}$Ile$^{28}$hPYY(4-36), Thr$^{27}$Val$^{28}$hPYY(4-36), Thr$^{27}$Gln$^{29}$hPYY(4-36), Thr$^{27}$Ile$^{30}$hPYY(4-36), Thr$^{27}$Val$^{31}$hPYY(4-36), Thr$^{27}$Ile$^{31}$hPYY(4-36), Thr$^{27}$Leu$^{31}$hPYY(4-36), Thr$^{27}$Ser$^{32}$hPYY(4-36), Thr$^{27}$Lys$^{33}$hPYY(4-36), Thr$^{27}$Asn$^{34}$hPYY(4-36), Thr$^{27}$Lys$^{35}$hPYY(4-36), Thr$^{27}$Thr$^{36}$hPYY(4-36), Thr$^{27}$Phe$^{36}$hPYY(4-36), Phe$^{27}$Ile$^{28}$hPYY(4-36), Phe 27Val$^{28}$hPYY(4-36), Phe$^{27}$Gln$^{29}$hPYY(4-36), Phe$^{27}$Ile$^{30}$hPYY(4-36), Phe$^{27}$Val$^{30}$hPYY(4-36), Phe$^{27}$Ile$^{31}$hPYY(4-36), Phe$^{27}$Leu$^{31}$hPYY(4-36), Phe$^{27}$Ser$^{32}$hPYY(4-36), Phe$^{27}$Lys$^{33}$hPYY(4-36), Phe$^{27}$Asn$^{34}$hPYY(4-36), Phe$^{27}$Lys$^{35}$hPYY(4-36), Phe$^{27}$Thr$^{36}$hPYY(4-36), Phe$^{27}$Phe$^{36}$hPYY(4-36), Gln$^{29}$Ile$^{30}$hPYY(4-36), Gln$^{29}$Val$^{30}$hPYY(4-36), Gln$^{29}$Ile$^{31}$hPYY(4-36), Gln$^{29}$Leu$^{31}$hPYY(4-36), Gln$^{29}$Ser$^{32}$hPYY(4-36) Gln$^{29}$Leu$^{33}$hPYY(4-36), Gln$^{29}$Asn$^{34}$hPYY(4-36), Gln$^{29}$Leu$^{35}$hPYY(4-36), Gln$^{29}$Thr$^{36}$hPYY(4-36), Gln$^{29}$Phe$^{36}$hPYY(4-36), Ile$^{30}$Ile$^{31}$hPYY(4-36), Ile$^{31}$Leu$^{31}$hPYY(4-36), Ile$^{30}$Ser$^{32}$hPYY(4-36), Ile$^{30}$Lys$^{33}$hPYY(4-36), Ile$^{30}$Asn$^{34}$hPYY(4-36), Ile$^{30}$Lys$^{35}$hPYY(4-36), Ile$^{30}$Thr$^{36}$hPYY(4-36), Ile$^{30}$Phe$^{36}$hPYY(4-36), Val$^{30}$Ile$^{31}$hPYY(4-36), Val$^{30}$Leu$^{31}$hPYY(4-36), Val$^{30}$Ser$^{32}$hPYY(4-36), Val$^{30}$Lys$^{33}$hPYY(4-36), Val$^{30}$Asn$^{34}$hPYY(4-36), Val$^{30}$Lys$^{35}$hPYY(4-36), Val$^{30}$Thr$^{36}$hPYY(4-36), Val$^{30}$Phe$^{36}$hPYY(4-36), Ile$^{31}$Ser$^{32}$hPYY(4-36), Ile$^{31}$Lys$^{33}$hPYY(4-36), Ile$^{31}$Asn$^{34}$hPYY(4-36), Ile$^{31}$Lys$^{35}$hPYY(4-36), Ile$^{31}$Thr$^{36}$hPYY(4-36), Leu$^{31}$Phe$^{36}$hPYY(4-36), Leu$^{31}$Phe$^{36}$hPYY(4-36), Leu$^{31}$Ser$^{32}$hPYY(4-36), Val$^{31}$Lys$^{33}$hPYY(4-36), Leu$^{31}$Asn$^{34}$hPYY(4-36), Leu$^{31}$Lys$^{35}$hPYY(4-36), Leu$^{31}$Thr$^{36}$hPYY(4-36), Leu$^{31}$Phe$^{36}$hPYY(4-36), Ser$^{32}$Lys$^{33}$hPYY(4-36), Ser$^{32}$Asn$^{34}$hPYY(4-36), Ser$^{32}$Lys$^{35}$hPYY(4-36), Ser$^{32}$Thr$^{36}$hPYY(4-36), Ser$^{32}$Phe$^{36}$hPYY(4-36), Lys$^{33}$Asn$^{34}$hPYY(4-36), Lys$^{33}$Lys$^{35}$hPYY(4-36), Lys$^{33}$Thr$^{36}$hPYY(4-36), Lys$^{33}$Phe$^{36}$hPYY(4-36), Asn$^{34}$Lys$^{35}$hPYY(4-36), Asn$^{34}$Phe$^{36}$hPYY(4-36), Lys$^{35}$Thr$^{36}$hPYY(4-36), Lys$^{35}$Phe$^{36}$hPYY(4-36), Thr$^{27}$hPYY(5-36), Phe$^{27}$hPYY(5-36), Ile$^{28}$hPYY(5-36), Val$^{28}$hPYY(5-36), Gln$^{29}$hPYY(5-36), Ile$^{30}$hPYY(5-36), Val$^{30}$hPYY(5-36), Ile$^{31}$hPYY(5-36), Leu$^{31}$hPYY(5-36), Ser$^{32}$hPYY(5-36), Lys$^{33}$hPYY(5-36), Asn$^{34}$hPYY(5-36), Lys$^{35}$hPYY(5-36), Thr$^{36}$hPYY(5-36), Phe$^{36}$hPYY(5-36), Lys$^{25}$Thr$^{27}$hPYY(5-36), Lys$^{25}$Phe$^{27}$hPYY(5-36), Lys$^{25}$Ile$^{28}$hPYY(5-36), Lys$^{25}$Val$^{28}$hPYY(5-36), Lys$^{25}$Gln$^{29}$hPYY(5-36), Lys$^{25}$Ile$^{30}$hPYY(5-36), Lys$^{25}$Val$^{30}$hPYY(5-36), Lys$^{25}$Ile$^{31}$hPYY(5-36), Lys$^{25}$Leu$^{31}$hPYY(5-36), Lys$^{25}$Ser$^{32}$hPYY(5-36), Lys$^{25}$Lys$^{33}$hPYY(5-36), Lys$^{25}$Asn$^{24}$hPYY(5-36), Lys$^{25}$Lys$^{35}$hPYY(5-36), Lys$^{25}$Thr$^{36}$hPYY(5-36), Lys$^{25}$Phe$^{36}$hPYY(5-36), Thr$^{17}$Ile$^{28}$hPYY(5-36), Thr$^{27}$Val$^{28}$hPYY(5-36), Thr$^{27}$Gln$^{29}$hPYY(5-36), Thr$^{27}$Ile$^{30}$hPYY(5-36), Thr$^{27}$Val$^{30}$hPYY(5-36), Thr$^{27}$Ile$^{31}$hPYY(5-36), Thr$^{27}$Leu$^{31}$hPYY(5-36), Thr$^{27}$Ser$^{32}$hPYY(5-36), Thr²⁷Lys³³hPYY(5-36), Thr²⁷Asn³⁴hPYY(5-36), Thr²⁷Lys³⁵hPYY(5-36), Thr²⁷Thr³⁶hPYY(5-36), Thr²⁷Phe³⁶hPYY(5-36), Phe²⁷Ile²⁸hPYY(5-36), Phe²⁷Val²⁸hPYY(5-36), Phe²⁷Gln²⁹hPYY(5-36), Phe²⁷Ile³⁰hPYY(5-36), Phe²⁷Val³⁰hPYY(5-36), Phe²⁷Ile³¹hPYY(5-36), Phe²⁷Leu³¹hPYY(5-36), Phe²⁷Ser³²hPYY(5-36), Phe²⁷Lys³³hPYY(5-36), Phe²⁷Asn³⁴hPYY(5-36), Phe²⁷Lys³⁵hPYY(5-36), Phe²⁷Thr³⁶hPYY(5-36), Phe²⁷Phe³⁶hPYY(5-36), Gln²⁹Ile³⁰hPYY(5-36), Gln²⁹Val³⁰hPYY(5-36), Gln²⁹Ile³¹hPYY(5-36), Gln²⁹Leu³¹hPYY(5-36), Gln²⁹Ser³²hPYY(5-36) Gln²⁹Leu³³hPYY(5-36), Gln²⁹Asn³⁴hPYY(5-36), Gln²⁹Leu³⁵hPYY(5-36), Gln²⁹Thr³⁶hPYY(5-36), Gln²⁹Phe³⁶hPYY(5-36), Ile³⁰Ile³¹hPYY(5-36), Ile³⁰Leu³¹hPYY(5-36), Ile³⁰Ser³²hPYY(5-36), Ile³⁰Lys³³hPYY(5-36), Ile³⁰Asn³⁴hPYY(5-36), Ile³⁰Lys³⁵hPYY(5-36), Ile³⁰Thr³⁶hPYY(5-36), Ile³⁰Phe³⁶hPYY(5-36), Val³⁰Ile³¹hPYY(5-36), Val³⁰Leu³¹hPYY(5-36), Val³⁰Ser³²hPYY(5-36), Val³⁰Lys³³hPYY(5-36), Val³⁰Asn³⁴hPYY(5-36), Val³⁰Lys³⁵hPYY(5-36), Val³⁰Thr³⁶hPYY(5-36), Val³⁰Phe³⁶hPYY(5-36), Ile³¹Ser³²hPYY(5-36), Ile³¹Lys³³hPYY(5-36), Ile³¹Asn³⁴hPYY(5-36), Ile³¹Lys³⁵hPYY(5-36), Ile³¹Thr³⁶hPYY(5-36), Leu³¹Phe³⁶hPYY(5-36), Leu³¹Phe³⁶hPYY(5-36), Leu³¹Ser³²hPYY(5-36), Val³¹Lys³³hPYY(5-36), Leu³¹Asn³⁴hPYY(5-36), Leu³¹Lys³⁵hPYY(5-36), Leu³¹Thr³⁶hPYY(5-36), Leu³¹Phe³⁶hPYY(5-36), Ser³²Lys³³hPYY(5-36), Ser³²Asn³⁴hPYY(5-36), Ser³²Lys³⁵hPYY(5-36), Ser³²Thr³⁶hPYY(5-36), Ser³²Phe³⁶hPYY(5-36), Lys³³Asn³⁴hPYY(5-36), Lys³³Lys³⁵hPYY(5-36), Lys³³Thr³⁶hPYY(5-36), Lys³³Phe³⁶hPYY(5-36), Asn³⁴Lys³⁵hPYY(5-36), Asn³⁴Phe³⁶hPYY(5-36), Lys³⁵Thr³⁶hPYY(5-36), or Lys³⁵Phe³⁶hPYY(5-36).

In another embodiment, the PPF polypeptides of the invention do not include any unnatural amino acid residues, and preferably comprise a C-terminal tail motif of hPYY. The C-terminal tail motif may preferably comprise amino acid residues 32-35 of hPYY, e.g., Thr, Arg, Gln, Arg (SEQ ID NO: 351). In such an embodiment, the PPF polypeptides of the invention do not include any native PPF polypeptides (e.g., NPY(1-36), NPY(3-36), PYY(1-36), PYY(3-36)), NPY(2-36), PYY(4-36), PYY(5-36)), (2-36)NPY, (2-36) PYY, Gln³⁴hPP, Ile³¹Gln³⁴PP, Ala¹NPY, Tyr¹NPY, Ala²NPY, Leu²NPY, Phe²NPY, His²NPY, Ala³NPY, Ala⁴NPY, Ala⁶NPY, Tyr⁷pNPY, Ala⁷NPY, Ala⁹NPY, Ala¹⁰NPY, Ala¹¹NPY, Gly¹²NPY, Ala¹³NPY, Gly¹⁴NPY, Ala¹⁵NPY, Ala¹⁶NPY, Ala¹⁷NPY, Gly¹⁸NPY Ala¹⁹NPY, Lys¹⁹NPY, Ala²⁰NPY, Ala²¹NPY, Ala²²NPY, Gly²³NPY, Ala²⁴NPY Trp²⁴pNPY, Ala²⁵NPY, Lys²⁵NPY, Ala²⁶NPY, Ala²⁷NPY, Phe²⁷NPY, Ala²⁸NPY, Ala²⁹NPY, Gln²⁹NPY, Ala³⁰NPY, Phe³⁰NPY, Ala³¹NPY, Trp³¹pNPY, Ala³⁶NPY, Phe³⁶NPY, His³⁶NPY, Ahx(9-22)pNPY, Ahx(9-17)pNPY, des-AA(10-17)-pNPY, des-AA(10-17)-Cys²,²⁷-pNPY des-AA(10-17)-Ala⁷,²¹-pNPY, des-AA(10-17)-Cys⁷,²¹-pNPY, des-AA(10-17)-Glu⁷Lys²¹-pNPY, Lys²⁵hPYY(5-36), Arg⁴hPYY(4-36), Gln⁴hPYY(4-36), Asn⁴hPYY(4-36), Lys²⁵hPYY(4-36), Leu³hPYY(3-36), Val³ hPYY(3-36), Lys²⁵hPYY(3-36), Tyr¹,³⁶pPYY, Pro¹³Ala¹⁴hPYY, FMS-PYY, FMS-PYY(3-36), Fmoc-PYY, Fmoc-PYY(3-36), FMS₂-PYY, FMS₂-PYY(3-36), Fmoc₂-PYY, Fmoc₂-PYY(3-36), hPP(1-7)-pNPY, hPP(1-17)-pNPY, hPP(19-23)-pNPY, rPP(19-23)-pNPY, hPP(1-7)-pNPY, hPP(1-17)-pNPY, hPP(19-23)-pNPY, rPP(19-23)-pNPY, pNPY(19-23)-Gln³⁴hPP, pNPY(19-23)-Phe⁶Gln³⁴hPP, or pNPY(1-7,19-23)-Gln³⁴hPP.

In another aspect, such PPF polypeptides of the invention comprising a C-terminal tail motif of hPYY also do not include: Thr²⁷hPYY(3-36), Ile³⁰hPYY(3-36), Thr³⁶hPYY(3-36), Lys²⁵Thr²⁷hPYY(3-36), Lys²⁵Ile³⁰hPYY(3-36), Lys²⁵Asn²⁴hPYY(3-36), Lys²⁵Thr³⁶hPYY(3-36), Thr²⁷Ile²⁸hPYY(3-36), Thr²⁷Val²⁸hPYY(3-36), Thr²⁷Gln²⁹hPYY(3-36), Thr²⁷Ile³⁰hPYY(3-36), Thr²⁷Val³⁰hPYY(3-36), Thr²⁷Ile³¹hPYY(3-36), Thr²⁷Leu³²hPYY(3-36), Thr²⁷Thr³⁶hPYY(3-36), Thr²⁷Phe³⁶hPYY(3-36), Phe²⁷Ile³⁰hPYY(3-36), Phe²⁷Thr³⁶hPYY(3-36), Gln²⁹Ile³⁰hPYY(3-36), Gln²⁹Thr³⁶hPYY(3-36), Ile³⁰Ile³¹hPYY(3-36), Ile³⁰Leu³¹hPYY(3-36), Ile³⁰Thr³⁶ hPYY(3-36), Ile³⁰Phe³⁶hPYY(3-36), Val³⁰Thr³⁶hPYY(3-36), Ile³¹Thr³⁶hPYY(3-36), Ile³¹Phe³⁶hPYY(3-36), Leu³¹Thr³⁶hPYY(3-36), Thr²⁷hPYY(4-36), Phe²⁷hPYY(4-36), Ile²⁸hPYY(4-36), Val²⁸hPYY(4-36), Gln²⁹hPYY(4-36), Ile³⁰hPYY(4-36), Val³⁰hPYY(4-36), Ile³¹hPYY(4-36), Leu³¹hPYY(4-36), Thr³⁶hPYY(4-36), Phe³⁶hPYY(4-36), Lys²⁵Thr²⁷hPYY(4-36), Lys²⁵Phe²⁷hPYY(4-36), Lys²⁵Ile²⁸hPYY(4-36), Lys²⁵Val²⁸hPYY(4-36), Lys²⁵Gln²⁹hPYY(4-36), Lys²⁵Ile³⁰hPYY(4-36), Lys²⁵Val³⁰hPYY(4-36), Lys²⁵Ile³¹hPYY(4-36), Lys²⁵Leu³¹hPYY(4-36), Lys²⁵Thr³⁶hPYY(4-36), Lys²⁵Phe³⁶hPYY(4-36), Thr²⁷Ile²⁸hPYY(4-36), Thr²⁷Val²⁸hPYY(4-36), Thr²⁷Gln²⁹hPYY(4-36), Thr²⁷Ile³⁰hPYY(4-36), Thr²⁷Val³⁰hPYY(4-36), Thr²⁷Ile³¹hPYY(4-36), Thr²⁷Leu³¹hPYY(4-36), Thr²⁷Thr³⁶hPYY(4-36), Thr²⁷Phe³⁶hPYY(4-36), Phe²⁷Ile²⁸hPYY(4-36), Phe²⁷Val²⁸hPYY(4-36), Phe²⁷Gln²⁹hPYY(4-36), Phe²⁷Ile³⁰hPYY(4-36), Phe²⁷Val³⁰hPYY(4-36), Phe²⁷Ile³¹hPYY(4-36), Phe²⁷Leu³¹hPYY(4-36), Phe²⁷Thr³⁶hPYY(4-36), Phe²⁷Phe³⁶hPYY(4-36), Gln²⁹Ile³⁰hPYY(4-36), Gln²⁹Val³⁰hPYY(4-36), Gln²⁹Ile³¹hPYY(4-36), Gln²⁹Leu³¹hPYY(4-36), Gln²⁹Thr³⁶hPYY(4-36), Gln²⁹Phe³⁶hPYY(4-36), Ile³⁰Ile³¹hPYY(4-36), Ile³⁰Leu³¹hPYY(4-36), Ile³⁰Thr³⁶hPYY(4-36), Ile³⁰Phe³⁶hPYY(4-36), Val³⁰Ile³¹hPYY(4-36), Val³⁰Leu³¹hPYY(4-36), Val³⁰Thr³⁶hPYY(4-36), Val³⁰Phe³⁶hPYY(4-36), Ile³¹Thr³⁶hPYY(4-36), Leu³¹Phe³⁶hPYY(4-36), Leu³¹Thr³⁶hPYY(4-36), Leu³¹Phe³⁶hPYY(4-36), Thr²⁷hPYY(5-36), Phe²⁷hPYY(5-36), Ile²⁸hPYY(5-36), Val²⁸hPYY(5-36), Gln²⁹hPYY(5-36), Ile³⁰hPYY(5-36), Val³⁰hPYY(5-36), Ile³¹hPYY(5-36), Leu³¹hPYY(5-36), Thr³⁶hPYY(5-36), Phe³⁶hPYY(5-36), Lys²⁵Thr²⁷hPYY(5-36), Lys²⁵Phe²⁷hPYY(5-36), Lys²⁵Ile²⁸hPYY(5-36), Lys²⁵Val²⁸hPYY(5-36), Lys²⁵Gln²⁹hPYY(5-36), Lys²⁵Ile³⁰hPYY(5-36), Lys²⁵Val³⁰hPYY(5-36), Lys²⁵Ile³¹hPYY(5-36), Lys²⁵Leu³¹hPYY(5-36), Lys²⁵Thr³⁶hPYY(5-36), Lys²⁵Phe³⁶hPYY(5-36), Thr²⁷Ile²⁸hPYY(5-36), Thr²⁷Val²⁸hPYY(5-36), Thr²⁷Gln²⁹hPYY(5-36), Thr²⁷Ile³⁰hPYY(5-36), Thr²⁷Val³⁰hPYY(5-36), Thr²⁷Ile³¹hPYY(5-36), Thr²⁷Leu³¹hPYY(5-36), Thr²⁷Thr³⁶hPYY(5-36), Thr²⁷Phe³⁶hPYY(5-36), Phe²⁷Ile²⁸hPYY(5-36), Phe²⁷Val²⁸hPYY(5-36), Phe²⁷Gln²⁹hPYY(5-36), Phe²⁷Ile³⁰hPYY(5-36), Phe²⁷Val³⁰hPYY(5-36), Phe²⁷Ile³¹hPYY(5-36), Phe²⁷Leu³¹hPYY(5-36), Phe²⁷Thr³⁶hPYY(5-36), Phe²⁷Phe³⁶hPYY(5-36), Gln²⁹Ile³⁰hPYY(5-36), Gln²⁹Val³⁰hPYY(5-36), Gln²⁹Ile³¹hPYY(5-36), Gln²⁹Leu³¹hPYY(5-36), Gln²⁹Thr³⁶hPYY(5-36), Gln²⁹Phe³⁶hPYY(5-36), Ile³⁰Ile³¹hPYY(5-36), Ile³⁰Leu³¹hPYY(5-36), Ile³⁰Thr³⁶hPYY(5-36), Ile³⁰Phe³⁶hPYY(5-36), Val³⁰Ile³¹hPYY(5-36), Val³⁰Leu³¹hPYY(5-36), Val³⁰Thr³⁶hPYY(5-36), Val³⁰Phe³⁶hPYY(5-36), Ile³¹Thr³⁶hPYY(5-36), Leu³¹Phe³⁶hPYY(5-36),
Leu³¹Phe³⁶hPYY(5-36), Leu³¹Thr³⁶hPYY(5-36),
Leu³¹Phe³⁶hPYY(5-36).

In yet another embodiment, the PPF polypeptides of the invention do not include those PPF-related polypeptides disclosed in WO 03/026591 and WO 03/057235, which are herein incorporated by reference in their entirety.

In another embodiment, the polypeptides of the invention are at least 34 amino acids in length. In other embodiments, the PPF polypeptides may be at least 21, 22, 23, 24, 25, 26, 27, 28, 29, 30, 31, 32, or 33 amino acids in length. Further, in one embodiment, the polypeptides of the invention include only natural L amino acid residues and/or modified natural L amino acid residues. Alternatively, in another embodiment, the polypeptides of the invention do not include unnatural amino acid residues.

In yet another embodiment, PPF polypeptides of the invention may exhibit at least 60%, 65%, 70%, 80%, or 90% sequence identity to a native PYY(3-36) over the entire length of the PYY(3-36). Such PPF polypeptides of the invention may also exhibit at least 50%, 60%, 65%, 70%, 80%, or 90% sequence identity to a native PP. In yet another embodiment, such PPF polypeptides of the invention may exhibit at least 50%, 60%, 65%, 70%, 80%, or 90% sequence identity to a native NPY.

More specifically, in a first aspect, the present invention relates to novel PPF polypeptides comprising at least two PPF motifs, wherein the at least two PPF motifs include at least the N-terminal polyproline PPF motif and the C-terminal tail PPF motif, and the PPF polypeptide does not include any unnatural amino acid residues. Such PPF polypeptides of the invention will exhibit at least 50% sequence identity to a native PYY(3-36) over the entire length of the PYY(3-36). In a preferred embodiment, such PPF polypeptides have at least 34 amino acid residues. In another preferred embodiment, such PPF polypeptides of the invention may exhibit at least 60%, 65%, 70%, 80%, or 90% sequence identity to a native PYY(3-36) over the entire length of the PYY(3-36). Such PPF polypeptides of the invention may also exhibit at least 50%, 60%, 65%, 70%, 80%, or 90% sequence identity to a native PP. In yet another embodiment, such PPF polypeptides of the invention may exhibit at least 50%, 60%, 65%, 70%, 80%, or 90% sequence identity to a native NPY.

In another aspect, the PPF polypeptides of the invention include PYY analog polypeptides. In yet another aspect of the invention, the PPF polypeptides of the invention include PPF chimeric polypeptides comprising a fragment of a PP, PYY or NPY polypeptide covalently linked to at least one additional fragment of a PP, PYY or NPY polypeptide, wherein each PP, PYY or NPY fragment includes a PPF motif. Such PPF analog polypeptides and PPF chimeric polypeptides of the invention will exhibit at least 50% sequence identity to a native PYY(3-36) over the entire length of the PYY(3-36). In a preferred embodiment, such PPF polypeptides of the invention may exhibit at least 60%, 65%, 70%, 80%, or 90% sequence identity to a native PYY(3-36) over the entire length of the PYY(3-36). PPF polypeptides of the invention may also exhibit at least 50%, 60%, 65%, 70%, 80%, or 90% sequence identity to a native PP. In yet another embodiment, PPF polypeptides of the invention may exhibit at least 50%, 60%, 65%, 70%, 80%, or 90% sequence identity to a native NPY. In certain embodiments, desirable PPF polypeptides may not include N-terminal PP fragments in combination with C-terminal NPY fragments.

By way of background, PYY, NPY, and PP constitute a family of C-terminally amidated peptides involved in the regulation of gastrointestinal function, blood pressure, and feeding behavior. Without intending to be limited by theory, the ability of these peptides to selectively bind and activate Y receptor subtypes is believed to depend strongly on a stable solution structure, including the so-called "PP-fold". Table 1 (below) shows PP family ligand potencies at the known receptors and the rank order of potencies of various ligands.

TABLE 1

Summary of receptor pharmacology for the PP family of receptors

| RECEPTORS | PHARMACOLOGY | REFERENCE |
|---|---|---|
| Food Intake Inhibition (peripheral) | PYY(3-36) ≥ PYY >> NPY, NPY(3-36), PP, Ac-PYY(22-36) | |
| Gastric Emptying | PYY(3-36) ≥ PYY >> NPY, NPY(3-36), PP, Ac-PYY(22-36) | |
| Food Intake Stimulation (central) | PYY ≥ PYY(3-36) = NPY = NPY(3-36) > PP | Iyengar et al., J. Pharmacol. Exp. Ther. 289: 1031-40, 1999 |
| Y1 | NPY = PYY > NPY(3-36) = PYY(3-36) = PP | Iyengar et al., J. Pharmacol. Exp. Ther. 289: 1031-40, 1999; Gehlert, Proc. Soc. Exp. Biol. Med. 218: 7-22, 1998; Michel et al., Pharmacol. Rev. 50: 143-50, 1998; U.S. Pat. No. 5,968,819 |
| Y2 | NPY = PYY = PYY(3-36) = NPY(3-36) >> PP | Iyengar et al., J. Pharmacol. Exp. Ther. 289: 1031-40, 1999; Gehlert, Proc. Soc. Exp. Biol. Med. 218: 7-22, 1998; Michel et al., Pharmacol. Rev. 50: 143-50, 1998; U.S. Pat. No. 5,968,819 |
| Y3 | NPY > PP > PYY | Gehlert, Proc. Soc. Exp. Biol. Med. 218: 7-22, 1998; Michel et al., Pharmacol. Rev. 50: 143-50, 1998. |
| Y4 | PP > PYY > NPY > PYY(3-36) = NPY(3-36) | Iyengar et al., J. Pharmacol. Exp. Ther. 289: 1031-40, 1999; Gehlert, Proc. Soc. Exp. Biol. Med. 218: 7-22, 1998; Michel et al., Pharmacol. Rev. 50: 143-50, 1998; U.S. Pat. No. 5,968,819 |
| Y5 | NPY = PYY ≥ PP ≥ PYY(3-36) = NPY(3-36) | Iyengar et al., J. Pharmacol. Exp. Ther. 289: 1031-40, 1999; Gehlert, Proc. Soc. Exp. Biol. Med. 218: 7-22, 1998; Michel et al., Pharmacol. Rev. 50: 143-50, 1998; U.S. Pat. No. 5,968,819 |

TABLE 1-continued

Summary of receptor pharmacology for the PP family of receptors

| RECEPTORS | PHARMACOLOGY | REFERENCE |
|---|---|---|
| Y6 | NPY = PYY ≥ NPY(3-36) > PP | Iyengar et al., J. Pharmacol. Exp. Ther. 289: 1031-40, 1999; Gehlert, Proc. Soc. Exp. Biol. Med. 218: 7-22, 1998; Michel et al., Pharmacol. Rev. 50: 143-50, 1998; U.S. Pat. No. 5,968,819 |
| (Y7) | PYY > NPY >> PYY(3-36) = PP | Yang et al., Br. J. Pharmacol. 123: 1549-54, 1998 |
| (Y7) | PYY(3-36) ≥ PYY > NPY >> PP | Haynes et al., Br. J. Pharmacol. 122: 1530-6, 1997 |
| (Y7) | PYY >> NPY = PYY(3-36) = PP | Kawakubo et al., Brain Res. 854: 30-4, 2000 |

Research has suggested that the differences in Y receptor binding affinities are correlated with secondary and tertiary structural differences. See, e.g., Keire et al., *Biochemistry* 2000, 39, 9935-9942. Native porcine PYY has been characterized as including two C-terminal helical segments from residues 17 to 22 and 25 to 33 separated by a kink at residues 23, 24, and 25, a turn centered around residues 12-14, and the N-terminus folded near residues 30 and 31. Further, full-length porcine PYY has been characterized as including the PP fold, stabilized by hydrophobic interactions among residues in the N- and C-termini. See id.

By "PP" is meant a pancreatic peptide polypeptide obtained or derived from any species. Thus, the term "PP" includes both the human full length, 36 amino acid peptide as set forth in SEQ ID NO: 1, and species variations of PP, including, e.g., murine, hamster, chicken, bovine, rat, and dog PP. In this sense, "PP," "wild-type PP," and "native PP," i.e., unmodified PP, are used interchangeably.

By "NPY" is meant a neuropeptide Y polypeptide obtained or derived from any species. Thus, the term "NPY" includes both the human full length, 36 amino acid peptide as set forth in SEQ ID NO: 4, and species variations of NPY, including, e.g., murine, hamster, chicken, bovine, rat, and dog NPY. In this sense, "NPY," "wild-type NPY," and "native NPY", i.e., unmodified NPY, are used interchangeably.

By "PYY" is meant a peptide YY polypeptide obtained or derived from any species. Thus, the term "PYY" includes both the human full length, 36 amino acid peptide as set forth in SEQ ID NO: 2, and species variations of PYY, including e.g., murine, hamster, chicken, bovine, rat, and dog PYY. In this sense, "PYY" and "wild-type PYY" and "native PYY," i.e., unmodified PYY, are used interchangeably. In the context of the present invention, all modifications discussed with reference to the PYY analog polypeptides of the present invention are based on the 36 amino acid sequence of native human PYY (SEQ ID NO: 2).

By "PP agonist", "PYY agonist", or "NPY agonist" is meant a compound which elicits a biological activity of native human PP, PYY, or NPY, respectively. In a preferred embodiment, the terms refer to a compound which elicits a biological effect in the reduction of nutrient availability similar to that of native human PP, PYY, or NPY, for example a compound (1) having activity in the food intake, gastric emptying, pancreatic secretion, or weight loss assays similar to native human PP, PYY, or NPY, and (2) which binds specifically in a Y receptor assay or in a competitive binding assay with labeled PP, PYY, PYY(3-36), or NPY from certain tissues having an abundance of Y receptors, including, e.g., area postrema. In a preferred embodiment, the agonist is not PP, PYY, PYY(3-36), and/or NPY. Preferably, the agonists will bind in such assays with an affinity of greater than 1 μM, and more preferably with an affinity of greater than 1-5 nM. Such agonists may comprise a polypeptide having a PPF motif, an active fragment of PP, PYY, or NPY, or a small chemical molecule.

By "amino acid" and "amino acid residue" is meant natural amino acids, unnatural amino acids, and modified amino acid. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to homolysine, homoarginine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid, thioproline, sarcosine and citrulline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine. Additional residues that can be incorporated are described in Sandberg et al., *J. Med. Chem.* 41: 2481-91, 1998.

By "Ahx" is meant 6-amino hexanoic acid.

Certain human sequences of peptides in the PPF are as follows (in conventional one-letter amino acid code):

```
                                            (SEQ ID NO: 1)
PP:          APLEPVYPGD NATPEQMAQY AADLRRYINM LTRPRY (SEQ ID NO: 2)
PYY:         YPIKPEAPGE DASPEELNRY YASLRHYLNL VTRQRY (SEQ ID NO: 3)
PYY(3-36):     IKPEAPGE DASPEELNRY YASLRHYLNL VTRQRY (SEQ ID NO: 4)
NPY:         YPSKPDNPGE DAPAEDMARY YSALRHYINL ITRQRY
```

Species homologs of human PYY include those amino acid sequences of SEQ ID NOs. 7-29.

As mentioned above, these peptides are C-terminally amidated when expressed physiologically, but need not be for the purposes of the instant invention. In other words, the C-terminus of these peptides, as well as the PPF polypeptides of the present invention, may have a free —OH or —NH$_2$ group. These peptides may also have other post-translational modifications. One skilled in the art will appreciate that the PPF polypeptides of the present invention may also be constructed with an N-terminal methionine residue.

Preferred PPF polypeptides of the invention include the PPF polypeptides of the Formula (I) (SEQ ID NO: 30):

$Xaa_1$ $Xaa_2$ $Xaa_3$ $Xaa_4$ Pro $Xaa_6$ $Xaa_7$ Pro $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ Tyr $Xaa_{21}$ $Xaa_{22}$ $Xaa_{23}$ Leu $Xaa_{25}$ $Xaa_{26}$ $Xaa_{27}$ $Xaa_{28}$ $Xaa_{29}$ $Xaa_{30}$ $Xaa_{31}$ Thr Arg Gln Arg $Xaa_{36}$ wherein:
$Xaa_1$ is Tyr, Ala, Phe, Trp, or absent;
$Xaa_2$ is Pro, Gly, d-Ala, homoPro, hydroxyPro, or absent;
$Xaa_3$ is Ile, Ala, NorVal, Val, Leu, Pro, Ser, Thr or absent;
$Xaa_4$ is Lys, Ala, Gly, Arg, d-Ala, homoLys, homo-Arg, Glu, Asp, or absent;
$Xaa_6$ is Glu, Ala, Val, Asp, Asn, or Gln;
$Xaa_7$ is Ala, Asn, His, Ser, or Tyr;
$Xaa_9$ is Gly, Ala Ser, sarcosine, Pro, or Aib;
$Xaa_{10}$ is Glu, Ala, Asp, Asn, Gln, Pro, Aib, or Gly;
$Xaa_{11}$ is Asp, Ala, Glu, Asn, Gln, Pro, Aib, or Gly;
$Xaa_{12}$ is Ala or d-Ala;
$Xaa_{13}$ is Ser, Ala, Thr, Pro, or homoSer;
$Xaa_{14}$ is Pro, Ala, homo-Pro, hydroxyPro, Aib, or Gly;
$Xaa_{15}$ is Glu, Ala, Asp, Asn, Gln, Pro, Aib, or Gly;
$Xaa_{16}$ is Glu, Ala, Asp, Asn, or Gln;
$Xaa_{17}$ is Leu, Ala, Met, Trp, Ile, Val, or NorVal;
$Xaa_{18}$ is Asn, Asp, Ala, Glu, Gln, Ser, or Thr;
$Xaa_{19}$ is Arg, Tyr, Lys, Ala, Gln, or N(Me)Ala;
$Xaa_{21}$ is Tyr, Ala, Met, Phe, or Leu;
$Xaa_{22}$ is Ala, Ser, Thr, or d-Ala;
$Xaa_{23}$ is Ser, Ala, Asp, Thr, or homoSer;
$Xaa_{25}$ is Arg, homoArg, Lys, homoLys, Orn, or Cit;
$Xaa_{26}$ is His, Ala, Arg, homoArg, homoLys, Orn, or Cit;
$Xaa_{27}$ is Tyr or Phe;
$Xaa_{28}$ is Leu, Ile, Val, or Ala;
$Xaa_{29}$ is Asn or Gln;
$Xaa_{30}$ is Leu, Ala, NorVal, Val, Ile, or Met;
$Xaa_{31}$ is Ala, Val, Ile, or Leu; and
$Xaa_{36}$ is Tyr, N(Me)Tyr, His, Trp, or Phe;
with the proviso that said PPF polypeptide is not a native PPF polypeptide, NPY(2-36), NPY(4-36), PYY(2-36), PYY(4-36), PP(2-36), PP(4-36), Ala$^1$NPY, Ala$^3$NPY, Ala$^4$NPY, Ala$^6$NPY, Ala$^7$NPY, Tyr$^7$pNPY, Ala$^9$NPY, Ala$^{10}$NPY, Ala$^{11}$NPY, Ala$^{13}$NPY, Gly$^{14}$NPY, Ala$^{15}$NPY, Ala$^{16}$NPY, Ala$^{17}$NPY, Ala$^{19}$NPY, Lys$^{19}$NPY, Ala$^{21}$NPY, Ala$^{22}$NPY, Lys$^{25}$NPY, Ala$^{26}$NPY, Phe$^{27}$NPY, Ala$^{28}$NPY, Gln$^{29}$NPY, Ala$^{30}$NPY, Ala$^{31}$NPY, Phe$^{36}$NPY, His$^{36}$NPY, Leu$^3$hPYY(3-36), Val$^3$hPYY(3-36), Lys$^{25}$hPYY(3-36), Pro$^{13}$Ala$^{14}$hPYY, hPP(1-7)-pNPY, hPP(1-17)-pNPY, Tyr$^1$NPY, Ala$^7$NPY or hPP(19-23)-pNPY.

In another embodiment, the PPF polypeptides of Formula I also do not include: Phe$^{27}$hPYY(3-36), Ile$^{28}$hPYY(3-36), Val$^{28}$hPYY(3-36), Gln$^{29}$hPYY(3-36), Val$^{30}$hPYY(3-36), Ile$^{31}$hPYY(3-36), Leu$^{31}$hPYY(3-36), Phe$^{36}$hPYY(3-36), Lys$^{25}$Phe$^{27}$hPYY(3-36), Lys$^{25}$Ile$^{28}$hPYY(3-36), Lys$^{25}$Val$^{28}$hPYY(3-36), Lys$^{25}$Gln$^{29}$hPYY(3-36), Lys$^{25}$Val$^{30}$hPYY(3-36), Lys$^{25}$Ile$^{31}$hPYY(3-36), Lys$^{25}$Leu$^{31}$hPYY(3-36), Lys$^{25}$Phe$^{36}$hPYY(3-36), Phe$^{27}$Ile$^{28}$hPYY(3-36), Phe$^{27}$Val$^{28}$hPYY(3-36), Phe$^{27}$Gln$^{29}$hPYY(3-36), Phe$^{27}$Val$^{30}$hPYY(3-36), Phe$^{27}$Ile$^{31}$hPYY(3-36), Phe$^{27}$Leu$^{31}$hPYY(3-36), Phe$^{27}$Phe$^{36}$hPYY(3-36), Gln$^{29}$Val$^{30}$hPYY(3-36), Gln$^{29}$Ile$^{31}$hPYY(3-36), Gln$^{29}$Leu$^{31}$hPYY(3-36), Gln$^{29}$Phe$^{36}$hPYY(3-36), Val$^{30}$Ile$^{31}$hPYY(3-36), Val$^{30}$Leu$^{31}$hPYY(3-36), Val$^{30}$Phe$^{36}$hPYY(3-36), or Leu$^{31}$Phe$^{36}$hPYY(3-36).

As will be recognized by one of skill in the art, the polypeptides of Formula I may be in the free acid form, or may be C-terminally amidated.

1. PYY Analog Polypeptides of the Present Invention

The PYY analog polypeptides of the present invention will generally include at least two PPF motifs including the N-terminal polyproline PPF motif and the C-terminal tail PPF motif, and will generally retain, at least in part, a biological activity of native human PYY, e.g., the PYY analog polypeptides of the present invention will generally be PYY agonists. Moreover, the PYY analog polypeptide will have at least 50% sequence identity to PYY(3-36). In a preferred embodiment, the PYY analog polypeptides of the present invention will exhibit PYY activity in the treatment and prevention of metabolic conditions and disorders.

In one embodiment, the PYY analog polypeptides of the invention do not include any unnatural amino acid resides, and further with the provisio that the PYY analog polypeptides of the invention do not include any native PYY polypeptides or 1-4 N-terminal deletions thereof (e.g., PYY(1-36), PYY(2-36), PYY(3-36)), PYY(4-36)). The PYY analog polypeptides of the invention also preferably do not include: Pro$^{34}$PYY, His$^{34}$PYY Lys$^{25}$hPYY(5-36), Arg$^4$hPYY(4-36), Gln$^4$hPYY(4-36), Asn$^4$hPYY(4-36), Lys$^{25}$hPYY(4-36), Leu$^3$hPYY(3-36), Val$^3$hPYY(3-36), Lys$^{25}$hPYY(3-36), Tyr$^{1,36}$pPYY, Pro$^{13}$Ala$^{14}$hPYY, Leu$^3$hPYY, FMS-PYY, FMS-PYY(3-36), Fmoc-PYY, Fmoc-PYY(3-36), FMS$_2$-PYY, FMS$_2$-PYY(3-36), Fmoc$_2$-PYY, or Fmoc$_2$-PYY(3-36).

In another embodiment, such PYY analog polypeptides of the invention also do not include: Thr$^{27}$hPYY(3-36), Ile$^{30}$hPYY(3-36), Ser$^{32}$hPYY(3-36), Lys$^{33}$hPYY(3-36), Asn$^{34}$hPYY(3-36), Lys$^{35}$hPYY(3-36), Thr$^{36}$hPYY(3-36), Lys$^{25}$Thr$^{27}$hPYY(3-36), Lys$^{25}$Ile$^{30}$hPYY(3-36), Lys$^{25}$Ser$^{32}$hPYY(3-36), Lys$^{25}$Lys$^{33}$hPYY(3-36), Lys$^{25}$Asn$^{34}$hPYY(3-36), Lys$^{25}$Lys$^{35}$hPYY(3-36), Lys$^{25}$Thr$^{36}$hPYY(3-36), Thr$^{27}$Ile$^{28}$hPYY(3-36), Thr$^{27}$Val$^{28}$hPYY(3-36), Thr$^{27}$Gln$^{29}$hPYY(3-36), Thr$^{27}$Ile$^{30}$hPYY(3-36), Thr$^{27}$Val$^{30}$hPYY(3-36), Thr$^{27}$Ile$^{31}$hPYY(3-36), Thr$^{27}$Leu$^{31}$hPYY(3-36), Thr$^{27}$Ser$^{32}$hPYY(3-36), Thr$^{27}$Lys$^{33}$hPYY(3-36), Thr$^{27}$Asn$^{34}$hPYY(3-36), Thr$^{27}$Lys$^{35}$hPYY(3-36), Thr$^{27}$Thr$^{36}$hPYY(3-36), Thr$^{27}$Phe$^{36}$hPYY(3-36), Phe$^{27}$Ile$^{30}$hPYY(3-36), Phe$^{27}$Ser$^{32}$hPYY(3-36), Phe$^{27}$Lys$^{33}$hPYY(3-36), Phe$^{27}$Asn$^{34}$hPYY(3-36), Phe$^{27}$Lys$^{35}$hPYY(3-36), Phe$^{27}$Thr$^{36}$hPYY(3-36), Gln$^{29}$Ile$^{30}$hPYY(3-36), Gln$^{29}$Ser$^{32}$hPYY(3-36), Gln$^{29}$Leu$^{33}$hPYY(3-36), Gln$^{29}$Asn$^{34}$hPYY(3-36), Gln$^{29}$Leu$^{35}$hPYY(3-36), Gln$^{29}$Thr$^{36}$hPYY(3-36), Ile$^{30}$Ile$^{31}$hPYY(3-36), Ile$^{30}$Leu$^{31}$hPYY(3-36), Ile$^{30}$Ser$^{32}$hPYY(3-36), Ile$^{30}$Lys$^{33}$hPYY(3-36), Ile$^{30}$Asn$^{34}$hPYY(3-36), Ile$^{30}$Lys$^{35}$hPYY(3-36), Ile$^{30}$Thr$^{36}$hPYY(3-36), Ile$^{30}$Phe$^{36}$hPYY(3-36), Val$^{30}$Ser$^{32}$hPYY(3-36), Val$^{30}$Lys$^{33}$hPYY(3-36), Val$^{30}$Asn$^{34}$hPYY(3-36), Val$^{30}$Lys$^{35}$hPYY(3-36), Val$^{30}$Thr$^{36}$hPYY(3-36), Ile$^{31}$Ser$^{32}$hPYY(3-36), Ile$^{31}$Lys$^{33}$hPYY(3-36), Ile$^{31}$Asn$^{34}$hPYY(3-36), Ile$^{31}$Lys$^{35}$hPYY(3-36), Ile$^{31}$Thr$^{36}$hPYY(3-36), Ile$^{31}$Phe$^{36}$hPYY(3-36), Leu$^{31}$Ser$^{32}$hPYY(3-36), Leu³¹Lys³³hPYY(3-36), Leu³¹Asn³⁴hPYY(3-36), Leu³¹Lys³⁵hPYY(3-36), Leu³¹Thr³⁶hPYY(3-36), Ser³²Lys³³hPYY(3-36), Ser³²Asn³⁴hPYY(3-36), Ser³²Lys³⁵hPYY(3-36), Ser³²Thr³⁶hPYY(3-36), Ser³²Phe³⁶hPYY(3-36), Lys³³Asn³⁴hPYY(3-36), Lys³³Lys³⁵hPYY(3-36), Lys³³Thr³⁶hPYY(3-36), Lys³³Phe³⁶hPYY(3-36), Asn³⁴Lys³⁵hPYY(3-36), Asn³⁴Phe³⁶hPYY(3-36), Lys³⁵Thr³⁶hPYY(3-36), Lys³⁵Phe³⁶hPYY(3-36), Thr²⁷hPYY(4-36), Phe²⁷hPYY(4-36), Ile²⁸hPYY(4-36), Val²⁸hPYY(4-36), Gln²⁹hPYY(4-36), Ile³⁰hPYY(4-36), Val³⁰hPYY(4-36), Ile³¹hPYY(4-36), Leu³¹hPYY(4-35), Ser³²hPYY(4-36), Lys³³hPYY(4-36), Asn³⁴hPYY(4-36), Lys³⁵hPYY(4-36), Thr³⁶hPYY(4-36), Phe³⁶hPYY(4-36), Lys²⁵Thr²⁷hPYY(4-36), Lys²⁵Phe²⁷hPYY(4-36), Lys²⁵Ile²⁸hPYY(4-36), Lys²⁵Val²⁸hPYY(4-36), Lys²⁵Gln²⁹hPYY(4-36), Lys²⁵Ile³⁰hPYY(4-36), Lys²⁵Val³⁰hPYY(4-36), Lys²⁵Ile³¹hPYY(4-36), Lys²⁵Leu³¹hPYY(4-36), Lys²⁵Ser³²hPYY(4-36), Lys²⁵Lys³³hPYY(4-36), Lys²⁵Asn²⁴hPYY(4-36), Lys²⁵Lys³⁵hPYY(4-36), Lys²⁵Thr³⁶hPYY(4-36), Lys²⁵Phe³⁶hPYY(4-36), Thr²⁷Ile²⁸hPYY(4-36), Thr²⁷Val²⁸hPYY(4-36), Thr²⁷Gln²⁹hPYY(4-36), Thr²⁷Ile³⁰hPYY(4-36), Thr²⁷Val³⁰hPYY(4-36), Thr²⁷Ile³¹hPYY(4-36), Thr²⁷Leu³¹hPYY(4-36), Thr²⁷Ser³²hPYY(4-36), Thr²⁷Lys³³hPYY(4-36), Thr²⁷Asn³⁴hPYY(4-36), Thr²⁷Lys³⁵hPYY(4-36), Thr²⁷Thr³⁶hPYY(4-36), Thr²⁷Phe³⁶hPYY(4-36), Phe²⁷Ile²⁸hPYY(4-36), Phe²⁷Val²⁸hPYY(4-36), Phe²⁷Gln²⁹hPYY(4-36), Phe²⁷Ile³⁰hPYY(4-36), Phe²⁷Val³⁰hPYY(4-36), Phe²⁷Ile³¹hPYY(4-36), Phe²⁷Leu³¹hPYY(4-36), Phe²⁷Ser³²hPYY(4-36), Phe²⁷Lys³³hPYY(4-36), Phe²⁷Asn³⁴hPYY(4-36), Phe²⁷Lys³⁵hPYY(4-36), Phe²⁷Thr³⁶hPYY(4-36), Phe²⁷Phe³⁶hPYY(4-36), Gln²⁹Ile³⁰hPYY(4-36), Gln²⁹Val³⁰hPYY(4-36), Gln²⁹Ile³¹hPYY(4-36), Gln²⁹Leu³¹hPYY(4-36), Gln²⁹Ser³²hPYY(4-36), Gln²⁹Leu³³hPYY(4-36), Gln²⁹Asn³⁴hPYY(4-36), Gln²⁹Leu³⁵hPYY(4-36), Gln²⁹Thr³⁶hPYY(4-36), Gln²⁹Phe³⁶hPYY(4-36), Ile³⁰Ile³¹hPYY(4-36), Ile³⁰Leu³¹hPYY(4-36), Ile³⁰Ser³²hPYY(4-36), Ile³⁰Lys³³hPYY(4-36), Ile³⁰Asn³⁴hPYY(4-36), Ile³⁰Lys³⁵hPYY(4-36), Ile³⁰Thr³⁶hPYY(4-36), Ile³⁰Phe³⁶hPYY(4-36), Val³⁰Ile³¹hPYY(4-36), Val³⁰Leu³¹hPYY(4-36), Val³⁰Ser³²hPYY(4-36), Val³⁰Lys³³hPYY(4-36), Val³⁰Asn³⁴hPYY(4-36), Val³⁰Lys³⁵hPYY(4-36), Val³⁰Thr³⁶hPYY(4-36), Val³⁰Phe³⁶hPYY(4-36), Ile³¹Ser³²hPYY(4-36), Ile³¹Lys³³hPYY(4-36), Ile³¹Asn³⁴hPYY(4-36), Ile³¹Lys³⁵hPYY(4-36), Ile³¹Thr³⁶hPYY(4-36), Leu³¹Phe³⁶hPYY(4-36), Leu³¹Phe³⁶hPYY(4-36), Leu³¹Ser³²hPYY(4-36), Val³¹Lys³³hPYY(4-36), Leu³¹Asn³⁴hPYY(4-36), Leu³¹Lys³⁵hPYY(4-36), Leu³¹Thr³⁶hPYY(4-36), Leu³¹Phe³⁶hPYY(4-36), Ser³²Lys³³hPYY(4-36), Ser³²Asn³⁴hPYY(4-36), Ser³²Lys³⁵hPYY(4-36), Ser³²Thr³⁶hPYY(4-36), Ser³²Phe³⁶hPYY(4-36), Lys³³Asn³⁴hPYY(4-36), Lys³³Lys³⁵hPYY(4-36), Lys³³Thr³⁶hPYY(4-36), Lys³³Phe³⁶hPYY(4-36), Asn³⁴Lys³⁵hPYY(4-36), Asn³⁴Phe³⁶hPYY(4-36), Lys³⁵Thr³⁶hPYY(4-36), Lys³⁵Phe³⁶hPYY(4-36), Thr²⁷hPYY(5-36), Phe²⁷hPYY(5-36), Ile²⁸hPYY(5-36), Ile²⁸hPYY(5-36), Val²⁸hPYY(5-36), Gln²⁹hPYY(5-36), Ile³⁰hPYY(5-36), Val³⁰hPYY(5-36), Ile³¹hPYY(5-36), Leu³¹hPYY(5-36), Ser³²hPYY(5-36), Lys³³ hPYY(5-36), Asn³⁴hPYY(5-36), Lys³⁵hPYY(5-36), Thr³⁶hPYY(5-36), Phe³⁶hPYY(5-36), Lys²⁵Thr²⁷hPYY(5-36), Lys²⁵Phe²⁷hPYY(5-36), Lys²⁵Ile²⁸hPYY(5-36), Lys²⁵Val²⁸hPYY(5-36), Lys²⁵Gln²⁹hPYY(5-36), Lys²⁵Ile³⁰hPYY(5-36), Lys²⁵Val³⁰hPYY(5-36), Lys²⁵Ile³¹hPYY(5-36), Lys²⁵Leu³¹hPYY(5-36), Lys²⁵Ser³²hPYY(5-36), Lys²⁵Lys³³hPYY(5-36), Lys²⁵Asn²⁴hPYY(5-36), Lys²⁵Lys³⁵hPYY(5-36), Lys²⁵Thr³⁶hPYY(5-36), Lys²⁵Phe³⁶hPYY(5-36), Thr²⁷Ile²⁸hPYY(5-36), Thr²⁷Val²⁸hPYY(5-36), Thr²⁷Gln²⁹hPYY(5-36), Thr²⁷Ile³⁰hPYY(5-36), Thr²⁷Val³⁰hPYY(5-36), Thr²⁷Ile³¹hPYY(5-36), Thr²⁷Leu³¹hPYY(5-36), Thr²⁷Ser³²hPYY(5-36), Thr²⁷Lys³³hPYY(5-36), Thr²⁷Asn³⁴hPYY(5-36), Thr²⁷Lys³⁵hPYY(5-36), Thr²⁷Thr³⁶hPYY(5-36), Thr²⁷Phe³⁶hPYY(5-36), Phe²⁷Ile²⁸hPYY(5-36), Phe²⁷Val²⁸hPYY(5-36), Phe²⁷Gln²⁹hPYY(5-36), Phe²⁷Ile³⁰hPYY(5-36), Phe²⁷Val³⁰hPYY(5-36), Phe²⁷Ile³¹hPYY(5-36), Phe²⁷Leu³¹hPYY(5-36), Phe²⁷Ser³²hPYY(5-36), Phe²⁷Lys³³hPYY(5-36), Phe²⁷Asn³⁴hPYY(5-36), Phe²⁷Lys³⁵hPYY(5-36), Phe²⁷Thr³⁶hPYY(5-36), Phe²⁷Phe³⁶hPYY(5-36), Gln²⁹Ile³⁰hPYY(5-36), Gln²⁹Val³⁰hPYY(5-36), Gln²⁹Ile³¹hPYY(5-36), Gln²⁹Leu³¹hPYY(5-36), Gln²⁹Ser³²hPYY(5-36), Gln²⁹Leu³³hPYY(5-36), Gln²⁹Asn³⁴hPYY(5-36), Gln²⁹Leu³⁵hPYY(5-36), Gln²⁹Thr³⁶hPYY(5-36), Gln²⁹Phe³⁶hPYY(5-36), Ile³⁰Ile³¹hPYY(5-36), Ile³⁰Leu³¹hPYY(5-36), Ile³⁰Ser³²hPYY(5-36), Ile³⁰Lys³³hPYY(5-36), Ile³⁰Asn³⁴hPYY(5-36), Ile³⁰Lys³⁵hPYY(5-36), Ile³⁰Thr³⁶hPYY(5-36), Ile³⁰Phe³⁶hPYY(5-36), Val³⁰Ile³¹hPYY(5-36), Val³⁰Leu³¹hPYY(5-36), Val³⁰Ser³²hPYY(5-36), Val³⁰Lys³³hPYY(5-36), Val³⁰Asn³⁴hPYY(5-36), Val³⁰Lys³⁵hPYY(5-36), Val³⁰Thr³⁶hPYY(5-36), Val³⁰Phe³⁶hPYY(5-36), Ile³¹Ser³²hPYY(5-36), Ile³¹Lys³³hPYY(5-36), Ile³¹Asn³⁴hPYY(5-36), Ile³¹Lys³⁵hPYY(5-36), Ile³¹Thr³⁶hPYY(5-36), Leu³¹Phe³⁶hPYY(5-36), Leu³¹Phe³⁶hPYY(5-36), Leu³¹Ser³²hPYY(5-36), Val³¹Lys³³hPYY(5-36), Leu³¹Asn³⁴hPYY(5-36), Leu³¹Lys³⁵hPYY(5-36), Leu³¹Thr³⁶hPYY(5-36), Leu³¹Phe³⁶hPYY(5-36), Ser³²Lys³³hPYY(5-36), Ser³²Asn³⁴hPYY(5-36), Ser³²Lys³⁵hPYY(5-36), Ser³²Thr³⁶hPYY(5-36), Ser³²Phe³⁶hPYY(5-36), Lys³³Asn³⁴hPYY(5-36), Lys³³Lys³⁵hPYY(5-36), Lys³³Thr³⁶hPYY(5-36), Lys³³Phe³⁶hPYY(5-36), Asn³⁴Lys³⁵hPYY(5-36), Asn³⁴Phe³⁶hPYY(5-36), Lys³⁵Thr³⁶hPYY(5-36), or Lys³⁵Phe³⁶hPYY(5-36), In another embodiment, the PYY analog polypeptides of the invention do not include any unnatural amino acid residues, and preferably comprise a C-terminal tail motif of hPYY. The C-terminal motif may preferably comprise amino acid residues 32-35 of hPYY, e.g., Thr, Arg, Gln, Arg (SEQ ID NO: 351). In such an embodiment, the PYY analog polypeptides of the invention do not include any native PYY polypeptides or 1-4 N-terminal deletions thereof (e.g., PYY(1-36), PYY(2-36), PYY(3-36) and, PYY(4-36)). Such PYY analogs also preferably do not include: Lys²⁵hPYY(5-36), Arg⁴hPYY(4-36), Gln⁴hPYY(4-36), Asn⁴hPYY(4-36), Lys²⁵hPYY(4-36), Leu³hPYY(3-Val³hPYY(3-36), Lys²⁵hPYY(3-36), Tyr¹,³⁶pPYY, Pro¹³Ala¹⁴hPYY, FMS-PYY, FMS-PYY(3-36), Fmoc-PYY, Fmoc-PYY(3-36), FMS₂-PYY, FMS₂-PYY (3-36), Fmoc₂-PYY, or Fmoc₂-PYY(3-36).

In another aspect, such PYY analog polypeptides of the invention comprising a C-terminal tail motif of hPYY also do not include: Thr²⁷hPYY(3-36), Ile³⁰hPYY(3-36), Thr³⁶hPYY(3-36), Lys²⁵Thr²⁷hPYY(3-36), Lys²⁵Ile³¹hPYY(3-36), Lys²⁵Asn²⁴hPYY(3-36), Lys²⁵Thr³⁶hPYY(3-36), Thr²⁷Ile²⁸hPYY(3-36), Thr²⁷Val²⁸hPYY(3-36), Thr²⁷Gln²⁹hPYY(3-36), Thr²⁷Ile³⁰hPYY(3-36), Thr²⁷Val³⁰hPYY(3-36), Thr²⁷Ile³¹hPYY(3-36), Thr²⁷Leu³¹hPYY(3-36), Thr²⁷Thr³⁶hPYY(3-36), Thr²⁷Phe³⁶hPYY(3-36), Phe²⁷Ile³⁰hPYY(3-36), Phe²⁷Thr³⁶hPYY(3-36), Gln²⁹Ile³⁰hPYY(3-36), Gln²⁹Thr³⁶hPYY(3-36), Ile³⁰Ile³¹hPYY(3-36), Ile³⁰Leu³¹hPYY(3-36), Ile³⁰Thr³⁶hPYY(3-36), Ile³⁰Phe³⁶hPYY(3-36), Val³⁰Thr³⁶hPYY(3-36), Ile³¹Thr³⁶hPYY(3-36), Ile³²Phe³⁶hPYY(3-36), Leu³¹Thr³⁶hPYY(3-36), Thr²⁷hPYY(4-36), Phe²⁷hPYY(4-36), Ile²⁸hPYY(4-36), Val²⁸hPYY(4-36), Gln²⁹hPYY(4-36), Ile³⁰hPYY(4-36), Val³⁰hPYY(4-36), Ile³¹hPYY(4-36), Leu³¹hPYY(4-36), Thr³⁶hPYY(4-36), Phe³⁶hPYY(4-36), Lys²⁵Thr²⁷hPYY(4-36), Lys²⁵Phe²⁷hPYY(4-36), Lys²⁵Ile²⁸hPYY(4-36), Lys²⁵Val²⁸hPYY(4-36), Lys²⁵Gln²⁹hPYY(4-36), Lys²⁵Ile³⁰hPYY(4-36), Lys²⁵Val³⁰hPYY(4-36), Lys²⁵Ile³¹hPYY(4-36), Lys²⁵Leu³¹hPYY(4-36), Lys²⁵Thr³⁶hPYY(4-36), Lys²⁵Phe³⁶hPYY(4-36), Thr²⁷Ile²⁸hPYY(4-36), Thr²⁷Val²⁸hPYY(4-36), Thr²⁷Gln²⁹hPYY(4-36), Thr²⁷Ile³⁰hPYY(4-36), Thr²⁷Val³⁰hPYY(4-36), Thr²⁷Ile³¹hPYY(4-36), Thr²⁷Leu³¹hPYY(4-36), Thr²⁷Thr³⁶hPYY(4-36), Thr²⁷Phe³⁶hPYY(4-36), Phe²⁷Ile²⁸hPYY(4-36), Phe²⁷Val²⁸hPYY(4-36), Phe²⁷Gln²⁹hPYY(4-36), Phe²⁷Ile³⁰hPYY(4-36), Phe²⁷Val³⁰hPYY(4-36), Phe²⁷Ile³¹hPYY(4-36), Phe²⁷Leu³¹hPYY(4-36), Phe²⁷Thr³⁶hPYY(4-36), Phe²⁷Phe³⁶hPYY(4-36), Gln²⁹Ile³¹hPYY(4-36), Gln²⁹Val³⁰hPYY(4-36), Gln²⁹Ile³¹hPYY(4-36), Gln²⁹Leu³¹hPYY(4-36), Gln²⁹Thr³⁶hPYY(4-36), Gln²⁹Phe³⁶hPYY(4-36), Ile³⁰Ile³¹hPYY(4-36), Ile³⁰Leu³¹hPYY(4-36), Ile³⁰Thr³⁶hPYY(4-36), Ile³⁰Phe³⁶hPYY(4-36), Val³⁰Ile³¹hPYY(4-36), Val³⁰Leu³¹hPYY(4-36), Val³⁰Thr³⁶hPYY(4-36), Val³⁰Phe³⁶hPYY(4-36), Ile³¹Thr³⁶hPYY(4-36), Leu³¹Phe³⁶hPYY(4-36), Leu³¹Phe³⁶hPYY(4-36), Leu³¹Thr³⁶hPYY(4-36), Leu³¹Phe³⁶ hPYY(4-36), Thr²⁷hPYY(5-36), Phe²⁷hPYY(5-36), Ile²⁸hPYY(5-36), Val²⁸hPYY(5-36), Gln²⁹hPYY(5-36), Ile³⁰hPYY(5-36), Val³⁰hPYY(5-36), Ile³¹hPYY(5-36), Leu³¹hPYY(5-36), Thr³⁶hPYY(5-36), Phe³⁶hPYY(5-36), Lys²⁵Thr²⁷hPYY(5-36), Lys²⁵Phe²⁷hPYY(5-36), Lys²⁵Ile²⁸hPYY(5-36), Lys²⁵Val²⁸hPYY(5-36), Lys²⁵Gln²⁹hPYY(5-36), Lys²⁵Ile³⁰hPYY(5-36), Lys²⁵Val³⁰hPYY(5-36), Lys²⁵Ile³¹hPYY(5-36), Lys²⁵Leu³¹hPYY(5-36), Lys²⁵Thr³⁶hPYY(5-36), Lys²⁵Phe³⁶hPYY(5-36), Thr²⁷Ile²⁸hPYY(5-36), Thr²⁷Val²⁸hPYY(5-36), Thr²⁷Gln²⁹hPYY(5-36), Thr²⁷Ile³⁰hPYY(5-36), Thr²⁷Val³⁰hPYY(5-36), Thr²⁷Ile³¹hPYY(5-36), Thr²⁷Leu³¹hPYY(5-36), Thr²⁷Thr³⁶hPYY(5-36), Thr²⁷Phe³⁶hPYY(5-36), Phe²⁷Ile²⁸hPYY(5-36), Phe²⁷Val²⁸hPYY(5-36), Phe²⁷Gln²⁹hPYY(5-36), Phe²⁷Ile³⁰hPYY(5-36), Phe²⁷Val³⁰hPYY(5-36), Phe²⁷Ile³¹hPYY(5-36), Phe²⁷Leu³¹hPYY(5-36), Phe²⁷Thr³⁶hPYY(5-36), Phe²⁷Phe³⁶hPYY(5-36), Gln²⁹Ile³¹hPYY(5-36), Gln²⁹Val³⁰hPYY(5-36), Gln²⁹Ile³¹hPYY(5-36), Gln²⁹Leu³¹hPYY(5-36), Gln²⁹Thr³⁶hPYY(5-36), Gln²⁹Phe³⁶hPYY(5-36), Ile³⁰Ile³¹hPYY(5-36), Ile³⁰Leu³¹hPYY(5-36), Ile³⁰Thr³⁶hPYY(5-36), Ile³⁰Phe³⁶hPYY(5-36), Val³⁰Ile³¹hPYY(5-36), Val³⁰Leu³¹hPYY(5-36), Val³⁰Thr³⁶hPYY(5-36), Val³⁰Phe³⁶hPYY(5-36), Ile³¹Thr³⁶hPYY(5-36), Leu³¹Phe³⁶hPYY(5-36), Leu³¹Phe³⁶hPYY(5-36), Leu³¹Thr³⁶hPYY(5-36), or Leu³¹Phe³⁶hPYY(5-36).

The PYY analog polypeptides of the invention are also preferably at least 34 amino acids in length. Further, in a preferred embodiment, the PYY analog polypeptides of the invention include only natural L amino acid residues and/or modified natural L amino acid residues. Alternatively, in a preferred embodiment, the PYY analog polypeptides of the invention do not include unnatural amino acid residues.

More particularly, in one aspect, the present invention relates to PYY analog polypeptides including one or more amino acid sequence modifications. Such modifications include substitutions, insertions, and/or deletions, alone or in combination. In a preferred aspect, the PYY analog polypeptides of the invention include one or more modifications of a "non-essential" amino acid residue. In the context of the invention, a "non-essential" amino acid residue is a residue that can be altered, i.e., deleted or substituted, in the native human PYY amino acid sequence without abolishing or substantially reducing the PYY agonist activity of the PYY analog polypeptide. Preferably, the PYY analog polypeptides of the invention retain at least about 25%, preferably about 30%, 40%, 50%, 60%, 70%, 80%, 90%, 95%, 98%, or 99% percent of the biological activity of native human PYY with regard to the reduction of nutrient availability. In another embodiment, the PYY analog polypeptides of the invention exhibit improved PYY agonist activity. Preferably, the PYY analog polypeptides of the invention exhibits at least about 110%, 125%, 130%, 140%, 150%, 200%, or more of the biological activity of native human PYY with regard to the reduction of nutrient availability.

Preferred PYY analog polypeptide are those having a potency in one of the assays described herein (preferably food intake, gastric emptying, pancreatic secretion, or weight reduction assays) which is equal to or greater than the potency of NPY, PYY, or PYY(3-36) in that same assay. Alternatively, preferred PYY analog polypeptides of the invention may exhibit improved ease of manufacture, stability, and/or ease of formulation, as compared to PP, NPY, PYY, or PYY(3-36).

a. Substitutions

In one embodiment, the PYY analog polypeptides of the invention may have one or more substitutions in the amino acid sequence of native human PYY (SEQ ID NO: 2), alone or in combination with one or more insertions or deletions. Preferably, the substitution does not abolish or substantially reduce the PYY agonist activity of the PYY analog polypeptide. In one aspect, the present invention relates to PYY analog polypeptides that have a single substitution, or consecutive or non-consecutive substitution of more than one amino acid residues in the amino acid sequence of native human PYY (SEQ ID NO: 2). Preferably, the PYY analog polypeptides of the invention include one, two, or three amino acid substitutions.

Preferably, the amino acid residues of native human PYY (SEQ ID NO: 2) at the helical C-terminus region of PYY (e.g., residues 20, 24, 25, 27 and 29), the tail end residues (32-36), and/or the N-terminus prolines at position 5 and 8 are not substituted. In a preferred embodiment, amino acid residues are not substituted at positions 32 through 36 of native human PYY (SEQ ID NO: 2). In another embodiment, amino acid residues of native human PYY (SEQ ID NO: 2) are not substituted at one or more amino acid sequence positions selected from: 5, 7, 8, 20, 24, 25, 27, 29, 32, 33, 34, 35, 36, and any combination thereof.

Preferred substitutions include conserved amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine).

In another embodiment, the PYY analog polypeptides of the invention may include substitutions of one or more unnatural and/or non-amino acids, e.g., amino acid mimetics, into the sequence of PYY (SEQ ID NO: 2). In a preferred embodiment, the non-amino acids inserted into the sequence of PYY (SEQ ID NO: 2) may be β-turn mimetics or linker molecules, such as —NH—X—CO—, wherein $X=(CH_2)_n$ (where n can be 2-20) or —NH—$CH_2CH_2$—(O—$CH_2CH_2$—O—$)_m$—$CH_2$—CO— (where m=1-5). Preferred linker molecules include aminocaproyl ("Aca"), β-alanyl, and 8-amino-3,6-dioxaoctanoyl. β-turn mimetics are available commercially (BioQuadrant Inc, Quebec, Canada) and have been described in literature (Hanessian et al., Tetrahedron 12789-854 (1997); Gu et al., Tetrahedron Letters 44: 5863-6 (2003); Bourguet et al., Bioorganic & Medicinal Chemistry Letters 13: 1561-4 (2003); Grieco et al., Tetrahedron Letters 43: 6297-9 (2002); Souers et al., Tetrahedron 57: 7431-48 (2001); Tsai et al., Bioorganic & Medicinal Chemistry 7: 29-38 (1999); Virgilio et al., Tetrahedron 53: 6635-44 (1997)). Preferred β-turn mimetics include mimic A and mimic B illustrated below.

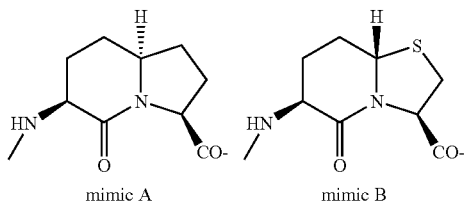

mimic A    mimic B

Preferred PYY analog polypeptides comprising amino acid sequence β-turn mimetic substitutions include native human PYY (SEQ ID NO: 2), wherein amino acids at positions x and x+1 are substituted with β-turn mimetics selected from the group consisting of mimic A and mimic B, wherein x is selected from the amino acids at amino acid positions 8 to 14 of native human PYY. Alternatively, known dipeptide turn inducers may be substituted, for example, Ala-Aib and Ala-Pro dipeptides.

Other preferred PYY analog polypeptides comprising amino acid sequence substitutions include the PYY analog polypeptides of the Formula (II) (SEQ ID NO: 88):

$Xaa_1$ $Xaa_2$ $Xaa_3$ $Xaa_4$ Pro $Xaa_6$ $Xaa_7$ Pro $Xaa_9$ $Xaa_{10}$
$Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ Tyr
$Xaa_{21}$ $Xaa_{22}$ $Xaa_{23}$ Leu Arg $Xaa_{26}$ Tyr $Xaa_{28}$ Asn $Xaa_{30}$
$Xaa_{31}$ Thr Arg Gln Arg $Xaa_{36}$ wherein:
$Xaa_1$ is Tyr, Ala, Phe, Trp, or absent;
$Xaa_2$ is Pro, Gly, d-Ala, homoPro, hydroxy-Pro, or absent;
$Xaa_3$ is Ile, Ala, NorVal, Val, Leu, Pro, Ser or Thr;
$Xaa_4$ is Lys, Ala, Gly, Arg, d-Ala, homoLys, homoArg, Glu, or Asp;
$Xaa_6$ is Glu, Ala, Val, Asp, Asn, or Gln;
$Xaa_7$ is Ala, Asn, His, Ser, or Tyr;
$Xaa_9$ is Gly, Ala Ser, sarcosine, Pro, or Aib;
$Xaa_{10}$ is Glu, Ala, Asp, Asn, Gln, Pro, Aib, or Gly;
$Xaa_{11}$ is Asp, Ala, Glu, Asn, Gln, Pro, Aib, or Gly;
$Xaa_{12}$ is Ala or d-Ala;
$Xaa_{13}$ is Ser, Ala, Thr, or homoSer;
$Xaa_{14}$ is Pro, Ala, homo-Pro, hydroxy-Pro, Aib, or Gly;
$Xaa_{15}$ is Glu, Ala, Asp, Asn, Gln, Pro, Aib, or Gly;
$Xaa_{16}$ is Glu, Ala, Asp, Asn, or Gln;
$Xaa_{17}$ is Leu, Ala, Met, Trp, Ile, Val, or NorVal;
$Xaa_{18}$ is Asn, Asp, Ala, Glu, Gln, Ser or Thr;
$Xaa_{19}$ is Arg, Tyr, Lys, Ala, Gln, or N(Me)Ala;
$Xaa_{21}$ is Tyr, Ala, Met, Phe, or Leu;
$Xaa_{22}$ is Ala, Ser, Thr, or d-Ala;
$Xaa_{23}$ is Ser, Ala, Thr, or homoSer;
$Xaa_{26}$ is His or Ala;
$Xaa_{28}$ is Leu, Ile, Val, or Ala;
$Xaa_{30}$ is Leu, Ala, NorVal, Val, Ile, or Met;
$Xaa_{31}$ is Ala, Val, Ile, or Leu; and
$Xaa_{36}$ is Tyr, N(Me)Tyr, His, Trp, or Phe;

with the proviso that said polypeptide is not a native PPF polypeptide, PYY(2-36), PP(2-36), $Ala^{13}$NPY, $Leu^3$hPYY (3-36), $Val^3$hPYY(3-36), hPP(1-7)-pNPY, or hPP(1-17)-pNPY.

In another embodiment, the PYY analog polypeptides of Formula II also do not include: $Ile^{28}$hPYY(3-36), $Val^{28}$hPYY(3-36), $Val^{30}$hPYY(3-36), $Ile^{31}$hPYY $Leu^{31}$hPYY(3-36), $Phe^{36}$hPYY(3-36), $Val^{31}Ile^{31}$hPYY(3-36), $Val^{30}Leu^{31}$hPYY(3-36), $Val^{30}Phe^{36}$hPYY(3-36), or $Leu^{31}Phe^{36}$hPYY(3-36).

As will be recognized by one of skill in the art, the polypeptides of Formula II may be in the free acid form, or may be C-terminally amidated.

Other preferred PYY analog polypeptides comprising amino acid sequence substitutions include the PYY analog polypeptides of the Formula (III) (SEQ ID NO: 348):

$Xaa_1$ $Xaa_2$ $Xaa_3$ $Xaa_4$ Pro $Xaa_6$ $Xaa_7$ Pro $Xaa_9$ $Xaa_{10}$
$Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ Tyr
$Xaa_{21}$ $Xaa_{22}$ $Xaa_{23}$ Leu Arg $Xaa_{26}$ Tyr $Xaa_{28}$ Asn $Xaa_{30}$
$Xaa_{31}$ Thr Arg Gln Arg $Xaa_{36}$ wherein:
$Xaa_1$ is Tyr, Phe, Trp, or absent;
$Xaa_2$ is Pro, Gly, d-Ala, homoPro, hydroxy-Pro, or absent;
$Xaa_3$ is Ile, Ala, NorVal, Val, Leu, Pro, Ser or Thr;
$Xaa_4$ is Lys, Ala, Gly, Arg, d-Ala, homoLys, homoArg, Glu, or Asp;
$Xaa_6$ is Glu, Ala, Val, Asp, Asn, or Gln;
$Xaa_7$ is Ala, Asn, His, Ser, or Tyr;
$Xaa_9$ is Gly, Ala Ser, sarcosine, Pro, or Aib;
$Xaa_{10}$ is Glu, Ala, Asp, Asn, Gln, Pro, Aib, or Gly;
$Xaa_{11}$ is Asp, Ala, Glu, Asn, Gln, Pro, Aib, or Gly;
$Xaa_{12}$ is Ala or d-Ala;
$Xaa_{13}$ is Ser, Ala, Thr, Pro, or homoSer;
$Xaa_{14}$ is Pro, Ala, homo-Pro, hydroxyPro, Aib, or Gly;
$Xaa_{15}$ is Glu, Ala, Asp, Asn, Gln, Pro, Aib, or Gly;
$Xaa_{16}$ is Glu, Ala, Asp, Asn, or Gln;
$Xaa_{17}$ is Leu, Ala, Met, Trp, Ile, Val, or NorVal;
$Xaa_{18}$ is Asn, Asp, Ala, Glu, Gln, Ser or Thr;
$Xaa_{19}$ is Arg, Tyr, Lys, Ala, Gln, or N(Me)Ala;
$Xaa_{21}$ is Tyr, Ala, Met, Phe, or Leu;
$Xaa_{22}$ is Ala, Ser, Thr, or d-Ala;
$Xaa_{23}$ is Ser, Ala, Thr, or homoSer;
$Xaa_{26}$ is His or Ala;
$Xaa_{28}$ is Leu, Ile, Val, or Ala;
$Xaa_{30}$ is Leu, Ala, NorVal, Val, Ile, or Met;
$Xaa_{31}$ is Ala, Val, Ile, or Leu; and
$Xaa_{36}$ is Tyr, N(Me)Tyr, His, Trp, or Phe;

with the proviso that said polypeptide is not a native PPF polypeptide, NPY(2-36), PYY(2-36), PP(2-36), $Ala^3$NPY, $Ala^4$NPY, $Ala^6$NPY, $Ala^7$NPY, $Tyr^7$pNPY, $Ala^9$NPY, Ala$^{10}$NPY, Ala$^{11}$NPY, Ala$^{13}$NPY, Gly$^{14}$NPY, Ala$^{15}$NPY, Ala$^{16}$NPY, Ala$^{17}$NPY, Ala$^{19}$NPY, Lys$^{19}$NPY, Ala$^{12}$NPY, Ala$^{22}$NPY, Lys$^{25}$NPY, Ala$^{26}$NPY, Phe$^{27}$NPY, Ala$^{28}$NPY, Gln$^{29}$NPY, Ala$^{30}$NPY, Ala$^{31}$NPY, Phe$^{36}$NPY, His$^{36}$NPY, Leu$^3$hPYY(3-36), Val$^3$hPYY(3-36), Lys$^{25}$hPYY(3-36), Pro$^{13}$Ala$^{14}$hPYY, Tyr$^1$NPY, Ala$^7$NPY, or hPP(19-23)-pNPY.

In another embodiment, the PYY analog polypeptides of Formula III also do not include: Ile$^{28}$hPYY(3-36), Val$^{28}$hPYY(3-36), Val$^{30}$hPYY(3-36), Ile$^{31}$hPYY(3-36), Leu$^{31}$hPYY(3-36), Phe$^{36}$hPYY(3-36), Val$^{30}$Ile$^{31}$hPYY(3-36), Val$^{30}$Leu$^{31}$hPYY(3-36), Val$^{30}$Phe$^{36}$hPYY(3-36), or Leu$^{31}$Phe$^{36}$hPYY(3-36).

As will be recognized by one of skill in the art, the polypeptides of Formula III may be in the free acid form, or may be C-terminally amidated.

Other preferred PYY analog polypeptides comprising amino acid sequence substitutions include the PYY analog polypeptides of the Formula (IV) (SEQ ID NO: 349):

Xaa$_1$ Xaa$_2$ Xaa$_3$ Xaa$_4$ Pro Xaa$_6$ Xaa$_7$ Pro Xaa$_9$ Xaa$_{10}$
Xaa$_{11}$ Xaa$_{12}$ Xaa$_{13}$ Xaa$_{14}$ Xaa$_{15}$ Xaa$_{16}$ Xaa$_{17}$ Xaa$_{18}$ Xaa$_{19}$ Tyr
Xaa$_{21}$ Xaa$_{22}$ Xaa$_{23}$ Leu Arg Xaa$_{26}$ Tyr Xaa$_{28}$ Asn Xaa$_{30}$
Xaa$_{31}$ Thr Arg Gln Arg Xaa$_{36}$ wherein:
Xaa$_1$ is Tyr, Phe, Trp, or absent;
Xaa$_2$ is Pro, Gly, d-Ala, homoPro, hydroxy-Pro, or absent;
Xaa$_3$ is Ile, Ala, NorVal, Val, Leu, Pro, Ser or Thr;
Xaa$_4$ is Lys, Ala, Gly, Arg, d-Ala, homoLys, homoArg, Glu, or Asp;
Xaa$_6$ is Glu, Ala, Val, Asp, Asn, or Gln;
Xaa$_7$ is Ala, Asn, His, Ser, or Tyr;
Xaa$_9$ is Gly, Ala Ser, sarcosine, Pro, or Aib;
Xaa$_{10}$ is Glu, Ala, Asp, Asn, Gln, Pro, Aib, or Gly;
Xaa$_{11}$ is Asp, Ala, Glu, Asn, Gln, Pro, Aib, or Gly;
Xaa$_{12}$ is Ala or d-Ala;
Xaa$_{13}$ is Ser, Ala, Thr, or homoSer;
Xaa$_{14}$ is Pro, Ala, homo-Pro, hydroxyPro, Aib, or Gly;
Xaa$_{15}$ is Glu, Ala, Asp, Asn, Gln, Pro, Aib, or Gly;
Xaa$_{16}$ is Glu, Ala, Asp, Asn, or Gln;
Xaa$_{17}$ is Leu, Ala, Met, Trp, Ile, Val, or NorVal;
Xaa$_{18}$ is Asn, Asp, Ala, Glu, Gln, Ser or Thr;
Xaa$_{19}$ is Arg, Tyr, Lys, Ala, Gln, or N(Me)Ala;
Xaa$_{21}$ is Tyr, Ala, Met, Phe, or Leu;
Xaa$_{22}$ is Ala, Ser, Thr, or d-Ala;
Xaa$_{23}$ is Ser, Ala, Thr, or homoSer;
Xaa$_{26}$ is His or Ala;
Xaa$_{28}$ is Leu, Ile, Val, or Ala;
Xaa$_{30}$ is Leu, Ala, NorVal, Val, Ile, or Met;
Xaa$_{31}$ is Ala, Val, Ile, or Leu; and
Xaa$_{36}$ is Tyr, N(Me)Tyr, His, Trp, or Phe;

with the proviso that said polypeptide is not a native PPF polypeptide, PYY(2-36), Ala$^{13}$NPY, Leu$^3$hPYY(3-36), or Val$^3$hPYY(3-36).

In another embodiment, the PYY analog polypeptides of Formula IV also do not include: Ile$^{28}$hPYY(3-36), Val$^{28}$hPYY(3-36), Val$^{30}$hPYY(3-36), Ile$^{31}$hPYY(3-36), Leu$^{31}$hPYY(3-36), Phe$^{36}$hPYY(3-36), Val$^{30}$Ile$^{31}$hPYY(3-36), Val$^{30}$Leu$^{31}$hPYY(3-36), Val$^{30}$Phe$^{36}$hPYY(3-36), or Leu$^{31}$Phe$^{36}$hPYY(3-36).

As will be recognized by one of skill in the art, the polypeptides of Formula IV may be in the free acid form, or may be C-terminally amidated.

Other preferred PYY analog polypeptides comprising amino acid sequence linker substitutions include PYY(1-4) Aminocaproyl(14-36) (IUPAC [Aca$^{5-13}$]PYY) (Aminocaproyl is abbreviated as "Aca"), PYY(1-4)Aca(15-36), PYY (1-4)Aca(16-36), PYY(1-4)Aca(22-36) (IUPAC [Aca$^{5-21}$] PYY), and PYY(1-4)Aca(25-36), (IUPAC [Aca$^{5-24}$]PYY) (SEQ ID NOS: 180-184).

b. Deletions and Truncations

In another embodiment, the PYY analog polypeptides of the invention may have one or more amino acid residues deleted from the amino acid sequence of native human PYY (SEQ ID NO: 2), alone or in combination with one or more insertions or substitutions. In one aspect, the PYY analog polypeptides of the invention may have one or more amino acid residues deleted from the N-terminus or C-terminus of native human PYY (SEQ ID NO: 2), with the proviso that the polypeptide is not SEQ ID NO: 3. In another embodiment, the PYY analog polypeptides of the invention may have one or more amino acid residues deleted at amino acid positions 2 through 35 of native human PYY (SEQ ID NO: 2). Such deletions may include more than one consecutive or non-consecutive deletions at amino acid positions 2 through 35 of native human PYY (SEQ ID NO: 2). In a preferred embodiment, the amino acid residues at positions 24 through 36 of native human PYY (SEQ ID NO: 2) are not deleted.

In another embodiment, the PPF polypeptides of the invention described in Formulas I to V (infra and supra) may include N or C-terminal truncations, or internal deletions at amino acid positions 2 to 35 of Formula I, II, III, IV, or V, so long as at least one biological activity of a native PPF polypeptide is retained. In preferred embodiments, the amino acid residues at positions 5 through 8 and 24 through 36, more preferably 5 through 8 and 32 through 35 are not deleted.

c. Insertions

In another embodiment, the PYY analog polypeptides of the invention may have one or more amino acid residues inserted into the amino acid sequence of native human PYY (SEQ ID NO: 2), alone or in combination with one or more deletions and/or substitutions. In one aspect, the present invention relates to PYY analog polypeptides that have a single insertion, or consecutive or non-consecutive insertions of more than one amino acid residues into the amino acid sequence of native human PYY (SEQ ID NO: 2). In a preferred embodiment, amino acid residues are not inserted at positions 24 through 36 of native human PYY (SEQ ID NO: 2).

In another embodiment, the PYY analog polypeptides of the invention may include insertions of one or more unnatural amino acids and/or non-amino acids into the sequence of PYY (SEQ ID NO: 2). In a preferred embodiment, the unnatural amino acids inserted into the sequence of PYY (SEQ ID NO: 2) may be β-turn mimetics or linker molecules. Preferred linker molecules include aminocaproyl ("Aca"), β-alanyl, and 8-amino-3,6-dioxaoctanoyl. Preferred β-turn mimetics include mimic A and mimic B illustrated below, also Ala-Aib and Ala-Pro dipeptides.

mimic A   mimic B

In another embodiment, PYY analog polypeptides of the invention may include insertions of polyamino acid sequences (e.g., poly-his, poly-arg, poly-lys, poly-ala, etc.) at either terminus of the polypeptide, known as "extensions" or "tails."

Preferred PYY analog polypeptides comprising amino acid sequence insertions include alanine substitutions at each amino acid position along the length of native human PYY. Such PYY analog polypeptides include PYY (+Axa), wherein x is selected from 1' to 36 (SEQ ID NOS: 54-87).

d. Derivatives

The present invention also relates to derivatives of the PYY analog polypeptides of the invention. Such derivatives include PYY analog polypeptides conjugated to one or more water soluble polymer molecules, such as polyethylene glycol ("PEG") or fatty acid chains of various lengths (e.g., stearyl, palmitoyl, octanoyl), by the addition of polyamino acids, such as poly-his, poly-arg, poly-lys, and poly-ala, or by addition of small molecule substituents include short alkyls and constrained alkyls (e.g., branched, cyclic, fused, adamantyl), and aromatic groups. The water soluble polymer molecules will preferably have a molecular weight ranging from about 500 to about 20,000 Daltons.

Such polymer-conjugations may occur singularly at the N- or C-terminus or at the side chains of amino acid residues within the sequence of the PYY analog polypeptides. Alternatively, there may be multiple sites of derivatization along the PYY analog polypeptide. Substitution of one or more amino acids with lysine, aspartic acid, glutamic acid, or cysteine may provide additional sites for derivatization. See, e.g., U.S. Pat. Nos. 5,824,784 and 5,824,778. Preferably, the PYY analog polypeptides may be conjugated to one, two, or three polymer molecules.

The water soluble polymer molecules are preferably linked to an amino, carboxyl, or thiol group, and may be linked by N or C termini, or at the side chains of lysine, aspartic acid, glutamic acid, or cysteine. Alternatively, the water soluble polymer molecules may be linked with diamine and dicarboxylic groups. In a preferred embodiment, the PYY analog polypeptides of the invention are conjugated to one, two, or three PEG molecules through an epsilon amino group on a lysine amino acid.

PYY analog polypeptide derivatives of the invention also include PYY analog polypeptides with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of the PYY analog polypeptides. In one embodiment, the C-terminus of these peptides may have a free —OH or —NH$_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group (isocap), an octanyl group, an octyl glycine group (G(Oct)), an 8-aminooctanic acid group or a Fmoc group. In a preferred embodiment, cyclization can be through the formation of disulfide bridges, see, e.g., SEQ ID NO. 171. Alternatively, there may be multiple sites of chemical alteration along the PYY analog polypeptide.

e. Preferred Analogs and Derivatives

In a preferred aspect of the invention, the PYY analog polypeptides include combinations of the above-described modifications, i.e., deletion, insertion, and substitution.

By way of example, preferred PYY analog polypeptides may include N-terminal deletions in combination with one or more amino acid substitutions. For instance, preferred PYY analog polypeptides include PYY (3-36) with the one or more of the following amino acid substitutions: Ala$^3$, Leu$^3$, Pro$^3$, Ala$^4$, Gly$^4$, d-Ala$^4$, homoLys$^4$, Glu$^4$, Ala$^5$, Ala$^6$, Val$^6$, d-Ala$^7$, Tyr$^7$, His$^7$, Ala$^8$, Ala$^9$, Ala$^{10}$, Ala$^{11}$, d-Ala$^{12}$, Ala$^{13}$, homoSer$^{13}$, Ala$^{14}$, Ala$^{15}$, Gln$^{15}$, Ala$^{16}$, Ala$^{17}$, Met$^{17}$, Ala$^{18}$, Ser$^{18}$, nor-Val$^{18}$, Ala$^{19}$, N-Me-Ala$^{19}$, Lys$^{19}$, homoArg$^{19}$, Ala$^{20}$, Ala$^{21}$, d-Ala$^{22}$, Ala$^{23}$, Ala$^{24}$, Ala$^{25}$, Lys$^{25}$, homoArg$^{25}$, Ala$^{26}$, Ala$^{27}$, Ala$^{28}$, Ala$^{29}$, Ala$^{30}$, Ala$^{31}$, Ala$^{32}$, Ala$^{33}$, Lys$^{33}$, Ala$^{34}$, Ala$^{35}$, Ala$^{36}$, His$^{36}$, Trp$^{36}$, N-Me-Tyr$^{36}$, and Phe$^{36}$. Preferably, the PYY analog polypeptide includes one, two, or three amino acid substitutions. Certain preferred PYY analog polypeptides comprising deletions in combination with amino acid insertions. (see, e.g., SEQ ID NOS: 89-174)

Preferred PYY analog polypeptides include the polypeptides of the Formula (V) (SEQ ID NO: 350):

Xaa$_3$ Xaa$_4$ Pro Xaa$_6$ Xaa$_7$ Pro Xaa$_9$ Xaa$_{10}$ Xaa$_{11}$ Xaa$_{12}$
Xaa$_{13}$ Xaa$_{14}$ Xaa$_{15}$ Xaa$_{16}$ Xaa$_{17}$ Xaa$_{18}$ Xaa$_{19}$ Tyr Xaa$_{21}$ Xaa$_{22}$
Xaa$_{23}$ Leu Arg Xaa$_{26}$ Tyr Xaa$_{28}$ Asn Xaa$_{30}$ Xaa$_{31}$ Thr Arg Gln Arg Xaa$_{36}$ wherein:
Xaa$_3$ is Ile, Ala, Pro, Ser, Thr, or NorVal;
Xaa$_4$ is Lys, Ala, Gly, Glu, Asp, d-Ala, homoLys, or homoArg;
Xaa$_6$ is Glu, Ala, Val, Asp, Asn, or Gln;
Xaa$_7$ is Ala, Asn, His, Ser, or Tyr;
Xaa$_9$ is Gly, Ala, Ser, sarcosine, Pro, or Aib;
Xaa$_{10}$ is Glu, Ala, Asp, Asn, Gln, Pro, Aib, or Gly;
Xaa$_{11}$ is Asp, Ala, Glu, Asn, Gln, Pro, Aib, or Gly;
Xaa$_{12}$ is Ala or d-Ala;
Xaa$_{13}$ is Ser, Ala, Thr, or homoSer;
Xaa$_{14}$ is Pro, Ala, homoPro, hydroxyPro, Aib, or Gly;
Xaa$_{15}$ is Glu, Ala, Asp, Asn, Gln, Pro, Aib, or Gly;
Xaa$_{16}$ is Glu, Ala, Asp, Asn, or Gln;
Xaa$_{17}$ is Leu, Ala, Met, Trp, Ile, Val, or NorVal;
Xaa$_{18}$ is Asn, Asp, Ala, Glu, Gln, Ser or Thr;
Xaa$_{19}$ is Arg, Tyr, Lys, Ala, Gln, or N(Me)Ala;
Xaa$_{21}$ is Tyr, Ala, Met, Phe, or Leu;
Xaa$_{22}$ is Ala, Ser, Thr, or d-Ala;
Xaa$_{23}$ is Ser, Ala, Thr, or homoSer;
Xaa$_{26}$ is His or Ala;
Xaa$_{28}$ is Leu or Ala;
Xaa$_{30}$ is Leu, Ala, NorVal, or Ile;
Xaa$_{31}$ is Ala or Val; and
Xaa$_{36}$ is Tyr, N(Me)Tyr, His, or Trp;
with the proviso that said polypeptide is not a native PPF polypeptide.

As will be recognized by one of skill in the art, the polypeptides of Formula V may be in the free acid form, or may be C-terminally amidated.

Other preferred PYY analog polypeptides include SEQ ID NOs: 31-87, 93, 95, 96, 110, 114-116, 118, 120, 124-129, 131-132, 137-141, 146-156, 158, 160-164, 167-168, 170-171, 174-217, 221-222, 225, 228-229, 231-239, 242-245, 247-249, 251, 255-258, 260, 264, 266-286, and 288-347.

Also included within the scope of the invention are PYY analog polypeptides of Formulas II to V, wherein the indicated amino acid residue is chemical modified or derivitized (e.g., through fatty acid derivitization, PEGylation, amidation, glycolization, etc.). Also contemplated within the scope of the invention are D-amino acid residues of the indicated amino acids.

In another embodiment, preferred PYY analog polypeptides include the polypeptides of Formulas II to V with internal deletions, particularly in areas not corresponding to the C-terminal tail PPF motif, as described herein.

Preferred PYY analog polypeptides comprising substitutions of unnatural amino acids include PYY(3-36), wherein amino acids at positions x and x+1 are substituted with β-turn mimetics selected from the group consisting of mimic A and mimic B, wherein x is selected from positions 8 to 14 (see, e.g., SEQ ID NOS: 211-217 and 231-237).

Preferred derivatives of the PYY analog polypeptides of the invention include polymer-conjugated PYY analog polypeptides, wherein the PYY analog polypeptide includes any of the above-described insertions, deletions, substitutions, or combinations thereof, and the polymer molecule is conjugated at a lysine residue. Other preferred derivatives of PYY analog polypeptides include PYY, PYY(3-36) or PYY (4-36) with the following substitutions and alterations: [Lys$^4$-fatty acid chain]PYY(3-36); [Lys$^4$-fatty acid chain]PYY(4-36); [Ala$^2$Lys$^{19}$-fatty acid chain]PYY(3-36); [Ile$^3$-fatty acid chain]PYY(3-36); [Ser$^{13}$-OAc]PYY(3-36) (OAc is O-Acylation with fatty acids or acetyl groups); [Ser$^{23}$-OAc]PYY(3-36); [Ile$^2$-Octanoyl chain]PYY(3-36); [Lys$^{19}$-Octanoyl chain]PYY(3-36); and [Lys$^{19}$-Stearyl chain]PYY(3-36). (see e.g., SEQ ID NOS: 185-208).

Further examples of the PYY analog polypeptides of the present invention are provided in the Sequence Listing and discussed in the Examples section below.

2. PPF Chimeric Polypeptides

In yet another aspect of the invention, the PPF polypeptides of the invention include PPF chimeric polypeptides comprising a fragment of a PP, PYY or NPY polypeptide covalently linked to at least one additional fragment of a second PP, PYY or NPY polypeptide, wherein each PP, PYY or NPY fragment includes a PPF motif. Alternatively, the PPF chimeric polypeptides of the invention may comprise a fragment of a PP family polypeptide linked to one, two, three, or four polypeptides segments, wherein at least one of the linked polypeptide segments is a fragment of a second PP family polypeptide. In certain embodiments, PPF polypeptides do not include an N-terminal PP fragment with a C-terminal NPY fragment. PPF chimeric polypeptides of the invention will exhibit at least 50% sequence identity to a native PYY (3-36) over the entire length of the PYY(3-36). In a preferred embodiment, such PPF chimeric polypeptides of the invention may exhibit at least 60%, 65%, 70%, 80%, or 90% sequence identity to a native PYY(3-36) over the entire length of the PYY(3-36). Such PPF chimeric polypeptides of the invention may also exhibit at least 50%, 60%, 65%, 70%, 80%, or 90% sequence identity to a native PP. In yet another embodiment, such PPF chimeric polypeptides of the invention may exhibit at least 50%, 60%, 65%, 70%, 80%, or 90% sequence identity to a native NPY. Further, the PPF chimeric polypeptides of the invention will preferably include at least the N-terminal polyproline PPF motif and the C-terminal tail PPF motif.

Again, the PPF polypeptides of the present invention will generally retain, at least in part, a biological activity of native human PP, PYY, or NPY. In a preferred embodiment, the PPF chimeric polypeptides of the present invention will exhibit biological activity in the treatment and prevention of metabolic conditions and disorders.

The polypeptide fragments may be covalently linked together in any manner known in the art, including but not limited to direct amide bonds or chemical linker groups. Chemical linker groups may include peptide mimetics which induce or stabilize polypeptide conformation. Preferred PPF chimeric polypeptides of the invention include PYY-PP, PYY-NPY, PP-PYY, PP-NPY, NPY-PP, or NPY-PYY chimeras.

The PPF chimeric polypeptides of the invention may be at least 21, 22, 23, 24, 25, 26, 27, 28, 29, 30, 31, 32, 33, or 34 amino acids in length. Further, in a preferred embodiment, the PYY analog polypeptides of the invention include only natural L amino acid residues and/or modified natural L amino acid residues. Alternatively, in a preferred embodiment, the PYY analog polypeptides of the invention do not include unnatural amino acid residues.

Further, as mentioned above, the PPF chimeric polypeptides of the invention preferably do not include: hPP(1-7)-pNPY, hPP(1-17)-pNPY, hPP(19-23)-pNPY, hPP(19-23)-Pro$^{34}$pNPY, hPP(19-23)-His$^{34}$pNPY, rPP(19-23)-pNPY, rPP(19-23)-Pro$^{34}$pNPY, rPP(19-23)-His$^{34}$pNPY, hPP(1-17)-His$^{34}$pNPY, pNPY(1-7)-hPP, pNPY(1-7, 19-23)-hPP, cPP(1-7)-pNPY(19-23)-hPP, cPP(1-7)-NPY(19-23)-His$^{34}$hPP, hPP(1-17)-His$^{34}$pNPY, hPP(19-23)-pNPY, hPP(19-23)-Pro$^{34}$pNPY, pNPY(1-7)-hPP, pNPY(19-23)-hPP, pNPY(19-23)-Gln$^{34}$hPP, pNPY(19-23)-His$^{34}$hPP, pNPY(19-23)-Phe$^6$Gln$^{34}$hPP, pNPY(19-23)-Phe$^6$His$^{34}$hPP, pNPY(1-7,19-23)-hPP, pNPY(1-7,19-23)-Gln$^{34}$hPP, cPP(20-23)-Pro$^{34}$-pNPY, cPP(21-23)-Pro$^{34}$-pNPY, cPP(22-23)-Pro$^{34}$-pNPY, cPP(1-7)-Pro$^{34}$-pNPY, cPP(20-23)-Pro$^{34}$-pNPY, cPP(1-7, 20-23)-Pro$^{34}$-pNPY, cPP(1-7)-pNPY(19-23)-hPP, cPP(1-7)-pNPY(19-23)-His$^{34}$hPP, cPP(1-7)-gPP(19-23)-hPP, cPP(1-7)-pNPY(19-23)-Ala$^{31}$Aib$^{32}$Gln$^{34}$-hPP, cPP(1-7)-pNPY (19-23)-Ala$^{31}$Aib$^{32}$His$^{34}$-hPP hPP(1-7)-Ala$^{31}$Aib$^{32}$-pNPY, hPP(1-17)-Ala$^{31}$Aib$^{32}$-pNPY, pNPY(1-7)-Ala$^{31}$Aib$^{32}$Gln$^{34}$-hPP, or pNPY(1-7, 19-23)-Ala$^{31}$ Aib$^{32}$Gln$^{34}$-hPP.

In a preferred embodiment, the PPF chimeric polypeptides of the invention may comprise fragments of PP family analog polypeptides. For instance, the PPF chimeric polypeptides may comprise PPY analog polypeptides described herein, as well as PP analog polypeptides, and NPY analog polypeptides.

Preferred PYY analog polypeptide are those having a potency in one of the assays described herein (preferably food intake, gastric emptying, pancreatic secretion, or weight reduction assays) which is equal to or greater than the potency of NPY, PYY, or PYY(3-36) in that same assay. Alternatively, preferred PYY analog polypeptides of the invention may exhibit improved ease of manufacture, stability, and/or ease of formulation, as compared to PP, NPY, PYY, or PYY(3-36).

Preferably, the PPF chimeric polypeptides of the invention retain at least about 25%, preferably about 30%, 40%, 50%, 60%, 70%, 80%, 90%, 95%, 98%, or 99% percent of the biological activity of native human PYY with regard to the reduction of nutrient availability, the reduction of food intake, the effect of body weight gain, and/or the treatment and prevention of metabolic conditions and disorders. In another embodiment, the PPF chimeric polypeptides of the invention exhibit improved PYY agonist activity. Preferably, the PPF chimeric polypeptides of the invention exhibits at least about 110%, 125%, 130%, 140%, 150%, 200%, or more of the biological activity of native human PYY with regard to the reduction of nutrient availability the reduction of food intake, the effect of body weight gain, and/or the treatment and prevention of metabolic conditions and disorders.

More particularly, in one aspect, the PPF chimeric polypeptides preferably comprise a fragment of PP linked to a fragment of PYY. In one embodiment, the PPF chimeric polypeptides of the invention comprise an N-terminal fragment of PP or a PP analog polypeptide linked at its C-terminal end to a C-terminal fragment of PYY or a PYY analog polypeptide. In another embodiment, the PPF chimeric polypeptides of the invention comprise an N-terminal fragment of PYY, PYY(3-36), or a PYY analog polypeptide linked at its C-terminal end to a C-terminal fragment of PP or a PP analog polypeptide.

In another aspect, the PPF chimeric polypeptides preferably comprise a fragment of PYY linked to a fragment of NPY. In one embodiment, the PPF chimeric polypeptides of the invention comprise an N-terminal fragment of PYY, PYY (3-36), or a PYY analog polypeptide linked at its C-terminal end to a C-terminal fragment of NPY or a NPY analog polypeptide. In another embodiment, the PPF chimeric polypeptides of the invention comprise an N-terminal fragment of NPY or a NPY analog polypeptide linked at its C-terminal end to a C-terminal fragment of PYY or a PYY analog polypeptide.

In yet another aspect, the PPF chimeric polypeptides preferably comprise a fragment of PP linked to a fragment of NPY. In one embodiment, the PPF chimeric polypeptides of the invention comprise an N-terminal fragment of PP or a PP analog polypeptide linked at its C-terminal end to a C-terminal fragment of NPY or a NPY analog polypeptide. In another embodiment, the PPF chimeric polypeptides of the invention comprise an N-terminal fragment of NPY or a NPY analog polypeptide linked at its C-terminal end to a C-terminal fragment of PP or a PP analog polypeptide.

A fragment of PP, a PP analog polypeptide, PYY, PYY(3-36), a PYY analog polypeptide, NPY, or an NPY analog polypeptide is preferably a fragment comprising anywhere from 4 to 20 amino acid residues of the PP, PP analog polypeptide, PYY, PYY(3-36), PYY analog polypeptide, NPY, or NPY analog polypeptide. In a preferred embodiment, the length of fragment is selected so as to obtain a final PPF chimeric polypeptide of at least 34 amino acids in length.

The PPF chimeric polypeptides of the present invention may also comprise further modifications including, but are not limited to, substitution, deletion, and insertion to the amino acid sequence of such PPF chimeric polypeptides and any combination thereof. In a preferred aspect, the PPF chimeric polypeptides of the invention include one or more modifications of a "non-essential" amino acid residue. In the context of the invention, a "non-essential" amino acid residue is a residue that can be altered, i.e., deleted or substituted, in the native human amino acid sequence of the fragment, e.g., the PP family polypeptide fragment, without abolishing or substantially reducing the PYY agonist activity of the PPF chimeric polypeptide.

The present invention also relates to derivatives of the PPF chimeric polypeptides. Such derivatives include PPF chimeric polypeptides conjugated to one or more water soluble polymer molecules, such as polyethylene glycol ("PEG") or fatty acid chains of various lengths (e.g., stearyl, palmitoyl, octanoyl, oleoyl etc.), or by the addition of polyamino acids, such as poly-his, poly-arg, poly-lys, and poly-ala. Modifications to the PPF chimeric polypeptides can also include small molecule substituents, such as short alkyls and constrained alkyls (e.g., branched, cyclic, fused, adamantyl), and aromatic groups. The water soluble polymer molecules will preferably have a molecular weight ranging from about 500 to about 20,000 Daltons.

Such polymer-conjugations and small molecule substituent modifications may occur singularly at the N- or C-terminus or at the side chains of amino acid residues within the sequence of the PPF chimeric polypeptides. Alternatively, there may be multiple sites of derivatization along the PPF chimeric polypeptide. Substitution of one or more amino acids with lysine, aspartic acid, glutamic acid, or cysteine may provide additional sites for derivatization. See, e.g., U.S. Pat. Nos. 5,824,784 and 5,824,778. Preferably, the PPF chimeric polypeptides may be conjugated to one, two, or three polymer molecules.

The water soluble polymer molecules are preferably lined to an amino, carboxyl, or thiol group, and may be linked by N or C terminus, or at the side chains of lysine, aspartic acid, glutamic acid, or cysteine. Alternatively, the water soluble polymer molecules may be linked with diamine and dicarboxylic groups. In a preferred embodiment, the PPF chimeric polypeptides of the invention are conjugated to one, two, or three PEG molecules through an epsilon amino group on a lysine amino acid.

PPF chimeric polypeptide derivatives of the invention also include PPF chimeric polypeptides with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of the PPF chimeric polypeptides. In one embodiment, the C-terminus of these peptides may have a free —OH or —NH$_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group (isocap), an octanyl group, an octyl glycine group (G(Oct)), or an 8-aminooctanic acid group. In a preferred embodiment, cyclization can be through the formation of disulfide bridges. Alternatively, there may be multiple sites of chemical alteration along the PYY analog polypeptide.

In a preferred aspect, the PPF chimeric polypeptides include those having an amino acid sequence of SEQ ID NOs. 238-347.

Examples of the PPF chimeric polypeptides of the present invention are provided in the Sequence Listing and further discussed in the Examples section below.

B. Use of PPF Polypeptides in the Treatment or Prevention of Metabolic Conditions or Disorders It has been generally accepted that endogenous NPY (reviewed in Schwartz et al., Nature 404: 661-71 (2000)) and PYY (Morley et al., Brain Res. 341: 200-3 (1985)), via their receptors, increase feeding behavior. Methods directed at therapies for obesity have invariably attempted to antagonize Y receptors, while claims for treating anorexia have been directed at agonists of this ligand family. However, as described and claimed in the commonly-owned pending U.S. patent application No. 20020141985, it has been surprisingly discovered that peripheral administration of PYY analog polypeptides has a potent effect to reduce nutrient availability (see also Batterham et al., Nature 418: 650-4, 2002; WO 03/026591; and WO 03/057235), rather than increase it as suggested by reports in the patent and scientific literature (see, e.g., U.S. Pat. Nos. 5,912,227 and 6,315,203 which disclose the use of PYY receptor agonists to increase weight gain). The spectrum of actions of inhibition of food intake, slowing of gastric emptying, inhibition of gastric acid secretion, and inhibition of pancreatic enzyme secretion, are useful to exert clinical benefit in metabolic diseases such as type 1, type 2, or gestational diabetes mellitus, obesity and other manifestations of insulin-resistance syndrome (Syndrome X), and in any other use for reducing nutrient availability.

As such, in another aspect of the invention, methods for treating or preventing obesity are provided, wherein the method comprises administering a therapeutically or prophylactically effective amount of a PPF polypeptide to a subject in need thereof. In a preferred embodiment, the subject is an obese or overweight subject. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method.

In other aspects of the invention, methods of reducing food intake, reducing nutrient availability, causing weight loss, affecting body composition, and altering body energy content or increasing energy expenditure, treating diabetes mellitus, and improving lipid profile (including reducing LDL cholesterol and triglyceride levels and/or changing HDL cholesterol levels) are provided, wherein the methods comprise administering to a subject an effective amount of a PPF polypeptide of the invention. In a preferred embodiment, the methods of the invention are used to treat or prevent conditions or disorders which can be alleviated by reducing nutrient availability in a subject in need thereof, comprising administering to said subject a therapeutically or prophylactically effective amount of a PPF polypeptide of the invention. Such conditions and disorders include, but are not limited to, hypertension, dyslipidemia, cardiovascular disease, eating disorders, insulin-resistance, obesity, and diabetes mellitus of any kind.

Without intending to be limited by theory, it is believed that the effects of peripherally-administered PPF polypeptides of the present invention in the reduction of food intake, in the delay of gastric emptying, in the reduction of nutrient availability, and in the causation of weight loss are determined by interactions with one or more unique receptor classes in, or similar to, those in the PP family. More particularly, it appears that a receptor or receptors similar to the PYY-preferring (or Y7) receptors are involved.

Additional assays useful to the invention include those that can determine the effect of PPF compounds on body composition. An exemplary assay can be one that involves utilization of a diet-induced obese (DIO) mouse model for metabolic disease. Prior to the treatment period, male C57BL/6J mice can be fed a high-fat diet (#D12331, 58% of calories from fat; Research Diets, Inc.) for 6 weeks beginning at 4 weeks of age. During the study, the mice can continue to eat their high-fat diet. Water can be provided ad libitum throughout the study. One group of similarly-aged non-obese mice can be fed a low-fat diet (#D12329, 11% of calories from fat) for purposes of comparing metabolic parameters to DIO groups.

DIO mice can be implanted with subcutaneous (SC) intrascapular osmotic pumps to deliver either vehicle (50% dimethylsulfoxide [DMSO] in water) n=20 or a compound of the invention n=12. The pumps of the latter group can be set to deliver any amount, e.g., 1000 μg/kg/d of a compound of the invention for 7 days.

Body weights and food intake can be measured over regular intervals throughout the study periods. Respiratory quotient (RQ, defined as $CO_2$ production÷$O_2$ consumption) and metabolic rate can be determined using whole-animal indirect calorimetry (Oxymax, Columbus Instruments, Columbus, Ohio). The mice can be euthanized by isoflurane overdose, and an index of adiposity (bilateral epididymal fat pad weight) measured. Moreover, prior to determination of epididymal weight, body composition (lean mass, fat mass) for each mouse can be analyzed using a Dual Energy X-ray Absorptiometry (DEXA) instrument per manufacturer's instructions (Lunar Piximus, GE Imaging System). In the methods of the invention, preferred PPF polypeptide of the invention are those having a potency in one of the assays described herein (preferably food intake, gastric emptying, pancreatic secretion, weight reduction or body composition assays) which is greater than the potency of PP, NPY, PYY, or PYY(3-36) in that same assay.

In addition to the amelioration of hypertension in subjects in need thereof as a result of reduced food intake, weight loss, or treating obesity, compounds of the invention may be used to treat hypotension as described in Example 4.

Compounds of the invention may also be useful for potentiating, inducing, enhancing or restoring glucose responsivity in pancreatic islets or cells. These actions may be useful for treating or preventing conditions associated with metabolic disorders such as those described above and in U.S. patent application No. US20040228846. Assays for determining such activity are known in the art. For example, in published U.S. patent application No. US20040228846 (incorporated by reference in its entirety), assays are described for islet isolation and culture as well as determining fetal islet maturation. In the examples of patent application US20040228846, intestine-derived hormone peptides including pancreatic polypeptide (PP), neuropeptide Y (NPY), neuropeptide K (NPK), PYY, secretin, glucagon-like peptide-1 (GLP-1) and bombesin were purchased from Sigma. Collagenase type XI was obtained from Sigma. RPMI 1640 culture medium and fetal bovine serum were obtained from Gibco. A radioimmunoassay kit containing anti-insulin antibody ([$^{125}$I]-RIA kit) was purchased from Linco, St Louis.

Post-partem rat islets were obtained from P-02 year old rats. Adult rat islets were obtained from 6-8 week old rats. Fetal rat islets were obtained as follows. Pregnant female rats were sacrificed on pregnancy day e21. Fetuses were removed from the uterus. 10-14 pancreata were dissected from each litter and washed twice in Hanks buffer. The pancreas were pooled, suspended in 6 ml 1 mg/ml collagenase (Type XI, Sigma) and incubated at 37° C. for 8-10 minutes with constant shaking. The digestion was stopped by adding 10 volumes of ice-cold Hanks buffer followed by three washes with Hanks buffer. The islets were then purified by Ficoll gradient and cultured in 10% fetal bovine serum (FBS)/RPMI medium with or without addition of 1 μM IBMX. At the end of five days, 20 islets were hand picked into each tube and assayed for static insulin release. Generally, islets were first washed with KRP buffer and then incubated with 1 ml of KRP buffer containing 3 mM (low) glucose for 30 minutes at 37° C. with constant shaking. After collecting the supernatant, the islets were then incubated with 17 mM (high) glucose for one hour at 37° C. The insulin released from low or high glucose stimulation were assayed by radioimmunoassay (RIA) using the [$^{125}$I]-RIA kit. E21 fetal islets were cultured for 5 days in the presence of 200 ng/ml PYY, PP, CCK, NPK, NPY, Secretin, GLP-1 or Bombesin.

An exemplary in vivo assays is also provided using the Zucker Diabetic Fatty (ZDF) male rat, an inbred (>F30 Generations) rat model that spontaneously expresses diabetes in all fa/fa males fed a standard rodent diet Purina 5008. In ZDF fa-fa males, hyperglycemia begins to develop at about seven weeks of age and glucose levels (fed) typically reach 500 mg/DL by 10 to 11 weeks of age. Insulin levels (fed) are high during the development of diabetes. However, by 19 weeks of age insulin drops to about the level of lean control litter mates. Triglyceride and cholesterol levels of obese rats are normally higher than those of leans. In the assay, three groups of 7-week old ZDF rats, with 6 rats per group, received the infusion treatment by ALZA pump for 14 days: 1) vehicle control, 2) and 3), PYY with two different doses, 100 pmol/kg/hr and 500 pmol/kg/hr respectively. Four measurements were taken before the infusion and after the infusion at day 7 and day 14: 1) plasma glucose level, 2) plasma insulin level, and 3) plasma triglycerides (TG) level, as well as oral glucose tolerance (OGTT) test. Accordingly, these assays can be used with compounds of the invention to test for desired activity.

Other uses contemplated for the PPF polypeptides include methods for reducing aluminum (Al) concentrations in the central nervous system (see U.S. Pat. No. 6,734,166, incorporated by reference in its entirety) for treating, preventing, or delay the onset of Alzheimer's disease. Assays for determining effects on Al are known in the art and can be found in U.S. Pat. No. 6,734,166 using diploid and Ts mice. These mice were individually housed in Nalgene® brand metabolism or polypropylene cages and given three days to adjust to the cages before experimentation. Mice had free access to food (LabDiet® NIH Rat and Moust/Auto 6F5K52, St. Louis, Mo.) and water during the experiment except for the 16 hours prior to euthanasia when no food was provided. Mice were given daily subcutaneous injections of either active compound or saline. Mice were sacrificed at the end of day 13 for one experiment and day 3 for another, and samples were collected. Mice brain samples were weighted in clean teflon liners and prepared for analysis by microwave digestion in low trace element grade nitric acid. Sample were then analyzed for Al content using Inductively Coupled Plasma Mass Spectrometry (Nuttall et al., Annals of Clinical and Laboratory Science 25, 3, 264-271 (1995)). All tissue handling during analysis took place in a clean room environment utilizing HEPA air filtration systems to minimize background contamination.

The compounds of the invention exhibit a broad range of biological activities, some related to their antisecretory and antimotility properties. The compounds may suppress gastrointestinal secretions by direct interaction with epithelial cells or, perhaps, by inhibiting secretion of hormones or neurotransmitters which stimulate intestinal secretion. Antisecretory properties include inhibition of gastric and/or pancreatic secretions and can be useful in the treatment or prevention of diseases and disorders including gastritis, pancreatitis, Barrett's esophagus, and Gastroesophageal Reflux Disease.

Compounds of the invention are useful in the treatment of any number of gastrointestinal disorders (see e.g., Harrison's Principles of Internal Medicine, McGraw-Hill Inco, New York, 12th Ed.) that are associated with excess intestinal electrolyte and water secretion as well as decreased absorption, e.g., infectious diarrhea, inflammatory diarrhea, short bowel syndrome, or the diarrhea which typically occurs following surgical procedures, e.g., ileostomy. Examples of infectious diarrhea include, without limitation, acute viral diarrhea, acute bacterial diarrhea (e.g., salmonella, campylobacter, and clostridium or due to protozoal infections), or traveller's diarrhea (e.g., Norwalk virus or rotavirus). Examples of inflammatory diarrhea include, without limitation, malabsorption syndrome, tropical sprue, chronic pancreatitis, Crohn's disease, diarrhea, and irritable bowel syndrome. It has also been discovered that the peptides of the invention can be used to treat an emergency or life-threatening situation involving a gastrointestinal disorder, e.g., after surgery or due to cholera.

Compounds of the invention may also be useful for treating or preventing intestinal damage as opposed to merely treating the symptoms associated with the intestinal damage (for example, diarrhea). Such damage to the intestine may be, or a result of, ulcerative colitis, inflammatory bowel disease, bowel atrophy, loss bowel mucosa, and/or loss of bowel mucosal function (see WO 03/105763, incorporated herein by reference in its entirety). Assays for such activity, as described in WO 03/105763, include 11 week old male HSD rats, ranging 250-300 grams housed in a 12:12 light:dark cycle, and allowed ad libitum access to a standard rodent diet (Teklad LM 485, Madison, Wis.) and water. The animals were fasted for 24 hours before the experiment. A simple and reproducible rat model of chronic colonic inflammation has been previously described by Morris G P, et al., "Hapten-induced model of chronic inflammation and ulceration in the rat colon." Gastroenterology. 1989; 96: 795-803. It exhibits a relatively long duration of inflammation and ulceration, affording an opportunity to study the pathophysiology of colonic inflammatory disease in a specifically controlled fashion, and to evaluate new treatments potentially applicable to inflammatory bowel disease in humans.

Rats were anesthetized with 3% isofluorane and placed on a regulated heating pad set at 37° C. A gavage needle was inserted rectally into the colon 7 cm. The hapten trinitrobenzenesulfonic acid (TNBS) dissolved in 50% ethanol (v/v) was delivered into the lumen of the colon through the gavage needle at a dose of 30 mg/kg, in a total volume of 0 0.4-0.6 mL, as described in Mazelin, et al., "Protective role of vagal afferents in experimentally-induced colitis in rats." Juton Nerv Syst. 1998; 73: 38 45. Control groups received saline solution (NaCl 0.9%) intracolonically.

Four days after induction of colitis, the colon was resected from anesthetized rats, which were then euthanized by decapitation. Weights of excised colon and spleen were measured, and the colons photographed for scoring of gross morphologic damage. Inflammation was defined as regions of hyperemia and bowel wall thickening.

Compounds of the invention may also be used to treat or prevent pancreatic tumors (e.g., inhibit the proliferation of pancreatic tumors). Methods of the invention include reducing the proliferation of tumor cells. The types of benign pancreatic tumor cells which may be treated in accordance with the present invention include serous cyst adenomas, microcystic tumors, and solid-cystic tumors. The method is also effective in reducing the proliferation of malignant pancreatic tumor cells such as carcinomas arising from the ducts, acini, or islets of the pancreas. U.S. Pat. No. 5,574,010 (incorporated by reference in its entirety) provides exemplary assays for testing anti-proliferative properties. For example, the '010 patent provides that PANC-1 and MiaPaCa-2 are two human pancreatic adenocarcinoma cancer cell lines which are available commercially from suppliers such as American Type Culture Collection, ATCC (Rockville, Md.). The two tumor cells were grown in RPMI-1640 culture media supplemented with 10% fetal bovine serum, 29.2 mg/L of glutamine, 25 .mu·g gentamicin, 5 ml penicillin, streptomycin, and fungizone solution (JRH Biosciences, Lenexa, Kans.) at 37 degrees Celcius in a NAPCO water jacketed 5% $CO_2$ incubator. All cell lines were detached with 0.25% trypsin (Clonetics, San Diego, Calif.) once to twice a week when a confluent monolayer of tumor cells was achieved. Cells were pelleted for 7 minutes at 500 g in a refrigerated centrifuge at 4 degrees Celcius, and resuspended in trypsin free fortified RPMI 1640 culture media. Viable cells were counted on a hemocytometer slide with trypan blue.

Ten thousand, 20,000, 40,000 and 80,000 cells of each type were added to 96 well microculture plates (Costar, Cambridge, Mass.) in a total volume of 200 ul of culture media per well. Cells were allowed to adhere for 24 hours prior to addition of the PYY or test peptide. Fresh culture media was exchanged prior to addition of peptides. In vitro incubation of pancreatic tumor cells with either PYY or test compound was continued for 6 hours and 36 hours in length. PYY was added to cells at doses of 250 pmol, 25 pmol, and 2.5 pmol per well (N=14). Test compound was added to cells cultures at doses of 400 pmol, 40 pmol, and 4 pmol per well. Control wells received 2 ul of 0.9% saline to mimic the volume and physical disturbance upon adhered tumor cells. Each 96 well plate contained 18 control wells to allow for comparison within each plate during experimentation. Ninety-six (96) well plates were repeated 6 times with varying concentrations of PYY and test compound in both the PANC-1 and MiaPaCa-2 cells.

At the end of the incubation period, 3-(4,5-dimethylthiazolyl-2-yl)-2,5-diphenyltetrazolium Bromide, MTT tetrazolium bromide (Sigma, St. Louis, Mo.) was added to fresh culture media at 0.5 mg/ml. Culture media was exchanged and tumor cells were incubated for 4 hours with MTT tetrazolium bromide at 37 degrees Celcius. At the end of incubation, culture media was aspirated. Formazon crystal precipitates were dissolved in 200 ul of dimethyl sulfoxide (Sigma, St. Louis, Mo.). Quantitation of solubilized formazon was performed by obtaining absorption readings at 500 nm wavelength on an ELISA reader (Molecular Devices, Menlo Park, Calif.). The MTT assay measures mitochondrial NADH dependent dehydrogenase activity, and it has been among the most sensitive and reliable method to quantitative in vitro chemotherapy responses of tumor cells. (Alley, M. C., Scudiero, D. A., Monk, A., Hursey, M. L., Dzerwinski, M. J., Fine, D. L., Abbott, B. J., Mayo, J. G., Shoemaker, R. H. and Boyd, M. R., Feasibility of drug screening with panels of human tumor cell lines using a microculture tetrazolium assay Cancer Res., 48: 589-601, 1988; Carmichael, J., DeGraff, W. G., Gazdar, A. F., Minna, J. D. and Mitchell, J. B., Evaluation of a tetrazolium-based semiautomated colorimetric assay: Assessment of chemosensitivity testing. Cancer Res., 47: 936-942, 1987; McHale, A. P., McHale, L., Use of a tetrazolium based colorimetric assay in assessing photoradiation therapy in vitro. Cancer Lett., 41: 315-321, 1988; and Saxton, R. E., Huang, M. Z., Plante D., Fetterman, H. F., Lufkin, R. B., Soudant, J., Castro, D. J., Laser and daunomycin chemophototherapy of human carcinoma cells. J. Clin. Laser Med. and Surg., 10(5): 331-336, 1992.) Analysis of absorption readings at 550 nm were analyzed by grouping wells of the same test conditions and verifying differences occurring between control and the various peptide concentration treatments by one-way ANOVA.

An exemplary in vivo assay is also provided. The human pancreatic ductal adenocarcinoma Mia Paca-2 was examined for in vivo growth inhibition by peptide YY and test compound. Seventy thousand to 100,000 human Mia PaCa-2 cells were orthotopically transplanted into 48 male athymic mice. After one week, the animals were treated with either PYY or test compound at 200 pmol/kg/hr via mini-osmotic pumps for four weeks. The paired cultures received saline. At sacrifice, both tumor size and mass were measured. Control mice had significant human cancer growth within the pancreas as evidenced by histologic sections. At 9 weeks, ninety percent (90%) of control mice had substantial metastatic disease. Tumor mass was decreased by 60.5% in test treated mice and 27% in PYY treated mice.

For all indications, in preferred embodiments, the PPF polypeptide of the invention is administered peripherally at a dose of about 0.5 µg to about 5 mg per day in single or divided doses or controlled continual release, or at about 0.01 µg/kg to about 500 µg/kg per dose, more preferably about 0.05 µg/kg to about 250 µg/kg, most preferably below about 50 µg/kg. Dosages in these ranges will vary with the potency of each analog or derivative, of course, and may be determined by one of skill in the art.

In the methods of the present invention, PPF polypeptides of the invention may be administered separately or together with one or more other compounds and compositions that exhibit a long term or short-term action to reduce nutrient availability, including, but not limited to other compounds and compositions that comprise an amylin or amylin analog agonist, salmon calcitonin, a cholecystokinin (CCK) or CCK agonist, a leptin (OB protein) or leptin agonist, an exendin or exendin analog agonist, or a GLP-1 or GLP-1 analog agonist. Suitable amylin agonists include, for example, $[^{25,28,29}$Pro-$]$ human amylin (also known as "pramlintide," and described in U.S. Pat. Nos. 5,686,511 and 5,998,367). The CCK used is preferably CCK octopeptide (CCK-8). Leptin is discussed in, for example, (Pelleymounter et al., Science 269: 540-3 (1995); Halaas et al., Science 269: 543-6 (1995); Campfield et al., Science 269: 546-9 (1995)). Suitable exendins include exendin-3 and exendin-4, and exendin agonist compounds include, for example, those described in PCT Publications WO 99/07404, WO 99/25727, and WO 99/25728.

C. Polypeptide Production and Purification

The PPF polypeptides described herein may be prepared using standard recombinant techniques or chemical peptide synthesis techniques known in the art, e.g., using an automated or semi-automated peptide synthesizer, or both.

The PPF polypeptides of the invention can be synthesized in solution or on a solid support in accordance with conventional techniques. Various automatic synthesizers are commercially available and can be used in accordance with known protocols. See, e.g., Stewart and Young, Solid Phase Peptide Synthesis, 2d. ed., Pierce Chemical Co. (1984); Tam et al., J. Am. Chem. Soc. 105: 6442 (1983); Merrifield, Science 232: 341-7 (1986); and Barany and Merrifield, The Peptides, Gross and Meienhofer, eds., Academic Press, New York, 1-284 (1979). Solid phase peptide synthesis may be carried out with an automatic peptide synthesizer (e.g., Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Peptides may also be assembled using an Advanced ChemTech Synthesizer (Model MPS 350, Louisville, Ky.). Peptides may be purified by RP-HPLC (preparative and analytical) using, e.g., a Waters Delta Prep 3000 system and a C4, C8, or C18 preparative column (10µ, 2.2×25 cm; Vydac, Hesperia, Calif.). The active protein can be readily synthesized and then screened in screening assays designed to identify reactive peptides.

The PPF polypeptides of the present invention may alternatively be produced by recombinant techniques well known in the art. See, e.g., Sambrook et al., Molecular Cloning: A Laboratory Manual, 2d ed., Cold Spring Harbor (1989). These PYY analog polypeptides produced by recombinant technologies may be expressed from a polynucleotide. One skilled in the art will appreciate that the polynucleotides, including DNA and RNA, that encode such encoded PYY analog polypeptides may be obtained from the wild-type PYY cDNA, taking into consideration the degeneracy of codon usage. These polynucleotide sequences may incorporate codons facilitating transcription and translation of mRNA in microbial hosts. Such manufacturing sequences may readily be constructed according to the methods well known in the art. See, e.g., WO 83/04053. The polynucleotides above may also optionally encode an N-terminal methionyl residue. Non-peptide compounds useful in the present invention may be prepared by art-known methods. For example, phosphate-containing amino acids and peptides containing such amino acids may be prepared using methods known in the art. See, e.g., Bartlett and Landen, Bioorg. Chem. 14: 356-77 (1986).

A variety of expression vector/host systems may be utilized to contain and express a PPF polypeptide coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein are described herein below.

As such, polynucleotide sequences provided by the invention are useful in generating new and useful viral and plasmid DNA vectors, new and useful transformed and transfected procaryotic and eucaryotic host cells (including bacterial, yeast, and mammalian cells grown in culture), and new and useful methods for cultured growth of such host cells capable of expression of the present PPF polypeptides. The polynucleotide sequences encoding PPF polypeptides herein may be useful for gene therapy in instances where underproduction of PP, PYY, or NPY would be alleviated, or the need for increased levels of such would be met.

The present invention also provides for processes for recombinant DNA production of the present PPF polypeptides. Provided is a process for producing the PPF polypeptides from a host cell containing nucleic acids encoding such PPF polypeptides comprising: (a) culturing said host cell containing polynucleotides encoding such PPF polypeptides under conditions facilitating the expression of such DNA molecule; and (b) obtaining such PPF polypeptides.

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

Alternatively, a yeast system may be employed to generate the PPF polypeptides of the present invention. The coding region of the PPF polypeptide cDNA is amplified by PCR. A DNA encoding the yeast pre-pro-alpha leader sequence is amplified from yeast genomic DNA in a PCR reaction using one primer containing nucleotides 1-20 of the alpha mating factor gene and another primer complementary to nucleotides 255-235 of this gene (Kurjan and Herskowitz, Cell, 30: 933-43 (1982)). The pre-pro-alpha leader coding sequence and PPF polypeptide coding sequence fragments are ligated into a plasmid containing the yeast alcohol dehydrogenase (ADH2) promoter, such that the promoter directs expression of a fusion protein consisting of the pre-pro-alpha factor fused to the mature PPF polypeptide. As taught by Rose and Broach, Meth. Enz. 185: 234-79, Goeddel ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the E. coli β-lactamase gene, and an E. coli origin of replication. The β-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment (Stearns et al., Meth. Enz. 185: 280-97 (1990)). The ADH2 promoter is induced upon exhaustion of glucose in the growth media (Price et al., Gene 55: 287 (1987)). The pre-pro-alpha sequence effects secretion of the fusion protein from the cells. Concomitantly, the yeast KEX2 protein cleaves the pre-pro sequence from the mature PYY analog polypeptides (Bitter et al., Proc. Natl. Acad. Sci. USA 81: 5330-4 (1984)).

PPF polypeptides of the invention may also be recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted PPF polypeptide is purified from the yeast growth medium by, e.g., the methods used to purify PPF polypeptide from bacterial and mammalian cell supernatants.

Alternatively, the cDNA encoding PYY analog polypeptides may be cloned into the baculovirus expression vector pVL 1393 (PharMingen, San Diego, Calif.). This PPF polypeptides-containing vector is then used according to the manufacturer's directions (PharMingen) to infect *Spodoptera frugiperda* cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Proton 2090 Peptide Sequencer confirms its N-terminal sequence.

For example, the DNA sequence encoding the predicted mature PYY analog polypeptide may be cloned into a plasmid containing a desired promoter and, optionally, a leader sequence (see, e.g., Better et al., Science 240: 1041-3 (1988)). The sequence of this construct may be confirmed by automated sequencing. The plasmid is then transformed into E. coli, strain MC1061, using standard procedures employing CaCl2 incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will affect secretion of the mature PYY analog polypeptide and be cleaved during secretion. The secreted recombinant protein is purified from the bacterial culture media by the method described herein below.

Alternatively, the PPF polypeptides of the invention may be expressed in an insect system. Insect systems for protein expression are well known to those of skill in the art. In one such system, *Autographa californica* nuclear polyhedrosis virus (AcNPV) is used as a vector to express foreign genes in *Spodoptera frugiperda* cells or in *Trichoplusia* larvae. The PPF polypeptide coding sequence is cloned into a nonessential region of the virus, such as the polyhedrin gene, and placed under control of the polyhedrin promoter. Successful insertion of PYY analog polypeptide will render the polyhedrin gene inactive and produce recombinant virus lacking coat protein coat. The recombinant viruses are then used to infect *S. frugiperda* cells or *Trichoplusia* larvae in which PYY analog polypeptide is expressed (Smith et al., J. Virol. 46: 584 (1983); Engelhard et al., Proc. Natl. Acad. Sci. USA 91: 3224-7 (1994)).

In another example, the DNA sequence encoding the PPF polypeptide may be amplified by PCR and cloned into an appropriate vector, for example, pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR may be generated to include, for example, an appropriate cleavage site. The recombinant fusion protein may then be cleaved from the GST portion of the fusion protein. The pGEX-3X/PYY analog polypeptide construct is transformed into *E. coli* XL-1 Blue cells (Stratagene, La Jolla, Calif.), and individual transformants are isolated and grown at 37° C. in LB medium (supplemented with carbenicillin) to an optical density at wavelength 600 nm of 0.4, followed by further incubation for 4 hours in the presence of 0.5 mM Isopropyl β-D-Thiogalactopyranoside (Sigma Chemical Co., St. Louis, Mo.). Plasmid DNA from individual transformants is purified and partially sequenced using an automated sequencer to confirm the presence of the desired PPF polypeptide-encoding gene insert in the proper orientation.

The fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at room temperature. The lysate is cleared by sonication, and cell debris is pelleted by centrifugation for 10 min. at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/PYY analog polypeptide fusion protein is produced in bacteria as a soluble protein, it may be purified using the GST Purification Module (Pharmacia Biotech).

The fusion protein may be subjected to digestion to cleave the GST from the mature PYY analog polypeptide. The digestion reaction (20-40 μg fusion protein, 20-30 units human thrombin (4000 U/mg (Sigma) in 0.5 mL PBS) is incubated 16-48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of the PYY analog polypeptide may be confirmed by partial amino acid sequence analysis using an automated sequencer (Applied Biosystems Model 473A, Foster City, Calif.).

In a particularly preferred method of recombinant expression of the PPF polypeptides of the present invention, 293 cells may be co-transfected with plasmids containing the PYY analog polypeptide cDNA in the pCMV vector (5' CMV promoter, 3+ HGH poly A sequence) and pSV2neo (containing the neo resistance gene) by the calcium phosphate method. Preferably, the vectors should be linearized with ScaI prior to transfection. Similarly, an alternative construct using a similar pCMV vector with the neo gene incorporated can be used. Stable cell lines are selected from single cell clones by limiting dilution in growth media containing 0.5 mg/mL G418 (neomycin-like antibiotic) for 10-14 days. Cell lines are screened for PYY analog polypeptide expression by ELISA or Western blot, and high-expressing cell lines are expanded for large scale growth.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

Many of the PPF polypeptides of the present invention may be produced using a combination of both automated peptide synthesis and recombinant techniques. For example, a PPF polypeptide of the present invention may contain a combination of modifications including deletion, substitution, and insertion by PEGylation. Such a PPF polypeptide may be produced in stages. In the first stage, an intermediate PPF polypeptide containing the modifications of deletion, substitution, insertion, and any combination thereof, may be produced by recombinant techniques as described. Then after an optional purification step as described below, the intermediate PPF polypeptide is PEGylated through chemical modification with an appropriate PEGylating reagent (e.g., from NeKtar Therapeutics, San Carlos, Calif.) to yield the desired PPF polypeptide. One skilled in the art will appreciate that the above-described procedure may be generalized to apply to a PPF polypeptide containing a combination of modifications selected from deletion, substitution, insertion, derivation, and other means of modification well known in the art and contemplated by the present invention.

It may be desirable to purify the PPF polypeptides generated by the present invention. Peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient method of purifying peptides is reverse phase HPLC, followed by characterization of purified product by liquid chromatography/mass spectrometry (LC/MS) and Matrix-Assisted Laser Desorption Ionization (MALDI) mass spectrometry. Additional confirmation of purity is obtained by determining amino acid analysis.

Certain aspects of the present invention concern the purification, and in particular embodiments, the substantial purification, of an encoded protein or peptide. The term "purified peptide" as used herein, is intended to refer to a composition, isolatable from other components, wherein the peptide is purified to any degree relative to its naturally obtainable state. A purified peptide therefore also refers to a peptide, free from the environment in which it may naturally occur.

Generally, "purified" will refer to a peptide composition that has been subjected to fractionation to remove various other components, and which composition substantially retains its expressed biological activity. Where the term "substantially purified" is used, this designation will refer to a composition in which the peptide forms the major component of the composition, such as constituting about 50%, about 60%, about 70%, about 80%, about 90%, about 95% or more of the peptides in the composition.

Various techniques suitable for use in peptide purification will be well known to those of skill in the art. These include, for example, precipitation with ammonium sulphate, PEG, antibodies, and the like; heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the peptides always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed, utilizing an HPLC apparatus, will generally result in a greater "-fold" purification than the same technique utilizing a low pressure chromatography system. Methods exhibiting a lower degree of relative purification may have advantages in total recovery of protein product, or in maintaining the activity of an expressed protein.

One may optionally purify and isolate such PPF polypeptides from other components obtained in the process. Methods for purifying a polypeptide can be found in U.S. Pat. No. 5,849,883. These documents describe specific exemplary methods for the isolation and purification of G-CSF compositions that may be useful in isolating and purifying the PPF polypeptides of the present invention. Given the disclosure of these patents, it is evident that one of skill in the art would be well aware of numerous purification techniques that may be used to purify PPF polypeptides from a given source.

Also it is contemplated that a combination of anion exchange and immunoaffinity chromatography may be employed to produce purified PPF polypeptide compositions of the present invention.

D. Pharmaceutical Compositions

The present invention also relates to pharmaceutical compositions comprising a therapeutically or prophylactically effective amount of at least one PPF polypeptide of the invention, or a pharmaceutically acceptable salt thereof, together with pharmaceutically acceptable diluents, preservatives, solubilizers, emulsifiers, adjuvants and/or carriers useful in the delivery of the PPF polypeptides. Such compositions may include diluents of various buffer content (e.g., acetate, citrate, tartrate, phosphate, TRIS), pH and ionic strength; additives such as surfactants and solubilizing agents (e.g., sorbitan monooleate, lecithin, Pluronics, Tween 20 & 80, Polysorbate 20 & 80, propylene glycol, ethanol, PEG-40, sodium dodecyl sulfate), anti-oxidants (e.g., monothioglyercol, ascorbic acid, acetylcysteine, sulfurous acid salts (bisulfise and metabisulfite), preservatives (e.g., phenol, meta-cresol, benzyl alcohol, parabens (methyl, propyl, butyl), benzalkonium chloride, chlorobutanol, thimersol, phenylmercuric salts, (acetate, borate, nitrate), and tonicity/bulking agents (glycerine, sodium chloride, mannitol, sucrose, trehalose, dextrose); incorporation of the material into particulate preparations of polymeric compounds, such as polylactic acid, polyglycolic acid, etc., or in association with liposomes. Such compositions will influence the physical state, stability, rate of in vivo release, and rate of in vivo clearance of the present PYY analog polypeptides. See, e.g., Remington's Pharmaceutical Sciences 1435-712, 18th ed., Mack Publishing Co., Easton, Pa. (1990).

In general, the present PPF polypeptides will be useful in the same way that PP, PYY, or NPY is useful in view of their pharmacological properties. One preferred use is to peripherally administer such PPF polypeptides for the treatment or prevention of metabolic conditions and disorders. In particular, the compounds of the invention possess activity as agents to reduce nutrient availability, reduce of food intake, and effect weight loss.

The present PPF polypeptides may be formulated for peripheral administration, including formulation for injection, oral administration, nasal administration, pulmonary administration, topical administration, or other types of administration as one skilled in the art will recognize. More particularly, administration of the pharmaceutical compositions according to the present invention may be via any common route so long as the target tissue is available via that route. In a preferred embodiment, the pharmaceutical compositions may be introduced into the subject by any conventional peripheral method, e.g., by intravenous, intradermal, intramusclar, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time. Controlled continual release of the compositions of the present invention is also contemplated.

The formulation may be liquid or may be solid, such as lyophilized, for reconstitution. Aqueous compositions of the present invention comprise an effective amount of the PPF polypeptide, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients also can be incorporated into the compositions. In some cases, it will be convenient to provide a PPF polypeptide and another food-intake-reducing, plasma glucose-lowering or plasma lipid-altering agent, such as an amylin, an amylin agonist analog, a CCK or CCK agonist, or a leptin or leptin agonist, or an exendin or exendin agonist analog, and small molecule cannabinoid CB1 receptor antagonists, beta-hydroxysteroid dehydrogenase-1 inhibitors, sibutramine and other drugs marketed for treatment of obesity in a single composition or solution for administration together. In other cases, it may be more advantageous to administer the additional agent separately from said PPF polypeptide.

The PPF polypeptide of the invention may be prepared for administration as solutions of free base, or pharmacologically acceptable salts in water suitably mixed with surface active agents (e.g., sorbitan monooleate, polyoxyethylene sorbitan monolaurate (Tween 20), polyoxyethylene sorbitan monooleate (Tween 80), lecithin, polyoxyethylene-polyoxypropylene copolymers (Pluronics), hydroxypropylcellulose,) or complexation agents (e.g., hydroxypropyl-b-cyclodextrin, sulfobutyether-b-cyclodextrin (Captisol), polyvinylpyrrolidone). Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like. Such products are readily prepared by procedures well known to those skilled in the art. Dispersions also can be prepared in glycerol, liquid polyethylene glycols, and mixtures thereof and in oils. Under ordinary conditions of storage and use, these preparations contain a preservative to prevent the growth of microorganisms.

In one embodiment, the pharmaceutical compositions of the present invention are formulated so as to be suitable for parenteral administration, e.g., via injection or infusion. Preferably, the PPF polypeptide is suspended in an aqueous carrier, for example, in an buffer solution at a pH of about 3.0 to about 8.0, preferably at a pH of about 3.5 to about 7.4, about 3.5 to about 6.0, about 3.5 to about 5.0 or about 3.7 to about 4.7. Useful buffers include sodium acetate/acetic acid, sodium lactate/lactic acid, ascorbic acid, sodium citrate-citric acid, sodium bicarbonate/carbonic acid, sodium succinate/succinic acid, Histidine, Sodium benzoate/benzoic acid, and sodium phosphates, and Tris(hydroxymethyl)aminomehane. A form of repository or "depot" slow release preparation may be used so that therapeutically effective amounts of the preparation are delivered into the bloodstream over many hours or days following transdermal injection or delivery.

The pharmaceutical compositions suitable for injectable use include sterile aqueous solutions or dispersions and sterile powders for the extemporaneous preparation of sterile injectable solutions or dispersions. In all cases, the form should be sterile and should be fluid to the extent that is easily syringable. It is also desirable for the PPF polypeptide of the invention to be stable under the conditions of manufacture and storage and must be preserved against the contaminating action of microorganisms, such as bacteria and fungi. The carrier can be a solvent or dispersion medium containing, for example, water, ethanol, polyol (e.g., sorbitol, glycerol, propylene glycol, and liquid polyethylene glycol, and the like), dimethylacetamide, cremorphor EL, suitable mixtures thereof, and oils (e.g., soybean, sesame, castor, cottonseed, ethyl oleate, isopropyl myristate, glycofurol, corn). The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, meta-cresol, benzyl alcohol, parabens (methyl, propyl, butyl), chlorobutanol, phenol, phenylmercuric salts (acetate, borate, nitrate), sorbic acid, thimerosal, and the like. In many cases, it will be preferable to include tonicity agents (for example, sugars, sodium chloride). Prolonged absorption of the injectable compositions can be brought about by the use in the compositions of agents delaying absorption (for example, aluminum monostearate and gelatin).

Sterile injectable solutions may be prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

In general, the PPF compounds may be formulated into a stable, safe pharmaceutical composition for administration to a patient. Pharmaceutical formulations contemplated for use in the methods of the invention may comprise approximately 0.01 to 20% (w/v), preferably 0.05 to 10%, of the PPF compound. The PPF compounds may be in an acetate, phosphate, citrate or glutamate buffer allowing a pH of the final composition of about 3.0 to about 7.0 containing carbohydrate or polyhydric alcohol as tonicity modifier and, optionally, approximately 0.005 to 5.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

In a particular embodiment of the present invention, a pharmaceutical formulation of the present invention may contain a range of concentrations of PPF compounds, e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in this embodiment. A sufficient amount of water for injection may be used to obtain the desired concentration of solution. The pharmaceutical formulations described herein may be lyophilized. An exemplary formulation can be 1 mg/mL PPF compound in 10 mM sodium acetate buffer solution, pH 4.2, containing 9.3% sucrose as an osmolality modifier.

Generally, a therapeutically or prophylactically effective amount of the present PPF polypeptides will be determined by the age, weight, and condition or severity of the diseases or metabolic conditions or disorders of the recipient. See, e.g., Remington's Pharmaceutical Sciences 697-773. See also Wang and Hanson, Parenteral Formulations of Proteins and Peptides: Stability and Stabilizers, Journal of Parenteral Science and Technology, Technical Report No. 10, Supp. 42:2S (1988). Typically, a dosage of between about 0.001 μg/kg body weight/day to about 1000 μg/kg body weight/day, may be used, but more or less, as a skilled practitioner will recognize, may be used. Dosing may be one, two, three, four or more times daily, or less frequently, such as once a week, once a month, or once a quarter, depending on the formulation, and may be in conjunction with other compositions as described herein. It should be noted that the present invention is not limited to the dosages recited herein.

Appropriate dosages may be ascertained through the use of established assays for determining level of metabolic conditions or disorders in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

An effective dose will typically be in the range of about 0.5 to 30 μg to about 5 mg/day, preferably about 10 to 30 μg to about 2 mg/day and more preferably about 5 to 100 μg to about 1 mg/day, most preferably about 5 μg to about 500 μg/day, administered in a single or divided doses of two, three, four or more administration. Accordingly, exemplary doses can be derived from the total amount of drug to be given a day and the number doses administered a day. For example, exemplary doses can range from about 0.125 μg/dose (0.5 fig given four times a day) to about 2 mg/dose (2 mg given once a day). Other dosages can be between about 0.01 to about 100 μg/kg/dose. The exact dose to be administered may be determined by one of skill in the art and is dependent upon the potency of the particular compound, as well as upon the age, weight and condition of the individual. Administration should begin whenever the suppression of nutrient availability, food intake, weight, blood glucose or plasma lipid lowering is desired, for example, at the first sign of symptoms or shortly after diagnosis of obesity, diabetes mellitus, or insulin-resistance syndrome. Administration may be by any route, e.g., injection, preferably subcutaneous or intramuscular, oral, nasal, transdermal, etc. Dosages for certain routes, for example oral administration, may be increased to account for decreased bioavailablity, for example, by about 5-100 fold.

In one embodiment, where the pharmaceutical formulation is to be administered parenterally, the composition is formulation so as to deliver a dose of PPF polypeptide ranging from 0.1 μg/kg to 100 mg/kg body weight/day, preferably at doses ranging from 1 μg/kg to about 50 mg/kg body weight/day. Exemplary daily amounts may be in the range of a lower limit of 2, 5, 10, 20, 40, 60 or 80 to an upper limit of 80 100, 150, 200, or 250. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, e.g., Remington's Pharmaceutical Sciences, supra, pages 1435-1712. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice, rats, rabbits, guinea pigs and hamsters; and poultry such as chickens, turkeys, ducks and geese.

In addition, the present invention contemplates a kit comprising a PPF polypeptide of the invention, components suitable for preparing said PPF polypeptide of the invention for pharmaceutical application, and instructions for using said PPF polypeptide and components for pharmaceutical application.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of the present PPF polypeptides, and the testing of these PPF polypeptides of the invention in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of PPF Polypeptides

Peptides of the invention may be assembled on a Symphony peptide synthesizer (Protein Technologies, Inc.) using Rink amide resin (Novabiochem) with a loading of 0.43-0.49 mmol/g at 0.050-0.100 mmol. Fmoc amino acid (5.0 eq, 0.250-0.500 mmol) residues are dissolved at a concentration of 0.10 M in 1-methyl-2-pyrrolidinone. All other reagents (HBTU, 1-hydroxybenzotriazole hydrate and N,N-Diisopropylethylamine) are prepared as 0.55 M dimethylformamide solutions. The Fmoc protected amino acids are then coupled to the resin-bound amino acid using, HBTU (2.0 eq, 0.100-0.200 mmol), 1-hydroxybenzotriazole hydrate (1.8 eq, 0.090-0.18 mmol), N,N-diisopropylethylamine (2.4 eq, 0.120-0.240 mmol) for 2 hours. Following the last amino acid coupling, the peptide is deprotected using 20% (v/v) piperidine in dimethylformamide for 1 hour. Once peptide sequence is complete, the Symphony peptide synthesizer is programmed to cleave the resin. Trifluoroacetic acid (TFA) cleavage of the peptide from resin is carried out using 93% TFA, 3% phenol, 3% water and 1% triisopropylsilane for 1 hour. The cleaved peptide is precipitated using tert-butyl methyl ether, pelleted by centrifugation and lyophilized. The pellet is re-dissolved in water (10-15 mL), filtered and purified via reverse phase HPLC using a C18 column and an acetonitrile/water gradient containing 0.1% TFA. The resulting peptides are purified to homogeneity by reverse phase HPLC and the purity is confirmed by LCMS.

A general procedure for N-capping the peptides of the invention with fatty acids (e.g., octanoic and stearic acids) is as follows: Peptide on rink amide resin (0.1 mmol) is suspended in NMP (5 mL). In a separate vial, HBTU (0.3 mmol), HOBt (0.3 mmol) is dissolved in DMF (5 mL) followed by the addition of DIEA (0.6 mmol). This solution is added to the resin and this suspension is shaken for 2 hrs. The solvent is filtered and washed thoroughly with NMP (5 mL×4) and $CH_2Cl_2$ (20 mL), dried and is subjected to the TFA cleavage for 1 hr. The yield of the desired peptide is ca. 40 mg after cleavage and purification.

PEG modification may be carried out in solution on a free epsilon-amino group of lysine or a terminal amino group of a purified peptide using commercially available activated PEG esters. The resulting PEGylated derivatives are purified to homogeneity by reverse phase HPLC and the purity is confirmed by LC/MS and MALDI-MS.

The PPF polypeptides of the invention may be tested in a variety of Y-receptor binding assays using binding assay methodologies generally known to those skilled in the art. Such assays include those described below.

NPY Y1 Receptor Binding Assay:

Membranes are prepared from confluent cultures of SK-N-MC cells that endogenously expresses the neuropeptide Y1 receptors. Membranes are incubated with 60 pM [$^{125}$I]-human Peptide YY (2200 Ci/mmol, PerkinElmer Life Sciences), and with unlabeled PPF polypeptide for 60 minutes at ambient temperature in a 96 well polystyrene plate. The well contents are then harvested onto a 96 well glass fiber plate using a Perkin Elmer plate harvestor. Dried glass fiber plates are combined with scintillant and counted on a Perkin Elmer scintillation counter.

NPY Y2 Receptor Binding Assay:

Membranes are prepared from confluent cultures of SK-N-BE cells that endogenously expresses the neuropeptide Y2 receptors. Membranes are incubated with 30 pM [$^{125}$I]-human Peptide YY (2200 Ci/mmol, PerkinElmer Life Sciences), and with unlabeled PPF polypeptide for 60 minutes at ambient temperature in a 96 well polystyrene plate. The well contents are then harvested onto a 96 well glass fiber plate using a Perkin Elmer plate harvestor. Dried glass fiber plates are combined with scintillant and counted on a Perkin Elmer scintillation counter.

NPY Y4 Receptor Binding Assay:

CHO-K1 cells are transiently transfected with cDNA encoding neuropeptide Y4 gene, and then forty-eight hours later membranes are prepared from confluent cell cultures. Membranes are incubated with 18 pM [$^{125}$I]-human Pancreatic Polypeptide (2200 Ci/mmol, PerkinElmer Life Sciences), and with unlabeled PPF polypeptide for 60 minutes at ambient temperature in a 96 well polystyrene plate. The well contents are then harvested onto a 96 well glass fiber plate using a Perkin Elmer plate harvester. Dried glass fiber plates are combined with scintillant and counted on a Perkin Elmer scintillation counter.

NPY Y5 Receptor Binding Assay:

CHO-K1 cells are transiently transfected with cDNA encoding neuropeptide Y5 gene, and then forty-eight hours later membranes are prepared from confluent cell cultures. Membranes are incubated with 44 pM [$^{125}$I]-human Peptide YY (2200 Ci/mmol, PerkinElmer Life Sciences), and with unlabeled PPF polypeptide for 60 minutes at ambient temperature in a 96 well polystyrene plate. The well contents are then harvested onto a 96 well glass fiber plate using a Perkin Elmer plate harvestor. Dried glass fiber plates are combined with scintillant and counted on a Perkin Elmer scintillation counter.

By way of example, Table 2 demonstrates certain preferred PPF polypeptides of the invention and their activity in various Y-receptor binding assays such as those described above.

| SEQ ID NO: | Y1RBA (nM) | Y2RBA (nM) | Y4 RBA (nM) | Y5RBA (nM) |
|---|---|---|---|---|
| 1 | | | 0.21 | |
| 2 | 0.2 | 0.058 | 4.5 | 0.31 |
| 3 | 6.2 | 0.041 | 54 | 0.85 |
| 4 | 0.48 | 0.24 | 39 | 0.43 |
| 5 | >1000 | 229 | >1000 | 0.59 |
| 6 | 0.42 | 0.19 | 0.84 | 0.19 |
| 7 | 1000 | 21 | 1000 | 1000 |
| 8 | 1000 | 12 | 1000 | 1000 |
| 9 | 0.61 | 0.085 | 51 | 0.47 |
| 10 | 1.3 | 0.023 | 107 | 0.49 |
| 11 | 2.6 | 0.059 | 96 | 0.41 |
| 12 | 1.7 | 0.14 | 16 | 0.31 |
| 13 | 3.2 | 0.42 | 169 | 0.54 |
| 14 | 1000 | 1.6 | 1000 | 6.8 |
| 15 | 1.6 | 0.026 | 52 | 0.33 |
| 16 | 4.1 | 0.048 | 29 | 0.15 |
| 17 | 11 | 0.037 | 104 | 0.36 |
| 18 | 0.32 | 0.031 | 19 | 0.32 |
| 19 | 5.4 | 0.036 | 117 | 0.73 |
| 20 | 2.9 | 0.04 | 93 | 0.42 |
| 21 | 24 | 0.31 | 182 | 3.3 |
| 22 | 12 | 0.1 | 75 | 7.4 |
| 23 | 13 | 0.2 | 54 | 3.2 |
| 26 | 4.4 | 0.04 | 120 | 0.42 |
| 27 | 7 | 0.18 | 104 | 1.3 |
| 28 | 0.55 | 0.032 | 9.2 | 0.23 |
| 29 | 14 | 0.46 | 178 | 0.95 |
| 50 | 0.86 | 0.15 | 14 | 0.6 |
| 51 | 0.68 | 0.14 | 7.7 | 0.56 |
| 52 | 2.7 | 0.19 | 21 | 0.93 |
| 53 | 2.2 | 0.084 | 7.4 | 0.64 |
| 89 | 4.7 | 0.11 | 38 | 0.99 |
| 90 | 15 | 0.46 | 50 | 7.3 |
| 91 | 9.2 | 0.35 | 99 | 1.9 |
| 92 | 9.8 | 0.36 | 107 | 5 |
| 93 | 8.6 | 0.28 | 99 | 5.6 |
| 94 | 1.8 | 0.048 | 27 | 0.54 |
| 95 | 8.2 | 0.67 | 101 | 7.3 |
| 96 | 7.4 | 0.29 | 56 | 6.6 |
| 97 | 8.6 | 0.19 | 54 | 2.9 |
| 98 | 4.4 | 0.099 | 49 | 2.1 |
| 99 | 3.5 | 0.065 | 43 | 0.99 |
| 100 | 5.9 | 0.28 | 70 | 4 |
| 101 | 8.6 | 0.18 | 65 | 3.4 |
| 102 | 7.8 | 0.09 | 58 | 1.8 |
| 103 | 1.8 | 0.038 | 22 | 0.66 |
| 104 | 4.6 | 0.053 | 27 | 0.89 |
| 105 | 4.4 | 0.3 | 68 | 3.3 |
| 106 | 5.4 | 0.081 | 37 | 0.92 |

-continued

| SEQ ID NO: | Y1RBA (nM) | Y2RBA (nM) | Y4 RBA (nM) | Y5RBA (nM) |
|---|---|---|---|---|
| 107 | 11 | 0.27 | 70 | 5.1 |
| 108 | 8.8 | 0.12 | 51 | 2.1 |
| 110 | 20 | 0.81 | 97 | 8.7 |
| 111 | 17 | 0.41 | 71 | 10 |
| 112 | 5.6 | 0.33 | 76 | 6.3 |
| 113 | 6.8 | 0.1 | 37 | 1.2 |
| 114 | 71 | 0.25 | 119 | 14 |
| 115 | 34 | 6.2 | 193 | 55 |
| 116 | 8.9 | 0.23 | 40 | 10 |
| 117 | 7.3 | 0.21 | 74 | 5.8 |
| 118 | 88 | 0.97 | 180 | 31 |
| 119 | 158 | 1.1 | 92 | 47 |
| 120 | 17 | 1.5 | 44 | 27 |
| 121 | 14 | 0.19 | 51 | 14 |
| 122 | 36 | 0.4 | 68 | 2.4 |
| 123 | 45 | 9.2 | 66 | 1.7 |
| 124 | >1000 | 86 | >1000 | 56 |
| 125 | 28 | 9.1 | 129 | 8.4 |
| 126 | 24 | 34 | 88 | 2.4 |
| 127 | >1000 | >1000 | >1000 | >1000 |
| 128 | >1000 | 113 | >1000 | >1000 |
| 142 | 6.2 | 0.12 | 61 | 1.2 |
| 143 | 3.8 | 0.19 | 56 | 2.3 |
| 144 | 4.5 | 0.39 | 52 | 4.6 |
| 145 | 5.4 | 0.12 | 47.5 | 1.5 |
| 146 | 8.7 | 0.19 | 73 | 2.3 |
| 147 | 5.1 | 0.092 | 48 | 1.7 |
| 150 | 276 | 11 | 1000 | 118 |
| 151 | 7.6 | 0.25 | 115 | 2.1 |
| 152 | 3.7 | 0.24 | 3.9 | 0.82 |
| 157 | 5.8 | 0.11 | 63 | 1.6 |
| 158 | 6.1 | 0.11 | 66 | 2.1 |
| 160 | 6.3 | 0.56 | 71 | 2.9 |
| 162 | 11 | 0.47 | 86 | 2.8 |
| 165 | 4.8 | 0.072 | 59 | 1.3 |
| 170 | 0.7 | 0.084 | 17 | 0.82 |
| 171 | 33 | 0.53 | 97 | 10 |
| 174 | 11 | 0.35 | 64 | 80 |
| 175 | 20 | 0.72 | >1000 | >1000 |
| 176 | 7.6 | 0.84 | 120 | 8.5 |
| 177 | 5.8 | 0.34 | 46 | 11 |
| 178 | 7.7 | 0.29 | 38 | 17 |
| 179 | 30 | 5.4 | 33 | 208 |
| 180 | 4.3 | 0.11 | 49 | 3.9 |
| 181 | 6.3 | 0.41 | 46 | 2.4 |
| 182 | 4.4 | 0.21 | 65 | 5.8 |
| 183 | 4.7 | 0.071 | 60 | 9.2 |
| 184 | 26 | 0.14 | 54 | 42 |
| 185 | 3 | 0.13 | 38 | 3.8 |
| 186 | 0.85 | 0.11 | 29 | 2.8 |
| 187 | 1000 | 62 | 1000 | 128 |
| 188 | 1000 | 102 | 1000 | 968 |
| 189 | 1000 | 57 | 1000 | 202 |
| 190 | 1000 | 24 | 1000 | 578 |
| 193 | 308 | 78 | 331 | 180 |
| 194 | 32 | 1.5 | 89 | 15 |
| 195 | 15 | 1.7 | 146 | 5.7 |
| 196 | 1000 | 612 | 1000 | 1000 |
| 197 | 1000 | 46 | 611 | 1000 |
| 198 | 10 | 0.7 | 88 | 9.9 |
| 199 | 38 | 4.1 | 143 | 58 |
| 200 | 106 | 7 | 426 | 74 |
| 201 | 27 | 2.2 | 99 | 29 |
| 202 | 36 | 148 | 23 | 80 |
| 203 | 33 | 4.4 | 108 | 78 |
| 204 | 47 | 1.1 | 223 | 37 |
| 205 | 44 | 1.5 | 172 | 18 |
| 206 | 66 | 15 | 204 | 45 |
| 207 | 180 | 0.69 | 1000 | 114 |
| 208 | 228 | 93 | 407 | 568 |
| 211 | 3.7 | 0.24 | 50 | 5.4 |
| 212 | 2.9 | 0.046 | 59 | 0.8 |
| 225 | 6.7 | 0.15 | 79 | 1.8 |
| 226 | 3 | 0.059 | 35 | 0.57 |
| 227 | 1 | 0.032 | 38 | 0.11 |
| 228 | 4.1 | 0.1 | 61 | 1.1 |
| 229 | 8.2 | 0.23 | 57 | 2.7 |
| 230 | 3.4 | 0.1 | 45 | 1.2 |
| 231 | 5.6 | 0.37 | 55 | 9.4 |
| 235 | 8.7 | 0.65 | 77 | 12 |
| 236 | 6.5 | 0.24 | 62 | 4.6 |
| 237 | 2.1 | 0.11 | 35 | 2.8 |
| 238 | >1000 | 229 | >1000 | 0.59 |
| 239 | 0.18 | 0.092 | 18 | 0.27 |
| 240 | 2.4 | 0.059 | 89 | 0.58 |
| 241 | 4 | 0.15 | 61 | 0.88 |
| 242 | 2.7 | 0.13 | 71 | 1 |
| 243 | 18 | 0.74 | 124 | 7.2 |
| 244 | 11 | 1.5 | 88 | 7.5 |
| 245 | 0.19 | 0.077 | 16 | 0.35 |
| 246 | 3.9 | 0.11 | 119 | 0.7 |
| 247 | 0.38 | 0.12 | 25 | 0.76 |
| 248 | 0.48 | 0.12 | 24 | 0.44 |
| 249 | 0.36 | 0.11 | 21 | 0.34 |
| 250 | 2.2 | 0.075 | 73 | 0.51 |
| 251 | 0.42 | 0.12 | 28 | 0.52 |
| 252 | 2.1 | 0.074 | 52 | 0.64 |
| 253 | 1.3 | 0.041 | 34 | 0.29 |
| 258 | 0.39 | 0.12 | 22 | 0.89 |
| 260 | 0.42 | 0.16 | 22 | 0.74 |
| 261 | 2.9 | 0.11 | 71 | 1 |
| 262 | 1.7 | 0.087 | 61 | 0.91 |
| 263 | 3.2 | 0.1 | 141 | 1.2 |
| 264 | 1.8 | 0.22 | 98 | 0.48 |
| 267 | 0.25 | 0.1 | 9.5 | 0.32 |
| 268 | 0.31 | 0.14 | 21 | 0.57 |
| 269 | 3.8 | 0.084 | 77 | 0.74 |
| 270 | 3.3 | 0.13 | 97 | 1.4 |
| 271 | 0.51 | 0.094 | 4.2 | 0.25 |
| 272 | 0.26 | 0.1 | 12 | 0.27 |
| 273 | 0.32 | 0.18 | 21 | 0.89 |
| 274 | 4.9 | 0.42 | 181 | 1.5 |
| 275 | 0.59 | 0.099 | 81 | 1.5 |
| 276 | 0.68 | 0.3 | 8.3 | 1.3 |
| 277 | 3.4 | 0.16 | 150 | 2.5 |
| 278 | 3.6 | 0.078 | 138 | 1.4 |
| 280 | 2.1 | 0.38 | 108 | 1.6 |
| 281 | 2.8 | 0.1 | 117 | 0.67 |
| 282 | 0.55 | 0.04 | 18 | 0.15 |
| 283 | 30 | 3.4 | 87 | 10.6 |
| 285 | 0.67 | 0.18 | 16 | 0.54 |
| 286 | 0.65 | 0.11 | 0.75 | 0.3 |
| 287 | 5.2 | 0.16 | 10 | 1.2 |
| 288 | 1.8 | 0.35 | 11 | 1.1 |
| 289 |  |  | 48 | 0.83 |
| 290 |  |  | 187 | 0.51 |
| 291 | 186 | 201 | 9.5 | 0.71 |
| 292 | 1.4 | 0.17 | 0.77 | 0.32 |
| 293 | 0.82 | 0.18 | 0.87 | 0.48 |
| 294 | 0.94 | 0.17 | 0.98 | 0.51 |
| 295 | 1 | 0.18 | 1 | 0.63 |
| 296 | 2.7 | 0.76 | 2.9 | 2.1 |
| 297 | 3.6 | 0.32 | 4 | 1.8 |
| 298 | 5.5 | 1.2 | 3.4 | 3.9 |
| 299 | 11 | 3.2 | 16 | 7.5 |
| 300 | 83 | 16 | 311 | 78 |
| 301 | 26 | 3.7 | 70 | 28 |
| 302 | 5.1 | 0.68 | 93 | 2.9 |
| 303 | 6 | 0.5 | 7.1 | 3.3 |
| 304 | 0.51 | 0.14 | 0.48 | 0.28 |
| 305 |  |  |  |  |
| 306 |  | 0.6 | 0.16 | 1.2 | 0.27 |
| 307 | 0.53 | 0.13 | 0.73 | 0.47 |
| 308 | 1 | 0.56 | 2.1 | 1.4 |
| 309 | 3.3 | 78 | 5.6 | 1.5 |
| 310 |  |  | 27 | 5.1 |
| 311 | 16 | 0.49 | 51 | 1.8 |
| 312 |  |  | 91 | 3.4 |
| 313 | 9.2 | 0.57 | 151 | 2.6 |
| 314 | 8.2 | 0.67 | 202 | 2.5 |
| 315 | 9.2 | 2.1 | 467 | 5.6 |
| 316 | 7.1 | 0.63 | 52 | 1.1 |
| 317 | 4.3 | 0.097 | 16 | 0.69 |
| 318 | 100 | 1.3 | 84 | 1.9 |

-continued

| SEQ ID NO: | Y1RBA (nM) | Y2RBA (nM) | Y4 RBA (nM) | Y5RBA (nM) |
|---|---|---|---|---|
| 319 | 35 | 1.04 | 77 | 1.2 |
| 320 | 77 | 3.1 | 243 | 13 |
| 321 | 12 | 3.7 | 57 | 5.6 |
| 333 | 4.8 | 0.54 | 37 | 0.87 |
| 334 | 21 | 0.45 | 101 | 2.4 |
| 335 | 34 | 0.72 | 109 | 3.6 |
| 338 | 8.1 | 0.68 | 46 | 1.1 |
| 341 | 1.8 | 0.15 | 11 | 0.3 |
| 342 | 15 | 0.62 | 84 | 1.4 |
| 343 | 12 | 0.38 | 69 | 1.3 |
| 347 | 35 | 18 | 740 | 51 |

Example 2

PPF Polypeptides Suppress Food Intake in Food Intake Assay

Female NIH/Swiss mice (8-24 weeks old) are group housed with a 12:12 hour light:dark cycle with lights on at 0600. Water and a standard pelleted mouse chow diet are available ad libitum, except as noted. Animals are fasted starting at approximately 1500 hrs, 1 day prior to experiment. The morning of the experiment, animals are divided into experimental groups. In a typical study, n=4 cages with 3 mice/cage.

At time=0 min, all animals are given an intraperitoneal injection of vehicle or compound in an amount ranging from about 10 nmol/kg to 100 nmol/kg, and immediately given a pre-weighed amount (10-15 g) of the standard chow. Food is removed and weighed at 30, 60, and 120 min to determine the amount of food consumed (Morley, Flood et al., Am. J. Physiol. 267: R178-R184, 1994). Food intake is calculated by subtracting the weight of the food remaining after the e.g., 30, 60, 120, 180 and/or 240 minute time point from the weight of the food provided initially at time=0. Significant treatment effects were identified by ANOVA (p<0.05). Where a significant difference exists, test means are compared to the control mean using Dunnett's test (Prism v. 2.01, GraphPad Software Inc., San Diego, Calif.).

FIGS. 1-4 demonstrate the ability of several preferred PPF polypeptides of the invention to reduce cumulative food intake in the food intake assay described above.

Example 3

PPF Polypeptides Decrease Body Weight Gain in High Fat Fed (Diet-Induced-Obesity or DIO) C57BL/6 Mice and High Fat-Fed HSD Rats Mice:
Male C57BL/6 mice (4 weeks old at start of study) are fed high fat (HF, 58% of dietary kcal as fat) or low fat (LF, 11% of dietary kcal as fat) chow. After 4 weeks on chow, each mouse is implanted with an osmotic pump (Alzet #2002) that subcutaneously delivers a predetermined dose of PPF polypeptide continuously for two weeks. Body weight and food intake are measured weekly (Surwit et al., Metabolism—Clinical and Experimental, 44: 645-51, 1995). Effects of the test compound are expressed as the mean+/−sd of % body weight change (i.e., % change from starting weight) of at least 14 mice per treatment group (p<0.05 ANOVA, Dunnett's test, Prism v. 2.01, GraphPad Software Inc., San Diego, Calif.).

Rats:
The night before treatment, male Sprague-Dawley® rats (average weight=415) consuming a high fat diet (45% kCal from fat) were assigned to two treatment groups based on equal 24 hr food intake. On test night, each animal received a single IP injection of Vehicle (10% DMSO) or Compound (1 mg/kg) just prior to lights off (1800 h), and were then placed individually into a DietPro automated feeding cage. Each cage contains a food hopper resting on a scale connected to a computer, and a water bottle. Hourly food intake (in grams) is recorded for the following 24 hours. Animals received injections for six consecutive nights. Body weights were recorded nightly.

Figure 5:
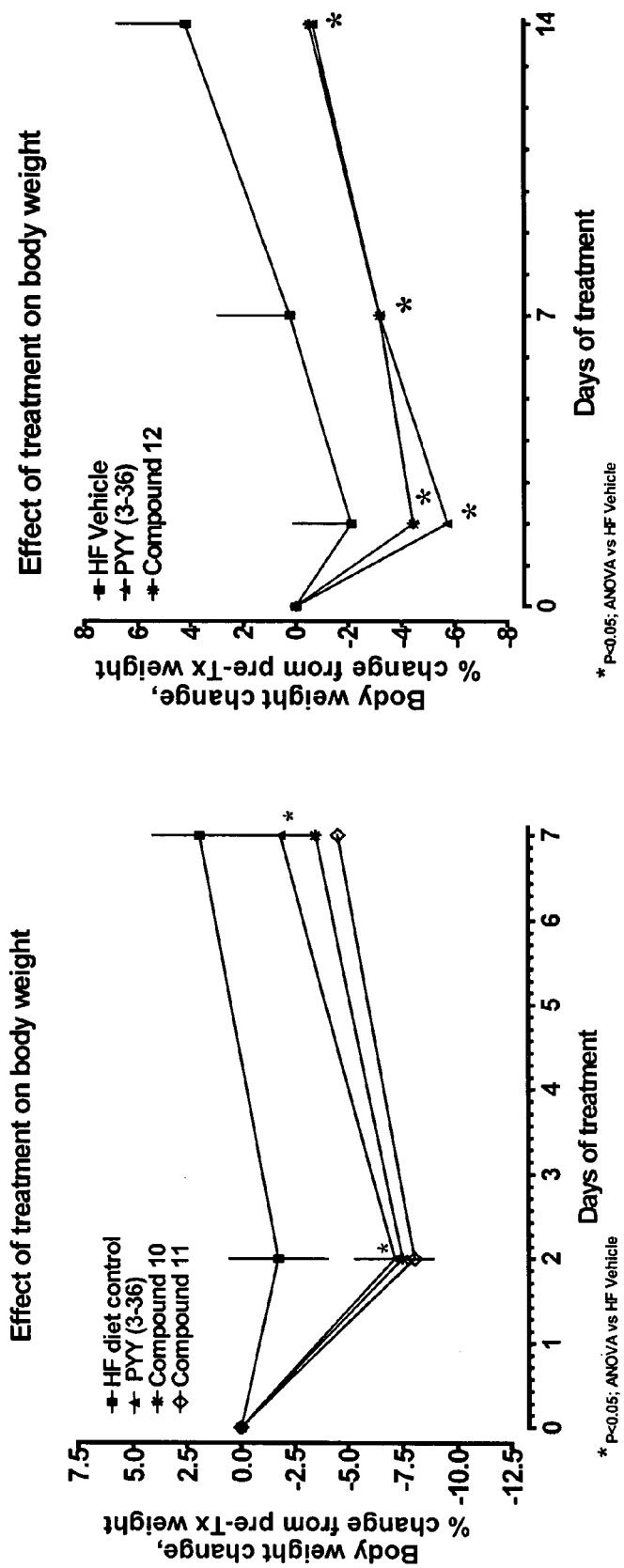
FIG. 5 demonstrates the activity of certain PPF polypeptides of the invention in the DIO mouse model.
Figure 6:
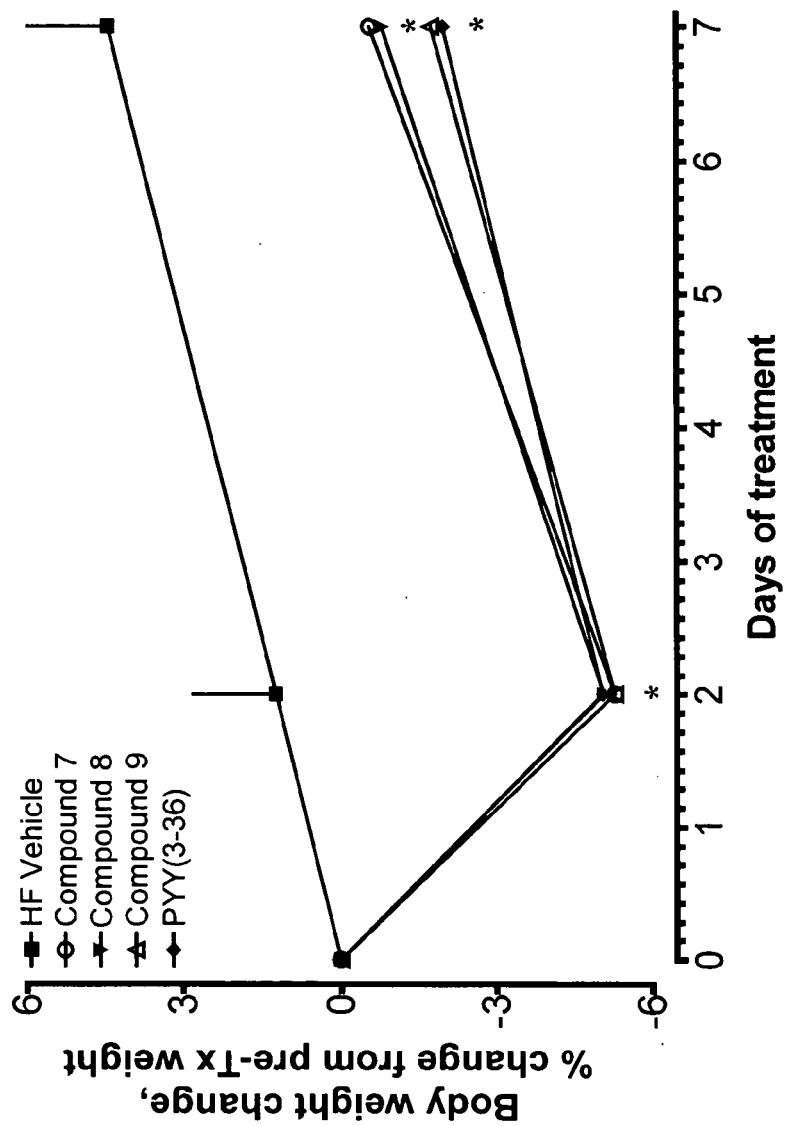
FIG. 6 demonstrates the activity of additional PPF polypeptides of the invention in the DIO mouse model.
Figure 7:
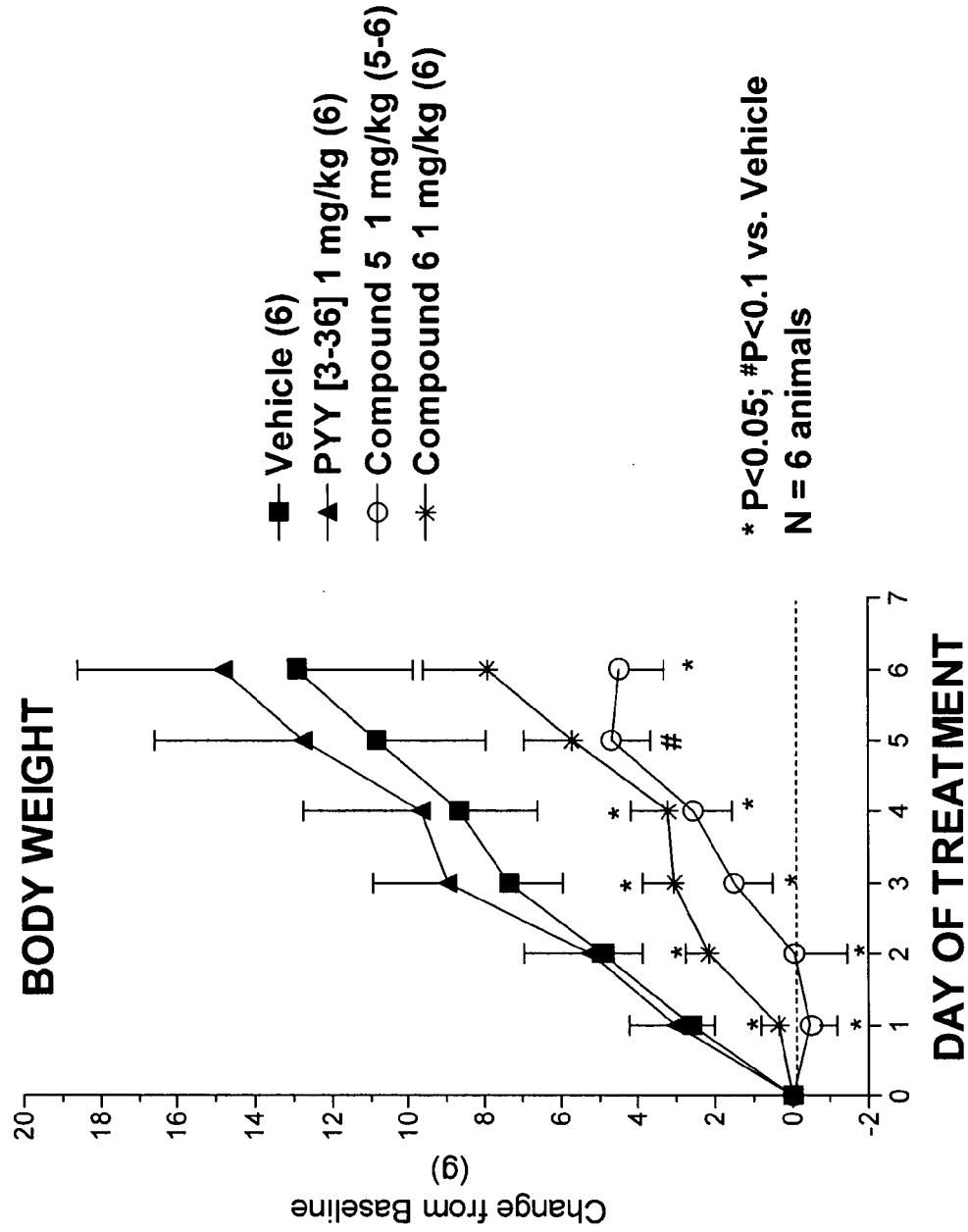
FIG. 7 shows weight gain in rats.
Figure 8:
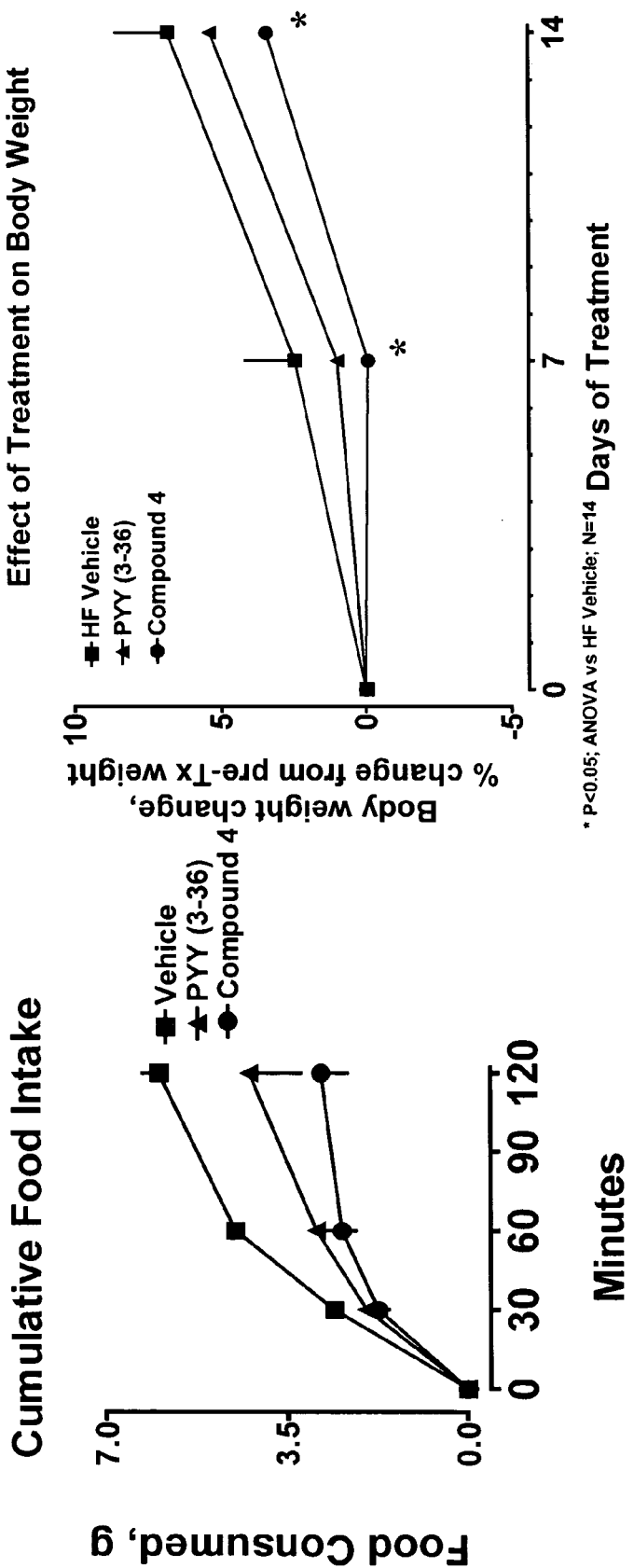
FIG. 8 demonstrates the activity of a PPF polypeptide of the invention in a food intake assay and the DIO mouse model, as compared to PYY(3-36).

FIGS. 5-6 demonstrate the ability of several PPF polypeptides of the invention to decrease body weight gain in the DIO mouse assay described above. FIG. 7 demonstrates that once daily injections resulted in a significant reduction in body weight gain on several nights (P<0.05) in high fat-fed rats. Further, FIG. 8 demonstrates that a PPF polypeptide of the invention exhibits greater efficacy than PYY(3-36) in both the food intake assay and the DIO mouse assay.

Example 4

PPF Polypeptides Reduce Blood Pressure

Male Harlan Sprague Dawley rats housed at 22.8±0.8° C. in a 12:12 hour light:dark cycle were used to study the effects of PPF Polypeptides on the circulatory system through the use of telemetry. The experiments were performed during the light cycle. Telemetry allows for real-time hemodynamic readings including arterial blood pressure, heart rate and arterial dP/dt, via an implanted radio transmitter in conscious, non-anesthetized, unrestrained rats. In the present Example, rats were injected with either vehicle, 10 nmol/kg PYY, 10 nmol/kg PYY(3-36) or 10 nmol/kg of several PPF polypeptides by remote intravenous dosing. Remote intravenous dosing was achieved through in-dwelling vascular access ports (Access Technologies (Skokie, Ill.). The port is secured to the underlying muscle just below the skin between the scapulae. The catheter resides in the jugular vein. Data were collected for up to 60 minutes following injection.

As shown in FIGS. 9A-B, the effect of compound 1 to increase mean arterial pressure are similar to those of PYY (3-36). FIGS. 9C-D show that while the effects of compound 3 to increase mean arterial pressure and decrease heart rate are similar to those of PYY(1-36), those effects are blunted with compound 2.

Example 5

Antisecretory Effects of PYY and PYY Agonists

Gastric Acid Secretion
Male Harlan Sprague Dawley rats were housed at 22.8±0.8° C. in a 12:12 hour light:dark cycle. The experiments were performed during the light cycle. Animals, fed rat chow (Teklad LM 485, Madison, Wis.), were fasted for approximately 20 hours before experimentation. They were given free access to water until the start of the experiment.

The rats (age 11-16 weeks, body mass 291-365 g) were surgically fitted with gastric fistulae custom made by David Osborne, Department of Biology, UCLA. Overnight fasted rats were weighed and their gastric fistulae were uncapped and attached to flexible Tygon tubing (⅜×¹⁄₁₆) into which was fitted a piece of PE205 tubing that would extend into the stomach. Saline was injected through the narrower PE205 tubing and the effluent collected from the Tygon tubing. To ensure proper flow through the fistulae and an empty stomach, the stomach was flushed several times with ~5 ml of room temperature saline solution until flow was easy and the effluent was clean. Gastric acid secretion was measured at 10 min intervals by injecting 5 mL of saline (pH 7.0) followed by 3 ml of air and collecting the effluent. Three ml of each gastric aspirate were titrated to 7.0 with 0.01 N sodium hydroxide using a pH meter (Beckman model number PHI34 Fullerton, Calif.). The amount of base required for each titration, corrected to the total volume collected, was used to calculate the moles of acid in each sample.

After a baseline sample was collected, and the recovered volume recorded, the animal was given a subcutaneous injection of 125 µg/kg pentagastrin (Sigma, lot#40K0616) and then 10 min. gastric sampling was continued for a further 2 hours. Forty minutes after pentagastrin injection, when a stable plateau of gastric acid secretion was typically observed, the rats were given a subcutaneous injection of (PYY[3-36]) at a dose per animal of 1, 3, 10, 100 µg or saline (n=3, 2, 4, 4, 6 respectively), (3.45, 10.34, 34.5, 344.8 µg/kg).

Figure 10:
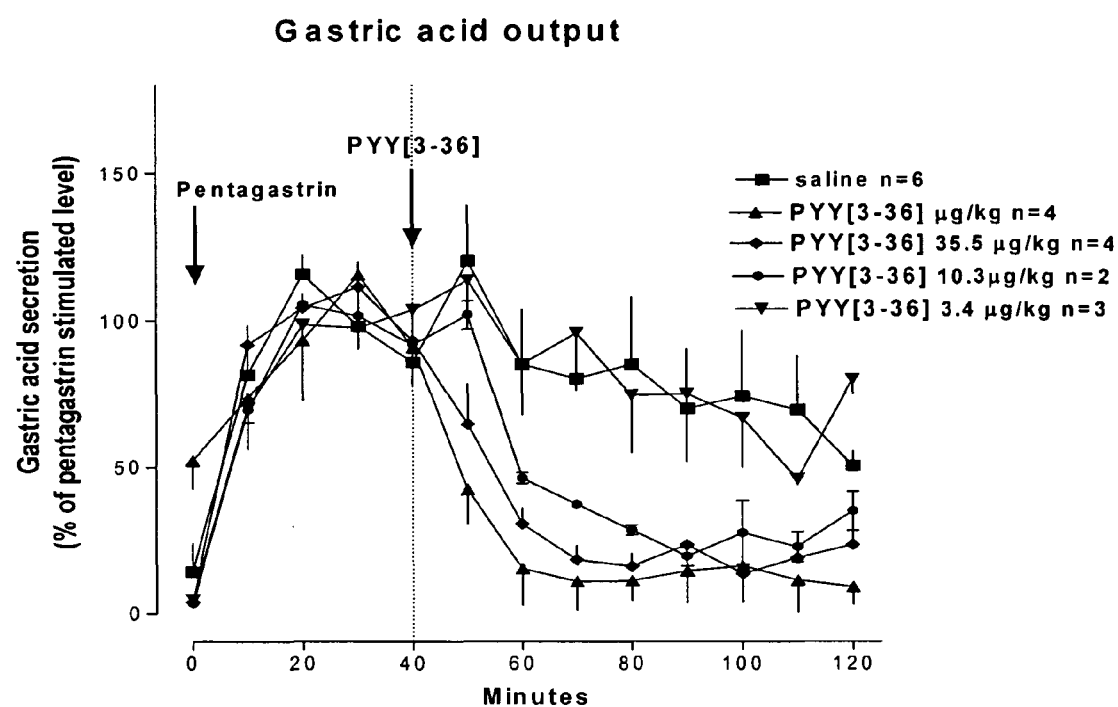
FIG. 10 demonstrates the activity of PPF polypeptides of the invention on gastric acid secretion.
Figure 11:
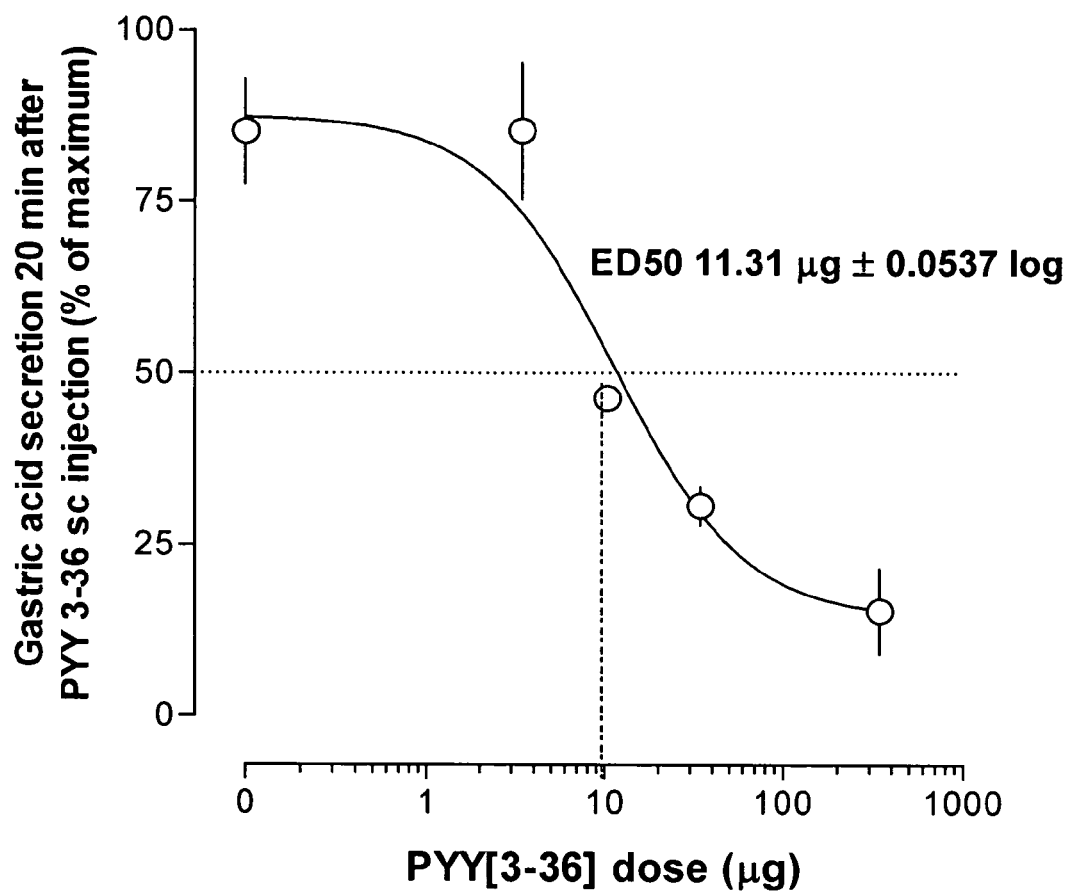
FIG. 11 demonstrates the activity of PPF polypeptides of the invention on gastric acid secretion.

As shown in FIG. 10, gastric acid output was expressed as % of pentagastrin-stimulated secretion, calculated as the average of time points 20, 30, and 40 minutes after injection of pentagastrin. In response to pentagastrin, gastric acid secretion increased 6.8-fold from a basal rate of 9.3±5.8 µmol/10 min to 62.8±3.8 µmol/10 min 40 min after injection (grand means: $P<0.01$). PYY(3-36) injected 40 min after pentagastrin dose-dependently and significantly inhibited gastric acid production. With doses of 10 µg and 100 µg PYY(3-36), acid secretion was reduced by 74.7±7.2% and 84.7±9.7%, respectively ($P<0.05$, $P<0.01$ and $P<0.01$; t-test, 20 minutes after PYY(3-36) injection) (see t=60 min in FIGS. 11-17). The dose response for PYY(3-36) inhibition of pentagastrin-stimulated acid secretion is shown in FIG. 11. The $ED_{50}$ for the antacid effect of PYY(3-36) was 11.31 µg/kg±0.054 log units.

Gastric Emptying

To determine the effects of PYY [3-36] on gastric emptying, conscious, non-fasted male Harlan Sprague Dawley rats with vacuum-aspiration lesions of area postrema (APx) and sham-operated rats were used. Experiments were performed at least 2 weeks post surgery (weight 426±8 g) and again three weeks later (weight 544±9 g). The rats were randomly assigned to treatment groups. All rats were housed at 22.7° C. in a 12:12 h light:dark cycle (experiments performed during light cycle) and were fed and watered ad libitum (diet LM-485 Teklad, Madison, Wis., USA).

PYY[3-36] dissolved in saline was administered as a 0.1 ml subcutaneous bolus in doses of 0, 1 or 10 µg 5 min before gavage of 5 µCi D-[3-$^3$H]-glucose (lot #3165036 Dupont, Wilmington, Del., USA) in 1 ml water. The vehicle or different doses of PYY was given s.c. after animals had been given an oral liquid meal. There were 15 Treatment Groups:

| (1) Control saline | n = 4 |
|---|---|
| (2) Control 3 µg/kg | n = 3 |
| (3) Control 30 µg/kg | n = 4 |
| (4) Control 90 µg/kg | n = 5 |
| (5) Control 300 µg/kg | n = 5 |
| (6) Sham saline | n = 5 |
| (7) Sham 3 µg/kg | n = 2 |
| (8) Sham 30 µg/kg | n = 4 |
| (9) Sham 90 µg/kg | n = 3 |
| (10) Sham 300 µg/kg | n = 5 |
| (11) APx saline | n = 5 |
| (12) APx 3 µg/kg | n = 3 |
| (13) APx 30 µg/kg | n = 3 |
| (14) APx 90 µg/kg | n = 3 |
| (15) APx 300 µg/kg | n = 5 |

Blood was collected from anesthetized tails of the rats at −15, 0, 5, 15, 30, 60 and 90 min after gavage for measurements and the plasma separated to measure the plasma glucose-derived tritium (CPM per 10 µl counted in β-counter). The appearance of tritium in plasma has previously been shown to reflect gastric emptying. The integrated tritium appearance in plasma was calculated using the trapezoidal method as the increment above the levels before the tritium gavage (the area-under-the-curve for 30 minutes).

Figure 12:
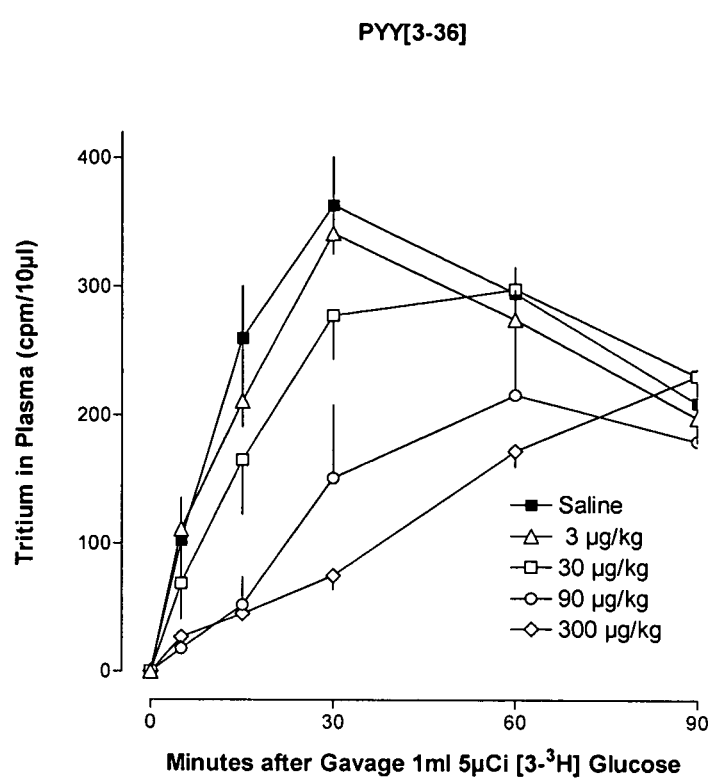
FIG. 12 demonstrates the activity of PPF polypeptides of the invention on gastric emptying.
Figure 13:
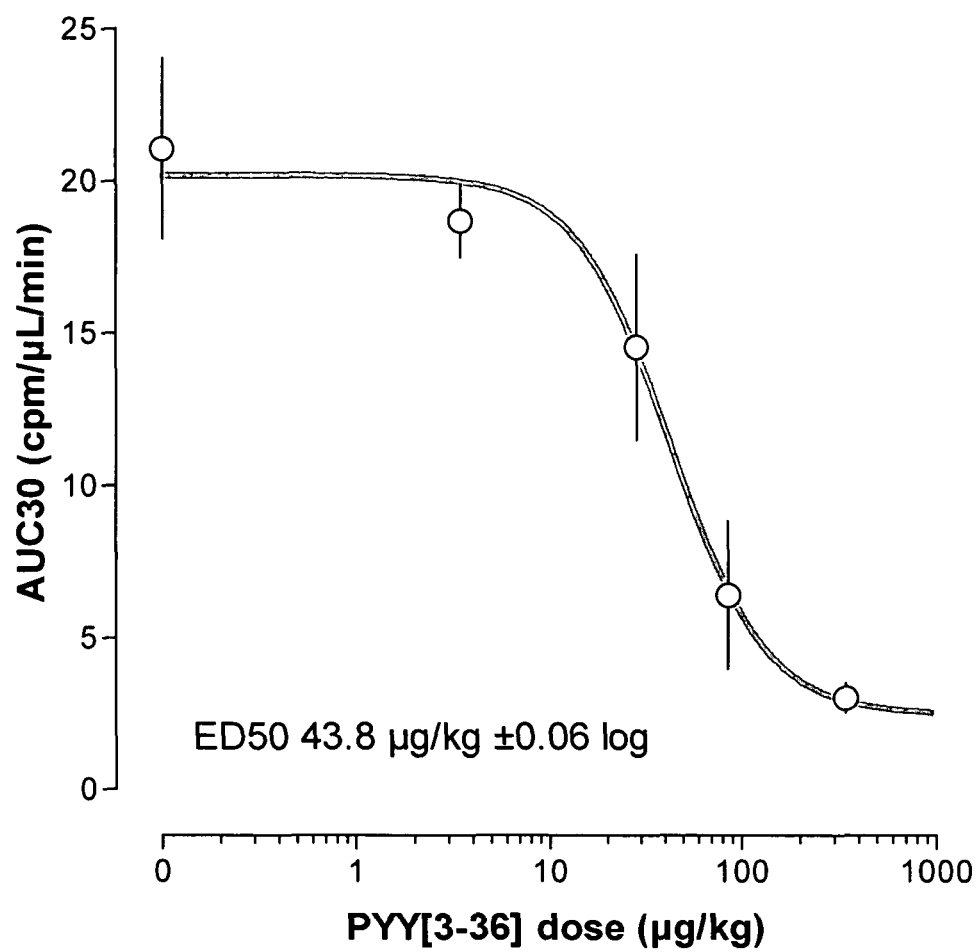
FIG. 13 demonstrates the activity of PPF polypeptides of the invention on gastric emptying.
Figure 14:
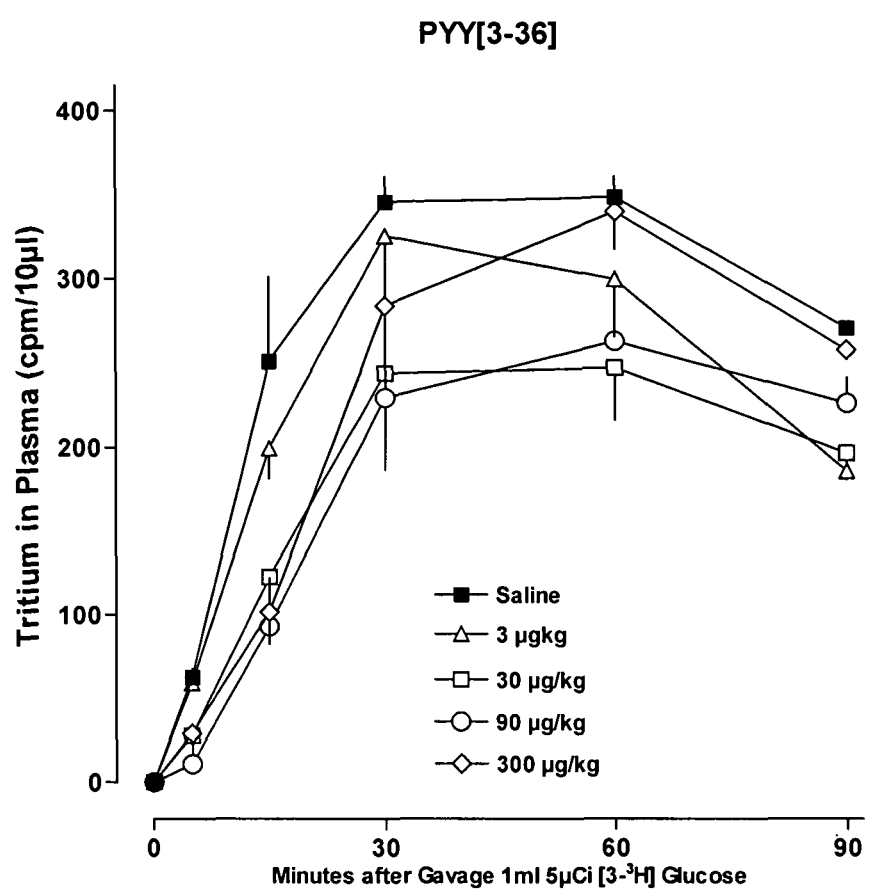
FIG. 14 demonstrates the activity of PPF polypeptides of the invention on gastric emptying.
Figure 15:
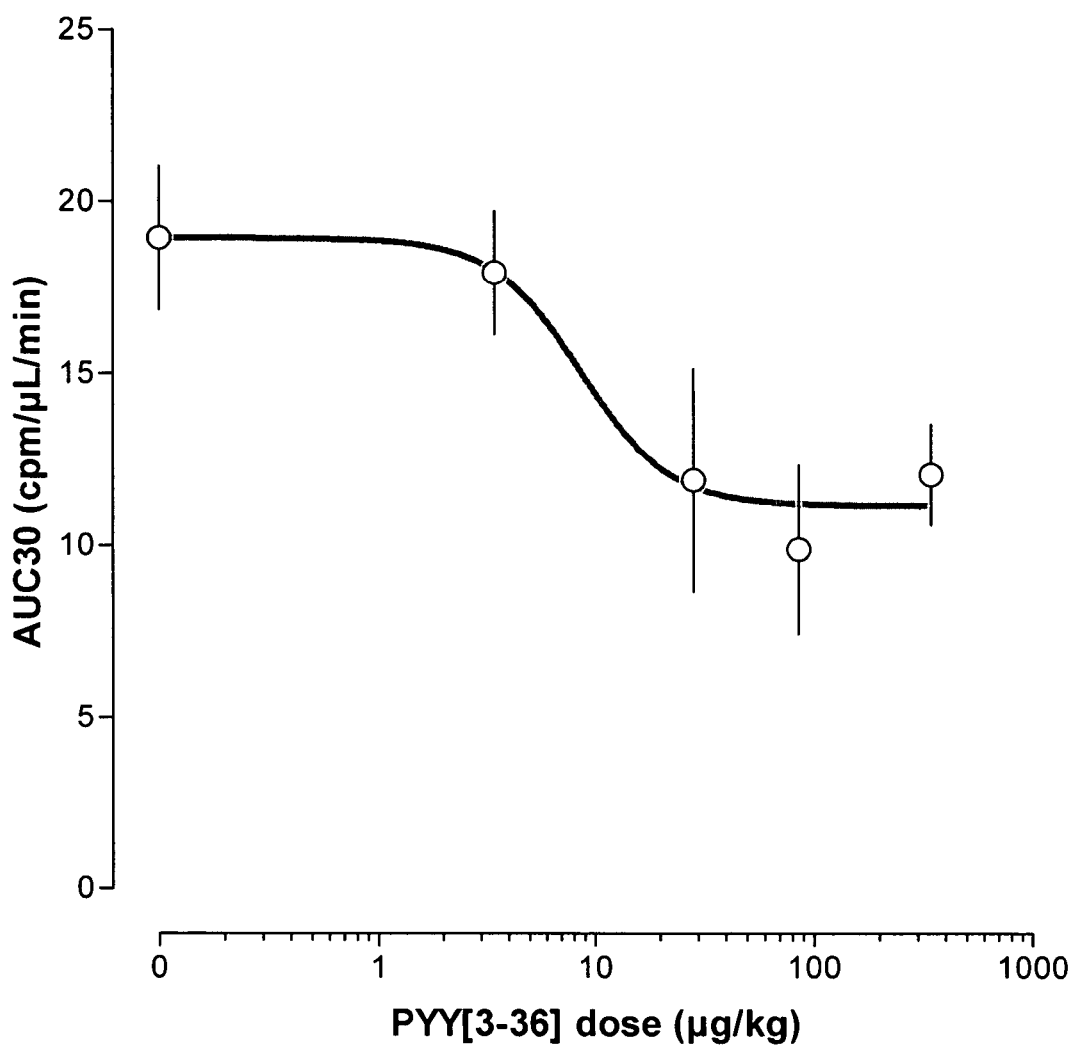
FIG. 15 demonstrates the activity of PPF polypeptides of the invention on gastric emptying.
Figure 16:
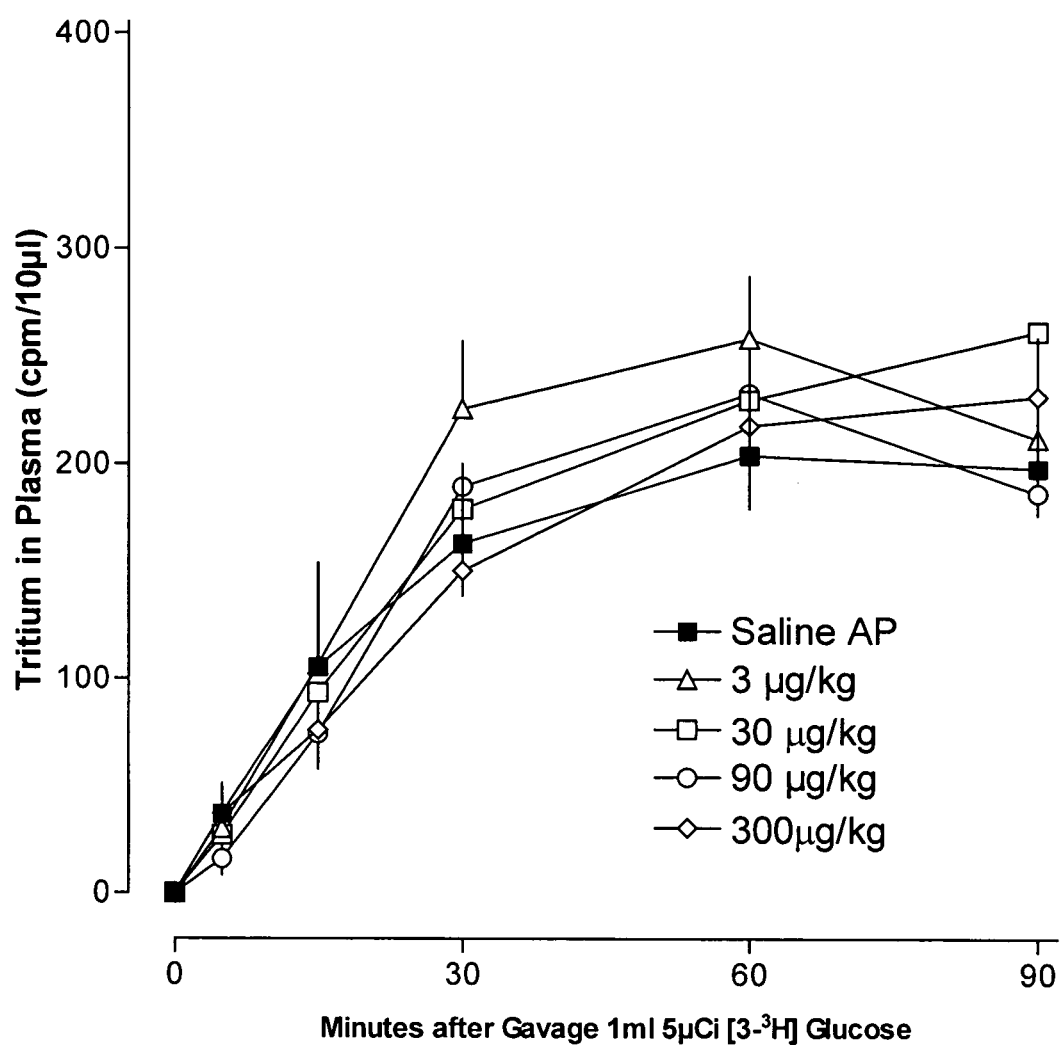
FIG. 16 demonstrates the activity of PPF polypeptides of the invention on gastric emptying.
Figure 17:
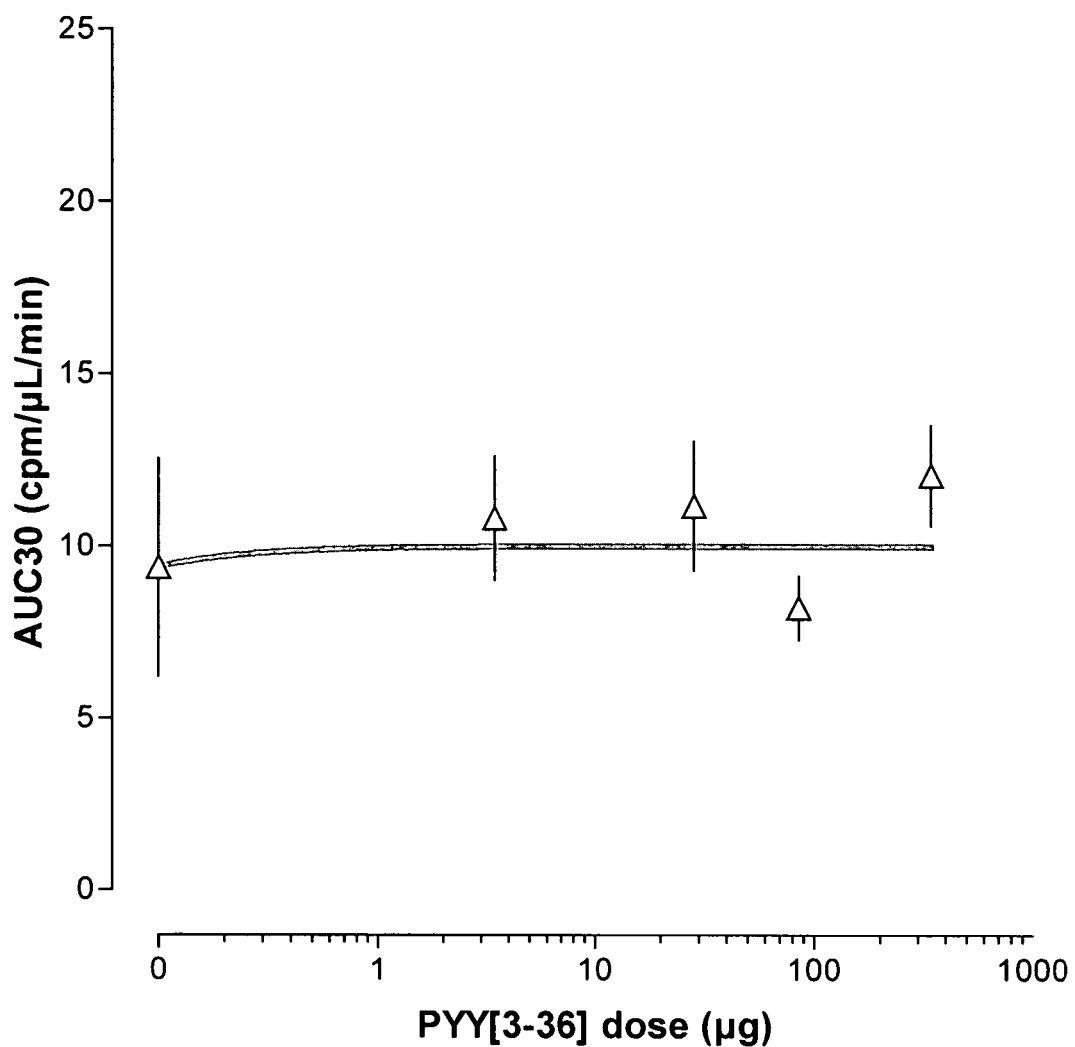
FIG. 17 demonstrates the activity of PPF polypeptides of the invention on gastric emptying.

In unoperated rats, PYY[3-36]dose-dependently inhibited label appearance, (10.5±1.5, 7.26±1.52 and 3.20±1.21 cpm/µL·min for 30 µg/kg, 90 µg/kg, 300 µg/kg PYY[3-36], respectively; $P<0.0001$ ANOVA; FIG. 12). In sham-AP rats, 10 µg (n=4) and 30 µg PYY[3-36] injections (n=3) also delayed appearance of label compared to saline-injected controls (n=5) in dose dependent manner (11.89±3.23, 9.88±2.45, 18.94±3.23 cpm/µL/min, respectively; $P<0.05$). Maximal effect of PYY in sham animals was less compared to intact non-operated rats with $ED_{50}$ also lower than in non-operated animals (decreases from 43.77 to 10.20 µg/kg PYY [3-36]. In APx rats, gastric emptying was slowed compared to that in sham-APx or unoperated rats (9.38±3.25 cpm/µL/min; $P<0.05$, 0.05), but was not altered by administration of PYY [3-36]. Regression analysis confirmed absence of dose dependency.

Results showed that PYY9 [3-36] potently regulates the rate of gastric emptying in normal Sprague Dawley rats. A dose-dependent inhibition of gastric emptying was observed following the injection of PYY (10, 30 and 100 µg/rat). The 100 µg dose of PYY produced an inhibition of similar magnitude as that caused by amylin (10 µg). AP-lesioned animals had a tendency to delay gastric emptying compared to non-operated and sham operated rats (n.s.). PYY[3-36] administration had no additional effect on gastric emptying rate in the AP-lesioned animals.

Gallbladder Emptying

To determine the effect of PYY [3-36] on gallbladder emptying, eight week old, male NIH Swiss mice were housed at 22.8±0.8° in a 12:12 light:dark cycle, and allowed ad libitum access to a standard rodent diet (Teklad LM 7012, Madison, Wis.) and water. The mice were food deprived for 3 hours prior to experimentation. At t=0, PYY(3-36), CCK-8 or saline was injected subcutaneously in conscious mice. Thirty min later, mice were euthanized by cervical dislocation, a midline laparotomy was performed and the gallbladder was excised and weighed.

Treatment Groups:

Group A: saline 100 µl subcutaneously at t=0, n=14.
Group B: PYY(3-36) 1 µg/kg subcutaneously at t=0, n=6.
Group C: PYY(3-36) 10 µg/kg subcutaneously at t=0, n=10.
Group D: PYY(3-36) 100 µg/kg subcutaneously at t=0, n=8.
Group E: CCK-8 1 µg/kg subcutaneously at t=0, n=3.
Group F: CCK-8 10 µg/kg subcutaneously at t=0, n=3.
Group G: PYY(3-36) 10 µg/kg+CCK-8 1 µg/kg subcutaneously at t=0, n=4.
Group H: PYY(3-36) 10 µg/kg+CCK-8 10 µg/kg subcutaneously at t=0, n=4.

Figure 18:
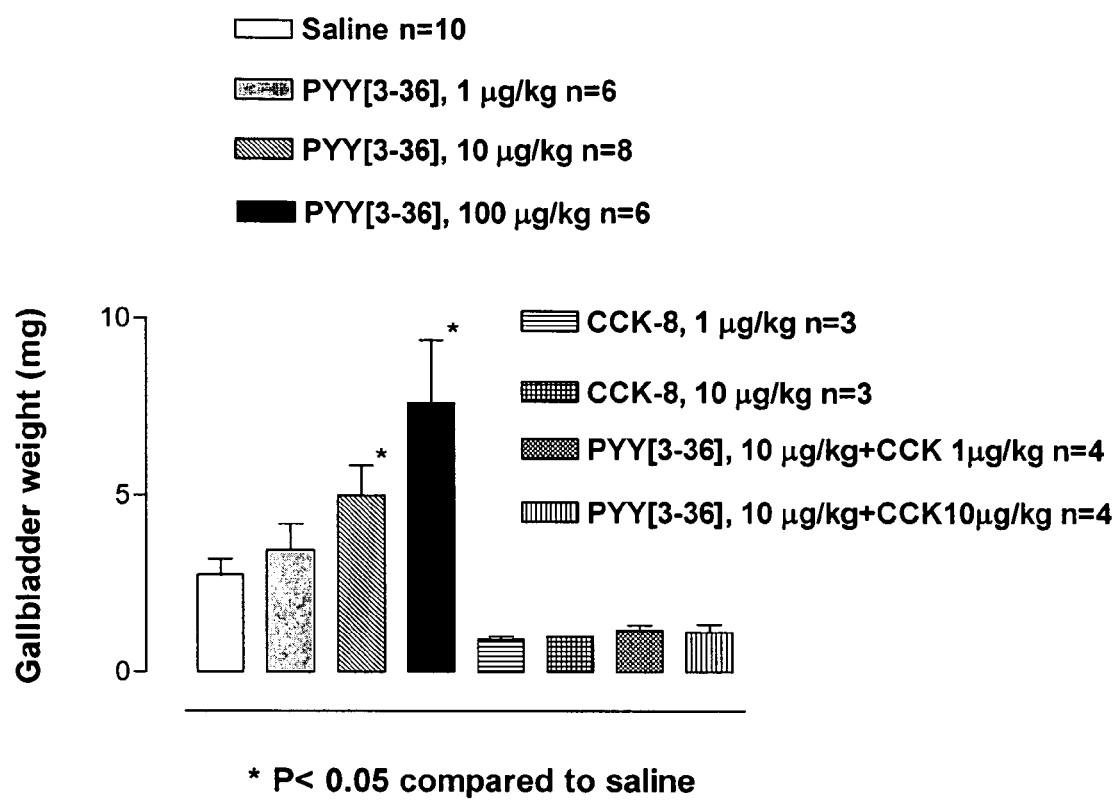
FIG. 18 demonstrates the activity of PPF polypeptides of the invention on gallbladder emptying.
Figure 19:
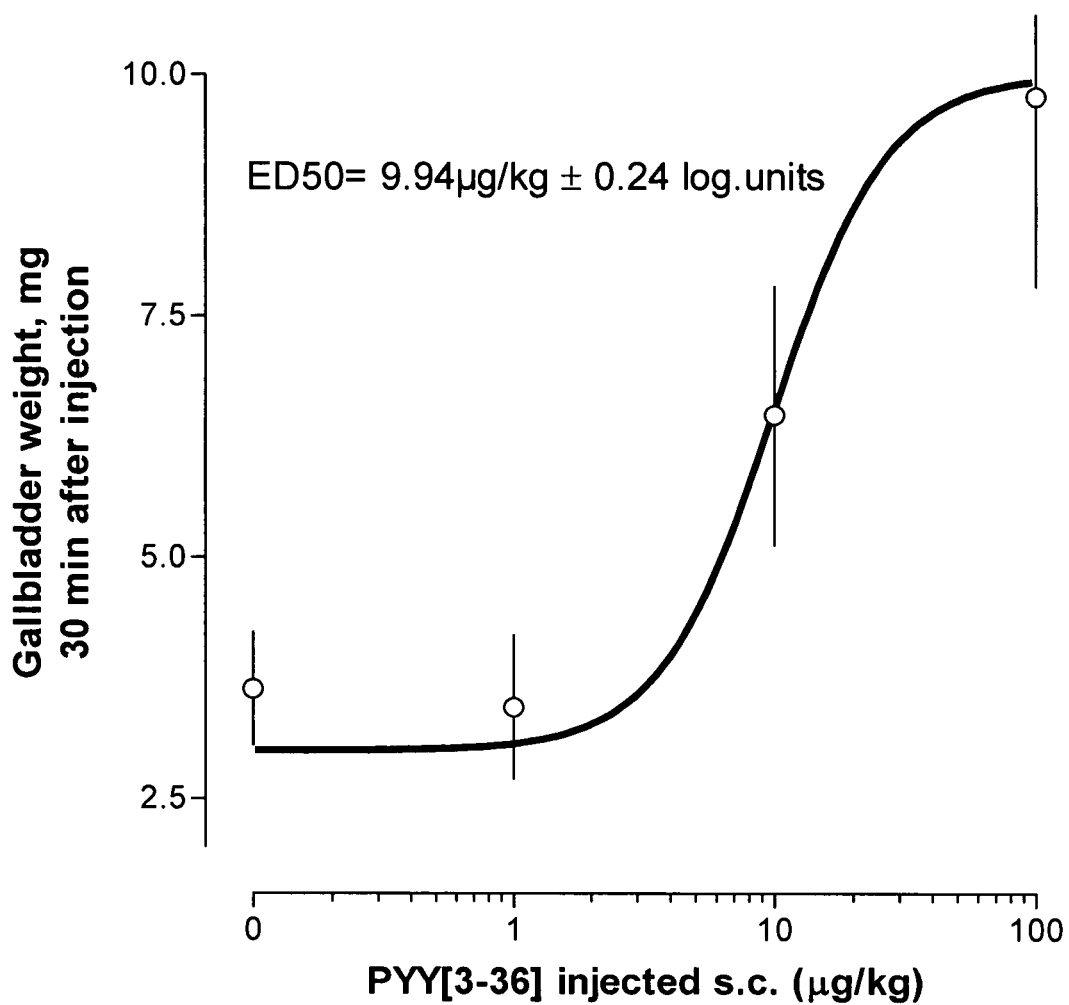
FIG. 19 demonstrates the activity of PPF polypeptides of the invention on gallbladder emptying.

The results are shown in FIGS. 18 and 19. PYY(3-36) dose dependently inhibited basal gallbladder emptying with an $ED_{50}$ of 9.94 µg/kg±0.24 log units. The highest dose (Group D) increased gallbladder weight by 168% over that observed in saline injected controls (Group A) (P<0.005). PYY(3-36) did not affect CCK-8 stimulated gallbladder emptying. The data indicate that PYY[3-36] inhibits gallbladder emptying via CCK-independent pathways. Gallbladder emptying in response to exogenous CCK was not affected by PYY(3-36). A similar result was obtained with PYY[1-36] in conscious dogs; a 400 ng/kg bolus+800 pmol/kg/h infusion did not inhibit CCK-8-stimulated gallbladder contraction.

It is possible that the effects of PYY(3-36) on gallbladder emptying are mediated by vagal-cholinergic pathways. This idea is supported by findings that specific peptide YY (PYY) binding sites have recently been autoradiographically identified in the area postrema, nucleus of the solitary tract, and dorsal motor nucleus regions (collectively referred to as the dorsal vagal complex (DVC)) in rats. These medullary brain stem regions are responsible for vagovagal reflex control of gastrointestinal functions, including motility and secretion. PYY(3-36) inhibits other digestive functions that are mediated by vagal-cholinergic mechanisms, such as gastric emptying.

Example 6

Gastroprotective Effects of PYY and PYY Agonists

Male Harlan Sprague Dawley rats were housed at 22.8±0.80 in a 12:12 light:dark cycle, and allowed ad libitum access to a standard rodent diet (Teklad LM 485, Madison, Wis.) and water. The rats, 200-220 gm, were fasted for approximately 20 hours prior to experimentation.

At t=−30, PYY(3-36) or saline was injected s.c. At t=0, a 1 ml gavage of absolute ethanol (ethyl alcohol-200 proof dehydrated alcohol, U.S.P. punctilious) or saline was administered. At t=30, the rats were anesthetized with 5% isofluorane. A midline laparotomy incision was made. The stomach was exposed and ligated at the pyloric and lower esophageal sphincters. The stomach was excised, opened along the lesser curvature and everted to expose the mucosa. The mucosa was gently rinsed with saline and assessed for damage (ulcerations, dilated blood vessels, sloughing off of the mucosal lining) by observers blinded to the treatment. Mucosal damage was scored between 0 (no damage) and 5 (100% of stomach covered by hyperemia and ulceration).

Treatment Groups:

Group A: saline 100 μl s.c. at t=−30, gavage 1 ml H2O at t=0, n=4.

Group B: saline 100 μl s.c. at t=−30, gavage 1 ml absolute ethanol at t=0, n=6.

Group C: PYY(3-36) 1 μg/kg at t=−30, gavage 1 ml absolute ethanol at t=0, n=5.

Group D: PYY(3-36) 10 μg/kg at t=−30, gavage 1 ml absolute ethanol at t=0, n=4.

Group E: PYY(3-36) 100 μg/kg at t=−30, gavage 1 ml absolute ethanol at t=0, n=5.

Group F: PYY(3-36) 300 μg/kg at t=−30, gavage 1 ml absolute ethanol at t=0, n=5.

Figure 20:
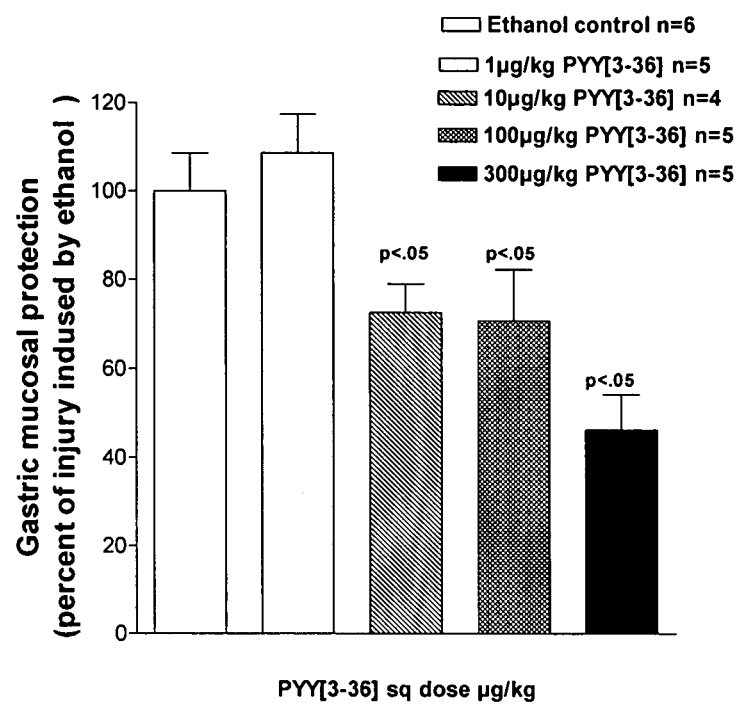
FIG. 20 demonstrates the activity of PPF polypeptides of the invention on gastric mucosal protection.

PYY(3-36) dose dependently reduced the injury score by 27.4±6.4, 29.3±11.6 and 53.7±7.9% (n=4,5,5, p<0.05 ANOVA) after injection of 10, 100, and 300 μg/kg of PYY (3-36), respectively (FIG. 20). PYY [3-36] showed a gastroprotective effect, in rats. Endogenously circulating PYY [3-36] may play a physiologic role in controlling gastric acid secretion and protecting the gastric mucosa.

Certain preferred PPF polypeptides are shown in the table below, although other polypeptides are envisioned.

| ID | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| 1 | A | P | L | E | P | V | Y | P | G | D | N | A | T | P | E | Q | M | A | Q | Y | A | A | D | L |
| 2 | Y | P | I | K | P | E | A | P | G | E | D | A | S | P | E | E | L | N | R | Y | Y | S | S | L |
| 3 |  |  | I |  | P | E |  | P | G | E | D | A | S | A | E | D | M | A | R | Y | Y | S | A | L |
| 4 | Y | P | S | K | P | D | N | P | G | E | D | A | P | A | E | Q | M | A | R | Y | I | S | A | L |
| 5 | A | P | L | K | P | V | Y | P | G | D | D | A | T | P | E | Q | M | A | R | Y | I | T | A | L |
| 6 | A | P | L | E | P | V | Y | P | G | D | D | A | T | P | E | Q | M | A | R | Y | Y | S | A | L |
| 7 | Y |  | P | K | P | E | S | P | G | E | D | A | P | A | E | D | L | A | K | Y | Y | T | A | L |
| 8 | A | P | P | K | P | E | S | P | G | E | D | A | S | P | E | D | L | S | K | Y | Y | S | A | L |
| 9 |  |  | P | K | P | E | H | P | G | E | D | A | P | A | E | D | V | A | K | Y | Y | L | A | L |
| 10 |  | P | P | K | P | E | N | P | G | E | D | A | P | A | E | D | L | A | K | Y | Y | L | A | D |
| 11 |  |  | P | K | P | E | S | P | G | E | D | A | P | A | E | D | L | A | K | Y | Y | L | A | D |
| 12 | A | P | P | K | P | E | N | P | S | S | D | A | S | P | E | Q | I | A | Q | Y | F | L | A | L |
| 13 | A | P | P | K | P | E | E | P | G | D | D | A | S | P | E | D | L | A | K | Y | M | S | A | V |
| 14 |  |  | P | K | P | E | H | P | G | E | D | A | S | P | E | D | L | I | K | Y | M | L | A | V |
| 15 |  |  | T | K | P | E | N | P | G | E | D | A | S | P | E | D | L | A | K | Y | K | L | A | V |
| 16 |  |  | P | K | P | E | N | P | G | E | D | A | S | P | E | D | M | L | R | Y | F | S | A | V |
| 17 | Y |  | I | K | P | E | Z | P | G | E | D | A | S | P | E | E | M | A | A | Y | M | T | A | L |
| 18 |  |  | S | K | P | E | N | P | G | E | D | A | P | A | E | D | L | T | K | Y | L | T | A | L |
| 19 |  |  | P | K | P | E | N | P | G | E | D | A | P | A | E | D | M | A | K | Y | L | T | A | L |
| 20 |  |  | P | K | P | D | N | P | G | E | D | A | S | P | E | Q | V | A | R | Y | Y | A | A | L |
| 21 |  | P | P | K | P | E | N | P | G | E | D | A | S | P | E | D | V | N | Q | Y | Y | S | A | L |
| 22 |  |  | P | K | P | D | N | P | G | E | D | A | S | P | E | D | V | A | R | Y | Y | S | A | L |
| 23 |  |  | P | K | P | E | N | P | G | E | D | A | P | A | E | D | V | A | R | Y | Y | A | A | L |
| 24 |  | P | P | K | P | E | A | P | G | E | D | A | P | A | E | D | V | A | K | Y | A | A | D | L |
| 25 |  |  | P | K | P | E | N | P | G | E | D | A | P | A | E | D | L | A | K | Y | Y | S | A | L |
| 26 |  |  | P | K | P | E | H | P | G | E | D | A | P | A | E | D | L | A | K | Y | Y | S | A | L |
| 27 |  |  | I |  | P | E | H | P | G | E | D | A | P | A | E | D | L | A | R |  | Y | S | A | L |
| 28 | Y | P | P | K | P | E | H | P | G | E | D | A | S | P | E | D | M | A | Q | Y | Y | A | A | L |
| 29 |  |  | A | K | P | E | N | P | G | S | N | A | P | A | E | Q | A | A | K | Y | L | T | A | L |
| 30 FORMULA I |  |  |  |  |  |  |  |  |  |  |  |  |  |  |  |  |  |  |  |  |  |  |  |  |
| 31 | Y | P | I | hK | P | E | A | P | G | E | D | A | S | P | E | E | L | N | R | Y | Y | A | S | L |
| 32 | Y | P | I | K | P | E | A | P | G | E | D | A | S | P | E | E | L | N | R | Y | Y | A | S | L |
| 33 | Y | P | I | K | P | E | A | P | G | E | D | A | S | P | E | E | L | N | R | Y | Y | A | S | L |
| 34 | Y | P | I | K | P | E | A | P | G | E | D | A | S | A | E | E | L | N | R | Y | Y | A | S | L |
| 35 | Y | P | I | K | P | E | A | P | G | A | D | A | S | P | E | A | L | N | R | Y | Y | A | S | L |
| 36 | Y | P | I | K | P | E | A | P | G | E | D | A | S | P | E | E | L | N | R | Y | Y | A | S | L |
| 37 | Y | P | I | K | P | E | A | P | G | E | D | A | S | P | E | E | L | N | R | Y | Y | A | S | L |
| 38 | Y | P | I | K | P | E | A | P | G | E | D | A | S | P | E | E | L | A | R | Y | Y | A | S | L |
| 39 | Y | P | I | K | P | E | A | P | G | E | D | A | S | P | E | E | L | N | R | Y | Y | A | S | L |
| 40 | Y | P | I | K | P | E | A | P | G | E | D | A | S | P | E | E | L | L | R | Y | Y | A | S | L |
| 41 | Y | P | I | K | P | E | A | P | G | E | D | A | S | P | E | E | L | N | R | Y | Y | A | S | L |
| 42 | Y | P | I | K | P | E | A | P | G | E | D | A | S | A | E | E | L | N | R | Y | Y | A | S | L |
| 43 | Y | P | I | K | P | E | A | P | G | E | D | A | S | P | E | E | L | N | R | Y | Y | A | S | L |
| 44 | Y | P | I | K | P | E | A | P | G | E | D | A | S | P | E | E | L | N | K | Y | Y | A | S | L |
| 45 | Y | P | I | K | P | E | A | P | G | E | D | A | S | P | E | E | L | N | R | Y | Y | A | S | L |
| 46 | Y | P | I | K | P | E | A | P | G | E | D | A | S | P | E | E | L | N | R | Y | Y | A | S | L |
| 47 | Y | P | I | K | P | E | A | P | G | E | D | A | S | A | E | E | L | A | R | Y | Y | A | S | L |
| 48 | Y | P | I | K | P | E | A | P | G | E | D | A | S | P | E | E | L | L | R | Y | Y | A | S | L |
| 49 | Y | P | I | K | P | E | A | P | G | E | D | A | S | A | E | E | L | L | R | Y | Y | A | S | L |

-continued

FORMULA II

| # | | | | | | | | | | | | | | | | | | | | |
|---|---|---|---|---|---|---|---|---|---|---|---|---|---|---|---|---|---|---|---|---|
| 103 | | I | K | P | E | A | P | G | E | D | A | S | P | E | L | N | R | Y | A | S | L |
| 104 | | I | K | P | E | A | P | G | E | D | A | S | P | E | L | N | R | Y | A | S | L |
| 105 | | I | K | P | E | A | P | G | E | D | A | S | P | E | A | N | R | Y | A | S | L |
| 106 | | I | K | P | E | A | P | G | E | D | A | S | P | E | L | A | R | Y | A | S | L |
| 107 | | I | K | P | E | A | P | G | E | D | A | S | P | E | L | N | A | Y | A | S | L |
| 108 | | I | K | P | E | A | P | G | E | D | A | S | P | E | L | N | R | A | A | S | L |
| 109 | | I | K | P | E | A | P | G | E | D | A | S | P | E | L | N | K(NMe)A | Y | A | A | L |
| 110 | | I | K | P | E | A | P | G | E | D | A | S | P | E | L | N | R | Y | dA | S | L |
| 111 | | I | K | P | E | A | P | G | E | D | A | S | P | E | L | N | R | Y | A | S | L |
| 112 | | I | K | P | E | A | P | G | E | D | A | S | P | E | L | N | R | Y | A | S | L |
| 113 | | I | K | P | E | A | P | G | E | D | A | S | P | E | L | N | R | Y | A | S | L |
| 114 | | I | K | P | E | A | P | G | E | D | A | S | P | E | L | N | R | Y | A | S | L |
| 115 | | I | K | P | E | A | P | G | E | D | A | S | P | E | L | N | R | Y | A | S | L |
| 116 | | I | K | P | E | A | P | G | E | D | A | S | P | E | L | N | R | Y | A | S | L |
| 117 | | I | K | P | E | A | P | G | E | D | A | S | P | E | L | N | R | Y | A | S | L |
| 118 | | I | K | P | E | A | P | G | E | D | A | S | P | E | L | N | R | Y | A | S | L |
| 119 | | I | K | P | E | A | P | G | E | D | A | S | P | E | L | N | R | Y | A | S | L |
| 120 | | I | K | P | E | A | P | G | E | D | A | S | P | E | L | N | R | Y | A | S | L |
| 121 | | I | K | P | E | A | P | G | E | D | A | S | P | E | L | N | R | Y | A | S | L |
| 122 | | I | K | P | E | A | P | G | E | D | A | S | P | E | L | N | R | Y | A | S | L |
| 123 | | I | K | P | E | A | P | G | E | D | A | S | P | E | L | N | R | Y | A | S | L |
| 124 | | I | K | P | E | A | P | G | E | D | A | S | P | E | L | N | R | Y | A | S | L |
| 125 | | I | K | P | E | A | P | G | E | D | A | S | P | E | L | N | R | Y | A | S | L |
| 126 | | I | K | P | E | A | P | G | E | D | A | S | P | E | L | N | R | Y | A | S | L |
| 127 | | I | K | P | E | A | P | G | E | D | A | S | P | E | L | N | R | Y | A | S | L |
| 128 | | I | K | P | E | A | P | G | E | D | A | S | P | E | M | N | R | Y | A | S | L |
| 129 | isocap | S | K | P | D | N | P | G | E | D | A | P | A | E | L | N | R | Y | s | A | L |
| 130 | AC | P | K | P | E | A | P | G | E | D | A | S | P | E | L | N | R | Y | A | S | L |
| 131 | | P | K | P | E | A | P | G | E | D | A | S | A | E | L | N | R | Y | A | S | L |
| 132 | | I | K | P | E | A | P | G | E | D | A | S | P | E | L | N | R | Y | A | S | L |
| 133 | | I | K | P | E | A | P | G | E | D | A | S | P | E | L | N | R | Y | A | S | L |
| 134 | | I | K | P | E | A | P | G | E | D | A | S | P | E | L | N | R | Y | A | S | L |
| 135 | | I | K | P | E | A | P | G | E | D | A | S | P | E | L | N | R | Y | A | S | L |
| 136 | | I | K | P | E | A | P | G | E | D | A | S | P | E | L | N | R | Y | A | S | L |
| 137 | | I | K | P | E | A | P | G | E | D | A | S | P | E | L | N | R | Y | A | S | L |
| 138 | | I | K | P | E | A | P | G | E | D | A | S | P | E | L | N | R | Y | A | S | L |
| 139 | | I | K | P | E | A | P | G | E | D | A | S | P | E | L | A | R | Y | A | S | L |
| 140 | | I | K | P | E | A | P | G | E | D | A | S | P | E | L | N | R | Y | A | S | L |
| 141 | | I | K | P | E | A | P | G | E | D | A | S | P | E | L | N | R | Y | A | S | L |
| 142 | | I | hK | P | E | A | P | G | E | D | A | S | P | E | L | N | R | Y | A | S | L |
| 143 | | I | K | P | E | A | P | G | E | D | A | S(Ac) | P | E | L | N | R | Y | A | S | L |
| 144 | | I | K | P | E | A | P | G | E | D | A | S | P | E | L | N | R | Y | A | S | L |
| 145 | | I | K | P | E | A | P | G | E | D | A | S | P | E | L | N | R | Y | A | S | L |
| 146 | | I | K | P | E | A | P | G | E | D | A | S | P | E | L | N | R | Y | A | S | L |
| 147 | | I | K | P | E | A | P | G | E | D | A | S | P | E | L | N | hR | Y | A | S | L |
| 148 | | I | K | P | E | A | P | G | E | D | A | S | P | E | L | N | R | Y | A | S(Ac) | L |
| 149 | | I | K | P | E | A | P | G | E | D | A | S | P | E | L | N | R | Y | A | S | L |
| 150 | FmocSO3H | I | K(FmocSO3H) | P | E | A | P | G | E | D | A | S | P | E | L | N | R | Y | A | S | L |
| 151 | isocaproyl | I | K | P | E | A | P | G | E | D | A | S | P | E | L | N | R | Y | A | S | L |
| 152 | Fmoc | I | K | P | E | A | P | G | E | D | A | S | P | E | L | N | R | Y | A | S | L |
| 153 | isobutyloxycarbonyl | I | K | P | E | A | P | G | E | D | A | S | P | E | L | N | R | Y | A | S | L |
| 154 | isopropyloxycarbonyl | I | K | P | E | A | P | G | E | D | A | S | P | E | L | N | R | Y | A | S | L |
| 155 | n- | I | K | P | E | A | P | G | E | D | A | S | P | E | L | N | R | Y | A | S | L |

| # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| 156 | butyloxycarbonyl | | I | K | P | E | A | P | G | E | D | A | S | P | E | E | L | A | R | Y | A | S | L |
| 157 | ethoxycarbonyl | | I | K | P | E | A | P | G | E | D | A | S | P | E | E | L | A | R | Y | A | S | L |
| 158 | | | I | K | P | E | A | P | G | E | D | A | S | P | E | E | L | A | R | Y | A | S | L |
| 159 | | | I | hK | P | E | A | P | G | E | D | A | S | P | E | E | L | s | R | Y | A | S | L |
| 160 | isocapryl | | I | hK | P | E | A | P | G | E | D | A | S | P | E | E | L | nV | R | Y | A | S | L |
| 161 | | | I | K | P | E | A | P | G | E | D | A | S | P | E | E | L | A | R | Y | A | S | L |
| 162 | isocapryl | | I | hK | P | E | A | P | G | E | D | A | S | P | E | E | L | A | hR | Y | A | S | L |
| 163 | isocapryl | | I | hK | P | E | A | P | G | E | D | A | S | P | E | E | L | A | hR | Y | A | S | L |
| 164 | | | I | hK | P | E | A | P | G | E | D | A | S | P | E | E | L | A | hR | Y | A | S | L |
| 165 | | | I | K | P | E | A | P | G | E | D | A | hS | P | E | E | M | A | R | Y | A | S | L |
| 166 | | | I | hK | P | E | A | P | G | E | D | A | S | P | E | E | L | A | hR | Y | A | S | L |
| 167 | | | I | hK | P | E | A | P | G | E | D | A | S | A | Q | E | L | A | R | Y | A | S | L |
| 168 | | | L | hK | P | E | A | P | G | E | D | A | S | A | E | E | L | A | R | Y | A | S | L |
| 169 | | | I | hK | P | E | A | P | G | E | D | A | S | A | E | E | L | A | R | Y | A | S | L |
| 170 | | | I | KA | P | E | C | P | G | E | D | A | S | P | E | E | C | A | R | Y | A | S | L |
| 171 | | | I | K | P | V | Y | P | G | E | D | A | S | P | E | E | L | A | R | Y | A | S | L |
| 172 | | | L | E | P | V | Y | P | G | E | D | A | S | P | E | E | L | A | R | Y | A | S | L |
| 173 | | | I | E | P | E | A | P | G | E | D | A | S | P | E | E | L | N | R | Y | A | S | L |
| 174 | | | L | E | P | E | A | P | G | E | D | A | S | P | E | E | L | N | R | YY | A | S | L |
| 175 | | | I | K | P | E | A | P | G | E | D | A | S | P | E | E | L | N | R | Y | A | S | L |
| 176 | | | | | | | | | | | | | | | | | | | | | | | |
| 177 | | | | | | | | | | | | | | | | | | | | | | | |
| 178 | | | | | | | | | | | | | | | | | | | | | | | |
| 179 | | Y | P | K | P | E | A | P | G | Aminocaproyl | E | D | A | S | P | E | E | L | N | R | Y | A | S | L |
| 180 | | Y | P | K | P | E | A | P | G | Aminocaproyl | E | D | A | S | P | E | E | L | N | R | Y | A | S | L |
| 181 | | Y | P | K | P | E | A | P | G | Aminocaproyl | E | D | A | S | Aminocaproyl | E | E | L | | R | Y | A | S | L |
| 182 | | Y | P | K | P | E | A | P | | | E | D | A | S | Aminocaproyl | E | E | L | | R | Y | A | S | L |
| 183 | | Y | P | K | P | E | A | P | | | E | D | A | Aminocaproyl | A | E | E | L | | R | Y | A | S | L |
| 184 | | Y | P | K | P | E | A | P | | | E | D | A | Aminocaproyl | Ado | E | E | | | R | Y | A | S | L |
| 185 | | | Fmoc | K | P | E | A | P | G | E | D | A | S | P | E | E | L | L | R | Y | A | S | L |
| 186 | | | | K(PEG 5000) | P | E | A | P | G | E | D | A | S | P | E | E | L | L | R | Y | A | S | L |
| 187 | | | Fmoc | K(PEG 5000) | P | E | A | P | G | E | D | A | S | P | E | E | L | L | R | Y | A | S | L |
| 188 | | | Fmoc | A | P | E | A | P | G | E | D | A | S | P | E | E | L | L | K(PEG 5000) | Y | A | S | L |
| 189 | | | | A | P | E | A | P | G | E | D | A | S | P | E | E | L | L | R | Y | A | S | L |
| 190 | | PEG 5000 | | A | P | E | A | P | G | E | D | A | S | P | E | E | L | L | R | Y | A | S | L |
| 191 | | | | K | P | E | A | P | G | E | D | A | acylation with fatty acids | P | E | E | L | L | R | Y | A | acylation with fatty acids | L |
| 192 | | Fmoc | | K | P | E | A | P | G | E | D | A | S | P | E | E | L | L | R | Y | A | S | L |
| 193 | | | | A | P | E | A | P | G | E | D | A | S | P | E | E | L | L | K(oct) | Y | A | S | L |
| 194 | | Octanoic acid | | A | P | E | A | P | G | E | D | A | S | P | E | E | L | L | K(oct) | Y | A | S | L |
| 195 | | | | A | P | E | A | P | G | E | D | A | S | P | E | E | L | A | R | Y | A | S | L |
| 196 | | Fmoc | | A | P | E | A | P | G | E | D | A | S | P | E | E | L | L | K(stea) | Y | A | S | L |
| 197 | | | | A | P | E | A | P | G | E | D | A | S | P | E | E | L | L | K(stea) | Y | A | S | L |
| 198 | | | | | | | | Ac | | | | | | | | | | | R | Y | A | S | L |

| # | | | | | | | | | | | | | | | | | | | | | | |
|---|---|---|---|---|---|---|---|---|---|---|---|---|---|---|---|---|---|---|---|---|---|---|
| 199 | | | | | | | | | stearyl | E | D | A | S | P | E | L | N | R | Y | A | S | L |
| 200 | | | | | | | | | octyl | E | D | A | S | P | E | L | N | R | Y | A | S | L |
| 201 | | | | | | | | | succinyl | E | D | A | S | P | E | L | N | R | Y | A | S | L |
| 202 | | | I | A | P | E | A | P | G | E | D | A | S | P | E | L | N | R | Y | A | S | L |
| 203 | | | I | A | P | E | A | P | G | E | D | A | S | P | E | L | N | R | Y | A | S | L |
| 204 | Fmoc | | I | A | P | E | A | P | G | E | D | A | S | P | E | L | N | R | Y | A | S | L |
| 205 | | | I | K | P | E | A | P | G | E | D | A | S | P | E | K(PEG) | L | N | R | Y | A | S | L |
| 206 | | | I | K | P | E | A | P | G | E | D | A | S | P | E | K(Oct) | L | N | R | Y | A | S | L |
| 207 | | | I | K | P | E | A | P | G | E | D | A | S | P | E | K(Oct) | L | N | R | Y | A | S | L |
| 208 | | | I | K | P | E | A | P | G | E | D | A | S | P | E | L | N | R | Y | A | S | L |
| 209 | | | I | K | P | E | A | P | G | E | D | A | S | P | E | L | N | R | Y | A | S | L |
| 210 | | | I | K | P | E | A | P | G | E | D | A | S | P | E | L | N | R | Y | A | S | L |
| 211 | | | I | K | P | E | A | P | mimic A | mimic A | mimic A | mimic A | mimic A | P | E | L | N | R | Y | A | S | L |
| 212 | | | I | K | P | E | A | P | G | E | D | A | S | P | E | L | N | R | Y | A | S | L |
| 213 | | | I | K | P | E | A | P | G | E | mimic A | mimic A | mimic A | P | E | L | N | R | Y | A | S | L |
| 214 | | | I | K | P | E | A | P | G | mimic A | D | A | S | P | E | L | N | R | Y | A | S | L |
| 215 | | | I | K | P | E | A | P | G | E | D | A | S | P | E | L | N | R | Y | A | S | L |
| 216 | | | I | K | P | E | A | P | G | E | D | A | S | mimic A | E | L | N | R | Y | A | S | L |
| 217 | | | I | K | P | E | A | P | Aib | Aib | Aib | Aib | Aib | Aib | Aib | L | N | R | Y | A | S | L |
| 218 | | | I | K | P | E | A | P | A | A | A | A | A | A | E | L | N | R | Y | A | S | L |
| 219 | | | I | K | P | E | A | P | G | E | D | A | S | P | E | L | N | R | Y | A | S | L |
| 220 | | | I | K | P | E | A | P | G | E | D | A | S | P | E | L | N | R | Y | A | S | L |
| 221 | | | I | K | P | E | A | P | A | Aib | Aib | Aib | Aib | Aib | E | L | N | R | Y | A | S | L |
| 222 | | | I | K | P | E | A | P | G | E | D | A | S | P | E | L | N | R | Y | A | S | L |
| 223 | | | I | K | P | E | A | P | G | E | D | A | S | P | E | L | N | R | Y | A | S | L |
| 224 | | | I | K | P | E | A | P | P | A | P | P | P | A | E | L | N | R | Y | A | S | L |
| 225 | | | I | K | P | E | A | P | G | E | D | A | S | P | E | L | N | R | Y | A | S | L |
| 226 | | | I | K | P | E | A | P | G | E | D | A | S | P | E | L | N | R | Y | A | S | L |
| 227 | | | I | K | P | E | A | P | G | E | D | A | S | P | E | L | N | R | Y | A | S | L |
| 228 | | | I | K | P | E | A | P | G | E | D | A | S | P | E | L | N | R | Y | A | S | L |
| 229 | | | I | K | P | E | A | P | G | E | D | A | S | P | E | L | N | R | Y | A | S | L |
| 230 | | | I | K | P | E | A | P | G | E | D | A | S | P | E | L | N | R | Y | A | S | L |
| 231 | | | I | K | P | E | A | P | mimic B | mimic B | mimic B | mimic B | mimic B | mimic B | E | L | N | R | Y | A | S | L |
| 232 | | | I | K | P | E | A | P | G | E | D | A | S | P | E | L | N | R | Y | A | S | L |
| 233 | | | I | K | P | E | A | P | G | E | D | A | T | P | E | L | N | R | Y | A | S | L |
| 234 | | | I | K | P | E | A | P | G | D | N | A | S | P | E | L | N | R | Y | A | S | L |
| 235 | | | I | K | Y | E | A | P | G | E | D | A | S | P | E | Q | M | A | R | Y | A | A | L |
| 236 | | | I | K | Y | V | A | P | G | E | D | A | S | P | E | L | L | A | K | Y | S | S | L |
| 237 | | | L | E | P | E | A | P | G | E | D | A | S | P | E | L | L | A | R | Y | A | A | L |
| 238 | | P | A | I | K | P | E | A | P | G | E | D | A | S | P | E | L | L | A | R | Y | A | A | L |
| 239 | | P | Y | I | K | P | E | A | P | G | E | D | A | S | P | E | L | L | A | R | Y | S | S | L |
| 240 | | | | | | | | | | | | | | | | | | | | | | | |
| 241 | | | | | | | | | | | | | | | | | | | | | | | |
| 242 | isocap | | I | K | P | E | A | P | G | E | D | A | S | P | E | L | L | A | R | Y | A | A | L |
| 243 | | | | | | | | | | | | | | | | | | | | | | | |
| 244 | | P | Y | I | K | P | E | A | P | G | E | D | A | S | P | E | L | L | A | R | Y | S | S | L |
| 245 | | P | Y | I | K | P | E | A | P | G | E | D | A | S | P | E | L | L | A | R | Y | A | A | L |
| 246 | | P | Y | I | K | P | E | A | P | G | E | D | A | S | P | E | L | L | A | R | Y | S | S | L |
| 247 | | P | Y | I | K | P | E | A | P | G | E | D | A | S | P | E | L | L | A | R | Y | A | A | L |
| 248 | | P | | I | hK | P | E | A | P | G | E | D | A | S | P | E | L | L | A | R | Y | A | A | L |
| 249 | | | | I | hK | P | E | A | P | G | E | D | A | S | P | E | L | L | A | R | Y | A | A | L |
| 250 | | | | I | hK | P | E | A | P | G | E | D | A | S | P | E | L | L | A | R | Y | A | A | L |
| 251 | | P | Y | I | | P | E | A | P | G | E | D | A | S | P | E | L | L | A | R | Y | A | S | L |

| # | | | | | | | | | | | | | | | | | | | | |
|---|---|---|---|---|---|---|---|---|---|---|---|---|---|---|---|---|---|---|---|---|
| 252 | | | | I | hK | P | E | A | P | G | E | D | A | S | P | E | E | L | A | Y | R | Y | A | S | L |
| 253 | | | | P | hK | P | E | A | P | G | E | D | A | S | P | E | E | L | A | Y | R | Y | A | S | L |
| 254 | isocap | | | P | K | P | E | A | P | G | E | D | A | S | P | E | E | L | A | Y | R | Y | A | S | L |
| 255 | | | | P | K | P | E | A | P | G | E | D | A | S | P | E | E | L | A | Y | R | Y | A | S | L |
| 256 | | | | P | K | P | E | A | P | G | E | D | A | P | P | E | E | L | A | Y | R | Y | A | S | L |
| 257 | | | | I | hK | P | E | H | P | G | E | D | A | S | P | E | E | L | A | Y | R | Y | A | S | L |
| 258 | | Y | | I | hK | P | E | A | P | G | E | D | A | S | P | E | E | L | A | Y | R | Y | A | S | L |
| 259 | | | P | I | hK | P | E | A | P | G | E | D | A | S | P | E | E | L | A | Y | R | Y | A | S | L |
| 260 | | Y | | I | hK | P | E | A | P | G | E | D | A | S | P | E | E | L | A | Y | R | Y | A | S | L |
| 261 | | | P | I | hK | P | E | A | P | G | E | D | A | S | P | E | E | L | A | Y | R | Y | A | S | L |
| 262 | | | P | P | K | P | E | A | P | G | E | D | A | S | P | E | E | L | A | Y | R | Y | A | S | L |
| 263 | isocap | | | P | K | P | E | A | P | G | E | D | A | S | P | E | E | L | A | Y | R | Y | A | S | L |
| 264 | | | P | I | K | P | E | A | P | G | E | D | A | S | P | E | E | L | A | Y | R | Y | A | S | L |
| 265 | | Y | | I | R | P | E | A | P | G | E | D | A | S | P | E | E | L | A | Y | R | Y | A | S | L |
| 266 | isocap | Y | | I | R | P | E | A | P | G | E | D | A | S | P | E | E | L | A | Y | R | Y | A | S | L |
| 267 | | Y | P | I | R | P | E | A | P | G | E | D | A | S | P | E | E | L | A | Y | R | Y | A | S | L |
| 268 | | Y | P | I | R | P | E | A | P | G | E | D | A | P | P | E | E | L | A | Y | R | Y | A | S | L |
| 269 | | | P | I | K | P | E | A | P | G | E | D | A | S | P | E | E | L | A | Y | R | Y | A | S | L |
| 270 | | | | P | K | P | E | A | P | G | E | D | A | S | P | E | E | L | A | Y | R | Y | S | S | L |
| 271 | 8-amino octanoyl | | | P | K | P | E | A | P | G | E | D | A | S | A | E | E | L | A | Y | R | Y | A | A | L |
| 272 | | Y | P | I | K | P | E | A | P | G | E | D | A | S | P | E | E | L | A | Y | R | Y | A | A | L |
| 273 | | Y | | I | K | P | E | A | P | G | E | D | A | P | A | E | E | L | A | Y | R | Y | A | A | L |
| 274 | P | | P | I | K | P | E | A | P | G | E | D | A | P | A | E | E | L | A | Y | R | Y | A | A | L |
| 275 | 8-amino octanoyl | Y | | I | K | P | E | A | P | G | E | D | A | S | A | E | E | L | A | Y | R | Y | A | A | L |
| 276 | | | | | P | K | P | E | A | P | G | E | D | A | S | A | E | E | L | A | Y | R | Y | A | A | L |
| 277 | isocap | Y | | | P | K | P | E | A | P | G | E | D | A | S | A | E | E | L | A | Y | R | Y | A | S | L |
| 278 | | | | | S | K | P | E | A | P | G | E | D | A | T | A | E | E | L | A | Y | R | Y | A | S | L |
| 279 | | | | isocap | G(Oct) | E | P | D | N | P | D | N | N | T | P | D | M | A | R | Y | S | L |
| 280 | | | | G(Oct) | L | E | P | V | Y | P | G | D | N | A | T | P | E | Q | M | A | R | Y | A | S | L |
| 281 | | | | Fmoc-G(Oct) | L | E | P | V | Y | P | G | D | N | A | T | P | E | Q | M | A | R | Y | A | S | L |
| 282 | | | | | Y | L | E | P | V | Y | P | G | D | N | A | T | P | E | Q | M | A | R | Y | A | S | L |
| 283 | | A | | | L | E | P | V | Y | P | G | D | N | A | T | P | E | Q | M | A | R | Y | S | S | L |
| 284 | | A | | | L | E | P | V | Y | P | G | D | N | A | T | P | E | Q | M | A | R | Y | A | S | L |
| 285 | | A | P | | L | E | P | V | Y | P | G | D | N | A | T | P | E | Q | M | A | R | Y | A | S | L |
| 286 | | A | P | | L | E | P | V | Y | P | G | D | N | A | T | P | E | Q | M | A | R | Y | A | S | L |
| 287 | | A | P | | L | E | P | V | Y | P | G | D | N | A | T | P | E | Q | M | A | R | Y | A | A | L |
| 288 | | A | P | | L | E | P | V | Y | P | G | D | N | A | T | P | E | Q | L | A | R | Y | A | S | L |
| 289 | | A | P | | L | E | P | V | Y | P | G | D | N | A | T | P | E | Q | L | A | R | Y | A | S | L |
| 290 | | A | P | | L | E | P | V | Y | P | G | D | N | A | T | P | E | Q | L | A | R | Y | A | S | L |
| 291 | | A | P | | L | E | P | V | Y | P | G | D | N | A | T | P | E | Q | M | A | K | Y | A | S | L |
| 292 | | A | P | | L | E | P | V | Y | P | G | N | N | A | T | P | E | Q | M | A | R | Y | A | S | L |
| 293 | | A | P | | L | E | P | V | Y | P | G | D | N | A | T | P | E | Q | M | A | R | Y | A | S | L |
| 294 | | A | P | | L | E | P | V | Y | P | G | E | N | A | T | P | E | Q | M | A | R | Y | A | S | L |
| 295 | | A | P | | L | E | P | A | Y | P | G | D | N | A | T | P | E | Q | L | A | R | Y | A | S | L |
| 296 | | A | P | | L | E | P | Y | Y | P | G | D | N | A | T | P | E | E | L | A | R | Y | A | S | L |
| 297 | | A | P | | L | E | P | E | Y | P | G | D | N | A | T | P | E | E | L | A | R | Y | A | S | L |
| 298 | | A | P | | L | E | P | V | A | P | G | D | N | A | T | P | E | E | L | A | R | Y | A | S | L |
| 299 | | A | P | | L | K | P | E | A | P | G | E | D | A | S | P | E | E | L | A | R | Y | A | S | L |
| 300 | | A | P | | L | E | P | V | Y | P | G | D | N | A | T | P | E | E | L | A | R | Y | A | S | L |
| 301 | | A | P | | L | E | P | V | Y | P | G | D | N | A | T | P | E | E | L | A | R | Y | A | S | L |
| 302 | | A | P | | L | E | P | E | A | P | G | D | D | A | S | P | E | Q | L | A | R | Y | A | S | L |
| 303 | isocap A | | | L | E | P | V | Y | P | G | D | N | A | T | P | E | Q | M | N | R | Y | A | S | L |
| 304 | A | | | L | E | P | V | Y | P | G | D | N | A | T | P | E | Q | M | N | hR | Y | A | S | L |

-continued

| SEQ ID | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 305 | isocap A | P | L | E | P | V | Y | P | G | D | A | T | P | E | Q | M | hR | Y | Y | A | S | L |
| 306 | A | P | L | E | P | V | Y | P | G | N | A | T | P | E | Q | M | hK | Y | Y | A | S | L |
| 307 | A | P | M | E | P | V | Y | P | G | N | A | T | P | E | Q | M | R | Y | Y | A | D | L |
| 308 | A | P | L | E | P | V | Y | P | G | D | A | S | P | E | L | N | Q | Y | Y | A | S | L |
| 309 | Y | P | I | K | P | E | A | P | G | E | D | A | S | P | E | L | L | Q | Y | A | D | L |
| 310 | Y | P | I | K | P | E | A | P | G | E | D | A | S | P | E | L | A | Q | Y | A | D | L |
| 311 | Y | P | I | K | P | E | A | P | G | E | D | A | S | P | E | L | A | Q | Y | A | D | L |
| 312 | Y | P | I | K | P | E | A | P | G | E | D | A | S | P | E | L | A | Q | Y | A | D | L |
| 313 | Y | P | I | K | P | E | A | P | G | E | D | A | S | P | E | L | A | Q | Y | A | D | L |
| 314 | Y | P | I | K | P | E | A | P | G | E | D | A | S | P | E | L | A | Q | Y | A | A | L |
| 315 | Y | P | I | K | P | E | A | P | G | E | D | A | S | P | E | L | A | Q | Y | A | S | L |
| 316 | Y | P | I | K | P | E | A | P | G | E | D | A | S | P | E | N | A | Q | Y | A | D | L |
| 317 | Y | P | I | K | P | E | A | P | G | E | D | A | S | P | E | L | A | Q | Y | A | D | L |
| 318 | Y | dA | I | K | P | E | A | P | G | E | D | A | S | P | E | L | A | Q | Y | A | D | L |
| 319 | A | P | I | K | P | E | A | P | G | E | D | A | S | P | E | L | A | Q | Y | A | D | L |
| 320 | isocap Y | P | I | K | P | E | A | P | G | E | D | A | S | P | E | L | A | Q | Y | A | D | L |
| 321 | Y | P | I | K | P | E | A | P | G | E | D | A | S | P | E | L | A | Q | Y | A | D | L |
| 322 | Y | P | I | K | P | E | A | P | G | E | D | A | S | P | E | L | A | Q | Y | A | D | L |
| 323 | Y | P | I | K | P | E | A | P | G | E | D | A | S | P | E | L | A | Q | Y | A | D | L |
| 324 | Y | P | I | K | P | E | A | P | G | E | D | A | S | P | E | L | A | Q | Y | A | D | L |
| 325 | Y | P | I | K | P | E | A | P | G | E | D | A | S | P | E | L | A | Q | Y | A | D | L |
| 326 | Y | P | I | K | P | E | A | P | G | E | D | A | S | P | E | L | A | Q | Y | A | D | L |
| 327 | Y | P | I | K | P | E | A | P | G | E | D | A | S | P | E | L | A | Q | Y | A | D | L |
| 328 | Y | P | I | K | P | E | A | P | G | E | D | A | S | P | E | L | A | Q | Y | A | D | L |
| 329 | Y | P | I | K | P | E | A | P | G | E | D | A | S | P | E | L | A | Q | Y | A | D | L |
| 330 | Y | P | I | hK | P | E | A | hP | G | E | D | A | S | P | E | L | A | Q | Y | A | D | L |
| 331 | Y | P | I | hR | P | E | A | Aib | P | E | D | A | hS | hP | E | L | A | Q | Y | A | D | L |
| 332 | isocap Y | P | I | K | P | E | A | G | Sar | E | D | A | Dap | Aib | E | L | A | Q | Y | A | D | L |
| 333 | Y | P | I | K | P | E | A | P | G | E | D | A | S | P | E | L | A | Q | Y | A | D | L |
| 334 | Y | P | I | K | P | E | A | P | G | E | D | A | S | P | E | L | A | Q | Y | A | D | L |
| 335 | Y | P | I | K | P | E | A | P | G | E | D | A | S | P | E | L | A | Q | Y | A | D | L |
| 336 | Y | P | I | K | P | E | A | P | G | E | D | A | S | P | E | L | A | Q | Y | A | D | L |
| 337 | Y | P | I | K | P | E | A | P | G | E | D | A | S | P | Q | L | A | Q | Y | A | D | L |
| 338 | Y | P | I | K | P | E | A | P | G | E | D | A | S | P | D | L | A | Q | Y | A | D | L |
| 339 | Y | P | I | K | P | E | A | P | G | E | D | A | S | P | E | L | A | Q | Y | A | D | L |
| 340 | Y | P | I | K | P | E | A | P | G | E | D | A | S | P | Q | L | A | Q | Y | A | D | L |
| 341 | Y | P | I | K | P | E | A | P | G | E | D | A | S | A | S | L | A | Q | Y | A | D | L |
| 342 | Y | P | I | K | P | E | A | P | G | E | D | A | S | A | Q | M | A | Q | Y | A | D | L |
| 343 | Y | P | I | K | P | E | A | P | G | E | D | A | S | P | E | L | A | Q | Y | A | D | L |
| 344 | Y | P | I | hK | P | E | A | P | G | E | D | A | S | P | E | L | A | Q | Y | A | D | L |
| 345 | Y | P | I | hK | P | E | A | P | G | E | D | A | S | P | E | M | A | Q | Y | A | D | L |
| 346 | Y | P | I | hK | P | E | A | P | G | E | D | A | S | P | E | L | A | Q | Y | A | D | L |
| 347 | Y | P | I | K | P | E | A | P | G | E | D | A | S | P | E | M | A | Q | Y | A | A | L |
| 348 | Formula III | | | | | | | | | | | | | | | | | | | | | |
| 349 | Formula IV | | | | | | | | | | | | | | | | | | | | | |
| 350 | Formula V | | | | | | | | | | | | | | | | | | | | | |
| 351 | hPYY C-terminal Motif - 32-35 | | | | | | | | | | | | | | | | | | | | | E |

-continued

| ID | 25 | 26 | 27 | 28 | 29 | 30 | 31 | 32 | 33 | 34 | 35 | 36 | 37 |
|---|---|---|---|---|---|---|---|---|---|---|---|---|---|
| 1 | R | R | Y | I | N | M | L | T | R | P | R | Y | |
| 2 | R | H | Y | L | N | L | V | T | R | Q | R | Y | |
| 3 | R | H | Y | I | N | L | V | T | R | Q | R | Y | |
| 4 | R | H | Y | L | N | L | I | T | R | Q | R | Y | |
| 5 | R | H | Y | I | N | L | A | Aib | R | Q | R | Y | |
| 6 | R | H | Y | I | N | L | I | T | R | Q | R | Y | |
| 7 | R | H | Y | I | N | L | V | T | R | Q | R | Y | |
| 8 | R | H | Y | I | N | L | I | T | R | Q | R | Y | |
| 9 | R | H | Y | I | N | L | I | T | R | Q | R | Y | |
| 10 | R | H | Y | I | N | L | V | T | R | Q | R | Y | |
| 11 | R | N | Y | I | N | L | I | T | R | Q | R | Y | |
| 12 | R | H | Y | I | N | L | V | T | R | Q | R | Y | |
| 13 | R | H | Y | I | N | L | I | T | R | Q | R | Y | |
| 14 | R | H | Y | I | N | L | V | T | R | Q | R | Y | |
| 15 | R | H | Y | I | N | L | I | T | R | Q | R | Y | |
| 16 | R | H | Y | I | N | L | V | T | R | Q | R | Y | |
| 17 | R | H | Y | I | N | L | L | T | R | Q | R | Y | |
| 18 | R | A | Y | V | N | L | I | T | R | Q | R | Y | |
| 19 | R | R | Y | I | N | L | I | T | R | Q | R | Y | |
| 20 | R | A | Y | I | N | L | I | T | R | Q | R | Y | |
| 21 | R | H | Y | L | N | L | V | T | R | Q | R | Y | |
| 22 | R | A | Y | L | N | M | I | T | R | Q | R | Y | |
| 23 | R | H | Y | I | N | L | I | T | R | Q | R | Y | |
| 24 | R | A | Y | I | N | L | V | T | R | Q | R | Y | |
| 25 | R | H | Y | I | N | L | I | T | R | Q | R | Y | |
| 26 | R | A | Y | I | N | L | V | T | R | Q | R | Y | |
| 27 | R | H | Y | V | N | L | I | T | R | Q | R | Y | |
| 28 | R | | Y | | N | L | | T | R | Q | R | Y | |
| 29 | R | | Y | | N | L | | T | R | Q | R | Y | |
| 30 | R | | Y | | N | L | | T | R | Q | R | Y | |
| 31 | R | H | Y | L | N | L | V | T | R | Q | R | Y | |
| 32 | R | H | Y | L | N | L | V | T | R | Q | R | Y | |
| 33 | R | H | Y | L | N | L | V | T | R | Q | R | Y | |
| 34 | R | H | Y | L | N | L | V | T | R | Q | R | Y | |
| 35 | R | H | Y | L | N | L | V | T | R | Q | R | Y | |
| 36 | R | H | Y | L | N | L | V | T | R | Q | R | Y | |
| 37 | R | H | Y | L | N | L | V | T | R | Q | R | Y | |
| 38 | R | H | Y | L | N | L | V | T | R | Q | R | Y | |
| 39 | R | H | Y | L | N | L | V | T | R | Q | R | Y | |
| 40 | R | H | Y | L | N | L | V | T | R | Q | R | Y | |
| 41 | R | A | Y | L | N | L | V | T | R | Q | R | Y | |
| 42 | R | H | Y | L | N | L | V | T | R | Q | R | Y | |
| 43 | R | H | Y | L | N | A | V | T | R | Q | R | Y | |
| 44 | R | A | Y | L | N | L | V | T | R | Q | R | Y | |
| 45 | R | H | Y | L | N | L | V | T | R | Q | R | Y | |
| 46 | R | A | Y | L | N | L | V | T | R | Q | R | Y | |
| 47 | R | H | Y | L | N | L | V | T | R | Q | R | Y | |
| 48 | R | H | Y | L | N | L | V | T | R | Q | R | Y | |
| 49 | R | A | Y | L | N | L | V | T | R | R | R | Y | |
| 50 | R | H | Y | L | N | L | V | T | R | Q | R | Y | |
| 51 | R | H | Y | L | N | L | V | T | R | Q | R | Y | |

| Pos | S1 | S2 | S3 | S4 | S5 | S6 | S7 | S8 | S9 | S10 | S11 | S12 | S13 |
|---|---|---|---|---|---|---|---|---|---|---|---|---|---|
| 52 | R | H | Y | L | N | V | T | R | Q | R | Y |   |   |
| 53 | R | H | Y | L | N | V | T | R | Q | R | Y | Y |   |
| 54 | L | R | H | Y | L | N | V | T | R | Q | R | Y | Y |
| 55 | L | R | H | Y | L | N | V | T | R | Q | R | Y | Y |
| 56 | L | R | H | Y | L | N | V | T | R | Q | R | Y | Y |
| 57 | L | R | H | Y | L | N | V | T | R | Q | R | Y | Y |
| 58 | L | R | H | Y | L | N | V | T | R | Q | R | Y | Y |
| 59 | L | R | H | Y | L | N | V | T | R | Q | R | Y | Y |
| 60 | L | R | H | Y | L | N | V | T | R | Q | R | Y | Y |
| 61 | L | R | H | Y | L | N | V | T | R | Q | R | Y | Y |
| 62 | L | R | H | Y | L | N | V | T | R | Q | R | Y | Y |
| 63 | L | R | H | Y | L | N | V | T | R | Q | R | Y | Y |
| 64 | L | R | H | Y | L | N | V | T | R | Q | R | Y | Y |
| 65 | L | R | H | Y | L | N | V | T | R | Q | R | Y | Y |
| 66 | L | R | H | Y | L | N | V | T | R | Q | R | Y | Y |
| 67 | L | R | H | Y | L | N | V | T | R | Q | R | Y | Y |
| 68 | L | R | H | Y | L | N | V | T | R | Q | R | Y | Y |
| 69 | L | R | H | Y | L | N | V | T | R | Q | R | Y | Y |
| 70 | L | R | H | Y | L | N | V | T | R | Q | R | Y | Y |
| 71 | L | R | H | Y | L | N | V | T | R | Q | R | Y | Y |
| 72 | L | R | H | Y | L | N | V | T | R | Q | R | Y | Y |
| 73 | L | R | H | Y | L | N | V | T | R | Q | R | Y | Y |
| 74 | L | R | H | Y | L | N | V | T | R | Q | R | Y | Y |
| 75 | L | R | H | Y | L | N | V | T | R | Q | R | Y | Y |
| 76 | L | R | H | Y | L | N | V | T | R | Q | R | Y | Y |
| 77 | L | R | H | Y | L | N | V | T | R | Q | R | Y | Y |
| 78 | L | R | H | Y | L | N | V | T | R | Q | R | Y | Y |
| 79 | L | R | H | Y | L | N | V | T | R | Q | R | Y | Y |
| 80 | L | R | H | Y | L | N | V | T | R | Q | R | Y | Y |
| 81 | L | R | H | Y | L | N | V | T | R | Q | R | Y | Y |
| 82 | L | R | H | Y | L | N | V | T | R | Q | R | Y | Y |
| 83 | L | R | H | A | Y | N | V | T | R | Q | R | Y | Y |
| 84 | L | R | H | Y | A | N | V | T | R | Q | R | Y | Y |
| 85 | L | A | A | Y | L | A | A | A | A | A | A | A | A |
| 86 | A | R | H | Y | L | N | V | T | R | Q | R | Y | Y |
| 87 | R | H | Y | L | N | V | T | R | Q | R | Y | Y | Y |
| 88 | R | H | Y | L | N | V | T | R | Q | R | Y | Y | Y |
| 89 | R | H | Y | L | N | V | T | R | Q | R | Y |   |   |
| 90 | R | H | Y | L | N | V | T | R | Q | R | Y |   |   |
| 91 | R | H | Y | L | N | V | T | R | Q | R | Y |   |   |
| 92 | R | H | Y | L | N | V | T | R | Q | R | Y |   |   |
| 93 | R | H | Y | L | N | V | T | R | Q | R | Y |   |   |
| 94 | R | H | Y | L | N | V | T | R | Q | R | Y |   |   |
| 95 | R | H | Y | L | N | V | T | R | Q | R | Y |   |   |
| 96 | R | H | Y | L | N | V | T | R | Q | R | Y |   |   |
| 97 | R | H | Y | L | N | V | T | R | Q | R | Y |   |   |
| 98 | R | H | Y | L | N | V | T | R | Q | R | Y |   |   |
| 99 | R | H | Y | L | N | V | T | R | Q | R | Y |   |   |
| 100 | R | H | Y | L | N | V | T | R | Q | R | Y |   |   |
| 101 | R | H | Y | L | N | V | T | R | Q | R | Y |   |   |
| 102 | R | H | Y | L | N | V | T | R | Q | R | Y |   |   |
| 103 | R | H | Y | L | N | V | T | R | Q | R | Y |   |   |
| 104 | R | H | Y | L | N | V | T | R | Q | R | Y |   |   |

| Pos | | | | | | | | | | |
|---|---|---|---|---|---|---|---|---|---|---|
| 105 | R | H | Y | L | N | L | V | T | R | Q | R | Y |
| 106 | R | H | Y | L | N | L | V | T | R | Q | R | Y |
| 107 | R | H | Y | L | N | L | V | T | R | Q | R | Y |
| 108 | R | H | Y | L | N | L | V | T | R | Q | R | Y |
| 109 | R | H | Y | L | N | L | V | T | R | Q | R | Y |
| 110 | R | H | Y | L | N | L | V | T | R | Q | R | Y |
| 111 | R | H | Y | L | N | L | V | T | R | Q | R | Y |
| 112 | R | H | Y | L | N | L | V | T | R | Q | R | Y |
| 113 | A | H | Y | L | N | L | V | T | R | Q | R | Y |
| 114 | K | H | Y | L | N | L | V | T | R | Q | R | Y |
| 115 | R | A | Y | L | N | L | V | T | R | Q | R | Y |
| 116 | R | H | A | L | N | L | V | T | R | Q | R | Y |
| 117 | R | H | Y | A | N | L | V | T | R | Q | R | Y |
| 118 | R | H | Y | L | A | L | V | T | R | Q | R | Y |
| 119 | R | H | Y | L | N | A | V | T | R | Q | R | Y |
| 120 | R | H | Y | L | N | L | A | T | R | Q | R | Y |
| 121 | R | A | Y | L | N | L | V | A | R | Q | R | Y |
| 122 | R | H | Y | L | N | L | V | T | A | Q | R | Y |
| 123 | R | H | Y | L | N | L | V | T | K | A | R | Y |
| 124 | R | H | A | L | N | L | V | T | R | Q | A | Y |
| 125 | R | H | Y | L | N | L | V | T | R | Q | R | A |
| 126 | R | H | Y | L | N | L | V | T | R | Q | R | Y |
| 127 | R | H | Y | L | N | L | V | T | R | Q | R | Y |
| 128 | A | H | Y | A | N | L | V | T | R | Q | R | Y |
| 129 | R | H | Y | L | N | L | V | T | R | Q | R | Y |
| 130 | R | H | Y | L | N | L | V | T | R | Q | R | Y |
| 131 | R | H | Y | L | N | L | V | T | R | Q | R | Y |
| 132 | R | H | Y | L | N | L | V | T | R | Q | R | Y |
| 133 | R | H | Y | L | N | L | V | T | R | Q | R | Y(NMe)Y |
| 134 | R | H | Y | L | N | L | V | T | R | Q | R | H |
| 135 | R | H | Y | L | N | L | V | T | R | Q | R | H |
| 136 | R | H | Y | L | N | L | V | T | R | Q | R | W |
| 137 | R | H | Y | L | N | L | V | T | R | Q | R | F |
| 138 | R | H | Y | L | N | L | V | T | R | Q | R | F |
| 139 | hR | H | Y | L | N | L | V | T | R | Q | R | Y(CH2SO3) |
| 140 | R | H | Y | L | N | L | V | T | R | Q | R | P(OH) |
| 141 | R | H | Y | L | N | L | V | T | R | Q | R | Y |
| 142 | R | H | Y | L | N | L | V | T | R | Q | R | Y |
| 143 | R | H | Y | L | N | L | V | T | R | Q | R | Y |
| 144 | R | H | Y | L | N | L | V | T | R | Q | R | Y |
| 145 | R | H | Y | L | N | L | V | T | R | Q | R | Y |
| 146 | R | H | Y | L | N | L | V | T | R | Q | R | Y |
| 147 | R | H | Y | L | N | L | V | T | R | Q | R | Y |
| 148 | R | H | Y | L | N | L | V | T | R | Q | R | Y |
| 149 | R | H | Y | L | N | L | V | T | R | Q | R | Y |
| 150 | R | H | Y | L | N | L | V | T | R | Q | R | Y |
| 151 | R | H | Y | L | N | L | V | T | R | Q | R | Y |
| 152 | R | H | Y | L | N | L | V | T | R | Q | R | Y |
| 153 | R | H | Y | L | N | L | V | T | R | Q | R | Y |
| 154 | R | H | Y | L | N | L | V | T | R | Q | R | Y |
| 155 | R | H | Y | L | N | L | V | T | R | Q | R | Y |
| 156 | R | H | Y | L | N | L | V | T | R | Q | R | Y |
| 157 | R | H | Y | L | N | L | V | T | R | Q | R | Y |

-continued

| Pos | | | | | | | | | | | | |
|---|---|---|---|---|---|---|---|---|---|---|---|---|
| 158 | R | H | Y | L | N | L | V | T | R | Q | R | Y |
| 159 | R | H | Y | L | N | L | V | T | R | Q | R | Y |
| 160 | R | H | Y | L | N | L | V | T | R | Q | R | Y |
| 161 | R | H | Y | L | N | L | V | T | R | Q | R | Y |
| 162 | R | H | Y | L | N | L | V | T | R | Q | R | Y |
| 163 | R | H | Y | L | N | L | V | T | R | Q | R | Y |
| 164 | R | A | Y | L | N | L | V | T | R | Q | R | Y |
| 165 | R | A | Y | L | N | L | V | T | R | Q | R | Y |
| 166 | R | A | Y | L | N | L | V | T | R | Q | R | Y |
| 167 | R | A | Y | L | N | L | V | T | R | Q | R | Y |
| 168 | R | H | Y | L | N | L | V | T | R | Q | R | Y |
| 169 | K | H | Y | L | N | L | V | T | R | Q | R | Y |
| 170 | R | H | Y | L | N | L | V | T | R | Q | R | Y |
| 171 | R | H | Y | L | N | L | V | T | R | Q | R | Y |
| 172 | R | A | Y | L | N | L | V | T | R | Q | R | Y |
| 173 | R | H | Y | L | N | L | I | T | R | Q | R | Y |
| 174 | R | H | Y | L | N | L | I | T | R | Q | R | Y |
| 175 | R | H | Y | L | N | L | V | T | R | Q | R | Y |
| 176 | R | H | Y | L | N | L | V | T | R | Q | R | Y |
| 177 | R | H | Y | L | N | A | V | T | R | Q | R | Y |
| 178 | R | H | Y | L | N | L | V | T | R | Q | R | Y |
| 179 | R | H | Y | L | N | L | V | T | R | Q | R | Y |
| 180 | R | H | Y | L | N | L | V | T | R | Q | R | Y |
| 181 | R | H | Y | L | N | L | V | T | R | Q | R | Y |
| 182 | R | H | Y | L | N | L | V | T | R | Q | R | Y |
| 183 | R | H | Y | L | N | L | V | T | R | Q | R | Y |
| 184 | R | H | Y | L | N | L | V | T | R | Q | R | Y |
| 185 | R | H | Y | L | N | L | V | T | R | Q | R | Y |
| 186 | R | H | Y | L | N | L | V | T | R | Q | R | Y |
| 187 | R | H | Y | L | N | L | V | T | R | Q | R | Y |
| 188 | R | H | Y | L | N | L | V | T | R | Q | R | Y |
| 189 | R | H | Y | L | N | L | V | T | R | Q | R | Y |
| 190 | R | H | Y | L | N | L | V | T | R | Q | R | Y |
| 191 | R | H | Y | L | N | L | V | T | R | Q | R | Y |
| 192 | R | H | Y | L | N | L | V | T | R | Q | R | Y |
| 193 | R | H | Y | L | N | L | V | T | R | Q | R | Y |
| 194 | R | H | Y | L | N | L | V | T | R | Q | R | Y |
| 195 | R | H | Y | L | N | L | V | T | R | Q | R | Y |
| 196 | R | H | Y | L | N | L | V | T | R | Q | R | Y |
| 197 | R | H | Y | L | N | L | V | T | R | Q | R | Y |
| 198 | R | H | Y | L | N | L | V | T | R | Q | R | Y |
| 199 | R | H | Y | L | N | L | V | T | R | Q | R | Y |
| 200 | R | H | Y | L | N | L | V | T | R | Q | R | Y |
| 201 | R | H | Y | L | N | L | V | T | R | Q | R | Y |
| 202 | R | H | Y | L | N | L | V | T | R | Q | R | Y |
| 203 | R | H | Y | L | N | L | V | T | R | Q | R | Y |
| 204 | R | H | Y | L | N | L | V | T | R | Q | R | Y |
| 205 | R | H | Y | L | N | L | V | T | R | Q | R | Y |
| 206 | R | H | Y | L | N | L | V | T | R | Q | R | Y |
| 207 | R | H | Y | L | N | L | V | T | R | Q | R | Y(8-Am-3,6-dioxaoct) |

-continued

| | | | | | | | | | | | Y(11-Am-undecanoyl) Y(12 Ado) Y(8-Oct) |
|---|---|---|---|---|---|---|---|---|---|---|---|
| 208 | R | H | Y | L | N | L | V | T | R | Q | R | Y |
| 209 | R | H | Y | L | N | L | V | T | R | Q | R | Y |
| 210 | R | H | Y | L | N | L | V | T | R | Q | R | Y |
| 211 | R | H | Y | L | N | L | V | T | R | Q | R | Y |
| 212 | R | H | Y | L | N | L | V | T | R | Q | R | Y |
| 213 | R | H | Y | L | N | L | V | T | R | Q | R | Y |
| 214 | R | H | Y | L | N | L | V | T | R | Q | R | Y |
| 215 | R | H | Y | L | N | L | V | T | R | Q | R | Y |
| 216 | R | H | Y | L | N | L | V | T | R | Q | R | Y |
| 217 | R | H | Y | L | N | L | V | T | R | Q | R | Y |
| 218 | R | H | Y | L | N | L | V | T | R | Q | R | Y |
| 219 | R | H | Y | L | N | L | V | T | R | Q | R | Y |
| 220 | R | H | Y | L | N | L | V | T | R | Q | R | Y |
| 221 | R | H | Y | L | N | L | V | T | R | Q | R | Y |
| 222 | R | H | Y | L | N | L | V | T | R | Q | R | Y |
| 223 | R | H | Y | L | N | L | V | T | R | Q | R | Y |
| 224 | R | H | Y | L | N | L | V | T | R | Q | R | Y |
| 225 | R | H | Y | L | N | L | V | T | R | Q | R | Y |
| 226 | R | H | Y | L | N | L | V | T | R | Q | R | Y |
| 227 | R | H | Y | L | N | L | V | T | R | Q | R | Y |
| 228 | R | H | Y | L | N | L | V | T | R | Q | R | Y |
| 229 | R | H | Y | L | N | L | V | T | R | Q | R | Y |
| 230 | R | H | Y | L | N | L | V | T | R | Q | R | Y |
| 231 | R | H | Y | L | N | L | V | T | R | Q | R | Y |
| 232 | R | H | Y | L | N | L | A | T | R | Q | R | Y |
| 233 | R | H | Y | L | N | L | I | T | R | Q | R | Y |
| 234 | R | H | Y | L | N | L | I | T | R | Q | R | Y |
| 235 | R | H | Y | L | N | L | I | T | R | Q | R | Y |
| 236 | R | H | Y | L | N | L | I | T | R | Q | R | Y |
| 237 | R | H | Y | L | N | I | I | T | R | Q | R | Y |
| 238 | R | H | Y | L | N | I | I | T | R | Q | R | Y |
| 239 | R | H | Y | I | N | I | I | T | R | Q | R | Y |
| 240 | R | H | A | I | N | I | I | T | R | Q | R | Y |
| 241 | R | H | Y | I | N | I | I | T | R | Q | R | Y |
| 242 | R | H | Y | I | N | I | I | T | R | Q | R | Y |
| 243 | R | H | A | I | N | I | I | T | R | Q | R | Y |
| 244 | R | A | Y | I | N | I | I | T | R | Q | R | Y |
| 245 | R | H | Y | I | N | I | I | T | R | Q | R | Y |
| 246 | R | H | A | I | N | I | I | T | R | Q | R | Y |
| 247 | R | A | Y | I | N | I | I | T | R | Q | R | Y |
| 248 | R | H | Y | I | N | I | I | T | R | Q | R | Y |
| 249 | R | H | Y | I | N | I | I | T | R | Q | R | Y |
| 250 | R | H | Y | I | N | I | I | T | R | Q | R | Y |
| 251 | R | H | Y | I | N | I | I | T | R | Q | R | Y |
| 252 | R | H | Y | I | N | I | I | T | R | Q | R | Y |
| 253 | R | H | Y | I | N | I | I | T | R | Q | R | Y |
| 254 | R | H | Y | I | N | I | I | T | R | Q | R | Y |
| 255 | R | H | Y | I | N | I | I | T | R | Q | R | Y |
| 256 | R | H | Y | I | N | I | I | T | R | Q | R | Y |
| 257 | R | A | Y | I | N | I | I | T | R | Q | Q | Y |
| 258 | R | A | Y | I | N | I | I | T | R | Q | R | Y |
| 259 | R | A | Y | L | N | I | I | T | R | Q | R | Y |

-continued

| Pos | | | | | | | | | | | | |
|---|---|---|---|---|---|---|---|---|---|---|---|---|
| 260 | R | A | Y | I | N | L | I | T | R | Q | R | Y |
| 261 | R | R | Y | I | N | L | I | T | R | Q | R | Y |
| 262 | R | A | Y | I | N | L | I | T | R | Q | R | Y |
| 263 | R | A | Y | I | N | L | I | T | R | Q | R | Y |
| 264 | R | A | Y | I | N | L | I | T | R | Q | R | Y |
| 265 | R | A | Y | I | N | L | I | T | R | Q | R | Y |
| 266 | R | A | Y | I | N | L | I | T | R | Q | R | Y |
| 267 | R | H | Y | I | N | L | I | T | R | Q | R | Y |
| 268 | R | A | Y | I | N | L | I | T | R | Q | R | Y |
| 269 | R | H | Y | I | N | L | I | T | R | Q | R | Y |
| 270 | R | H | Y | I | N | L | I | T | R | Q | R | Y |
| 271 | R | A | Y | I | N | L | I | T | R | Q | R | Y |
| 272 | R | A | Y | I | N | L | I | T | R | Q | R | Y |
| 273 | R | A | Y | I | N | L | I | T | R | Q | R | Y |
| 274 | R | A | Y | I | N | L | I | T | R | Q | R | Y |
| 275 | R | A | Y | I | N | L | I | T | R | Q | R | Y |
| 276 | R | H | Y | I | N | L | I | T | R | Q | R | Y |
| 277 | R | A | Y | F | N | L | I | T | R | Q | R | Y |
| 278 | R | H | Y | Y | N | L | I | T | R | Q | R | Y |
| 279 | R | H | Y | Y | N | L | I | T | R | Q | R | Y |
| 280 | R | H | Y | Y | L | N | V | T | R | Q | R | Y |
| 281 | R | H | Y | Y | L | N | V | T | R | Q | R | Y |
| 282 | R | H | Y | Y | L | N | V | T | R | Q | R | Y |
| 283 | R | H | Y | Y | L | N | V | T | R | Q | R | Y |
| 284 | R | H | Y | Y | L | N | I | T | R | Q | R | Y |
| 285 | R | H | Y | Y | L | N | A | T | R | Q | R | Y |
| 286 | R | H | Y | Y | L | N | A | T | R | Q | R | Y |
| 287 | R | H | Y | Y | L | N | A | P | R | Q | R | Y |
| 288 | R | H | Y | Y | L | N | A | Aib | R | Q | R | Y |
| 289 | R | H | Y | Y | L | N | A | Sar | R | Q | R | Y |
| 290 | R | H | Y | Y | L | N | V | T | R | Q | R | Y |
| 291 | R | H | Y | Y | L | N | V | T | R | Q | R | Y |
| 292 | R | H | Y | Y | L | N | V | T | R | Q | R | Y |
| 293 | R | H | Y | Y | L | N | V | T | R | Q | R | Y |
| 294 | R | H | Y | Y | L | N | V | T | R | Q | R | Y |
| 295 | R | H | Y | Y | L | N | V | T | R | Q | R | Y |
| 296 | R | H | Y | Y | L | N | V | T | R | Q | R | Y |
| 297 | R | H | Y | Y | L | N | V | T | R | Q | R | Y |
| 298 | R | H | Y | Y | L | N | V | T | R | Q | R | Y |
| 299 | R | H | Y | Y | L | N | V | T | R | Q | R | Y |
| 300 | R | H | Y | Y | L | N | V | T | R | Q | R | Y |
| 301 | R | H | Y | Y | L | N | V | T | R | Q | R | Y |
| 302 | R | H | Y | Y | L | N | V | T | R | Q | R | Y |
| 303 | R | H | Y | Y | L | N | V | T | R | Q | R | Y |
| 304 | R | H | Y | Y | L | N | V | T | R | Q | R | Y |
| 305 | R | A | Y | I | L | N | V | T | R | Q | R | Y |
| 306 | R | A | Y | Y | L | N | L | T | R | Q | R | Y |
| 307 | R | A | Y | Y | L | N | L | T | R | P | R | Y |
| 308 | R | R | Y | Y | I | M | L | T | R | P | R | Y |
| 309 | R | R | Y | I | N | M | L | T | R | Q | R | Y |
| 310 | R | R | Y | I | N | M | L | T | R | Q | R | Y |
| 311 | R | R | Y | I | N | M | L | T | R | Q | R | Y |
| 312 | R | R | Y | I | N | M | L | T | R | Q | R | Y |

-continued

| | | | | | | | | | | | |
|---|---|---|---|---|---|---|---|---|---|---|---|
| 313 | R | H | Y | I | N | L | T | R | Q | R | Y |
| 314 | R | H | Y | I | N | M | L | T | R | Q | R | Y |
| 315 | R | H | Y | I | N | M | L | T | R | Q | R | Y |
| 316 | R | R | Y | I | N | M | L | T | R | Q | R | Y |
| 317 | R | R | Y | I | N | M | L | T | R | Q | R | Y |
| 318 | R | R | Y | I | N | M | L | T | R | Q | R | Y |
| 319 | R | R | Y | I | N | M | L | T | R | Q | R | Y |
| 320 | hK | R | Y | I | N | M | L | T | R | Q | R | Y |
| 321 | hR | R | Y | I | N | M | L | T | R | Q | R | Y |
| 322 | Om | R | Y | I | N | M | L | T | R | Q | R | Y |
| 323 | Cit | R | Y | I | N | M | L | T | R | Q | R | Y |
| 324 | R | hK | Y | I | N | M | L | T | R | Q | R | Y |
| 325 | R | hR | Y | I | N | M | L | T | R | Q | R | Y |
| 326 | R | Om | Y | I | N | M | L | T | R | Q | R | Y |
| 327 | R | Cit | Y | I | N | M | L | T | R | Q | R | Y |
| 328 | hR | R | Y | I | N | M | L | T | R | Q | R | Y |
| 329 | R | R | Y | I | N | M | L | T | R | Q | R | Y |
| 330 | R | R | Y | I | N | M | L | T | R | Q | R | Y |
| 331 | R | R | Y | I | N | M | L | T | R | Q | R | Y |
| 332 | R | R | Y | I | N | M | L | T | R | Q | R | Y |
| 333 | R | R | Y | I | N | M | L | T | R | Q | R | Y |
| 334 | R | R | Y | I | N | M | L | T | R | Q | R | Y |
| 335 | R | R | Y | I | N | M | L | T | R | Q | R | Y |
| 336 | R | R | Y | I | N | M | L | T | R | Q | R | Y |
| 337 | R | R | Y | I | N | M | L | T | R | Q | R | Y |
| 338 | R | R | Y | I | N | M | L | T | R | Q | R | Y |
| 339 | R | R | Y | I | N | M | L | T | R | Q | R | Y |
| 340 | R | R | Y | I | N | M | L | T | R | Q | R | Y |
| 341 | R | R | Y | I | N | M | L | T | R | Q | R | Y |
| 342 | R | R | Y | I | N | M | L | T | R | Q | R | Y |
| 343 | R | R | Y | I | N | M | L | T | R | Q | R | Y |
| 344 | R | R | Y | I | N | M | L | T | R | Q | R | Y |
| 345 | R | R | Y | I | N | M | L | T | R | Q | R | Y |
| 346 | R | R | Y | I | N | M | L | T | R | Q | R | Y |
| 347 | R | R | Y | I | Q | M | L | T | R | Q | R | Y |
| 348 | | | | | | | | T | R | Q | R | |
| 349 | | | | | | | | | | | | |
| 350 | | | | | | | | | | | | |
| 351 | | | | | | | | | | | | |

While the present invention has been described in terms of preferred examples and embodiments, it is understood that variations and modifications will occur to those skilled in the art. Therefore, it is intended that the appended claims cover all such equivalent variations which come within the scope of the invention as claimed.

What is claimed is:

1. A PPF polypeptide, wherein said polypeptide comprises an amino acid sequence selected from the group consisting of SEQ ID NO:54 through SEQ ID NO: 87.

2. A PPF polypeptide, wherein said polypeptide comprises an amino acid sequence selected from the group consisting of SEQ ID NOs: 131 to 132, 150 to 156, 160, 180 to 186, 207 to 210, 219 to 220, 252, 265, 275, 281, 286, 287, 292 to 293, and 313.

3. A PPF polypeptide, wherein said polypeptide comprises an amino acid sequence selected from the group consisting of SEQ ID NOs: 187 to 197.

* * * * *